US006592865B2

(12) United States Patent
Parry et al.

(10) Patent No.: US 6,592,865 B2
(45) Date of Patent: Jul. 15, 2003

(54) METHODS AND COMPOSITIONS FOR MODULATING ACE-2 ACTIVITY

(75) Inventors: Tom J. Parry, Walkersville, MD (US); Les Sekut, Ijamsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 10/158,847

(22) Filed: Jun. 3, 2002

(65) Prior Publication Data

US 2003/0091557 A1 May 15, 2003

Related U.S. Application Data

(60) Provisional application No. 60/295,004, filed on Jun. 4, 2001.

(51) Int. Cl.[7] ........................ A61K 38/00; A61K 38/08
(52) U.S. Cl. ................................ 424/94; 514/2; 514/15
(58) Field of Search ....................................... 514/2, 15

(56) References Cited

U.S. PATENT DOCUMENTS

| | | |
|---|---|---|
| 5,444,067 A | 8/1995 | Kivlighn et al. |
| 5,508,266 A | 4/1996 | Fink |
| 6,194,556 B1 | 2/2001 | Acton et al. |

FOREIGN PATENT DOCUMENTS

| | | |
|---|---|---|
| WO | WO 99/52540 A1 | 10/1999 |
| WO | WO 00/18899 A2 | 4/2000 |
| WO | WO 00/066104 A9 | 11/2000 |
| WO | WO 02/12471 A2 | 2/2002 |
| WO | WO 02/39997 A2 | 5/2002 |

OTHER PUBLICATIONS

Bramucci et al., "Bradykinin is not involved in angiotensin converting enzyme modulation of ovarian steroidogenesis and prostaglandin production in frog *Rana esculenta,"* *Acta. Physiol. Scand.,* 175:123–128 (2002).

Bramucci et al., "Different modulation of steroidogenesis and prostaglandin production in frog ovary in vitro by ACE and ANG II," *Am. J. Physiol.,* 273 (Regulatory Integrative Comp. Physiol.. 42:R2089–R2096 (1997).

Dasarathy et al., "Calcium ionophore A23187 elevates angiotensin–converting enzyme in cultured bovine endothelial cells," *Biochimica et Biophysica Acta,* 1010:16–19 (1989).

Donoghue, et al., "A Novel Angiotensin–Covnerting Enzyme–Related Carboxypeptidase (ADE2) Converts Angiotensin I to Angiotensin 1–9," *Circ. Res.,* 87:e1–e9 (2000).

Drummer et al., Effects of Chronic Enalapril Treatment on Enzymes Resposible for the Catabolism of Angiotensin I and Formation of Angiotensin II, *Biochemical Pharmacology,* 39(3):513–518 (1990).

Ito et al., "Pharmacological profile of depressor response elicited by sarthran in rat ventrolateral medulla," *Am. J. Physiol. Heart Circ. Physiol.,* 279:H2961–H2966 (2000).

Johnson et al., "Radioimmunoassay for Immunoreactive [des–Leu$^{10}$]–Angiotensin I," *Peptides,* 10:489–492 (1989).

Lembeck et al., "Demonstration of extrapulmonary activity of angiotensin converting enzyme in intact tissue preparations," *Br. J. Pharmacol.,* 100:49–54 (1990).

Miano et al., "Different modulation of aromatase activity in frog testis in vitro by ACE and ANG II," *Am. J. Physiol.,* 277 (Regulatory Integrative Comp. Physiol. 46):R1261–R1267 (1999).

Oparil et al., "Mechanism of Pulmonary Conversion of Angiotensin I to Angiotensin II in the Dog," *Circ. Res.,* 29:682–690 (Dec. 1971).

Sibinga et al., "A Pair of ACEs for Openers?," *Circ. Res.,* 87:523–525 (2000).

Snyder et al., "Inhibition of angiotensin–converting enzyme by des–Leu$^{10}$–angiotensin I: a potential mechanism of endogenous angiotensin–converting enzyme regulation," *Biochimica et Biophysica Acta,* 871:1–5 (1996).

Tipnis et al., "A Human Homolog of Angiotensin–converting Enzyme," *J. Biol. Chem.,* 275(43):33238–33243 (Oct. 27, 2000).

Turner et al., "The angiotensin–converting enzyme gene family: genomics and pharmacology," *TiPS,* 23(4):177–183 (Apr. 2002).

Turner et al., "ACEH/ACE2 is a novel mammalian metallocarboxypeptidase and a homologue of angiotensin–converting enzyme insensitive to ACE inhibitors," *Can. J. Physiol. Pharmacol.,* 80:346–353 (2002).

Vickers et al., "Hydrolysis of Biological Peptides by Human Angiotensin–converting Enzyme–related Carboxypeptidase," *J. Biol. Chem.,* 277(17):14838–14843 (Apr. 26, 2002).

*Primary Examiner*—Rebecca E. Prouty
*Assistant Examiner*—Sheridan L. Swope
(74) *Attorney, Agent, or Firm*—Human Genome Sciences, Inc.

(57) ABSTRACT

The invention relates to the use of angiotensin II in combination with angiotesin 1-9 to potentiate angiotensin II activity. The invention also relates to the use of combinations of angiotensin II and angiotensin 1-9 to increase vasoconstriction and to treat disorders associated with low blood pressure.

5 Claims, 4 Drawing Sheets

SEQUENCE LISTING

```
<160> NUMBER OF SEQ ID NOS: 158

<210> SEQ ID NO 1
<211> LENGTH: 10
<212> TYPE: PRT
<213> ORGANISM: homo sapiens
<220> FEATURE:
<221> NAME/KEY: MISC_FEATURE
<222> LOCATION: (2)..(2)
```

-continued

<223> OTHER INFORMATION: X equals any amino acid
<220> FEATURE:
<221> NAME/KEY: MISC_FEATURE
<222> LOCATION: (4)..(5)
<223> OTHER INFORMATION: X equals any amino acid
<220> FEATURE:
<221> NAME/KEY: MISC_FEATURE
<222> LOCATION: (7)..(8)
<223> OTHER INFORMATION: X equals any amino acid

<400> SEQUENCE: 1

Glx Xaa Ala Xaa Xaa Cys Xaa Xaa Phe Glx
1 5 10

<210> SEQ ID NO 2
<211> LENGTH: 7
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: X equals any amino acid
<220> FEATURE:
<221> NAME/KEY: MISC_FEATURE
<222> LOCATION: (4)..(6)
<223> OTHER INFORMATION: X equals any amino acid

<400> SEQUENCE: 2

Glx Xaa Cys Xaa Xaa Xaa Glx
1 5

<210> SEQ ID NO 3
<211> LENGTH: 17
<212> TYPE: PRT
<213> ORGANISM: homo sapiens
<220> FEATURE:
<221> NAME/KEY: MISC_FEATURE
<222> LOCATION: (2)..(4)
<223> OTHER INFORMATION: X equals any amino acid
<220> FEATURE:
<221> NAME/KEY: MISC_FEATURE
<222> LOCATION: (6)..(15)
<223> OTHER INFORMATION: X equals any amino acid

<400> SEQUENCE: 3

Glx Xaa Xaa Xaa Cys Xaa Xaa Xaa Xaa Xaa Xaa Xaa Xaa Xaa Xaa Cys
1 5 10 15

Glx

<210> SEQ ID NO 4
<211> LENGTH: 11
<212> TYPE: PRT
<213> ORGANISM: homo sapiens
<220> FEATURE:
<221> NAME/KEY: MISC_FEATURE
<222> LOCATION: (3)..(6)
<223> OTHER INFORMATION: X equals any amino acid
<220> FEATURE:
<221> NAME/KEY: MISC_FEATURE
<222> LOCATION: (9)..(9)
<223> OTHER INFORMATION: X equals any amino acid

<400> SEQUENCE: 4

Glx Arg Xaa Xaa Xaa Xaa Asp Ser Xaa Cys Glx
1 5 10

<210> SEQ ID NO 5
<211> LENGTH: 9
<212> TYPE: PRT
<213> ORGANISM: homo sapiens

-continued

<220> FEATURE:
<221> NAME/KEY: MISC_FEATURE
<222> LOCATION: (3)..(5)
<223> OTHER INFORMATION: X equals any amino acid
<220> FEATURE:
<221> NAME/KEY: MISC_FEATURE
<222> LOCATION: (8)..(8)
<223> OTHER INFORMATION: X equals any amino acid

<400> SEQUENCE: 5

Glx Cys Xaa Xaa Xaa Asp Cys Xaa Glx
1               5

<210> SEQ ID NO 6
<211> LENGTH: 7
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: X equals any amino acid
<220> FEATURE:
<221> NAME/KEY: MISC_FEATURE
<222> LOCATION: (6)..(6)
<223> OTHER INFORMATION: X equals any amino acid

<400> SEQUENCE: 6

Glx Cys Phe Xaa Trp Xaa Glx
1               5

<210> SEQ ID NO 7
<211> LENGTH: 13
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: X equals any amino acid
<220> FEATURE:
<221> NAME/KEY: MISC_FEATURE
<222> LOCATION: (4)..(4)
<223> OTHER INFORMATION: X equals any amino acid
<220> FEATURE:
<221> NAME/KEY: MISC_FEATURE
<222> LOCATION: (7)..(8)
<223> OTHER INFORMATION: X equals any amino acid
<220> FEATURE:
<221> NAME/KEY: MISC_FEATURE
<222> LOCATION: (10)..(11)
<223> OTHER INFORMATION: X equals any amino acid

<400> SEQUENCE: 7

Glx Xaa Glu Xaa Cys His Xaa Xaa Pro Xaa Xaa Cys Glx
1               5                   10

<210> SEQ ID NO 8
<211> LENGTH: 15
<212> TYPE: PRT
<213> ORGANISM: homo sapiens
<220> FEATURE:
<221> NAME/KEY: MISC_FEATURE
<222> LOCATION: (9)..(10)
<223> OTHER INFORMATION: X equals any amino acid
<220> FEATURE:
<221> NAME/KEY: MISC_FEATURE
<222> LOCATION: (13)..(13)
<223> OTHER INFORMATION: X equals any amino acid

<400> SEQUENCE: 8

Glx Lys Glu Cys Lys Phe Gly Tyr Xaa Xaa Cys Leu Xaa Trp Glx
1               5                   10                  15

-continued

```
<210> SEQ ID NO 9
<211> LENGTH: 12
<212> TYPE: PRT
<213> ORGANISM: homo sapiens
<220> FEATURE:
<221> NAME/KEY: MISC_FEATURE
<222> LOCATION: (2)..(3)
<223> OTHER INFORMATION: X equals any amino acid
<220> FEATURE:
<221> NAME/KEY: MISC_FEATURE
<222> LOCATION: (5)..(6)
<223> OTHER INFORMATION: X equals any amino acid
<220> FEATURE:
<221> NAME/KEY: MISC_FEATURE
<222> LOCATION: (8)..(9)
<223> OTHER INFORMATION: X equals any amino acid

<400> SEQUENCE: 9

Glx Xaa Xaa Cys Xaa Xaa Trp Xaa Xaa Pro Cys Glx
1               5                   10


<210> SEQ ID NO 10
<211> LENGTH: 14
<212> TYPE: PRT
<213> ORGANISM: homo sapiens
<220> FEATURE:
<221> NAME/KEY: MISC_FEATURE
<222> LOCATION: (3)..(5)
<223> OTHER INFORMATION: X equals any amino acid
<220> FEATURE:
<221> NAME/KEY: MISC_FEATURE
<222> LOCATION: (7)..(8)
<223> OTHER INFORMATION: X equals any amino acid
<220> FEATURE:
<221> NAME/KEY: MISC_FEATURE
<222> LOCATION: (11)..(12)
<223> OTHER INFORMATION: X equals any amino acid

<400> SEQUENCE: 10

Glx Cys Xaa Xaa Xaa Arg Xaa Xaa Pro Trp Xaa Xaa Cys Glx
1               5                   10


<210> SEQ ID NO 11
<211> LENGTH: 21
<212> TYPE: PRT
<213> ORGANISM: homo sapiens

<400> SEQUENCE: 11

Gly Ser Asn Arg Glu Cys His Ala Leu Phe Cys Met Asp Phe Ala Pro
1               5                   10                  15

Gly Glu Gly Gly Gly
            20


<210> SEQ ID NO 12
<211> LENGTH: 21
<212> TYPE: PRT
<213> ORGANISM: homo sapiens

<400> SEQUENCE: 12

Gly Ser Ser Pro Thr Cys Arg Ala Leu Phe Cys Val Asp Phe Ala Pro
1               5                   10                  15

Gly Glu Gly Gly Gly
            20


<210> SEQ ID NO 13
<211> LENGTH: 21
<212> TYPE: PRT
<213> ORGANISM: homo sapiens
```

-continued

<400> SEQUENCE: 13

```
Gly Ser Leu Glu Met Cys Glu Ala Leu Phe Cys Val Glu Phe Ala Pro
1               5                   10                  15

Gly Glu Gly Gly Gly
            20
```

<210> SEQ ID NO 14
<211> LENGTH: 21
<212> TYPE: PRT
<213> ORGANISM: homo sapiens

<400> SEQUENCE: 14

```
Gly Ser Asp Gln Asn Cys Phe Ala Met Tyr Cys Phe Glu Phe Ala Pro
1               5                   10                  15

Gly Glu Gly Gly Gly
            20
```

<210> SEQ ID NO 15
<211> LENGTH: 22
<212> TYPE: PRT
<213> ORGANISM: homo sapiens

<400> SEQUENCE: 15

```
Ala Gly Glu Gly Asn Cys Phe Leu Ile Gly Pro Trp Cys Phe Glu Phe
1               5                   10                  15

Gly Thr Glu Gly Gly Gly
            20
```

<210> SEQ ID NO 16
<211> LENGTH: 21
<212> TYPE: PRT
<213> ORGANISM: homo sapiens

<400> SEQUENCE: 16

```
Gly Ser Asp Gln Asn Cys Phe Ala Met Tyr Cys Phe Glu Phe Ala Pro
1               5                   10                  15

Gly Glu Gly Gly Gly
            20
```

<210> SEQ ID NO 17
<211> LENGTH: 22
<212> TYPE: PRT
<213> ORGANISM: homo sapiens

<400> SEQUENCE: 17

```
Ala Gly Glu Gly Asn Cys Phe Leu Ile Gly Pro Trp Cys Phe Glu Phe
1               5                   10                  15

Gly Thr Glu Gly Gly Gly
            20
```

<210> SEQ ID NO 18
<211> LENGTH: 24
<212> TYPE: PRT
<213> ORGANISM: homo sapiens

<400> SEQUENCE: 18

```
Gly Ser Asn Asp Tyr Cys Thr Val Phe Thr Gly Ala Leu Phe Cys Leu
1               5                   10                  15

Asp Phe Ala Pro Glu Gly Gly Gly
            20
```

-continued

<210> SEQ ID NO 19
<211> LENGTH: 24
<212> TYPE: PRT
<213> ORGANISM: homo sapiens

<400> SEQUENCE: 19

Gly Ser Tyr Asp Asn Cys Leu Gly Leu Ala Asn Leu Asn Phe Cys Phe
1 5 10 15

Asp Phe Ala Pro Glu Gly Gly Gly
20

<210> SEQ ID NO 20
<211> LENGTH: 26
<212> TYPE: PRT
<213> ORGANISM: homo sapiens

<400> SEQUENCE: 20

Gly Asp Asp Asp His Cys Glu Trp Ala Ser Tyr Trp Lys Trp Asp Leu
1 5 10 15

Cys Leu His Asp Asp Pro Glu Gly Gly Gly
20 25

<210> SEQ ID NO 21
<211> LENGTH: 26
<212> TYPE: PRT
<213> ORGANISM: homo sapiens

<400> SEQUENCE: 21

Gly Asp Asp Asp Asp Cys Gly Trp Ile Gly Phe Ala Asn Phe His Leu
1 5 10 15

Cys Leu His Gly Asp Pro Glu Gly Gly Gly
20 25

<210> SEQ ID NO 22
<211> LENGTH: 26
<212> TYPE: PRT
<213> ORGANISM: homo sapiens

<400> SEQUENCE: 22

Gly Asp Pro Phe Glu Cys Asp Trp Gly Pro Trp Thr Leu Glu Met Leu
1 5 10 15

Cys Gly Pro Pro Asp Pro Glu Gly Gly Gly
20 25

<210> SEQ ID NO 23
<211> LENGTH: 26
<212> TYPE: PRT
<213> ORGANISM: homo sapiens

<400> SEQUENCE: 23

Gly Asp Arg Leu His Cys Lys Pro Gln Arg Gln Ser Pro Trp Met Lys
1 5 10 15

Cys Gln His Leu Asp Pro Glu Gly Gly Gly
20 25

<210> SEQ ID NO 24
<211> LENGTH: 26
<212> TYPE: PRT
<213> ORGANISM: homo sapiens

<400> SEQUENCE: 24

Gly Asp Leu His Ala Cys Arg Pro Val Arg Gly Asp Pro Trp Trp Ala

-continued

```
1               5                   10                  15

Cys Thr Leu Gly Asp Pro Glu Gly Gly Gly
            20                  25


<210> SEQ ID NO 25
<211> LENGTH: 25
<212> TYPE: PRT
<213> ORGANISM: homo sapiens

<400> SEQUENCE: 25

Gly Ser Pro Asn Gln Cys Gly Val Asp Ile Trp Ala Leu Phe Cys Val
1               5                   10                  15

Asp Phe Ala Pro Glu Gly Gly Gly Lys
            20                  25


<210> SEQ ID NO 26
<211> LENGTH: 25
<212> TYPE: PRT
<213> ORGANISM: homo sapiens

<400> SEQUENCE: 26

Gly Ser Pro Asn Gln Cys Gly Val Asp Ile Trp Ala Leu Phe Cys Val
1               5                   10                  15

Asp Phe Ala Pro Glu Gly Gly Gly Lys
            20                  25


<210> SEQ ID NO 27
<211> LENGTH: 21
<212> TYPE: PRT
<213> ORGANISM: homo sapiens

<400> SEQUENCE: 27

Gly Ser Arg Ile Gly Cys Arg Asp Ser Arg Cys Asn Trp Trp Ala Pro
1               5                   10                  15

Gly Glu Gly Gly Gly
            20


<210> SEQ ID NO 28
<211> LENGTH: 21
<212> TYPE: PRT
<213> ORGANISM: homo sapiens

<400> SEQUENCE: 28

Gly Ser Arg Gly Phe Cys Arg Asp Ser Ser Cys Ser Phe Pro Ala Pro
1               5                   10                  15

Gly Glu Gly Gly Gly
            20


<210> SEQ ID NO 29
<211> LENGTH: 21
<212> TYPE: PRT
<213> ORGANISM: homo sapiens

<400> SEQUENCE: 29

Gly Ser Trp Pro Thr Cys Leu Thr Met Asp Cys Val Tyr Asn Ala Pro
1               5                   10                  15

Gly Glu Gly Gly Gly
            20


<210> SEQ ID NO 30
<211> LENGTH: 21
<212> TYPE: PRT
```

-continued

<213> ORGANISM: homo sapiens

<400> SEQUENCE: 30

```
Ala Gly Trp Val Leu Cys Phe Glu Trp Glu Asp Cys Asp Glu Lys Gly
1               5                   10                  15

Thr Glu Gly Gly Gly
            20
```

<210> SEQ ID NO 31
<211> LENGTH: 22
<212> TYPE: PRT
<213> ORGANISM: homo sapiens

<400> SEQUENCE: 31

```
Ala Gly Val Tyr Phe Cys Phe Asp Trp Glu Gln Asp Cys Asp Glu Met
1               5                   10                  15

Gly Thr Glu Gly Gly Gly
            20
```

<210> SEQ ID NO 32
<211> LENGTH: 22
<212> TYPE: PRT
<213> ORGANISM: homo sapiens

<400> SEQUENCE: 32

```
Ala Gly Trp Glu Val Cys His Trp Ala Pro Met Met Cys Lys His Gly
1               5                   10                  15

Gly Thr Glu Gly Gly Gly
            20
```

<210> SEQ ID NO 33
<211> LENGTH: 22
<212> TYPE: PRT
<213> ORGANISM: homo sapiens

<400> SEQUENCE: 33

```
Ala Gly Gln Lys Glu Cys Lys Phe Gly Tyr Pro His Cys Leu Pro Trp
1               5                   10                  15

Gly Thr Glu Gly Gly Gly
            20
```

<210> SEQ ID NO 34
<211> LENGTH: 22
<212> TYPE: PRT
<213> ORGANISM: homo sapiens

<400> SEQUENCE: 34

```
Ala Gly Ser Asp Trp Cys Gly Thr Trp Asn Asn Pro Cys Phe His Gln
1               5                   10                  15

Gly Thr Glu Gly Gly Gly
            20
```

<210> SEQ ID NO 35
<211> LENGTH: 27
<212> TYPE: PRT
<213> ORGANISM: homo sapiens

<400> SEQUENCE: 35

```
Gly Asp Leu His Ala Cys Arg Pro Val Arg Gly Asp Pro Trp Trp Ala
1               5                   10                  15

Cys Thr Leu Gly Asp Pro Glu Gly Gly Gly Lys
            20                  25
```

```
<210> SEQ ID NO 36
<211> LENGTH: 26
<212> TYPE: PRT
<213> ORGANISM: homo sapiens

<400> SEQUENCE: 36

Gly Asp Arg Tyr Leu Cys Leu Pro Gln Arg Asp Lys Pro Trp Lys Phe
1               5                   10                  15

Cys Asn Trp Phe Asp Pro Glu Gly Gly Gly
            20                  25


<210> SEQ ID NO 37
<211> LENGTH: 26
<212> TYPE: PRT
<213> ORGANISM: homo sapiens

<400> SEQUENCE: 37

Gly Asp Tyr Ser His Cys Ser Pro Leu Arg Tyr Tyr Pro Trp Trp Lys
1               5                   10                  15

Cys Thr Tyr Pro Asp Pro Glu Gly Gly Gly
            20                  25


<210> SEQ ID NO 38
<211> LENGTH: 26
<212> TYPE: PRT
<213> ORGANISM: homo sapiens

<400> SEQUENCE: 38

Gly Asp Gly Phe Thr Cys Ser Pro Ile Arg Met Phe Pro Trp Phe Arg
1               5                   10                  15

Cys Asp Leu Gly Asp Pro Glu Gly Gly Gly
            20                  25


<210> SEQ ID NO 39
<211> LENGTH: 26
<212> TYPE: PRT
<213> ORGANISM: homo sapiens

<400> SEQUENCE: 39

Gly Asp Phe Ser Pro Cys Lys Ala Leu Arg His Ser Pro Trp Trp Val
1               5                   10                  15

Cys Pro Ser Gly Asp Pro Glu Gly Gly Gly
            20                  25


<210> SEQ ID NO 40
<211> LENGTH: 12
<212> TYPE: PRT
<213> ORGANISM: homo sapiens

<400> SEQUENCE: 40

Asn Arg Glu Cys His Ala Leu Phe Cys Met Asp Phe
1               5                   10


<210> SEQ ID NO 41
<211> LENGTH: 12
<212> TYPE: PRT
<213> ORGANISM: homo sapiens

<400> SEQUENCE: 41

Ser Pro Thr Cys Arg Ala Leu Phe Cys Val Asp Phe
1               5                   10
```

<210> SEQ ID NO 42
<211> LENGTH: 12
<212> TYPE: PRT
<213> ORGANISM: homo sapiens

<400> SEQUENCE: 42

Ser Glu Asn Cys Gln Ala Leu Phe Cys Val Asp Phe
1 5 10

<210> SEQ ID NO 43
<211> LENGTH: 12
<212> TYPE: PRT
<213> ORGANISM: homo sapiens

<400> SEQUENCE: 43

Ser Pro Thr Cys Arg Ala Leu Phe Cys Val Asp Phe
1 5 10

<210> SEQ ID NO 44
<211> LENGTH: 12
<212> TYPE: PRT
<213> ORGANISM: homo sapiens

<400> SEQUENCE: 44

Leu Glu Met Cys Glu Ala Leu Phe Cys Val Glu Phe
1 5 10

<210> SEQ ID NO 45
<211> LENGTH: 12
<212> TYPE: PRT
<213> ORGANISM: homo sapiens

<400> SEQUENCE: 45

Asn Pro Glu Cys Gly Ala Leu Phe Cys Met Glu Phe
1 5 10

<210> SEQ ID NO 46
<211> LENGTH: 12
<212> TYPE: PRT
<213> ORGANISM: homo sapiens

<400> SEQUENCE: 46

Asp Phe Gly Cys Asn Ala Met Phe Cys Val Glu Phe
1 5 10

<210> SEQ ID NO 47
<211> LENGTH: 12
<212> TYPE: PRT
<213> ORGANISM: homo sapiens

<400> SEQUENCE: 47

Asp Gln Asn Cys Phe Ala Met Tyr Cys Phe Glu Phe
1 5 10

<210> SEQ ID NO 48
<211> LENGTH: 16
<212> TYPE: PRT
<213> ORGANISM: homo sapiens

<400> SEQUENCE: 48

Asn Asp Tyr Cys Thr Val Phe Thr Gly Ala Leu Phe Cys Leu Asp Phe
1 5 10 15

<210> SEQ ID NO 49

-continued

<211> LENGTH: 16
<212> TYPE: PRT
<213> ORGANISM: homo sapiens

<400> SEQUENCE: 49

Pro Asn Gln Cys Gly Val Asp Ile Trp Ala Leu Phe Cys Val Asp Phe
1 5 10 15

<210> SEQ ID NO 50
<211> LENGTH: 14
<212> TYPE: PRT
<213> ORGANISM: homo sapiens

<400> SEQUENCE: 50

Glu Gly Asn Cys Phe Leu Ile Gly Pro Trp Cys Phe Glu Phe
1 5 10

<210> SEQ ID NO 51
<211> LENGTH: 14
<212> TYPE: PRT
<213> ORGANISM: homo sapiens

<400> SEQUENCE: 51

Glu Gly Asn Cys Phe Leu Ile Gly Pro Trp Cys Phe Glu Phe
1 5 10

<210> SEQ ID NO 52
<211> LENGTH: 14
<212> TYPE: PRT
<213> ORGANISM: homo sapiens

<400> SEQUENCE: 52

His Ile Glu Cys Glu Glu Trp Gly Tyr Trp Cys Ile Glu Met
1 5 10

<210> SEQ ID NO 53
<211> LENGTH: 14
<212> TYPE: PRT
<213> ORGANISM: homo sapiens

<400> SEQUENCE: 53

Trp Glu Asp Cys Leu Trp Ile Gly Met Met Cys Val Glu Phe
1 5 10

<210> SEQ ID NO 54
<211> LENGTH: 14
<212> TYPE: PRT
<213> ORGANISM: homo sapiens

<400> SEQUENCE: 54

Tyr Glu Asp Cys Ile Gly His Ala Leu Phe Cys Met Thr Phe
1 5 10

<210> SEQ ID NO 55
<211> LENGTH: 14
<212> TYPE: PRT
<213> ORGANISM: homo sapiens

<400> SEQUENCE: 55

Asp Asp Lys Cys Phe Gly Trp Ala His Phe Cys Phe Asp Phe
1 5 10

<210> SEQ ID NO 56
<211> LENGTH: 14
<212> TYPE: PRT

-continued

<213> ORGANISM: homo sapiens

<400> SEQUENCE: 56

Gly Gly Gln Cys Gly Thr Ser Tyr Leu Phe Cys Ile Asp Phe
1 5 10

<210> SEQ ID NO 57
<211> LENGTH: 14
<212> TYPE: PRT
<213> ORGANISM: homo sapiens

<400> SEQUENCE: 57

Tyr Ser Gly Cys Ala Asp Met Tyr Met Phe Cys Ile Asp Phe
1 5 10

<210> SEQ ID NO 58
<211> LENGTH: 14
<212> TYPE: PRT
<213> ORGANISM: homo sapiens

<400> SEQUENCE: 58

Gly Gly Gln Cys Gly Thr Ser Tyr Leu Phe Cys Ile Asp Phe
1 5 10

<210> SEQ ID NO 59
<211> LENGTH: 14
<212> TYPE: PRT
<213> ORGANISM: homo sapiens

<400> SEQUENCE: 59

Lys Phe Glu Cys Met Pro Ser Ser Leu Phe Cys Val Asp Phe
1 5 10

<210> SEQ ID NO 60
<211> LENGTH: 16
<212> TYPE: PRT
<213> ORGANISM: homo sapiens

<400> SEQUENCE: 60

Asp Asp Tyr Cys Phe Asn Ile Ser Ser Tyr Ser Tyr Cys Phe Asp Phe
1 5 10 15

<210> SEQ ID NO 61
<211> LENGTH: 16
<212> TYPE: PRT
<213> ORGANISM: homo sapiens

<400> SEQUENCE: 61

Leu His Asp Cys Phe Ile Tyr Ala Asp Tyr Glu Tyr Cys Phe Asp Phe
1 5 10 15

<210> SEQ ID NO 62
<211> LENGTH: 16
<212> TYPE: PRT
<213> ORGANISM: homo sapiens

<400> SEQUENCE: 62

Asn His His Cys Leu Glu Phe Ser Ser Phe Glu Tyr Cys Phe Asp Phe
1 5 10 15

<210> SEQ ID NO 63
<211> LENGTH: 16
<212> TYPE: PRT
<213> ORGANISM: homo sapiens -continued

<400> SEQUENCE: 63

Asp Asn Leu Cys Met Ser Gly Gly Ser Phe Asp Tyr Cys Phe Asp Phe
1 5 10 15

<210> SEQ ID NO 64
<211> LENGTH: 16
<212> TYPE: PRT
<213> ORGANISM: homo sapiens

<400> SEQUENCE: 64

Ser Asp Tyr Cys Val Gly Asn Asn Ala Val Thr Tyr Cys Phe Asp Phe
1 5 10 15

<210> SEQ ID NO 65
<211> LENGTH: 16
<212> TYPE: PRT
<213> ORGANISM: homo sapiens

<400> SEQUENCE: 65

Asn Leu Asp Cys Ile Tyr Leu Gln Asn His Ser Tyr Cys Phe Asp Phe
1 5 10 15

<210> SEQ ID NO 66
<211> LENGTH: 16
<212> TYPE: PRT
<213> ORGANISM: homo sapiens

<400> SEQUENCE: 66

Asp Asp Asp Cys Met Met Leu Pro Leu Thr Met Phe Cys Phe Asp Phe
1 5 10 15

<210> SEQ ID NO 67
<211> LENGTH: 16
<212> TYPE: PRT
<213> ORGANISM: homo sapiens

<400> SEQUENCE: 67

Tyr Asp Asn Cys Leu Gly Leu Ala Asn Leu Asn Phe Cys Phe Asp Phe
1 5 10 15

<210> SEQ ID NO 68
<211> LENGTH: 16
<212> TYPE: PRT
<213> ORGANISM: homo sapiens

<400> SEQUENCE: 68

His Leu Asp Cys Tyr Asn Leu Val Asp Asn Met Phe Cys Phe Asp Phe
1 5 10 15

<210> SEQ ID NO 69
<211> LENGTH: 16
<212> TYPE: PRT
<213> ORGANISM: homo sapiens

<400> SEQUENCE: 69

Asn Trp Asn Cys Leu Gly Thr Asn Glu Leu Gln Phe Cys Leu Asp Phe
1 5 10 15

<210> SEQ ID NO 70
<211> LENGTH: 16
<212> TYPE: PRT
<213> ORGANISM: homo sapiens

<400> SEQUENCE: 70

-continued

Tyr Phe Ala Cys Thr Asn Asn Asp Ser Tyr Leu Phe Cys Leu Asp Phe
1 5 10 15

<210> SEQ ID NO 71
<211> LENGTH: 16
<212> TYPE: PRT
<213> ORGANISM: homo sapiens

<400> SEQUENCE: 71

Tyr Asn Phe Cys Met Leu Ile Gly Glu Arg Asp Tyr Cys Leu Asp Phe
1 5 10 15

<210> SEQ ID NO 72
<211> LENGTH: 16
<212> TYPE: PRT
<213> ORGANISM: homo sapiens

<400> SEQUENCE: 72

Asp Asp Val Cys Tyr Ser Leu Ile Met Ala Asp Tyr Cys Leu Asp Phe
1 5 10 15

<210> SEQ ID NO 73
<211> LENGTH: 16
<212> TYPE: PRT
<213> ORGANISM: homo sapiens

<400> SEQUENCE: 73

Tyr Phe Ala Cys Thr Asn Asn Asp Ser Tyr Leu Phe Cys Leu Asp Phe
1 5 10 15

<210> SEQ ID NO 74
<211> LENGTH: 17
<212> TYPE: PRT
<213> ORGANISM: homo sapiens

<400> SEQUENCE: 74

Asp Asp Met Cys Arg Trp Tyr Pro Phe Ala Ser Phe Tyr Met Cys Leu
1 5 10 15

Phe

<210> SEQ ID NO 75
<211> LENGTH: 18
<212> TYPE: PRT
<213> ORGANISM: homo sapiens

<400> SEQUENCE: 75

Asp Asp His Cys Glu Trp Ala Ser Tyr Trp Lys Trp Asp Leu Cys Leu
1 5 10 15

His Asp

<210> SEQ ID NO 76
<211> LENGTH: 18
<212> TYPE: PRT
<213> ORGANISM: homo sapiens

<400> SEQUENCE: 76

Asp Asp Val Cys Glu Asn Ala Asp Phe Ala Trp Leu Gly Trp Cys Met
1 5 10 15

His Phe

<210> SEQ ID NO 77
<211> LENGTH: 18
<212> TYPE: PRT

-continued

<213> ORGANISM: homo sapiens

<400> SEQUENCE: 77

Asp Asp Asp Cys Gly Trp Ile Gly Phe Ala Asn Phe His Leu Cys Leu
1 5 10 15

His Gly

<210> SEQ ID NO 78
<211> LENGTH: 18
<212> TYPE: PRT
<213> ORGANISM: homo sapiens

<400> SEQUENCE: 78

Phe Asp Asp Cys Gln Thr Ser Trp Phe Gln Gly Phe Trp Leu Cys Ile
1 5 10 15

Asp Asp

<210> SEQ ID NO 79
<211> LENGTH: 18
<212> TYPE: PRT
<213> ORGANISM: homo sapiens

<400> SEQUENCE: 79

Phe His Asp Cys Ser Trp Gly Pro Trp Gly Pro Trp Glu Ile Cys Thr
1 5 10 15

Arg Leu

<210> SEQ ID NO 80
<211> LENGTH: 18
<212> TYPE: PRT
<213> ORGANISM: homo sapiens

<400> SEQUENCE: 80

Ser Asn Asp Cys Val Trp Leu Gln Phe Trp Gly Gly Asp Met Cys Phe
1 5 10 15

Leu Pro

<210> SEQ ID NO 81
<211> LENGTH: 18
<212> TYPE: PRT
<213> ORGANISM: homo sapiens

<400> SEQUENCE: 81

Asn Ala Asp Cys Glu Trp Val Asn Phe Asn His Val Asp Leu Cys Met
1 5 10 15

Trp Asn

<210> SEQ ID NO 82
<211> LENGTH: 18
<212> TYPE: PRT
<213> ORGANISM: homo sapiens

<400> SEQUENCE: 82

Gly Ser Asp Cys Glu Trp Val Asn Phe Thr Met Phe Gln Met Cys Ile
1 5 10 15

Ser Asn

<210> SEQ ID NO 83
<211> LENGTH: 18
<212> TYPE: PRT
<213> ORGANISM: homo sapiens -continued

<400> SEQUENCE: 83

Ala Trp Asp Cys Glu Trp Asn Leu Phe Asp Ser Thr Phe Phe Cys Pro
1               5                   10                  15

Gly Phe

<210> SEQ ID NO 84
<211> LENGTH: 18
<212> TYPE: PRT
<213> ORGANISM: homo sapiens

<400> SEQUENCE: 84

Leu Tyr Glu Cys Glu Trp Lys Gln Phe Gly Pro Val Glu Met Cys Leu
1               5                   10                  15

Asn Phe

<210> SEQ ID NO 85
<211> LENGTH: 18
<212> TYPE: PRT
<213> ORGANISM: homo sapiens

<400> SEQUENCE: 85

His Ser Glu Cys Arg Trp Glu Trp Phe Gly Arg Thr Met Ile Cys Met
1               5                   10                  15

Ser Phe

<210> SEQ ID NO 86
<211> LENGTH: 18
<212> TYPE: PRT
<213> ORGANISM: homo sapiens

<400> SEQUENCE: 86

Ser Gly Glu Cys Asn Trp Gln Gln Phe Ser Gly Trp Glu Ile Cys Leu
1               5                   10                  15

Arg Asp

<210> SEQ ID NO 87
<211> LENGTH: 18
<212> TYPE: PRT
<213> ORGANISM: homo sapiens

<400> SEQUENCE: 87

Ala Tyr Leu Cys Asp Trp Ile Leu Phe Asp Ser Phe Glu Met Cys Leu
1               5                   10                  15

Ala Pro

<210> SEQ ID NO 88
<211> LENGTH: 18
<212> TYPE: PRT
<213> ORGANISM: homo sapiens

<400> SEQUENCE: 88

Pro Phe Glu Cys Asp Trp Gly Pro Trp Thr Leu Glu Met Leu Cys Gly
1               5                   10                  15

Pro Pro

<210> SEQ ID NO 89
<211> LENGTH: 15
<212> TYPE: PRT
<213> ORGANISM: homo sapiens -continued

<400> SEQUENCE: 89

Arg Gly His Cys Arg Asp Ser Arg Cys Met Met Asn Ala Pro Gly
1 5 10 15

<210> SEQ ID NO 90
<211> LENGTH: 15
<212> TYPE: PRT
<213> ORGANISM: homo sapiens

<400> SEQUENCE: 90

Arg Ile Gly Cys Arg Asp Ser Arg Cys Asn Trp Trp Ala Pro Gly
1 5 10 15

<210> SEQ ID NO 91
<211> LENGTH: 12
<212> TYPE: PRT
<213> ORGANISM: homo sapiens

<400> SEQUENCE: 91

Arg Gly Phe Cys Arg Asp Ser Ser Cys Ser Phe Pro
1 5 10

<210> SEQ ID NO 92
<211> LENGTH: 12
<212> TYPE: PRT
<213> ORGANISM: homo sapiens

<400> SEQUENCE: 92

Arg Gly Trp Cys Leu Asp Ser Arg Cys Lys Val Phe
1 5 10

<210> SEQ ID NO 93
<211> LENGTH: 16
<212> TYPE: PRT
<213> ORGANISM: homo sapiens

<400> SEQUENCE: 93

Phe Leu Phe Cys Arg Leu Ala Ser Arg Asp Ser Arg Cys Ala Ser Pro
1 5 10 15

<210> SEQ ID NO 94
<211> LENGTH: 16
<212> TYPE: PRT
<213> ORGANISM: homo sapiens

<400> SEQUENCE: 94

Phe Asn Pro Cys Arg Leu Gln Ser Arg Asp Ser Ala Cys Arg Phe Arg
1 5 10 15

<210> SEQ ID NO 95
<211> LENGTH: 16
<212> TYPE: PRT
<213> ORGANISM: homo sapiens

<400> SEQUENCE: 95

Phe Phe Pro Cys Arg Ala Leu Glu Lys Asp Ser Arg Cys Ser Phe Phe
1 5 10 15

<210> SEQ ID NO 96
<211> LENGTH: 16
<212> TYPE: PRT
<213> ORGANISM: homo sapiens

<400> SEQUENCE: 96

-continued

His Phe Ser Cys Arg Leu Pro Ser Leu Asp Ser Arg Cys Gln Leu Trp
1 5 10 15

<210> SEQ ID NO 97
<211> LENGTH: 12
<212> TYPE: PRT
<213> ORGANISM: homo sapiens

<400> SEQUENCE: 97

Asn Asp Val Cys Leu Asn Asp Asp Cys Val Tyr Gly
1 5 10

<210> SEQ ID NO 98
<211> LENGTH: 12
<212> TYPE: PRT
<213> ORGANISM: homo sapiens

<400> SEQUENCE: 98

Trp Pro Thr Cys Leu Thr Met Asp Cys Val Tyr Asn
1 5 10

<210> SEQ ID NO 99
<211> LENGTH: 12
<212> TYPE: PRT
<213> ORGANISM: homo sapiens

<400> SEQUENCE: 99

His Tyr Asn Cys His Thr Asn Asp Cys Val Val Leu
1 5 10

<210> SEQ ID NO 100
<211> LENGTH: 12
<212> TYPE: PRT
<213> ORGANISM: homo sapiens

<400> SEQUENCE: 100

His Leu Arg Cys Met Thr Ser Asp Cys Ile His Phe
1 5 10

<210> SEQ ID NO 101
<211> LENGTH: 13
<212> TYPE: PRT
<213> ORGANISM: homo sapiens

<400> SEQUENCE: 101

Trp Val Leu Cys Phe Glu Trp Glu Asp Cys Asp Glu Lys
1 5 10

<210> SEQ ID NO 102
<211> LENGTH: 13
<212> TYPE: PRT
<213> ORGANISM: homo sapiens

<400> SEQUENCE: 102

Tyr Glu Tyr Cys Phe Glu Trp Glu Gln Cys Trp Glu Lys
1 5 10

<210> SEQ ID NO 103
<211> LENGTH: 13
<212> TYPE: PRT
<213> ORGANISM: homo sapiens

<400> SEQUENCE: 103

Gly Ile Phe Cys Phe Glu Trp Glu Thr Cys Tyr Gln Ala
1 5 10

-continued

<210> SEQ ID NO 104
<211> LENGTH: 11
<212> TYPE: PRT
<213> ORGANISM: homo sapiens

<400> SEQUENCE: 104

Pro Gln Phe Cys Phe Glu Trp Glu Pro Cys Phe
1               5                   10

<210> SEQ ID NO 105
<211> LENGTH: 13
<212> TYPE: PRT
<213> ORGANISM: homo sapiens

<400> SEQUENCE: 105

Ile Gly Phe Cys Phe Glu Trp Glu Val Cys Tyr Glu Gly
1               5                   10

<210> SEQ ID NO 106
<211> LENGTH: 13
<212> TYPE: PRT
<213> ORGANISM: homo sapiens

<400> SEQUENCE: 106

Ser Ile Tyr Cys Phe Asp Trp Glu Asp Cys Trp Asp Glu
1               5                   10

<210> SEQ ID NO 107
<211> LENGTH: 13
<212> TYPE: PRT
<213> ORGANISM: homo sapiens

<400> SEQUENCE: 107

Tyr Asp Trp Cys Phe Asp Trp Glu Gln Cys Trp Asp Gln
1               5                   10

<210> SEQ ID NO 108
<211> LENGTH: 13
<212> TYPE: PRT
<213> ORGANISM: homo sapiens

<400> SEQUENCE: 108

Val Gly Phe Cys Phe Asp Trp Glu Pro Cys Asp Glu Leu
1               5                   10

<210> SEQ ID NO 109
<211> LENGTH: 13
<212> TYPE: PRT
<213> ORGANISM: homo sapiens

<400> SEQUENCE: 109

Met Asp Phe Cys Phe Asp Trp Glu Glu Cys Trp Thr Asn
1               5                   10

<210> SEQ ID NO 110
<211> LENGTH: 13
<212> TYPE: PRT
<213> ORGANISM: homo sapiens

<400> SEQUENCE: 110

Asn Ile Phe Cys Phe Asp Trp Glu Pro Cys His Phe Gly
1               5                   10

-continued

<210> SEQ ID NO 111
<211> LENGTH: 13
<212> TYPE: PRT
<213> ORGANISM: homo sapiens

<400> SEQUENCE: 111

Phe Glu Ile Cys Phe Asp Trp Glu Val Cys His Glu Gln
1 5 10

<210> SEQ ID NO 112
<211> LENGTH: 13
<212> TYPE: PRT
<213> ORGANISM: homo sapiens

<400> SEQUENCE: 112

Asp Tyr Leu Cys Phe Asp Trp Glu Ala Cys Trp Leu Ser
1 5 10

<210> SEQ ID NO 113
<211> LENGTH: 13
<212> TYPE: PRT
<213> ORGANISM: homo sapiens

<400> SEQUENCE: 113

Tyr Ala Met Cys Phe Asp Trp Asp Glu Cys Phe Leu Gly
1 5 10

<210> SEQ ID NO 114
<211> LENGTH: 14
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: X equals any amino acid

<400> SEQUENCE: 114

Trp Xaa Trp Cys Phe Glu Trp Glu Asp Trp Cys Leu Val Glu
1 5 10

<210> SEQ ID NO 115
<211> LENGTH: 14
<212> TYPE: PRT
<213> ORGANISM: homo sapiens

<400> SEQUENCE: 115

Tyr Gln Phe Cys Phe Asp Trp Glu Thr Thr Cys Trp Leu Asp
1 5 10

<210> SEQ ID NO 116
<211> LENGTH: 14
<212> TYPE: PRT
<213> ORGANISM: homo sapiens

<400> SEQUENCE: 116

Val Tyr Phe Cys Phe Asp Trp Glu Gln Asp Cys Asp Glu Met
1 5 10

<210> SEQ ID NO 117
<211> LENGTH: 14
<212> TYPE: PRT
<213> ORGANISM: homo sapiens

<400> SEQUENCE: 117

Phe Gln Leu Cys Phe Asp Trp Glu Glu Glu Cys Glu Glu Ser
1 5 10

-continued

<210> SEQ ID NO 118
<211> LENGTH: 13
<212> TYPE: PRT
<213> ORGANISM: homo sapiens

<400> SEQUENCE: 118

Trp Ala Val Cys Phe Asp Trp Glu Asn Cys Gly Asp Lys
1 5 10

<210> SEQ ID NO 119
<211> LENGTH: 14
<212> TYPE: PRT
<213> ORGANISM: homo sapiens

<400> SEQUENCE: 119

Trp Gln Phe Cys Phe Asp Trp Asp Leu Asn Cys Asp Leu Arg
1 5 10

<210> SEQ ID NO 120
<211> LENGTH: 18
<212> TYPE: PRT
<213> ORGANISM: homo sapiens

<400> SEQUENCE: 120

Tyr Trp Phe Cys Phe Asp Trp Glu Glu Asp Ala Asn Gly His Cys Gly
1 5 10 15

Gly Asn

<210> SEQ ID NO 121
<211> LENGTH: 18
<212> TYPE: PRT
<213> ORGANISM: homo sapiens

<400> SEQUENCE: 121

Phe Leu Leu Cys Phe Asp Trp Asp Ile Asp Trp Glu Tyr Gly Cys Gln
1 5 10 15

His His

<210> SEQ ID NO 122
<211> LENGTH: 14
<212> TYPE: PRT
<213> ORGANISM: homo sapiens

<400> SEQUENCE: 122

Tyr Glu Glu Cys His Trp Arg Pro Met Ala Cys Ser Thr His
1 5 10

<210> SEQ ID NO 123
<211> LENGTH: 14
<212> TYPE: PRT
<213> ORGANISM: homo sapiens

<400> SEQUENCE: 123

Trp Glu Val Cys His Trp Ala Pro Met Met Cys Lys His Gly
1 5 10

<210> SEQ ID NO 124
<211> LENGTH: 14
<212> TYPE: PRT
<213> ORGANISM: homo sapiens

<400> SEQUENCE: 124

-continued

```
Tyr Glu Phe Cys His Tyr Ala Pro Gln Glu Cys Lys His Met
1               5                   10


<210> SEQ ID NO 125
<211> LENGTH: 14
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: X equals any amino acid
<220> FEATURE:
<221> NAME/KEY: MISC_FEATURE
<222> LOCATION: (10)..(10)
<223> OTHER INFORMATION: X equals any amino acid

<400> SEQUENCE: 125

Xaa Lys Glu Cys Lys Phe Gly Tyr Ser Xaa Cys Leu Ala Trp
1               5                   10


<210> SEQ ID NO 126
<211> LENGTH: 14
<212> TYPE: PRT
<213> ORGANISM: homo sapiens

<400> SEQUENCE: 126

Gln Lys Glu Cys Lys Phe Gly Tyr Pro His Cys Leu Pro Trp
1               5                   10


<210> SEQ ID NO 127
<211> LENGTH: 13
<212> TYPE: PRT
<213> ORGANISM: homo sapiens

<400> SEQUENCE: 127

Glu His Asn Cys Thr Trp Trp Asn Pro Cys Trp Thr Thr
1               5                   10


<210> SEQ ID NO 128
<211> LENGTH: 13
<212> TYPE: PRT
<213> ORGANISM: homo sapiens

<400> SEQUENCE: 128

Met Asp His Cys Thr Trp Tyr Gln Pro Cys Val Leu Lys
1               5                   10


<210> SEQ ID NO 129
<211> LENGTH: 13
<212> TYPE: PRT
<213> ORGANISM: homo sapiens

<400> SEQUENCE: 129

Trp Asp His Cys Asn Trp Ala His Pro Cys Ser Arg Lys
1               5                   10


<210> SEQ ID NO 130
<211> LENGTH: 14
<212> TYPE: PRT
<213> ORGANISM: homo sapiens

<400> SEQUENCE: 130

Ser Asp Trp Cys Gly Thr Trp Asn Asn Pro Cys Phe His Gln
1               5                   10


<210> SEQ ID NO 131
```

-continued

<211> LENGTH: 18
<212> TYPE: PRT
<213> ORGANISM: homo sapiens

<400> SEQUENCE: 131

Arg Tyr Leu Cys Leu Pro Gln Arg Asp Lys Pro Trp Lys Phe Cys Asn
1 5 10 15

Trp Phe

<210> SEQ ID NO 132
<211> LENGTH: 18
<212> TYPE: PRT
<213> ORGANISM: homo sapiens

<400> SEQUENCE: 132

Arg Leu His Cys Lys Pro Gln Arg Gln Ser Pro Trp Met Lys Cys Gln
1 5 10 15

His Leu

<210> SEQ ID NO 133
<211> LENGTH: 18
<212> TYPE: PRT
<213> ORGANISM: homo sapiens

<400> SEQUENCE: 133

Tyr Ser His Cys Ser Pro Leu Arg Tyr Tyr Pro Trp Trp Lys Cys Thr
1 5 10 15

Tyr Pro

<210> SEQ ID NO 134
<211> LENGTH: 18
<212> TYPE: PRT
<213> ORGANISM: homo sapiens

<400> SEQUENCE: 134

Leu His Ala Cys Arg Pro Val Arg Gly Asp Pro Trp Trp Ala Cys Thr
1 5 10 15

Leu Gly

<210> SEQ ID NO 135
<211> LENGTH: 18
<212> TYPE: PRT
<213> ORGANISM: homo sapiens

<400> SEQUENCE: 135

Gly Phe Thr Cys Ser Pro Ile Arg Met Phe Pro Trp Phe Arg Cys Asp
1 5 10 15

Leu Gly

<210> SEQ ID NO 136
<211> LENGTH: 18
<212> TYPE: PRT
<213> ORGANISM: homo sapiens

<400> SEQUENCE: 136

Phe Ser Pro Cys Lys Ala Leu Arg His Ser Pro Trp Trp Val Cys Pro
1 5 10 15

Ser Gly

<210> SEQ ID NO 137
<211> LENGTH: 2920

-continued

<212> TYPE: DNA
<213> ORGANISM: homo sapiens
<220> FEATURE:
<221> NAME/KEY: misc_feature
<222> LOCATION: (1707)..(1707)
<223> OTHER INFORMATION: n equals any amino acid
<220> FEATURE:
<221> NAME/KEY: misc_feature
<222> LOCATION: (2702)..(2702)
<223> OTHER INFORMATION: n equals any amino acid
<220> FEATURE:
<221> NAME/KEY: misc_feature
<222> LOCATION: (2749)..(2749)
<223> OTHER INFORMATION: n equals any amino acid
<220> FEATURE:
<221> NAME/KEY: misc_feature
<222> LOCATION: (2757)..(2757)
<223> OTHER INFORMATION: n equals any amino acid
<220> FEATURE:
<221> NAME/KEY: misc_feature
<222> LOCATION: (2788)..(2789)
<223> OTHER INFORMATION: n equals any amino acid
<220> FEATURE:
<221> NAME/KEY: misc_feature
<222> LOCATION: (2819)..(2819)
<223> OTHER INFORMATION: n equals any amino acid
<220> FEATURE:
<221> NAME/KEY: misc_feature
<222> LOCATION: (2835)..(2835)
<223> OTHER INFORMATION: n equals any amino acid
<220> FEATURE:
<221> NAME/KEY: misc_feature
<222> LOCATION: (2856)..(2856)
<223> OTHER INFORMATION: n equals any amino acid

<400> SEQUENCE: 137

```
gtggatgtga tcttggctcc ccggggacga tgtcagctct tcctggctcc ttctcagcct     60

tgttgctgta actgctgctc agtccaccat tgaggaacag gccaagacat tttgggaca     120

agtttaacca cgaagccgaa gacctgttct atcaaagttc acttgcttct tggaattata    180

acaccaatat tactgaagag aatgtccaaa acatgaataa tgctggggac aaatggtctg    240

cctttttaaa ggaacagtcc acacttgccc aaatgtatcc actacaagaa attcagaatc    300

tcacagtcaa gcttcagctg caggctcttc agcaaaatgg gtcttcagtg ctctcagaag    360

acaagagcaa acggttgaac acaattctaa atacaatgag caccatctac agtactggaa    420

aagtttgtaa cccagataat ccacaagaat gcttattact tgaaccaggt ttgaatgaaa    480

taatggcaaa cagtttagac tacaatgaga ggctctgggc ttgggaaagc tggagatctg    540

aggtcggcaa gcagctgagg ccattatatg aagagtatgt ggtcttgaaa aatgagatgg    600

caagagcaaa tcattatgag gactatgggg attattggag aggagactat gaagtaaatg    660

gggtagatgg ctatgactac agccgcggcc agttgattga agatgtggaa catacctttg    720

aagagattaa accattatat gaacatcttc atgcctatgt gaggccaaag ttgatgaatg    780

cctatccttc ctatatcagt ccaattggat gcctccctgc tcatttgctt ggtgatatgt    840

ggggtagatt ttggacaaat ytgtacwstt tgacagttcc ctttggacag aaaccaaaca    900

tagatgttac tgatgcaatg gtggaccagr cctgggatgc acagagaata ttcaaggagg    960

ccgagaagtt ctttgtatct gttggtcttc ctaatatgac tcaaggattc tgggaaaatt   1020

ccatgctaac ggacccagga aatgttcaga aagcagtctg ccatcccaca gcttgggacc   1080

tggggaaggg cgacttcagg atccttatgt gcacaaaggt gacaatggac gacttcctga   1140

cagctcatca tgagatgggg catatccagt atgatatggc atatgctgca caaccttttc   1200

tgctaagaaa tggagctaat gaaggattcc atgaagctgt tggggaaatc atgtcacttt   1260
```

-continued

```
ctgcagccac acctaagcat ttaaaatcca ttggtcttct gtcacccgat tttcaagaag   1320

acaatgaaac agaaataaac ttcctgctca aacaagcact cacgattgtt gggactctgc   1380

catttactta catgttagag aagtggaggt ggatggtctt taaaggggaa attcccaaag   1440

accagtggat gaaaaagtgg tgggagatga agcgagagat agttggggtg gtggaacctg   1500

tgccccatga tgaaacatac tgtgaccccg catctctgtt ccatgtttct aatgattact   1560

cattcattcg atattacaca aggacccttt accaattcca gtttcaagaa gcactttgtc   1620

aagcagctaa acatgaaggc cctctgcaca aatgtgacat ctcaaactct acagaagctg   1680

gacagaaact gttcaatatg ctgaggnttg gaaaatcaga accctggacc ctagcattgg   1740

aaaatgttgt aggagcaaag aacatgaatg taaggccact gctcaactac tttgagccct   1800

tatttacctg gctgaaagac cagaacaaga attcttttgt gggatggagt accgactgga   1860

gtccatatgc agaccaaagc atcaaagtga ggataagcct aaaatcagct cttggagata   1920

aagcatatga atggaacgac aatgaaatgt acctgttccg atcatctgtt gcatatgcta   1980

tgaggcagta ctttttaaaa gtaaaaaatc agatgattct tttggggag gaggatgtgc   2040

gagtggctaa tttgaaacca agaatctcct ttaatttctt tgtcactgca cctaaaaatg   2100

tgtctgatat cattcctaga actgaagttg aaaaggccat caggatgtcc cggagccgta   2160

tcaatgatgc tttccgtctg aatgacgaca gcctagagtt tctggggata cagccaacac   2220

ttggacctcc taaccagccc cctgtttcca tatggctgat tgtttttgga gttgtgatgg   2280

gagtgatagt ggttggcatt gtcatcctga tcttcactgg gatcagagat cggaagaagg   2340

gcctgtaaat ggaattcctg cattgctcta accatgtaca accttggact tagcttttac   2400

ctgtaactgg cttctgagag acaaagagga gaaaccttca ctcctagtac acctattaca   2460

gctgcagagg tagaggagac agttgcagaa ctagttacaa tgacgataag aaacaatact   2520

ttgttattcc atagcacctt taatgttcat gtgtattatc tcagctagcc ttgaaccgcc   2580

taagtaaggt gatgaggacg ggtttaagcc ccactgatat tttaaaagcc cagagaaaag   2640

tgttcgttcc tctactaacc tgttctttta gagcagggat ctgcatacta ggcctgcagc   2700

cnaaatgagt aggtagccca ctacctattt ttgtatagcc agagggctna gaatggnttt   2760

tacattttaa gtggttttac atttaagnnc aaaagaagga taatatttca tgacaagtna   2820

aaattatatg aactnaaaat tgtatgaatt ttatgnattt atatttcagt attcataatt   2880

aaagttttat tgaactacaa aaaaaaaaaa aaaaaaaaaa                         2920


<210> SEQ ID NO 138
<211> LENGTH: 711
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: Xaa equals any amino acid
<220> FEATURE:
<221> NAME/KEY: MISC_FEATURE
<222> LOCATION: (240)..(240)
<223> OTHER INFORMATION: Xaa equals any amino acid
<220> FEATURE:
<221> NAME/KEY: MISC_FEATURE
<222> LOCATION: (499)..(499)
<223> OTHER INFORMATION: Xaa equals any amino acid

<400> SEQUENCE: 138

Met Asn Asn Ala Gly Asp Lys Trp Ser Ala Phe Leu Lys Glu Gln Ser
1               5                   10                  15
```

-continued

```
Thr Leu Ala Gln Met Tyr Pro Leu Gln Glu Ile Gln Asn Leu Thr Val
            20                  25                  30

Lys Leu Gln Leu Gln Ala Leu Gln Gln Asn Gly Ser Ser Val Leu Ser
        35                  40                  45

Glu Asp Lys Ser Lys Arg Leu Asn Thr Ile Leu Asn Thr Met Ser Thr
    50                  55                  60

Ile Tyr Ser Thr Gly Lys Val Cys Asn Pro Asp Asn Pro Gln Glu Cys
65                  70                  75                  80

Leu Leu Leu Glu Pro Gly Leu Asn Glu Ile Met Ala Asn Ser Leu Asp
                85                  90                  95

Tyr Asn Glu Arg Leu Trp Ala Trp Glu Ser Trp Arg Ser Glu Val Gly
            100                 105                 110

Lys Gln Leu Arg Pro Leu Tyr Glu Glu Tyr Val Val Leu Lys Asn Glu
        115                 120                 125

Met Ala Arg Ala Asn His Tyr Glu Asp Tyr Gly Asp Tyr Trp Arg Gly
    130                 135                 140

Asp Tyr Glu Val Asn Gly Val Asp Gly Tyr Asp Tyr Ser Arg Gly Gln
145                 150                 155                 160

Leu Ile Glu Asp Val Glu His Thr Phe Glu Glu Ile Lys Pro Leu Tyr
                165                 170                 175

Glu His Leu His Ala Tyr Val Arg Pro Lys Leu Met Asn Ala Tyr Pro
            180                 185                 190

Ser Tyr Ile Ser Pro Ile Gly Cys Leu Pro Ala His Leu Leu Gly Asp
        195                 200                 205

Met Trp Gly Arg Phe Trp Thr Asn Leu Tyr Xaa Leu Thr Val Pro Phe
    210                 215                 220

Gly Gln Lys Pro Asn Ile Asp Val Thr Asp Ala Met Val Asp Gln Xaa
225                 230                 235                 240

Trp Asp Ala Gln Arg Ile Phe Lys Glu Ala Glu Lys Phe Phe Val Ser
                245                 250                 255

Val Gly Leu Pro Asn Met Thr Gln Gly Phe Trp Glu Asn Ser Met Leu
            260                 265                 270

Thr Asp Pro Gly Asn Val Gln Lys Ala Val Cys His Pro Thr Ala Trp
        275                 280                 285

Asp Leu Gly Lys Gly Asp Phe Arg Ile Leu Met Cys Thr Lys Val Thr
    290                 295                 300

Met Asp Asp Phe Leu Thr Ala His His Glu Met Gly His Ile Gln Tyr
305                 310                 315                 320

Asp Met Ala Tyr Ala Ala Gln Pro Phe Leu Leu Arg Asn Gly Ala Asn
                325                 330                 335

Glu Gly Phe His Glu Ala Val Gly Glu Ile Met Ser Leu Ser Ala Ala
            340                 345                 350

Thr Pro Lys His Leu Lys Ser Ile Gly Leu Leu Ser Pro Asp Phe Gln
        355                 360                 365

Glu Asp Asn Glu Thr Glu Ile Asn Phe Leu Leu Lys Gln Ala Leu Thr
    370                 375                 380

Ile Val Gly Thr Leu Pro Phe Thr Tyr Met Leu Glu Lys Trp Arg Trp
385                 390                 395                 400

Met Val Phe Lys Gly Glu Ile Pro Lys Asp Gln Trp Met Lys Lys Trp
                405                 410                 415

Trp Glu Met Lys Arg Glu Ile Val Gly Val Val Glu Pro Val Pro His
            420                 425                 430

Asp Glu Thr Tyr Cys Asp Pro Ala Ser Leu Phe His Val Ser Asn Asp
```

-continued

```
        435                 440                 445

Tyr Ser Phe Ile Arg Tyr Tyr Thr Arg Thr Leu Tyr Gln Phe Gln Phe
    450                 455                 460

Gln Glu Ala Leu Cys Gln Ala Ala Lys His Glu Gly Pro Leu His Lys
465                 470                 475                 480

Cys Asp Ile Ser Asn Ser Thr Glu Ala Gly Gln Lys Leu Phe Asn Met
                485                 490                 495

Leu Arg Xaa Gly Lys Ser Glu Pro Trp Thr Leu Ala Leu Glu Asn Val
            500                 505                 510

Val Gly Ala Lys Asn Met Asn Val Arg Pro Leu Leu Asn Tyr Phe Glu
        515                 520                 525

Pro Leu Phe Thr Trp Leu Lys Asp Gln Asn Lys Asn Ser Phe Val Gly
    530                 535                 540

Trp Ser Thr Asp Trp Ser Pro Tyr Ala Asp Gln Ser Ile Lys Val Arg
545                 550                 555                 560

Ile Ser Leu Lys Ser Ala Leu Gly Asp Lys Ala Tyr Glu Trp Asn Asp
                565                 570                 575

Asn Glu Met Tyr Leu Phe Arg Ser Ser Val Ala Tyr Ala Met Arg Gln
            580                 585                 590

Tyr Phe Leu Lys Val Lys Asn Gln Met Ile Leu Phe Gly Glu Glu Asp
        595                 600                 605

Val Arg Val Ala Asn Leu Lys Pro Arg Ile Ser Phe Asn Phe Phe Val
    610                 615                 620

Thr Ala Pro Lys Asn Val Ser Asp Ile Ile Pro Arg Thr Glu Val Glu
625                 630                 635                 640

Lys Ala Ile Arg Met Ser Arg Ser Arg Ile Asn Asp Ala Phe Arg Leu
                645                 650                 655

Asn Asp Asp Ser Leu Glu Phe Leu Gly Ile Gln Pro Thr Leu Gly Pro
            660                 665                 670

Pro Asn Gln Pro Pro Val Ser Ile Trp Leu Ile Val Phe Gly Val Val
        675                 680                 685

Met Gly Val Ile Val Val Gly Ile Val Ile Leu Ile Phe Thr Gly Ile
    690                 695                 700

Arg Asp Arg Lys Lys Gly Leu
705                 710


<210> SEQ ID NO 139
<211> LENGTH: 17
<212> TYPE: PRT
<213> ORGANISM: homo sapiens

<400> SEQUENCE: 139

Leu Ile Val Phe Gly Val Val Met Gly Val Ile Val Val Gly Ile Val
1               5                   10                  15

Ile


<210> SEQ ID NO 140
<211> LENGTH: 681
<212> TYPE: PRT
<213> ORGANISM: homo sapiens
<220> FEATURE:
<221> NAME/KEY: MISC_FEATURE
<222> LOCATION: (219)..(219)
<223> OTHER INFORMATION: Xaa equals any amino acid
<220> FEATURE:
<221> NAME/KEY: MISC_FEATURE
<222> LOCATION: (240)..(240)
<223> OTHER INFORMATION: Xaa equals any amino acid
```

-continued

```
<220> FEATURE:
<221> NAME/KEY: MISC_FEATURE
<222> LOCATION: (499)..(499)
<223> OTHER INFORMATION: Xaa equals any amino acid

<400> SEQUENCE: 140

Met Asn Asn Ala Gly Asp Lys Trp Ser Ala Phe Leu Lys Glu Gln Ser
1               5                   10                  15

Thr Leu Ala Gln Met Tyr Pro Leu Gln Glu Ile Gln Asn Leu Thr Val
            20                  25                  30

Lys Leu Gln Leu Gln Ala Leu Gln Gln Asn Gly Ser Ser Val Leu Ser
        35                  40                  45

Glu Asp Lys Ser Lys Arg Leu Asn Thr Ile Leu Asn Thr Met Ser Thr
    50                  55                  60

Ile Tyr Ser Thr Gly Lys Val Cys Asn Pro Asp Asn Pro Gln Glu Cys
65                  70                  75                  80

Leu Leu Leu Glu Pro Gly Leu Asn Glu Ile Met Ala Asn Ser Leu Asp
                85                  90                  95

Tyr Asn Glu Arg Leu Trp Ala Trp Glu Ser Trp Arg Ser Glu Val Gly
            100                 105                 110

Lys Gln Leu Arg Pro Leu Tyr Glu Glu Tyr Val Val Leu Lys Asn Glu
        115                 120                 125

Met Ala Arg Ala Asn His Tyr Glu Asp Tyr Gly Asp Tyr Trp Arg Gly
    130                 135                 140

Asp Tyr Glu Val Asn Gly Val Asp Gly Tyr Asp Tyr Ser Arg Gly Gln
145                 150                 155                 160

Leu Ile Glu Asp Val Glu His Thr Phe Glu Glu Ile Lys Pro Leu Tyr
                165                 170                 175

Glu His Leu His Ala Tyr Val Arg Pro Lys Leu Met Asn Ala Tyr Pro
            180                 185                 190

Ser Tyr Ile Ser Pro Ile Gly Cys Leu Pro Ala His Leu Leu Gly Asp
        195                 200                 205

Met Trp Gly Arg Phe Trp Thr Asn Leu Tyr Xaa Leu Thr Val Pro Phe
    210                 215                 220

Gly Gln Lys Pro Asn Ile Asp Val Thr Asp Ala Met Val Asp Gln Xaa
225                 230                 235                 240

Trp Asp Ala Gln Arg Ile Phe Lys Glu Ala Glu Lys Phe Phe Val Ser
                245                 250                 255

Val Gly Leu Pro Asn Met Thr Gln Gly Phe Trp Glu Asn Ser Met Leu
            260                 265                 270

Thr Asp Pro Gly Asn Val Gln Lys Ala Val Cys His Pro Thr Ala Trp
        275                 280                 285

Asp Leu Gly Lys Gly Asp Phe Arg Ile Leu Met Cys Thr Lys Val Thr
    290                 295                 300

Met Asp Asp Phe Leu Thr Ala His His Glu Met Gly His Ile Gln Tyr
305                 310                 315                 320

Asp Met Ala Tyr Ala Ala Gln Pro Phe Leu Leu Arg Asn Gly Ala Asn
                325                 330                 335

Glu Gly Phe His Glu Ala Val Gly Glu Ile Met Ser Leu Ser Ala Ala
            340                 345                 350

Thr Pro Lys His Leu Lys Ser Ile Gly Leu Leu Ser Pro Asp Phe Gln
        355                 360                 365

Glu Asp Asn Glu Thr Glu Ile Asn Phe Leu Leu Lys Gln Ala Leu Thr
    370                 375                 380
```

-continued

```
Ile Val Gly Thr Leu Pro Phe Thr Tyr Met Leu Glu Lys Trp Arg Trp
385                 390                 395                 400

Met Val Phe Lys Gly Glu Ile Pro Lys Asp Gln Trp Met Lys Lys Trp
                405                 410                 415

Trp Glu Met Lys Arg Glu Ile Val Gly Val Val Glu Pro Val Pro His
            420                 425                 430

Asp Glu Thr Tyr Cys Asp Pro Ala Ser Leu Phe His Val Ser Asn Asp
        435                 440                 445

Tyr Ser Phe Ile Arg Tyr Tyr Thr Arg Thr Leu Tyr Gln Phe Gln Phe
    450                 455                 460

Gln Glu Ala Leu Cys Gln Ala Ala Lys His Glu Gly Pro Leu His Lys
465                 470                 475                 480

Cys Asp Ile Ser Asn Ser Thr Glu Ala Gly Gln Lys Leu Phe Asn Met
                485                 490                 495

Leu Arg Xaa Gly Lys Ser Glu Pro Trp Thr Leu Ala Leu Glu Asn Val
            500                 505                 510

Val Gly Ala Lys Asn Met Asn Val Arg Pro Leu Leu Asn Tyr Phe Glu
        515                 520                 525

Pro Leu Phe Thr Trp Leu Lys Asp Gln Asn Lys Asn Ser Phe Val Gly
    530                 535                 540

Trp Ser Thr Asp Trp Ser Pro Tyr Ala Asp Gln Ser Ile Lys Val Arg
545                 550                 555                 560

Ile Ser Leu Lys Ser Ala Leu Gly Asp Lys Ala Tyr Glu Trp Asn Asp
                565                 570                 575

Asn Glu Met Tyr Leu Phe Arg Ser Ser Val Ala Tyr Ala Met Arg Gln
            580                 585                 590

Tyr Phe Leu Lys Val Lys Asn Gln Met Ile Leu Phe Gly Glu Glu Asp
        595                 600                 605

Val Arg Val Ala Asn Leu Lys Pro Arg Ile Ser Phe Asn Phe Phe Val
    610                 615                 620

Thr Ala Pro Lys Asn Val Ser Asp Ile Ile Pro Arg Thr Glu Val Glu
625                 630                 635                 640

Lys Ala Ile Arg Met Ser Arg Ser Arg Ile Asn Asp Ala Phe Arg Leu
                645                 650                 655

Asn Asp Asp Ser Leu Glu Phe Leu Gly Ile Gln Pro Thr Leu Gly Pro
            660                 665                 670

Pro Asn Gln Pro Pro Val Ser Ile Trp
        675                 680
```

<210> SEQ ID NO 141
<211> LENGTH: 3396
<212> TYPE: DNA
<213> ORGANISM: homo sapiens

<400> SEQUENCE: 141

```
gaattcggct tccatcctaa tacgactcac tatagggctc gagcggccgc ccggggcagg     60

tatcttggct cacaggggac gatgtcaagc tcttcctggc tccttctcag ccttgttgct    120

gtaactgctg ctcagtccac cattgaggaa caggccaaga catttttgga caagtttaac    180

cacgaagccg aagacctgtt ctatcaaagt tcacttgctt cttggaatta taacaccaat    240

attactgaag agaatgtcca aaacatgaat aatgctgggg acaaatggtc tgccttttta    300

aaggaacagt ccacacttgc ccaaatgtat ccactacaag aaattcagaa tctcacagtc    360

aagcttcagc tgcaggctct tcagcaaaat gggtcttcag tgctctcaga agacaagagc    420
```

-continued

```
aaacggttga acacaattct aaatacaatg agcaccatct acagtactgg aaaagtttgt    480
aacccagata atccacaaga atgcttatta cttgaaccag gtttgaatga aataatggca    540
aacagtttag actacaatga gaggctctgg gcttgggaaa gctggagatc tgaggtcggc    600
aagcagctga ggccattata tgaagagtat gtggtcttga aaaatgagat ggcaagagca    660
aatcattatg aggactatgg ggattattgg agaggagact atgaagtaaa tggggtagat    720
ggctatgact acagccgcgg ccagttgatt gaagatgtgg aacatacctt tgaagagatt    780
aaaccattat atgaacatct tcatgcctat gtgagggcaa agttgatgaa tgcctatcct    840
tcctatatca gtccaattgg atgcctccct gctcatttgc ttggtgatat gtggggtaga    900
ttttggacaa atctgtactc tttgacagtt ccctttggac agaaaccaaa catagatgtt    960
actgatgcaa tggtggacca ggcctgggat gcacagagaa tattcaagga ggccgagaag   1020
ttctttgtat ctgttggtct tcctaatatg actcaaggat tctgggaaaa ttccatgcta   1080
acggacccag gaaatgttca gaaagcagtc tgccatccca cagcttggga cctggggaag   1140
ggcgacttca ggatccttat gtgcacaaag gtgacaatgg acgacttcct gacagctcat   1200
catgagatgg ggcatatcca gtatgatatg gcatatgctg cacaaccttt tctgctaaga   1260
aatggagcta atgaaggatt ccatgaagct gttggggaaa tcatgtcact ttctgcagcc   1320
acacctaagc atttaaaatc cattggtctt ctgtcacccg attttcaaga agacaatgaa   1380
acagaaataa acttcctgct caaacaagca ctcacgattg ttgggactct gccatttact   1440
tacatgttag agaagtggag gtggatggtc tttaaagggg aaattcccaa agaccagtgg   1500
atgaaaaagt ggtgggagat gaagcgagag atagttgggg tggtggaacc tgtgccccat   1560
gatgaaacat actgtgaccc cgcatctctg ttccatgttt ctaatgatta ctcattcatt   1620
cgatattaca caaggaccct ttaccaattc cagtttcaag aagcactttg tcaagcagct   1680
aaacatgaag gccctctgca caaatgtgac atctcaaact ctacagaagc tggacagaaa   1740
ctgttcaata tgctgaggct tggaaaatca gaaccctgga ccctagcatt ggaaaatgtt   1800
gtaggagcaa agaacatgaa tgtaaggcca ctgctcaact actttgagcc cttatttacc   1860
tggctgaaag accagaacaa gaattctttt gtgggatgga gtaccgactg gagtccatat   1920
gcagaccaaa gcatcaaagt gaggataagc ctaaaatcag ctcttggaga taaagcatat   1980
gaatggaacg acaatgaaat gtacctgttc cgatcatctg ttgcatatgc tatgaggcag   2040
tactttttaa aagtaaaaaa tcagatgatt ctttttgggg aggaggatgt gcgagtggct   2100
aatttgaaac caagaatctc ctttaatttc tttgtcactg cacctaaaaa tgtgtctgat   2160
atcattccta gaactgaagt tgaaaaggcc atcaggatgt cccggagccg tatcaatgat   2220
gctttccgtc tgaatgacaa cagcctagag tttctgggga tacagccaac acttggacct   2280
cctaaccagc cccctgtttc catatggctg attgtttttg gagttgtgat gggagtgata   2340
gtggttggca ttgtcatcct gatcttcact gggatcagag atcggaagaa gaaaaataaa   2400
gcaagaagtg gagaaaatcc ttatgcctcc atcgatatta gcaaaggaga aaataatcca   2460
ggattccaaa acactgatga tgttcagacc tccttttaga aaaatctatg tttttcctct   2520
tgaggtgatt ttgttgtatg taaatgttaa tttcatggta tagaaaatat aagatgataa   2580
agatatcatt aaatgtcaaa actatgactc tgttcagaaa aaaaattgtc caaagacaac   2640
atggccaagg agagagcatc ttcattgaca ttgctttcag tatttatttc tgtctctgga   2700
tttgacttct gttctgtttc ttaataagga ttttgtatta gagtatatta gggaaagtgt   2760
gtatttggtc tcacaggctg ttcagggata atctaaatgt aaatgtctgt tgaatttctg   2820
```

-continued aagttgaaaa caaggatata tcattggagc aagtgttgga tcttgtatgg aatatggatg 2880
gatcacttgt aaggacagtg cctgggaact ggtgtagctg caaggattga gaatggcatg 2940
cattagctca ctttcattta atccattgtc aaggatgaca tgctttcttc acagtaactc 3000
agttcaagta ctatggtgat ttgcctacag tgatgtttgg aatcgatcat gctttcttca 3060
aggtgacagg tctaaagaga gaagaatcca gggaacaggt agaggacatt gctttttcac 3120
ttccaaggtg cttgatcaac atctccctga caacacaaaa ctagagccag gggcctccgt 3180
gaactcccag agcatgcctg atagaaactc atttctactg ttctctaact gtggagtgaa 3240
tggaaattcc aactgtatgt tcaccctctg aagtgggtac ccagtctctt aaatcttttg 3300
tatttgctca cagtgtttga gcagtgctga gcacaaagca gacactcaat aaatgctaga 3360
tttacacact caaaaaaaaa aaaaaagggc ggccgc 3396

<210> SEQ ID NO 142
<211> LENGTH: 805
<212> TYPE: PRT
<213> ORGANISM: homo sapiens

<400> SEQUENCE: 142

Met Ser Ser Ser Ser Trp Leu Leu Leu Ser Leu Val Ala Val Thr Ala
1 5 10 15

Ala Gln Ser Thr Ile Glu Glu Gln Ala Lys Thr Phe Leu Asp Lys Phe
20 25 30

Asn His Glu Ala Glu Asp Leu Phe Tyr Gln Ser Ser Leu Ala Ser Trp
35 40 45

Asn Tyr Asn Thr Asn Ile Thr Glu Glu Asn Val Gln Asn Met Asn Asn
50 55 60

Ala Gly Asp Lys Trp Ser Ala Phe Leu Lys Glu Gln Ser Thr Leu Ala
65 70 75 80

Gln Met Tyr Pro Leu Gln Glu Ile Gln Asn Leu Thr Val Lys Leu Gln
85 90 95

Leu Gln Ala Leu Gln Gln Asn Gly Ser Ser Val Leu Ser Glu Asp Lys
100 105 110

Ser Lys Arg Leu Asn Thr Ile Leu Asn Thr Met Ser Thr Ile Tyr Ser
115 120 125

Thr Gly Lys Val Cys Asn Pro Asp Asn Pro Gln Glu Cys Leu Leu Leu
130 135 140

Glu Pro Gly Leu Asn Glu Ile Met Ala Asn Ser Leu Asp Tyr Asn Glu
145 150 155 160

Arg Leu Trp Ala Trp Glu Ser Trp Arg Ser Glu Val Gly Lys Gln Leu
165 170 175

Arg Pro Leu Tyr Glu Glu Tyr Val Val Leu Lys Asn Glu Met Ala Arg
180 185 190

Ala Asn His Tyr Glu Asp Tyr Gly Asp Tyr Trp Arg Gly Asp Tyr Glu
195 200 205

Val Asn Gly Val Asp Gly Tyr Asp Tyr Ser Arg Gly Gln Leu Ile Glu
210 215 220

Asp Val Glu His Thr Phe Glu Glu Ile Lys Pro Leu Tyr Glu His Leu
225 230 235 240

His Ala Tyr Val Arg Ala Lys Leu Met Asn Ala Tyr Pro Ser Tyr Ile
245 250 255

Ser Pro Ile Gly Cys Leu Pro Ala His Leu Leu Gly Asp Met Trp Gly
260 265 270

-continued

```
Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685
```

-continued

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 143
<211> LENGTH: 10
<212> TYPE: PRT
<213> ORGANISM: homo sapiens

<400> SEQUENCE: 143

Asp Arg Val Tyr Ile His Pro Phe His Leu
1               5                   10

<210> SEQ ID NO 144
<211> LENGTH: 8
<212> TYPE: PRT
<213> ORGANISM: homo sapiens

<400> SEQUENCE: 144

Asp Arg Val Tyr Ile His Pro Phe
1               5

<210> SEQ ID NO 145
<211> LENGTH: 9
<212> TYPE: PRT
<213> ORGANISM: homo sapiens

<400> SEQUENCE: 145

Asp Arg Val Tyr Ile His Pro Phe His
1               5

<210> SEQ ID NO 146
<211> LENGTH: 8
<212> TYPE: PRT
<213> ORGANISM: homo sapiens

<400> SEQUENCE: 146

Pro Gly Pro Glu Gly Gly Gly Lys
1               5

<210> SEQ ID NO 147
<211> LENGTH: 8
<212> TYPE: PRT
<213> ORGANISM: homo sapiens

<400> SEQUENCE: 147

Asp Tyr Lys Asp Asp Asp Asp Lys
1               5

<210> SEQ ID NO 148
<211> LENGTH: 17
<212> TYPE: PRT
<213> ORGANISM: homo sapiens

<400> SEQUENCE: 148

```
Met Leu Gln Asn Ser Ala Val Leu Leu Leu Leu Val Ile Ser Ala Ser
1               5                   10                  15

Ala
```

<210> SEQ ID NO 149
<211> LENGTH: 22
<212> TYPE: PRT
<213> ORGANISM: homo sapiens

<400> SEQUENCE: 149

```
Met Pro Thr Trp Ala Trp Trp Leu Phe Leu Val Leu Leu Leu Ala Leu
1               5                   10                  15

Trp Ala Pro Ala Arg Gly
            20
```

<210> SEQ ID NO 150
<211> LENGTH: 733
<212> TYPE: DNA
<213> ORGANISM: homo sapiens

<400> SEQUENCE: 150

```
gggatccgga gcccaaatct tctgacaaaa ctcacacatg cccaccgtgc ccagcacctg     60

aattcgaggg tgcaccgtca gtcttcctct tccccccaaa acccaaggac accctcatga    120

tctcccggac tcctgaggtc acatgcgtgg tggtggacgt aagccacgaa gaccctgagg    180

tcaagttcaa ctggtacgtg gacggcgtgg aggtgcataa tgccaagaca aagccgcggg    240

aggagcagta caacagcacg taccgtgtgg tcagcgtcct caccgtcctg caccaggact    300

ggctgaatgg caaggagtac aagtgcaagg tctccaacaa agccctccca acccccatcg    360

agaaaaccat ctccaaagcc aaagggcagc cccgagaacc acaggtgtac accctgcccc    420

catcccggga tgagctgacc aagaaccagg tcagcctgac ctgcctggtc aaaggcttct    480

atccaagcga catcgccgtg gagtgggaga gcaatgggca gccggagaac aactacaaga    540

ccacgcctcc cgtgctggac tccgacggct ccttcttcct ctacagcaag ctcaccgtgg    600

acaagagcag gtggcagcag gggaacgtct tctcatgctc cgtgatgcat gaggctctgc    660

acaaccacta cacgcagaag agcctctccc tgtctccggg taaatgagtg cgacggccgc    720

gactctagag gat                                                       733
```

<210> SEQ ID NO 151
<211> LENGTH: 34
<212> TYPE: DNA
<213> ORGANISM: homo sapiens

<400> SEQUENCE: 151

```
atggatgatc agccatcatg tcaagctctt cctg                                 34
```

<210> SEQ ID NO 152
<211> LENGTH: 35
<212> TYPE: DNA
<213> ORGANISM: homo sapiens

<400> SEQUENCE: 152

-continued gtatgctcta gattaggaaa cagggggctg gttag 35

<210> SEQ ID NO 153
<211> LENGTH: 12
<212> TYPE: PRT
<213> ORGANISM: homo sapiens
<220> FEATURE:
<221> NAME/KEY: MISC_FEATURE
<222> LOCATION: (1)..(4)
<223> OTHER INFORMATION: X equals any amino acid
<220> FEATURE:
<221> NAME/KEY: MISC_FEATURE
<222> LOCATION: (5)..(9)
<223> OTHER INFORMATION: X equals any amino acid
<220> FEATURE:
<221> NAME/KEY: MISC_FEATURE
<222> LOCATION: (10)..(12)
<223> OTHER INFORMATION: X equals any amino acid

<400> SEQUENCE: 153

Xaa Xaa Xaa Cys Xaa Xaa Xaa Xaa Cys Xaa Xaa Xaa
1 5 10

<210> SEQ ID NO 154
<211> LENGTH: 13
<212> TYPE: PRT
<213> ORGANISM: homo sapiens
<220> FEATURE:
<221> NAME/KEY: MISC_FEATURE
<222> LOCATION: (1)..(4)
<223> OTHER INFORMATION: X equals any amino acid
<220> FEATURE:
<221> NAME/KEY: MISC_FEATURE
<222> LOCATION: (5)..(10)
<223> OTHER INFORMATION: X equals any amino acid
<220> FEATURE:
<221> NAME/KEY: MISC_FEATURE
<222> LOCATION: (11)..(13)
<223> OTHER INFORMATION: X equals any amino acid

<400> SEQUENCE: 154

Xaa Xaa Xaa Cys Xaa Xaa Xaa Xaa Xaa Cys Xaa Xaa Xaa
1 5 10

<210> SEQ ID NO 155
<211> LENGTH: 14
<212> TYPE: PRT
<213> ORGANISM: homo sapiens
<220> FEATURE:
<221> NAME/KEY: MISC_FEATURE
<222> LOCATION: (1)..(4)
<223> OTHER INFORMATION: X equals any amino acid
<220> FEATURE:
<221> NAME/KEY: MISC_FEATURE
<222> LOCATION: (5)..(11)
<223> OTHER INFORMATION: X equals any amino acid
<220> FEATURE:
<221> NAME/KEY: MISC_FEATURE
<222> LOCATION: (12)..(14)
<223> OTHER INFORMATION: X equals any amino acid

<400> SEQUENCE: 155

Xaa Xaa Xaa Cys Xaa Xaa Xaa Xaa Xaa Xaa Cys Xaa Xaa Xaa
1 5 10

<210> SEQ ID NO 156
<211> LENGTH: 15
<212> TYPE: PRT
<213> ORGANISM: homo sapiens
<220> FEATURE:
<221> NAME/KEY: MISC_FEATURE
<222> LOCATION: (1)..(3)

-continued

```
<223> OTHER INFORMATION: X equals any amino acid
<220> FEATURE:
<221> NAME/KEY: MISC_FEATURE
<222> LOCATION: (5)..(11)
<223> OTHER INFORMATION: X equals any amino acid
<220> FEATURE:
<221> NAME/KEY: MISC_FEATURE
<222> LOCATION: (13)..(15)
<223> OTHER INFORMATION: X equals any amino acid

<400> SEQUENCE: 156

Xaa Xaa Xaa Cys Xaa Xaa Xaa Xaa Xaa Xaa Xaa Cys Xaa Xaa Xaa
1               5                   10                  15


<210> SEQ ID NO 157
<211> LENGTH: 16
<212> TYPE: PRT
<213> ORGANISM: homo sapiens
<220> FEATURE:
<221> NAME/KEY: MISC_FEATURE
<222> LOCATION: (1)..(3)
<223> OTHER INFORMATION: X equals any amino acid
<220> FEATURE:
<221> NAME/KEY: MISC_FEATURE
<222> LOCATION: (5)..(12)
<223> OTHER INFORMATION: X equals any amino acid
<220> FEATURE:
<221> NAME/KEY: MISC_FEATURE
<222> LOCATION: (14)..(16)
<223> OTHER INFORMATION: X equals any amino acid

<400> SEQUENCE: 157

Xaa Xaa Xaa Cys Xaa Xaa Xaa Xaa Xaa Xaa Xaa Xaa Cys Xaa Xaa Xaa
1               5                   10                  15


<210> SEQ ID NO 158
<211> LENGTH: 18
<212> TYPE: PRT
<213> ORGANISM: homo sapiens
<220> FEATURE:
<221> NAME/KEY: MISC_FEATURE
<222> LOCATION: (1)..(3)
<223> OTHER INFORMATION: X equals any amino acid
<220> FEATURE:
<221> NAME/KEY: MISC_FEATURE
<222> LOCATION: (5)..(14)
<223> OTHER INFORMATION: X equals any amino acid
<220> FEATURE:
<221> NAME/KEY: MISC_FEATURE
<222> LOCATION: (16)..(18)
<223> OTHER INFORMATION: X equals any amino acid

<400> SEQUENCE: 158

Xaa Xaa Xaa Cys Xaa Xaa Xaa Xaa Xaa Xaa Xaa Xaa Xaa Xaa Cys Xaa
1               5                   10                  15

Xaa Xaa
```

METHODS AND COMPOSITIONS FOR MODULATING ACE-2 ACTIVITY

This application claims benefit under 35 U.S.C. §119(e) of U.S. Patent Application No. 60/295,004, filed Jun. 4, 2001, which is hereby incorporated by reference in its entirety.

FIELD OF THE INVENTION

The present invention relates to polypeptides that regulate production of Angiotensin 1-9 via such mechanisms as, for example, inhibition of ACE-2. Such polypeptides have uses for example, in the detection, isolation, and/or purification of ACE-2 and/or Angiotensin 1-9. The invention also relates to nucleic acid molecules encoding these ACE-2 binding polypeptides, vectors and host cells containing these nucleic acids, and methods for producing the same. The present invention also relates to methods and compositions for detecting, diagnosing, or prognosing a disease or disorder associated with aberrant ACE-2 or Angiotensin 1-9 expression or inappropriate function of ACE-2.or Angiotensin 1-9, comprising ACE-2 binding polypeptides or fragments or variants thereof, that specifically regulate ACE-2 action. The present invention further relates to methods and compositions for preventing, treating or ameliorating a disease or disorder associated with aberrant ACE-2 or Angiotensin 1-9 expression or inappropriate ACE-2 function or Angiotensin 1-9 function, comprising administering to an animal, preferably a human, an effective amount of one or more ACE-2 binding polypeptides or fragments or variants thereof, that specifically regulate ACE-2.

BACKGROUND OF THE INVENTION

The renin-angiotensin system (RAS) plays an important role in circulatory homeostasis at both systemic and local levels. Angiotensin converting enzyme (ACE), a 175 kD protein known to be widely distributed throughout the cardiovascular system, has been long recognized as the key enzyme in the generation of angiotensin II, a peptide that regulates fluid balance, blood pressure and local blood flow in a number of tissues (Peach, M. J. *Physiological Reviews* 57:313–370 (1997)). As part of an ongoing strategy to establish genes associated with cardiovascular function via high throughput cDNA sequencing, we identified a member of the RAS family of enzymes, ACE-2, from human kidney. This enzyme was also identified in a variety of tissues by others (Donoghue et al., *Circulation Research* 87:e1–e9 (2000), Tipinis et al., *The Journal of Biological Chemistry* 275:33238–33243 (2000)). The unmodified ACE-2 protein contains transmembrane and signal peptide domains, but unlike ACE, ACE-2 contains just one single extracellular $Zn^{+2}$ binding metalloprotease domain (Tipinis et al., *The Journal of Biological Chemistry* 275:33238–33243 (2000)). ACE-2 mRNA has a more limited expression pattern than ACE (Donoghue et al., *Circulation Research* 87:e1–e9 (2000)) and, remarkably, no detectable expression in lungs (unpublished data).

ACE-2 and related carboxypeptidases (Snyder et al., *The Journal of Biological Chemistry* 260:7857–7860 (1985); Kokkonen et al., *Circulation* 95:1455–1463 (1997)) catalyze the removal of the C-terminal leucine from angiotensin I to form the nonapeptide angiotensin 1-9 (A1-9) (SEQ ID NO:145) or des-$Leu^{10}$-angiotensin I (Donoghue et al., *Circulation Research* 87:e1–e9 (2000); Tipinis et al., *The Journal of Biological Chemistry* 260:7857–7860 (2000); Snyder et al., *The Journal of Biological Chemistry* 260: 7857–7860 (1985); Snyder et al., *Biochemica et Biophysica Acta* 871:1–5 (1986)). Circulating A1-9 has been detected in vivo at levels twice that of angiotensin II (Oparil et al., *Circulation Research* 29 682–690 (1971); Johnson et al., *Peptides* 10:489–492) (1989)). In the case of ACE-2, the above reaction is not blocked by captopril, lisinopril or enalaprilat (Donoghue et al., *Circulation Research* 87:e1–e9 (2000); Tipinis et al., *The Journal of Biological Chemistry* 275:33238–33243 (2000)). The unique expression profile of ACE-2, spectum of its enzymatic activity and inhibitory effects of its product A1-9 on ACE have led to the speculation that ACE-2 functions to affect circulatory homeostasis by promoting vasodilation (Donoghue et al., *Circulation Research* 87:e1–e9 (2000); Snyder et al., *The Journal of Biological Chemistry* 260:7857–7860 (1985)). However, A1-9 has been shown to be a weak vasoconstrictor in isolated rat aorta and have weak pressor activity in anesthetized rats and dogs (Oparil et al., *Circulation Research* 29:682–690 (1971)). Therefore, we hypothesized that one of the physiologic roles of ACE-2 is to increase arterial pressure through the actions of its catabolic product, A1-9. As such, ACE-2 might be a valid target for drug development in hypertension.

Accordingly, molecules that specifically bind ACE-2 would find a variety of uses in the study of ACE-2, angiotensin 1-9) (SEQ ID NO:145), and angiotensin, as well as ACE, and its known substrates: Angiotensin II (SEQ ID NO:144), Angiotensin 1-7, des-Asp, bradykinin, neurotensin, and Substance P. Further, molecules that specifically bind ACE-2 would also find a variety of uses in the manufacture and purification of ACE-2, ACE, angiotensin, angiotensin II, and/or Angiotensin 1-9 in commercial and medically pure quantities, and in the development new therapeutic or diagnostic reagents. ACE-2 binding polypeptides may also find medical utility in, for example, the treatment of cardiovascular disorders (e.g., hypertension, chronic heart failure, left ventricular failure, stroke, cerebral vasospasm after subarachnoid injury, atherosclerotic heart disease, and retinal hemorrhage), renal disorders (e.g., renal vein thrombosis, kidney infarction, renal artery embolism, renal artery stenosis, myocardial hypertrophy, hypertrophy and/or hyperplasia of conduit and/or resistance vessels, myocyte hypertrophy, and fibroblast proliferative diseases), inflammatory diseases (e.g., SIRS (systemic Inflammatory Response Syndromes), sepsis, polytrauma, inflammatory bowl disease, acute and chronic pain, rheumatoid arthritis, and osteo arthritis), allergic disorders (e.g., asthma, adult respiratory distress syndrome, wound healing, and scar formation), as well as several other disorders and/or diseases (e.g., periodontal disease, dysmenorrhea, premature labor, brain edema following focal injury, diffuse axonal injury, and reperfusion injury).

SUMMARY OF THE INVENTION

The present invention provides new polypeptides and families of polypeptides that specifically bind ACE-2 and/or ACE-2-like polypeptides. In particular, the invention encompasses polypeptides that specifically bind to a polypeptide or polypeptide fragment of human ACE-2 (SEQ ID NOs:138 and/or 142).

In particular, the invention relates to ACE-2 binding polypeptides comprising, or alternatively consisting of, an amino acid sequence selected from the group consisting of SEQ ID NOs: 1–136, preferably SEQ ID NOs: 11–39, more preferably SEQ ID NOs:23–24 and 36–39, as referred to below, in Tables 1–2 and Example 1 below, and fragments and variants thereof.

In specific preferred embodiments, the ACE-2 binding polypeptides of the invention bind ACE-2 and/or ACE-2-like polypeptides with high affinity. In other embodiments, the ACE-2 binding polypeptides of the invention reversibly bind ACE-2 and/or ACE-2-like polypeptides. In still other embodiments, the ACE-2 binding polypeptides of the invention irreversibly bind ACE-2 and/or ACE-2-like polypeptides.

The cysteine residues in certain polypeptides according to the invention are believed to form a disulfide bond, which would cause the polypeptide containing these cysteine residues to form a stable loop structure under non-reducing conditions. Especially preferred ACE-2 binding polypeptides of the invention are polypeptide molecules that comprise amino acid sequences that form stable loop structures or other stable structures that bind ACE-2 or ACE-2-like polypeptides.

Preferred binding polypeptides specific for ACE-2 include two separated, invariant cyteine residues and are thus capable of forming a cyclic strucure under non-reducing conditions via a disulfide bond formed between the cysteine side chains. Specific ACE-2 binding polypeptides according to the present invention include polypeptides comprising amino acid sequences of the following general formulae I–X:

$Z_1$-$X_1$-A-$X_2$-$X_3$-C-$X_4$-$X_5$-F-$Z_2$ (SEQ ID NO:1) I.

wherein, $Z_1$ is a polypeptide of at least 2 amino acids;

$X_1$ is any amino acid except cysteine;

$X_2$ is L or M (preferably L);

$X_3$ is F or Y (preferably F);

$X_4$ is F, L, M, or V (preferably V);

$X_5$ is D or E;

$Z_2$ is a polypeptide of at least one amino acid or is absent; and $Z_1$ contains at least one cysteine residue such that formation of a disulfide bond with the invariant cysteine residue (C) forms a cyclic peptide of six or ten amino acids.

$Z_1$-$X_1$-C-$X_2$-$X_3$-$X_4$-$X_5$ (SEQ ID NO:2) II.

wherein, $Z_1$ is a polypeptide of at least six amino acids;

$X_1$ is F, M, W, or Y (preferably F or Y);

$X_2$ is F, I, L, M, or V (preferably F or L);

$X_3$ is D, E, or T (preferably D);

$X_4$ is F or M (preferably F);

$Z_2$ is a polypeptide of at least one amino acid or is absent; and $Z_1$ contains at least one cysteine residue such that formation of a disulfide bond with the invariant cysteine residue (C) forms a cyclic peptide of eight or ten amino acids.

$Z_1$-$X_1$-$X_2$-$X_3$-C-$X_4$-$X_5$-$X_6$-$X_7$-$X_8$-$X_9$-$X_{10}$-$X_{11}$-$X_{12}$-$X_{13}$-C-$Z_2$ (SEQ ID NO:3) III.

wherein, $Z_1$ is a polypeptide of at least one amino acid or is absent;

$X_1$ is A, D, F, G, H, L, N, P, or S (preferably D);

$X_2$ is A, D, F, G, H, N, S, W, or Y (preferably D);

$X_3$ is D, E, H, L, M, or V (preferably D or E);

$X_4$ is D, E, G, N, R, Q, S, or V (preferably D or E);

$X_5$ is N, T, or W (preferably W);

$X_6$ is any amino acid except cysteine;

$X_7$ is any amino acid except cysteine;

$X_8$ is F, W, or Y (preferably F);

$X_9$ is any amino acid except cysteine;

$X_{10}$ is any amino acid except cysteine;

$X_{11}$ is any amino acid except cysteine;

$X_{12}$ is any amino acid except cysteine;

$X_{13}$ is any amino acid except cysteine; and $Z_2$ is a polypeptide of at least one amino acid or is absent.

$Z_1$-R-$X_1$-$X_2$-$X_3$-$X_4$-D-S-$X_5$-C-$Z_2$ (SEQ ID NO:4) III.

wherein, $Z_1$ is a polypeptide of at least one amino acid or is absent;

$X_1$ is any amino acid except cysteine;

$X_2$ is any amino acid except cysteine;

$X_3$ is C, E, or S;

$X_4$ is K, L, or R (preferably R);

$X_5$ is A, R, or S (preferably R);

$Z_2$ is a polypeptide of at least one amino acid or is absent; and wherein, if $X_3$ is cysteine (C), then $Z_1$ contains a C-terminal cysteine residue.

$Z_1$-C-$X_1$-$X_2$-$X_3$-D-C-$X_4$-$Z_2$ (SEQ ID NO:5) V.

wherein, $Z_1$ is a polypeptide of at least one amino acid or is absent;

$X_1$ is any amino acid except cysteine (preferably L, H, or M);

$X_2$ is N or T (preferably T);

$X_3$ is any amino acid except cystein (preferably D, M, N, or S);

$X_4$ is V or I (preferably V);

$Z_2$ is a polypeptide of at least one amino acid or is absent.

$Z_1$-C-F-$X_1$-W-$X_2$-$Z_2$ (SEQ ID NO:6); VI.

wherein, $Z_1$ is a polypeptide of at least one amino acid or is absent;

$X_1$ is D or E;

$X_2$ is D or E;

$Z_2$ is a polypeptide of at least two amino acids and contains at least one cysteine residue such that formation of a disulfide bond with the invariant cysteine residue (C) forms a cyclic peptide of seven, eight or twelve amino acids.

$Z_1$-$X_1$-E-$X_2$-C-H-$X_3$-$X_4$-P-$X_5$-$X_6$-C-$Z_2$ (SEQ ID NO:7) VII.

wherein, $Z_1$ is a polypeptide of at least one amino acid or is absent;

$X_1$ is W or Y;

$X_2$ is any amino acid except cysteine;

$X_3$ is W or Y;

$X_4$ is any amino acid except cysteine;

$X_5$ is any amino acid except cysteine;

$X_6$ is any amino acid except cysteine; and $Z_2$ is a polypeptide of at least one amino acid or is absent.

$Z_1$-K-E-C-K-F-G-Y-$X_1$-$X_2$-C-L-$X_3$-W-$Z_2$ (SEQ ID NO: 8) VIII.

wherein, $Z_1$ is a polypeptide of at least one amino acid or is absent;

$X_1$ is any amino acid except cysteine;

$X_2$ is any amino acid except cysteine;

$X_3$ is any amino acid except cysteine; and $Z_2$ is a polypeptide of at least one amino acid or is absent.

$$Z_1\text{-}X_1\text{-}X_2\text{-}C\text{-}X_3\text{-}X_4\text{-}W\text{-}X_5\text{-}X_6\text{-}P\text{-}C\text{-}Z_2 \text{ (SEQ ID NO:9)} \qquad \text{IX.}$$

wherein, $Z_1$ is a polypeptide of at least one amino acid or is absent;

$X_1$ is D or H (preferably D);

$X_2$ is any amino acid except cysteine (preferably H, N, or W);

$X_3$ is G or is absent;

$X_4$ is T or N (preferably T);

$X_5$ is any amino acid except cysteine (preferably A, N, W, or Y);

$X_6$ is any amino acid except cysteine (preferably H, N, or Q); and $Z_2$ is a polypeptide of at least one amino acid or is absent.

$$Z_1\text{-}C\text{-}X_1\text{-}X_2\text{-}X_3\text{-}R\text{-}X_4\text{-}X_5\text{-}P\text{-}W\text{-}X_6\text{-}X_7\text{-}C\text{-}Z_2 \text{ (SEQ ID NO:10)} \qquad \text{X.}$$

wherein, $Z_1$ is a polypeptide of at least one amino acid or is absent;

$X_1$ is any amino acid except cysteine (preferably K, L, R, or S);

$X_2$ is A or P (preferably P);

$X_3$ is any amino acid except cysteine (preferably I, L, Q, or V);

$X_4$ is any amino acid except cysteine (preferably D, G, H, M, Q, or Y);

$X_5$ is any amino acid except cysteine (preferably D, F, K, S, or Y);

$X_6$ is any amino acid except cysteine (preferably F, K, M, or W; most preferably W);

$X_7$ is any amino acid except cysteine (preferably A, F, K, R, or V); and $Z_2$ is a polypeptide of at least one amino acid or is absent.

ACE-2 binding polypeptides of the present invention include polypeptides comprising amino acid sequences selected from the group consisting of:

| | SEQ ID NO: |
|---|---|
| N R E C H A L F C M D F | 40 |
| S P T C R A L F C V D F | 41 |
| S E N C Q A L F C V D F | 42 |
| S P T C R A L F C V D F | 43 |
| L E M C E A L F C V E F | 44 |
| N P E C G A L F C M E F | 45 |
| D F G C N A M F C V E F | 46 |
| D Q N C F A M Y C F E F | 47 |
| N D Y C T V F T G A L F C L D F | 48 |
| P N Q C G V D I W A L F C V D F | 49 |
| E G N C F L I G P W C F E F | 50 |
| E G N C F L I G P W C F E F | 51 |
| H I E C E E W G Y W C I E M | 52 |
| W E D C L W I G M M C V E F | 53 |
| Y E D C I G H A L F C M T F | 54 |
| D D K C F G W A H F C F D F | 55 |
| G G Q C G T S Y L F C I D F | 56 |
| Y S G C A D M Y M F C I D F | 57 |

-continued

| | SEQ ID NO: |
|---|---|
| G G Q C G T S Y L F C I D F | 58 |
| K F E C M P S S L F C V D F | 59 |
| D D Y C F N I S S Y S Y C F D F | 60 |
| L H D C F I Y A D Y E Y C F D F | 61 |
| N H H C L E F S S F E Y C F D F | 62 |
| D N L C M S G G S F D Y C F D F | 63 |
| S D Y C V G N N A V T Y C F D F | 64 |
| N L D C I Y L Q N H S Y C F D F | 65 |
| D D D C M M L P L T M F C F D F | 66 |
| Y D N C L G L A N L N F C F D F | 67 |
| H L D C Y N L V D N M F C F D F | 68 |
| N W N C L G T N E L Q F C L D F | 69 |
| Y F A C T N N D S Y L F C L D F | 70 |
| Y N F C M L I G E R D Y C L D F | 71 |
| D D V C Y S L I M A D Y C L D F | 72 |
| Y F A C T N N D S Y L F C L D F | 73 |
| D D M C R W Y P F A S F Y M C L F- | 74 |
| D D H C E W A S Y W K W D L C L H D | 75 |
| D D V C E N A D F A W L G W C M H F | 76 |
| D D D C G W I G F A N F H L C L H G | 77 |
| F D D C Q T S W F Q G F W L C I D D | 78 |
| F H D C S W G P W G P W E I C T R L | 79 |
| S N D C V W L Q F W G G D M C F L P | 80 |
| N A D C E W V N F N H V D L C M W N | 81 |
| G S D C E W V N F T M F Q M C I S N | 82 |
| A W D C E W N L F D S T F F C P G F | 83 |
| L Y E C E W K Q F G P V E M C L N F | 84 |
| H S E C R W E W F G R T M I C M S F | 85 |
| S G E C N W Q Q F S G W E I C L R D | 86 |
| A Y L C D W I L F D S F E M C L A P | 87 |
| P F E C D W G P W T L E M L C G P P | 88 |
| R G H C R D S R C M M N A P G | 89 |
| R I G C R D S R C N W W A P G | 90 |
| R G F C R D S S C S F P | 91 |
| R G W C L D S R C K V F | 92 |
| F L F C R L A S R D S R C A S P | 93 |
| F N P C R L Q S R D S A C R F R | 94 |
| F F P C R A L E K D S R C S F F | 95 |
| H F S C R L P S L D S R C Q L W | 96 |
| N D V C L N D D C V Y G | 97 |
| W P T C L T M D C V Y N | 98 |
| H Y N C H T N D C V V L | 99 |
| H L R C M T S D C I H F | 100 |
| W V L C F E W E D C D E K | 101 |
| Y E Y C F E W E Q C W E K | 102 |
| G I F C F E W E T C Y Q A | 103 |
| P Q F C F E W E P C F- - | 104 |
| I G F C F E W E V C Y E G | 105 |
| S I Y C F D W E D C W D E | 106 |
| Y D W C F D W E Q C W D Q | 107 |
| V G F C F D W E P C D E L | 108 |
| M D F C F D W E E C W T N | 109 |
| N I F C F D W E P C H F G | 110 |
| F E I C F D W E V C H E Q | 111 |
| D Y L C F D W E A C W L S | 112 |
| Y A M C F D W D E C F L G | 113 |
| W ? W C F E W E D W C L V E | 114 |
| Y Q F C F D W E T T C W L D | 115 |
| V Y F C F D W E Q D C D E M | 116 |
| F Q L C F D W E E E C E E S | 117 |
| W A V C F D W E N - C G D K | 118 |
| W Q F C F D W D L N C D L R | 119 |
| Y W F C F D W E E D A N G H C G G N | 120 |
| F L L C F D W D I D W E Y G C Q H H | 121 |
| Y E E C H W R P M A C S T H | 122 |
| W E V C H W A P M M C K H G | 123 |
| Y E F C H Y A P Q E C K H M | 124 |
| ? K E C K F G Y S ? C L A W | 125 |
| Q K E C K F G Y P H C L P W | 126 |
| E H N C T W W N P C W T T | 127 |
| M D H C T W Y Q P C V L K | 128 |
| W D H C N W A H P C S R K | 129 |
| S D W C G T W N N P C F H Q | 130 |
| R Y L C L P Q R D K P W K F C N W F | 131 |
| R L H C K P Q R Q S P W M K C Q H L | 132 |
| Y S H C S P L R Y Y P W W K C T Y P | 133 |

-continued

| | SEQ ID NO: |
|---|---|
| L H A C R P V R G D P W W A C T L G | 134 |
| G F T C S P I R M F P W F R C D L G | 135 |
| F S P C K A L R H S P W W V C P S G | 136 |

ACE-2 binding polypeptide molecules of the invention may also have an amino terminal (N-terminal) capping or functional group, such as an acetyl group, which, for example, blocks the amino terminal amino group from undesirable reactions or is useful in linking the ACE-2 binding polypeptide to another molecule, matrix, resin, or solid support. ACE-2 binding polypeptides of the invention may also have a carboxy terminal (C-terminal) capping or functional group, such as an amide group, which, for example, blocks the C-terminal carboxyl group from undesirable reactions or provides a functional group useful in conjugating the binding polypeptide to other molecules, matrices, resins, or solid supports. Preferably, the N- and/or C-terminal capping groups are polypeptide linker molecules. An especially preferred C-terminal linker molecule that is useful for immobilizing an ACE-2 binding polypeptide of the invention to a solid support or chromatographic matrix material comprises the amino acid sequence Pro-Gly-Pro-Glu-Gly-Gly-Gly-Lys (SEQ ID NO:146).

The invention also encompasses ACE-2 binding polypeptides that have been modified, for example, to increase or decrease the stability of the molecule, while retaining the ability to bind ACE-2 and/or ACE-2-like polypeptides. An example of a modified ACE-2 binding polypeptide of the invention is a polypeptide in which one of two cysteine residues is substituted with a non-naturally occurring amino acid that is capable of condensing with the remaining cysteine side chain to form a stable thioether bridge, thereby generating a cyclic BLyS binding polypeptide. Such cyclic thioether molecules of synthetic peptides may be routinely generated using techniques known in the art, e.g., as described in PCT publication WO 97/46251, incorporated herein by reference.

In another embodiment, the invention provides ACE-2 binding polypeptides of the invention attached, coupled, linked or adhered to a matrix or resin or solid support. Techniques for attaching, linking or adhering polypeptides to matrices, resins and solid supports are well known in the art. Suitable matrices, resins or solid supports for these materials may be any composition known in the art to which an ACE-2 binding polypeptide of the invention could be attached, coupled, linked, or adhered, including but not limited to, a chromatographic resin or matrix, such as SEPHAROSE-4 FF agarose beads, the wall or floor of a well in a plastic microtiter dish, such as used in an enzyme-liked immunosorbent assay (ELISA), or a silica based biochip. Materials useful as solid supports on which to immobilize binding polypeptides of the invention include, but are not limited to, polyacrylamide, agarose, silica, nitrocellulose, paper, plastic, nylon, metal, and combinations thereof. An ACE-2 binding polypeptide of the invention may be immobilized on a matrix, resin or solid support material by a non-covalent association or by covalent bonding, using techniques known in the art. Preferably, an ACE-2 binding polypeptide of the invention is immobilized on a chromatography material such as SEPHAROSE-4 FF agarose. In an even more preferred embodiment, an ACE-2 binding polypeptide of the invention is coupled to a chromatography material using a linker molecule. A preferred linker molecule according to the present invention is a polypeptide comprising the amino acid sequence Pro-Gly-Pro-Glu-Gly-Gly-Gly-Lys (SEQ ID NO:146). Most preferably, the affinity chromatography material of the invention comprises an ACE-2 binding polypeptide comprising an amino acid sequence selected from the group consisting of SEQ ID NOs:11–136, which is linked to a chromatography material by a polypeptide linker molecule having the amino acid sequence Pro-Gly-Pro-Glu-Gly-Gly-Gly-Lys (SEQ ID NO:146). ACE-2 binding polypeptides of the invention attached, coupled, linked or adhered to a matrix or resin or other solid support are useful for methods of detecting, isolating and purifying ACE-2 and/or ACE-2-like polypeptides as well as Angiotensin 1-9 and/or Angeiotensin 1-9-like polypeptides, particularly for purification of ACE-2 and/or ACE-2-like polypeptides as well as Angiotensin 1-9 and/or Angeiotensin 1-9-like polypeptides by affinity chromatography.

In certain preferred embodiments, the ACE-2 binding polypeptides of the present invention or phage displaying such binding polypeptides, irreversibly bind the ACE-2 protein in its native form.

In certain preferred embodiments, the ACE-2 binding polypeptides of the present invention or phage displaying such binding polypeptides, reversibly bind the ACE-2 protein in its native form.

In a further embodiment, the present invention encompasses a composition of matter comprising isolated nucleic acids, preferably DNA, encoding an ACE-2 binding polypeptide of the invention. In a specific embodiment, nucleic acid molecules of the invention encode an ACE-2 binding polypeptide of the invention as provided in SEQ ID NOs: 1–136. In additional embodiments, nucleic acid molecules of the invention encode a polypeptide variant or fragment of a polypeptide comprising an amino acid sequence of SEQ ID NOs: 1–136. In a further additional embodiment, nucleic acid molecules of the invention encode an ACE-2 binding polypeptide, the complementary strand of which nucleic acid hybridizes to a polynucleotide sequence encoding a polypeptide described in Tables 1–2 and in Example 1 (SEQ ID NOs: 1–136), under stringent conditions, e.g., hybridization to filter-bound DNA in 6×sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds. , 1989, *Current Protocols in Molecular Biology*, Vol. 1, Green Publishing Associates, Inc. and John Wiley & Sons, Inc., New York at pages 6.3.1–6.3.6 and 2.10.3).

The present invention also relates to recombinant vectors, which include the isolated nucleic acid molecules encoding the ACE-2 binding polypeptides of the present invention (as well as fragments and variants thereof), and to host cells containing the recombinant vectors, as well as to methods of making such vectors and host cells. The invention further provides for the use of such recombinant vectors in the production of ACE-2 binding polypeptides by recombinant techniques.

The ACE-2 binding polypeptides, nucleic acids, transformed host cells, and genetically engineered viruses and phage of the invention (e.g., recombinant phage), have uses that include, but are not limited to, the detection, isolation, and purification of ACE-2.

In another embodiment of the invention, recombinant bacteriophage displaying ACE-2 binding polypeptides on their surfaces are also provided. Such phage may be routinely generated using techniques known in the art and are useful, for example, as screening reagents and reagents for detecting ACE-2.

In another embodiment, an ACE-2 binding polypeptide of the invention is used to detect or isolate ACE-2 or ACE-2-like polypeptides in a solution. Such solutions include, but are not limited to, ACE-2 or ACE-2-like polypeptides suspended or dissolved in water or a buffer solution as well as any fluid and/or cell obtained from an individual, biological fluid, body tissue, body cell, cell line, tissue culture, or other source which may contain ACE-2 or ACE-2-like polypeptides, such as, cell culture medium, cell extracts, and tissue homogenates. Biological fluids include, but are not limited to, sera, plasma, lymph, blood, blood fractions, urine, synovial fluid, spinal fluid, saliva, and mucous.

In another embodiment, the present invention provides a method for detecting ACE-2 protein and/or ACE-2-like polypeptide in a solution comprising, contacting the solution with an ACE-2 binding polypeptide of the invention and detecting binding of ACE-2 or ACE-2-like polypeptide to the ACE-2 binding polypeptide. The ACE-2 binding polypeptide may be either free or immobilized. Preferably, the ACE-2 binding polypeptide is a polypeptide immobilized on a solid surface or chromatographic material or the well of a plastic microtiter assay dish.

Another embodiment of the present invention is a method for isolating ACE-2 protein and/or an ACE-2-like polypeptide from a solution, comprising:

(a) contacting the solution with an ACE-2 binding polypeptide under conditions that permit binding of the ACE-2 and/or ACE-2-like polypeptides to ACE-2 binding polypeptides, and (b) recovering the ACE-2 and/or ACE-2-like polypeptides.

A further embodiment of the present invention is a method for isolating ACE-2 protein and/or an ACE-2-like polypeptide from a solution, comprising:

(a) contacting the solution with an ACE-2 binding polypeptide under conditions that permit binding of the ACE-2 and/or ACE-2-like polypeptides to ACE-2 binding polypeptides, (b) separating the complex(es) formed by the ACE-2 binding polypeptide and ACE-2 and/or ACE-2-like polypeptides from other components of the solution, (c) dissociating the ACE-2 binding polypeptide from the ACE-2 and/or ACE-2 -like polypeptides, and (d) recovering the dissociated ACE-2 and/or ACE-2-like polypeptides.

In another embodiment, the invention provides kits containing a binding polypeptide of the invention for use in methods of detecting or isolating ACE-2 and/or ACE-2-like polypeptides.

The present invention also provides panels of ACE-2 binding polypeptides (including molecules comprising, or alternatively consisting of, ACE-2 binding polypeptide fragments or variants) wherein the panel members correspond to one, two, three, four, five, ten, fifteen, twenty, or more different ACE-2 binding polypeptides of the invention. The present invention further provides mixtures of ACE-2 binding polypeptides, wherein the mixture corresponds to one, two, three, four, five, ten, fifteen, twenty, or more different ACE-2 binding polypeptides of the invention. The present invention also provides for compositions comprising, or alternatively consisting of, one, two, three, four, five, ten, fifteen, twenty, or more ACE-2 binding polypeptides of the present invention (including molecules comprising, or alternatively consisting of, ACE-2 binding polypeptide fragments or variants thereof). A composition of the invention may comprise, or alternatively consist of, one, two, three, four, five, ten, fifteen, twenty, or more amino acid sequences of one or more ACE-2 binding polypeptides or fragments or variants thereof. Alternatively, a composition of the invention may comprise, or alternatively consist of, nucleic acid molecules encoding one or more ACE-2 binding polypeptides of the invention.

The present invention further provides for fusion proteins comprising an ACE-2 binding polypeptide (including molecules comprising, or alternatively consisting of, ACE-2 binding polypeptide fragments or variants thereof) of the invention, and a heterologous polypeptide. Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also encompasses methods and compositions for detecting, diagnosing, prognosing, and/or monitoring diseases or disorders associated with aberrant ACE-2 or ACE expression or inappropriate ACE-2 or ACE receptor function in an animal, preferably a mammal, and most preferably a human, comprising, or alternatively consisting of, use of ACE-2 binding polypeptides (including molecules which comprise, or alternatively consist of, ACE-2 binding polypeptide fragments or variants thereof) that specifically bind ACE-2. Diseases and disorders which can be detected, diagnosed, prognosed and/or monitored with the ACE-2 binding polypeptides of the invention include, but are not limited to, cardiovascular disorders (e.g., hypertension, chronic heart failure, left ventricular failure, stroke, cerebral vasospasm after subarachnoid injury, atherosclerotic heart disease, and retinal hemorrhage), renal disorders (e.g., renal vein thrombosis, kidney infarction, renal artery embolism, renal artery stenosis, and edema, hydronephritis), proliferative diseases or disorders (e.g., vascular stenosis, myocardial hypertrophy, hypertrophy and/or hyperplasia of conduit and/or resistance vessels, myocyte hypertrophy, and fibroblast proliferative diseases), inflammatory diseases (e.g., SIRS (systemic Inflammatory Response Syndromes), sepsis, polytrauma, inflammatory bowl disease, acute and chronic pain, rheumatoid arthritis, and osteo arthritis), allergic disorders (e.g., asthma, adult respiratory distress syndrome, wound healing, and scar formation), as well as several other disoders and/or diseases (e.g., periodontal disease, dysmenorrhea, premature labor, brain edema following focal injury, diffuse axonal injury, and reperfusion injury).

In specific embodiments, the present invention encompasses methods and compositions for detecting, diagnosing, prognosing and/or monitoring diseases or disorders for preventing, treating and/or ameliorating diseases or disorders associated with hypertension (e.g., accelerated hypertension, renal failure, vascular accidents, myocaridal infarction, and stroke).

In other specific embodiments, the present invention encompasses methods and compositions for detecting, diagnosing, prognosing and/or monitoring diseases or disorders associated with hypotension (e.g., shock, intracranial hypotension, and syncope).

The present invention further encompasses methods and compositions for preventing, treating and/or ameliorating diseases or disorders associated with aberrant ACE-2 or ACE expression or inappropriate ACE-2 or ACE function in an animal, preferably a mammal, and most preferably a human, comprising, or alternatively consisting of, administering to an animal in which such treatment, prevention or amelioration is desired one or more ACE-2 binding polypeptides (including molecules which comprise, or alternatively consist of, ACE-2 binding polypeptide fragments or variants thereof) in an amount effective to treat, prevent or ameliorate the disease or disorder. Diseases and disorders which can be prevented, treated, and/or ameliorated with the ACE-2 binding polypeptides of the invention include, but are not limited to, cardiovascular disorders (e.g., hypertension, chronic heart failure, left ventricular failure, stroke, cerebral vasospasm after subarachnoid injury, atherosclerotic heart disease, and retinal hemorrhage), renal disorders (e.g., renal vein thrombosis, kidney infarction, renal artery embolism, renal artery stenosis, and edema, hydronephritis), proliferative diseases or disorders (e.g., vascular stenosis, myocardial hypertrophy, hypertrophy and/or hyperplasia of conduit and/or resistance vessels, myocyte hypertrophy, and fibroblast proliferative diseases), inflammatory diseases (e.g., SIRS (systemic Inflammatory Response Syndromes), sepsis, polytrauma, inflammatory bowl disease, acute and chronic pain, rheumatoid arthritis, and osteo arthritis), allergic disorders (e.g., asthma, adult respiratory distress syndrome, wound healing, and scar formation), as well as several other disoders and/or diseases (e.g., periodontal disease, dysmenorrhea, premature labor, brain edema following focal injury, diffuse axonal injury, and reperfusion injury).

In specific embodiments, the present invention encompasses methods and compositions (e.g., ACE-2 binding polypeptides that antagonize ACE-2 activity) for preventing, treating and/or ameliorating diseases or disorders associated with hypertension (e.g., accelerated hypertension, renal failure, vascular accidents, myocaridal infarction, and stroke).

In a specific embodiment, this invention also provides a method for preventing, ameliorating, or treating diseases and/or disorders associated with hypotension (e.g., shock, syncope, and intracranial hypotension) comprising, or alternatively consisting of, administering to an animal in which such inhibition or reduction is desired, an effective amount of angiotensin H, or an angiotensin II-like compound, and an effective amount of angiotensin 1-9, or an angiotensin 1-9-like compound.

In specific embodiments, the present invention encompasses methods and compositions (e.g., ACE-2 binding polypeptides that antagonize ACE-2 or ACE activity) for preventing, treating and/or ameliorating other diseases or disorders associated with vasoconstriction, comprising, or alternatively consisting of, administering to an animal in which such treatment, prevention, and/or amelioration is desired, an ACE-2 binding polypeptide in an amount effective to treat, prevent and/or ameliorate the disease or disorder.

The present invention further encompasses methods and compositions for inhibiting or reducing stenosis, including aortic stenosis, buttonhole stenosis, coronary ostial stenosis, double aortic stenosis, fish-mouth mitral stenosis, bronchial stenosis, hypertrophic pyloric stenosis, pyloric stenosis, infundibular stenosis, idiopathic hypertrophic subaortic stenosis, idiopathic subglottic stenosis, pulmonary stenosis, muscular subaortic stenosis, laryngeal stenosis, mitral stenosis, supravalvar and subvalvar stenosis, subvalvular and supravalvular stenosis, and tricuspid stenosis, comprising, or alternatively consisiting of, contacting an effective amount of ACE-2 binding polypeptide, wherein the effective amount of ACE-2 binding polypeptide inhibits or reduces ACE-2 mediated enzymatic action.

The present invention further encompasses methods and compositions for inhibiting or reducing pain, comprising, or alternatively consisting of, administering to an animal in which such inhibition or reduction is desired, an ACE-2 binding polypeptide in an amount effective to inhibit or reduce ACE-2 enzymatic activity.

The present invention further encompasses methods and compositions for inhibiting or reducing inflammatory reactions in various tissues comprising, or alternatively consisting of, contacting an effective amount of ACE-2 binding polypeptide, wherein the effective amount of ACE-2 binding polypeptide inhibits or reduces ACE-2 enzymatic activity.

In a specific embodiment, the present invention encompasses methods and compositions for inhibiting or reducing inflammatory reactions in smooth muscle tissues comprising, or alternatively consisting of, contacting an effective amount of ACE-2 binding polypeptide, wherein the effective amount of ACE-2 binding polypeptide inhibits or reduces ACE-2 enzymatic activity.

The present invention further encompasses methods and compositions for inhibiting or reducing abnormal histamine release comprising, or alternatively consisting of, administering to an animal in which such inhibition or reduction is desired, an ACE-2 binding polypeptide in an amount effective to inhibit or reduce ACE-2 enzymatic activity.

In another embodiment, the present invention encompasses methods and compositions for inhibiting or reducing vasoconstriction and/or other diseases or disorders associated with vasoconstriction comprising, or alternatively consisting of, administering to an animal in which such inhibition or reduction is desired, an ACE-2 binding polypeptide in an amount effective to inhibit or reduce ACE-2 enzymatic activity.

In yet another embodiment, this invention also provides a method for reducing or inhibiting diseases and/or disorders associated with aberrant action of ACE-2 comprising, or alternatively consisting of, administering to an animal in which such inhibition or reduction is desired, an ACE-2 binding polypeptide and an effective amount of an ACE inhibiting compound.

Additionally, this invention also provides a method for reducing or inhibiting diseases and/or disorders associated with aberrant action of ACE comprising, or alternatively consisting of, administering to an animal in which such inhibition or reduction is desired, an ACE-2 binding polypeptide and an effective amount of an ACE inhibiting compound.

DEFINITIONS

Figure 1:
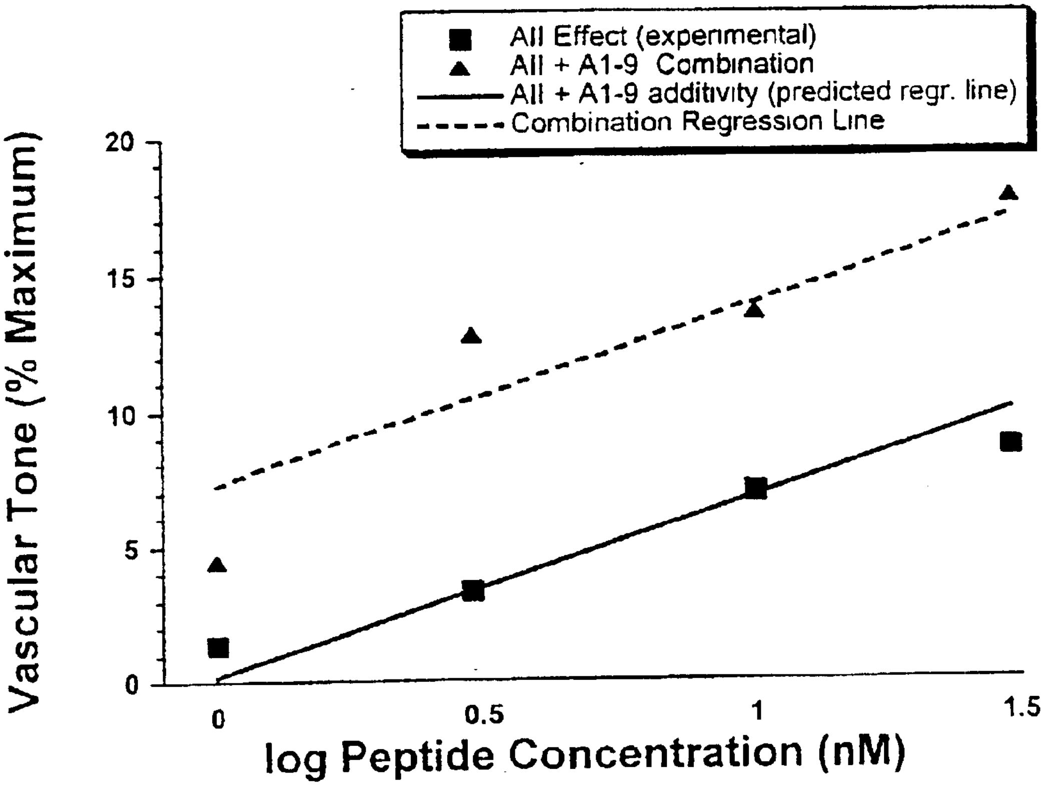
FIG. 1. Synergistic effects of Angiotensin1-9 (A1-9) on angiotensin II (AII)-induced vasoconstriction, representative experiment (experiment 9 from Table 3). Data are presented as the mean percentage of the maximal contractile response as defined by full KCl depolarization following treatment with angiotensin peptides for four separate rings used to determine average response at each concentration. Generated tension was plotted against peptide concentration and the resulting concentration-response curves were subjected to regression analysis to determine whether the effects of the combination of A1-9 and angiotensin II produced additivity or synergy. A1-9 had no effect on vascular tone in this experiment, hence the predicted effect of the combination that would be expected if A1-9 additively potentiated AII-mediated vasoconstriction is effectively that of AII alone (solid line). The synergistic or supraadditive potentiation of AII-mediated vasoconstriction by A1-9 is shown (squares and dotted line) as a leftward shift.

In order that the invention may be clearly understood, the following terms are defined:

The term "recombinant" is used to describe non-naturally altered or manipulated nucleic acids, host cells transfected with exogenous nucleic acids, or polypeptide molecules that are expressed non-naturally, through manipulation of isolated nucleic acid (typically, DNA) and transformation or transfection of host cells. "Recombinant" is a term that specifically encompasses nucleic acid molecules that have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

The term "bacteriophage" is defined as a bacterial virus containing a nucleic acid core and a protective shell built up by the aggregation of a number of different protein molecules. The terms "bacteriophage" and "phage" are synonymous and are used herein interchangeably.

The term "affinity ligand" is sometimes used herein and is synonymous with ACE-2 binding polypeptides of the invention.

The term "ACE-2 protein" as used herein encompasses both the membrane (e.g., SEQ ID NOs: 138 and 142) and soluble forms (e.g., SEQ ID NO: 140). ACE-2 protein may be monomeric, dimeric, or trimeric or multivalent, preferably, ACE-2 proteins are homotrimeric.

The term "ACE-2-like polypeptide" as used herein encompasses natural ACE-2 or full-length recombinant ACE-2 as well as fragments and variants thereof, such as, a modified or truncated form of natural ACE-2 or full-length recombinant ACE-2, which ACE-2 and ACE-2-like polypeptide retain an ACE-2 functional activity. ACE-2 or ACE-2 fragments that may be specifically bound and/or inhibited by the compositions of the invention include, but are not limited to, the ACE-2 polypeptide as shown in SEQ ID NO:138, the ACE-2 polypeptide as shown in SEQ ID NO:142, the ACE-2 extracellular domain (SEQ ID NO:140), and the ACE-2 transmembrane domain (SEQ ID NO:139). ACE-2 and ACE-2-like polypeptides retain at least one functional activity of the natural or full-length ACE-2, including but not limited to the following activities: cleaving angiotensin to angiotensin 1-9 and regulating the cleavage and/or synthesis of bradykinin, kinetensin, tachykinin, neurotensin, Substance P, and endothelin. In a preferred embodiment, the ACE-2 and ACE-2-like polypeptides retain the ability to cleave angiotensin to angiotesin 1-9. Assays that can be used to determine the functional activities of ACE-2 or ACE-2 like polypeptides can readily be determined by one skilled in the art (e.g., see assays disclosed in Moore et al., 1999, supra) "ACE-2-like polypeptides" also include fusion polypeptides in which all or a portion of ACE-2 is fused or conjugated to another polypeptide. ACE-2-like polypeptides that are fusion polypeptides retain at least one functional activity of ACE-2, preferably the ability to cleave angiotensin to angiotensin 1-9 and regulate the cleavage and/or synthesis of bradykinin, kinetensin, tachykinin, neurotensin, Substance P, and endothelin. In a preferred embodiment, the ACE-2 and ACE-2-like polypeptides that are fusion polypeptides retain the ability to cleave angiotensin to angiotensin 1-9. ACE-2.fusion polypeptides may be made by recombinant DNA techniques in which a gene or other polynucleotide coding sequence for ACE-2 or a fragment thereof is ligated in-frame (recombined) with the coding sequence of another protein or polypeptide. The resulting recombinant DNA molecule is then inserted into any of a variety of plasmid or phage expression vectors, which enable expression of the fusion protein molecule in an appropriate eukaryotic or prokaryotic host cell. ACE-2 fusion polypeptides may be generated by synthetic or semi-synthetic procedures as well.

The terms "ACE-2 target" or "ACE-2 target protein" are sometimes used herein and encompass ACE-2 and/or ACE-2-like polypeptides. Thus, the ACE-2 binding polypeptides of the invention bind "ACE-2 target proteins" and can be used to bind, detect, remove, and/or purify "ACE-2 target proteins."

The term "binding polypeptide" is used herein to refer to any polypeptide capable of forming a binding complex with another molecule, polypeptide, peptidomimetic or transformant.

A "ACE-2 binding polypeptide" is a molecule of the invention that can bind an ACE-2 target protein. Non-limiting examples of ACE-2 binding polypeptides of the invention are the polypeptide molecules having an amino acid sequence described herein (see SEQ ID NOs: 1–136). The term ACE-2 binding polypeptide also encompasses ACE-2 binding fragments and variants (including derivatives) of polypeptides having the specific amino acid sequences described herein (SEQ ID NOs: 1–136). By "variant" of an amino acid sequence as described herein is meant a polypeptide that binds ACE-2, but does not necessarily comprise an identical or similar amino acid sequence of an ACE-2 binding polypeptide specified herein. ACE-2 binding polypeptides of the invention which are variants of an ACE-2 binding polypeptide specified herein satisfy at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, least 99%, or 100% identical to the amino acid sequence of an ACE-2 binding polypeptide sequence disclosed herein (SEQ ID NOs: 1–136), (b) a polypeptide encoded by a nucleotide sequence, the complementary sequence of which hybridizes under stringent conditions to a nucleotide sequence encoding an ACE-2 binding polypeptide disclosed herein (e.g., a nucleic acid sequence encoding the amino acid sequence of SEQ ID NOs: 1–136), and/or a fragment of an ACE-2 binding polypeptide disclosed herein, of at least 5 amino acid residues, at least 10 amino acid residues, at least 15 amino acid residues, or at least 20 amino acid residues. ACE-2 binding polypeptides of the invention also encompass polypeptide sequences that have been modified for various applications provided that such modifications do not eliminate the ability to bind an ACE-2 target. Specific, non-limiting examples of modifications contemplated include C-terminal or N-terminal amino acid substitutions or peptide chain elongations for the purpose of linking the ACE-2 bindor to a chromatographic material or other solid support. Other substitutions contemplated herein include substitution of one or both of a pair of cysteine residues that normally form disulfide links, for example with non-naturally occurring amino acid residues having reactive side chains, for the purpose of forming a more stable bond between those amino acid positions than the former disulfide bond. All such modified binding polypeptides are also considered ACE-2 binding polypeptides according to this invention so long as the modified polypeptides retain the ability to bind ACE-2 and/or ACE-2-like polypeptides, and therefore, may be used in one or more of the various methods described herein, such as, to detect, purify, or isolate ACE-2 or ACE-2-like polypeptides in or from a solution. ACE-2 binding polypeptides of the invention also include variants of the specific ACE-2 binding polypeptide sequences disclosed herein (e.g., SEQ ID NOs: 1–136) which have an amino acid sequence corresponding to one of these polypeptide sequences, but in which the polypeptide sequence is altered by substitutions, additions or deletions that provide for moleucles that bind ACE-2. Thus, the ACE-2 binding polypeptides include polypeptides containing, as a primary amino acid sequence, all or part of the particular ACE-2 binding polypeptide sequence including altered sequences in which functionally equivalent amino acid residues are substituted for residues within the sequence, resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such ACE-2 binding polypeptides can be made either by chemical peptide synthesis or by recombinant production from a nucleic acid encoding the ACE-2 binding polypeptide which nucleic acid has been mutated. Any technique for mutagenesis known in the art can be used, including but not limited to, chemical mutagenesis, in vitro site-directed mutagenesis (Hutchinson et al., *J. Biol. Chem.,* 253:6551 (1978)), use of TAB.RTM. linkers (Pharmacia), etc.

As used and understood herein, percent homology or percent identity of two amino acid sequences or of two nucleic acid sequences is determined using the algorithm of Karlin and Atschul (*Proc. Natl. Acad. Sci. USA,* 87: 2264–2268 (1990)), modified as in Karlin and Altschul (*Proc. Natl. Acad. Sci. USA,* 90: 5873–5877 (1993)). Such an algorithm is incorporated into the NBLAST and XBLAST programs of Altschul et al. (*J. Mol. Biol.,* 215: 403–410 (1990)). BLAST nucleotide searches are performed with the NBLAST program to obtain nucleotide sequences homologous to a nucleic acid molecule described herein. BLAST protein searches are performed with the XBLAST program to obtain amino acid sequences homologous to a reference polypeptide. To obtain gapped alignments for comparison purposes, Gapped BLAST is utilized as described in Altschul et al. (*Nucleic Acids Res.,* 25: 3389–3402 (1997)). When utilizing BLAST and Gapped BLAST programs, the default parameters of the respective programs (e.g., XBLAST and NBLAST) are used. See, http://www.ncbi.nlm.nih.gov. Alternatively, the percent identity of two amino acid sequences or of two nucleic acid sequences can be determined once the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The term "polypeptide", as used herein, refers to a linear, branched, or cyclic (e.g., containing a loop structure) polymer of two or more amino acid residues linked with a peptide bond. The term "polypeptide" is not restricted to any particular upper limit of amino acid residues. Thus, the ACE-2 affinity ligands of the invention that comprise an amino acid sequence described herein are properly referred to as "ACE-2 binding polypeptides" because such binding polypeptides contain at least two amino acid residues held together by a peptide bond, even though such molecules may also contain one or more additional moieties or groups that are not amino acids, such as N-terminal and/or C-terminal capping or functional groups, and that may or may not be involved in a peptide bond. The polypeptides of the invention may be monovalent, divalent, trivalent, or multivalent and may comprise one or more of the ACE-2 binding polypeptides having the amino acid sequence of SEQ ID NOs: 1–136 and/or fragments or variants thereof. The term "peptide" is used herein to have the same meaning as "polypeptide." The term "antibody," as used herein, refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. Examples of molecules which are described by the term "antibody" in this application include, but are not limited to: single chain Fvs (scFvs), Fab fragments, Fab' fragments, $F(ab')_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody.

“Feed stream”: ACE-2 and ACE-2-like polypeptides that are bound by an ACE-2 binding polypeptide of this invention may be produced by any method known in the art, including, but not limited to, chemical synthesis; production in transformed host cells; secretion into culture medium by naturally occurring cells or recombinantly transformed bacteria, yeasts, fungi, insect cells, plant cells, and mammalian cells; production in genetically engineered organisms (for example, transgenic mammals); and production in non-genetically engineered organisms. The solution, sample, or mixture that contains an ACE-2 or ACE-2-like polypeptide as it is produced or is found present in a production solution will sometimes be referred to as the “feed stream”.

The term “binding” refers to the determination by standard techniques that a binding polypeptide recognizes and binds to a given target. Such standard techniques include, but are not limited to, affinity chromatography, equilibrium dialysis, gel filtration, enzyme linked immunosorbent assay (ELISA), FACS analysis, and the monitoring of spectroscopic changes that result from binding, e.g., using fluorescence anisotropy, either by direct binding measurements or competition assays with another binder.

The term “specificity” refers to a binding polypeptide of the invention that has a higher binding affinity for one target over another. Thus, the term “ACE-2 target protein specificity” refers to a molecule having a higher affinity for ACE-2 target protein as compared with another molecule that is not an ACE-2 target protein.

The term “epitopes” as used herein refers to portions of ACE-2 having antigenic or immunogenic activity in an animal, preferably a mammal. An epitope having immunogenic activity is a portion of ACE-2 that elicits an antibody response in an animal. An eptiope having antigenic activity is a portion of ACE-2 to which an antibody or ACE-2 binding polypeptide specifically binds as determined by any method known in the art, for example, by the immunoassays described herein. Antigenic epitopes need not necessarily be immunogenic.

The term “fragment” as used herein refers to a polypeptide comprising an amino acid sequence of at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, at least 15 amino acid residues, at least 16 amino acid residues, at least 17 amino acid residues, at least 18 amino acid residues, at least 19 amino acid residues, at least 20 amino acid residues, at least 21 amino acid residues, at least 22 amino acid residues, at least 23 amino acid residues, at least 24 amino acid residues, or at least 25 amino acid residues of the amino acid sequence of ACE-2, or an ACE-2 binding polypeptide (including molecules that comprise, or alternatively consist of, ACE-2 binding polypeptide fragments or variants thereof).

The term “fusion protein” as used herein refers to a polypeptide that comprises, or alternatively consists of, an amino acid sequence of an ACE-2 binding polypeptide of the invention and an amino acid sequence of a heterologous polypeptide (i.e., a polypeptide unrelated to the ACE-2 binding polypeptide).

The term “host cell” as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

Other terms are defined as necessary in the text below.

DETAILED DESCRIPTION OF THE INVENTION

The present invention provides novel binding moieties for ACE-2. Such binding moieties make possible the efficient detection and isolation of ACE-2 or ACE-2-like polypeptides in tissues or in a solution or system that contains ACE-2 or ACE-2-like polypeptides. The ACE-2 binding polypeptides disclosed herein can also be used to immobilize ACE-2 targets and provide a means of removing ACE-2 target proteins from solutions or systems containing them. The preferred binding moieties of the present invention bind ACE-2 with high affinity, i.e., acting at low concentrations.

The present invention also encompasses methods and compositions for detecting, diagnosing, prognosing, and/or monitoring diseases or disorders associated with aberrant ACE-2 or Angiotensin 1-9 expression or inappropriate ACE-2 or Angiotensin 1-9 function in an animal, preferably a mammal, and most preferably a human, comprising, or alternatively consisting of, use of ACE-2 binding polypeptides (including molecules which comprise, or alternatively consist of, ACE-2 binding polypeptide fragments or variants thereof) that specifically bind ACE-2. Diseases and disorders which can be detected, diagnosed, prognosed and/or monitored with the ACE-2 binding polypeptides of the invention include, but are not limited to, cardiovascular disorders (e.g., hypertension, chronic heart failure, left ventricular failure, stroke, cerebral vasospasm after subarachnoid injury, atherosclerotic heart disease, and retinal hemorrhage), renal disorders (e.g., renal vein thrombosis, kidney infarction, renal artery embolism, renal artery stenosis, and edema, hydronephritis), proliferative diseases or disorders (e.g., vascular stenosis, myocardial hypertrophy, hypertrophy and/or hyperplasia of conduit and/or resistance vessels, myocyte hypertrophy, and fibroblast proliferative diseases), inflammatory diseases (e.g., SIRS (systemic Inflammatory Response Syndromes), sepsis, polytrauma, inflammatory bowl disease, acute and chronic pain, rheumatoid arthritis, and osteo arthritis), allergic disorders (e.g., asthma, adult respiratory distress syndrome; wound healing, and scar formation), as well as several other disoders and/or diseases (e.g., periodontal disease, dysmenorrhea, premature labor, brain edema following focal injury, diffuse axonal injury, and reperfusion injury).

Preferably, the present invention also encompasses methods and compositions for detecting, diagnosing, prognosing, and/or monitoring diseases or disorders including, but not limited to, hypertension and diseases and/or disorders associated with hypertension, such as accelerated hypertension, episodic hypertension, paroxysmal hypertension, portal hypertension, primary hypertension, secondary hypertensoin, systemic venous hypertension, borderline hypertension, adrenal hypertension, benign hypertension, idiopathic hypertension, pale hypertension, postpartm hypertension, pregnancy-induced hypertension (gestational hypertension), essential hypertension, labile hypertension, pulmonary hypertension, renal and renovascular hypertension, and Goldblatt hypertension, left ventricular failure, atherosclerotic heart disease, stroke, retinal hemorrhage or infarction (Keith-Wagener-Barker changes), renal failure, renovascular disease, exudates, papilledema, vascular accidents, myocardial infarction, dissecting aneurysm.

The present invention further encompasses methods and compositions for preventing, treating and/or ameliorating diseases or disorders, especially diseases and disorders of vasoconstriction, or alternatively consisting of, administering to an animal in which such treatment, prevention or amelioration is desired one or more ACE-2 binding polypeptides (including molecules which comprise, or alternatively consist of, ACE-2 binding polypeptide fragments or variants thereof) in an amount effective to treat, prevent or ameliorate the disease or disorder. The present invention further encompasses methods and compositions for preventing, treating and/or ameliorating diseases or disorders associated with aberrant ACE-2 or Angiotensin 1-9 expression or inappropriate ACE-2 or Angiotensin 1-9 function in an animal, preferably a mammal, and most preferably a human, comprising, or alternatively consisting of, administering to an animal in which such treatment, prevention or amelioration is desired one or more ACE-2 binding polypeptides (including molecules which comprise, or alternatively consist of, ACE-2 binding polypeptide fragments or variants thereof) in an amount effective to treat, prevent or ameliorate the disease or disorder.

Diseases and disorders which can be prevented, treated, and/or ameliorated with the ACE-2 binding polypeptides of the invention include, but are not limited to, cardiovascular disorders (e.g., hypertension, chronic heart failure, left ventricular failure, stroke, cerebral vasospasm after subarachnoid injury, atherosclerotic heart disease, and retinal hemorrhage), renal disorders (e.g., renal vein thrombosis, kidney infarction, renal artery embolism, renal artery stenosis, and edema, hydronephritis), proliferative diseases or disorders (e.g., vascular stenosis, myocardial hypertrophy, hypertrophy and/or hyperplasia of conduit and/or resistance vessels, myocyte hypertrophy, and fibroblast proliferative diseases), inflammatory diseases (e.g., SIRS (systemic Inflammatory Response Syndromes), sepsis, polytrauma, inflammatory bowl disease, acute and chronic pain, rheumatoid arthritis, and osteo arthritis), allergic disorders (e.g., asthma, adult respiratory distress syndrome, wound healing, and scar formation), as well as several other disoders and/or diseases (e.g., periodontal disease, dysmenorrhea, premature labor, brain edema following focal injury, diffuse axonal injury, and reperfusion injury).

Preferably, the present invention also encompasses methods and compositions for preventing, treating and/or ameliorating diseases or disorders including, but not limited to, hypertension and diseases and/or disorders associated with hypertension, such as accelerated hypertension, episodic hypertension, paroxysmal hypertension, portal hypertension, primary hypertension, secondary hypertensoin, systemic venous hypertension, borderline hypertension, adrenal hypertension, benign hypertension, idiopathic hypertension, pale hypertension, postpartm hypertension, pregnancy-induced hypertension (gestational hypertension), essential hypertension, labile hypertension, pulmonary hypertension, renal and renovascular hypertension, and Goldblatt hypertension, left ventricular failure, atherosclerotic heart disease, stroke, retinal hemorrhage or infarction (Keith-Wagener-Barker changes), renal failure, renovascular disease, exudates, papilledema, .vascular accidents, myocardial infarction, dissecting aneurysm.

ACE-2 Binding Polypeptides

The present invention provides new polypeptides and families of polypeptides that specifically bind to ACE-2 (Angiotensin converting enzyme-2) and/or ACE-2-like polypeptides. In particular, the invention encompasses polypeptides that specifically bind to a polypeptide or polypeptide fragment of human ACE-2 (SEQ ID NO: AAA).

In specific preferred embodiments, the ACE-2 binding polypeptides of the invention bind ACE-2 and/or ACE-2-like polypeptides with high affinity. In other embodiments, the ACE-2 binding polypeptides of the invention reversibly bind ACE-2 and/or ACE-2-like polypeptides. In still other embodiments, the ACE-2 binding polypeptides of the invention irreversibly bind ACE-2 and/or ACE-2-like polypeptides.

In preferred embodiments, the ACE-2 binding polypeptides of the present invention (including molecules comprising, or alternatively consisting of, ACE-2 binding polypeptide fragments or variants thereof), specifically bind to ACE-2 and do not cross-react with any other antigens.

The cysteine residues in polypeptides are believed to form a disulfide bond, which would cause the polypeptide containing these cysteine residues to form a stable loop structure under non-reducing conditions. Especially preferred ACE-2 binding polypeptides of the invention are polypeptide molecules, which comprise amino acid sequences that form stable loop structures or other stable structures that bind ACE-2 or ACE-2-like polypeptides.

In specific embodiments, the invention relates to ACE-2 binding polypeptides comprising, or alternatively consisting of, an amino acid sequence selected from the group consisting of SEQ ID NOs: 1–136, preferably SEQ ID NOs:11–39, and most preferably SEQ ID NOs: 23–24 and 36–39, as referred to in Tables 1–2 and in Example 1 below. Ten consensus sequences (SEQ ID NOs:1–10) have been determined based on the specific ACE-2 binding polypeptides shown in paragraph 530 of Example 1. In specific embodiments, ACE-2 binding polypeptides of the invention comprise one or more of these sequences. Such preferred ACE-2 binding polypeptides include a polypeptide with the potential to form a loop structure comprising, or alternatively consisting of, an amino acid sequence selected from A–J (SEQ ID NOs:1–10):

$Z_1$-$X_1$-A-$X_2$-$X_3$-C-$X_4$-$X_5$-F-$Z_2$ (SEQ ID NO:1); A.

wherein, $Z_1$ is a polypeptide of at least 2 amino acids;

$X_1$ is any amino acid except cysteine;

$X_2$ is L or M (preferably L);

$X_3$ is F or Y (preferably F);

$X_4$ is F, L, M, or V (preferably V);

$X_5$ is D or E;

$Z_2$ is a polypeptide of at least one amino acid or is absent; and $Z_1$ contains at least one cysteine residue such that formation of a disulfide bond with the invariant cysteine residue (C) forms a cyclic peptide of six or ten amino acids.

$Z_1$-$X_1$-C-$X_2$-$X_3$-$X_4$-$Z_2$ (SEQ ID NO:2) B.

wherein, $Z_1$ is a polypeptide of at least six amino acids;

$X_1$ is F, M, W, or Y (preferably F or Y);

$X_2$ is F, I, L, M, or V (preferably F or L);

$X_3$ is D, E, or T (preferably D);

$X_4$ is F or M (preferably F);

$Z_2$ is a polypeptide of at least one amino acid or is absent; and $Z_1$ contains at least one cysteine residue such that formation of a disulfide bond with the invariant cysteine residue (C) forms a cyclic peptide of eight or ten amino acids.

$Z_1$-$X_1$-$X_2$-$X_3$-C-$X_4$-$X_5$-$X_6$-$X_7$-$X_8$-$X_9$-$X_{10}$-$X_{11}$-$X_{12}$-$X_{13}$-C-$Z_2$ (SEQ ID NO:3) C.

wherein, $Z_1$ is a polypeptide of at least one amino acid or is absent;
$X_1$ is A, D, F, G, H, L, N, P, or S (preferably D);
$X_2$ is A, D, F, G, H, N, S, W, or Y (preferably D);
$X_3$ is D, E, H, L, M, or V (preferably D or E);
$X_4$ is D, E, G, N, R, Q, S, or V (preferably D or E);
$X_5$ is N, T, or W (preferably W);
$X_6$ is any amino acid except cysteine;
$X_7$ is any amino acid except cysteine;
$X_8$ is F, W, or Y (preferably F);
$X_9$ is any amino acid except cysteine;
$X_{10}$ is any amino acid except cysteine;
$X_{11}$ is any amino acid except cysteine;
$X_{12}$ is any amino acid except cysteine;
$X_{13}$ is any amino acid except cysteine; and
$Z_2$ is a polypeptide of at least one amino acid or is absent.

$Z_1$-R-$X_1$-$X_2$-$X_3$-$X_4$-D-S-$X_5$-C-$Z_2$ (SEQ ID NO:4) D.

wherein, $Z_1$ is a polypeptide of at least one amino acid or is absent;
$X_1$ is any amino acid except cysteine;
$X_2$ is any amino acid except cysteine;
$X_3$ is C, E, or S;
$X_4$ is K, L, or R (preferably R);
$X_5$ is A, R, or S (preferably R);
$Z_2$ is a polypeptide of at least one amino acid or is absent; and wherein, if X3 is cysteine (C), then $Z_1$ contains a C-terminal cysteine residue.

$Z_1$-C-$X_1$-$X_2$-$X_3$-D-C-$X_4$-$Z_2$ (SEQ ID NO:5) E.

wherein, $Z_1$ is a polypeptide of at least one amino acid or is absent;
$X_1$ is L, H, or M;
$X_2$ is N or T (preferably T);
$X_3$ is D, M, N, or S;
$X_4$ is V or I (preferably V);
$Z_2$ is a polypeptide of at least one amino acid or is absent.

$Z_1$-C-F-$X_1$-W-$X_2$-$Z_2$ (SEQ ID NO:6); F.

wherein, $Z_1$ is a polypeptide of at least one amino acid or is absent;
$X_1$ is D or E;
$X_2$ is D or E;
$Z_2$ is a polypeptide of at least two amino acids and contains at least one cysteine residue such that formation of a disulfide bond with the invariant cysteine residue (C) form s a cyclic peptide of seven, eight or twelve amino acids.

$Z_1$-$X_1$-E-$X_2$-C-H-$X_3$-$X_4$-P-$X_5$-$X_6$-C-$Z_2$ (SEQ ID NO:7) G.

wherein, $Z_1$ is a polypeptide of at least one amino acid or is absent;
$X_1$ is W or Y;
$X_2$ is any amino acid except cysteine;
$X_3$ is W or Y;
$X_4$ is any amino acid except cysteine;
$X_5$ is any amino acid except cysteine;
$X_6$ is any amino acid except cysteine; and
$Z_2$ is a polypeptide of at least one amino acid or is absent.

$Z_1$-K-E-C-K-F-G-Y-$X_1$-$X_2$-C-L-$X_3$-W-$Z_2$ (SEQ ID NO:8) H.

wherein, $Z_1$ is a polypeptide of at least one amino acid or is absent;
$X_1$ is any amino acid except cysteine;
$X_2$ is any amino acid except cysteine;
$X_3$ is any amino acid except cysteine; and
$Z_2$ is a polypeptide of at least one amino acid or is absent.

$Z_1$-$X_1$-$X_2$-C-$X_3$-$X_4$-W-$X_5$-$X_6$-P-C-$Z_2$ (SEQ ID NO:9) I.

wherein, $Z_1$ is a polypeptide of at least one amino acid or is absent;
$X_1$ is D or H (preferably D);
$X_2$ is H, N, or W;
$X_3$ is G or is absent;
$X_4$ is T or N (preferably T);
$X_5$ is A, N, W, or Y;
$X_6$is H, N, or Q; and
$Z_2$ is a polypeptide of at least one amino acid or is absent.

$Z_1$-C-$X_1$-$X_2$-$X_3$-R-$X_4$-$X_5$-P-W-$X_6$-$X_7$-C-$Z_2$ (SEQ ID NO:10) I.

wherein, $Z_1$ is a polypeptide of at least one amino acid or is absent;
$X_1$ is K, L, R, or S;
$X_2$ is A or P (preferably P);
$X_3$ is 1, L, Q, or V;
$X_4$ is D, G, H, M, Q, or Y;
$X_5$ is D, F, K, S, or Y;
$X_6$ is F, K, M, or W (preferably W);
$X_7$ is A, F, K, R, or V; and
$Z_2$ is a polypeptide of at least one amino acid or is absent. wherein said polypeptides bind ACE-2 and/or ACE-2-like polypeptides.

ACE-2 binding polypeptide molecules of the invention may also have an amino terminal (N-terminal) capping or functional group, such as an acetyl group, which, for example, blocks the amino terminal amino group from undesirable reactions or is useful in linking the ACE-2 binding polypeptide to another molecule, matrix, resin, or solid support. The nature of the solid support, process for attachment of the ACE-2 binding polypeptide to the solid support, solvent, and conditions of the affinity isolation or selection procedure are largely conventional and well known to those skilled in the art. ACE-2 binding polypeptides of the invention may also have a carboxy terminal (C-terminal) capping or functional group, such as an amide group, which, for example, blocks the C-terminal carboxyl group from undesirable reactions or provides a functional group useful in conjugating the binding polypeptide to other molecules, matrices, resins, or solid supports. Preferably, the N- and/or C-terminal capping groups are polypeptide linker molecules. An especially preferred C-terminal linker molecule that is useful for immobilizing an ACE-2 binding polypeptide of the invention to a solid support or chromatographic matrix material comprises the amino acid sequence Pro-Gly-Pro-Glu-Gly-Gly-Gly-Lys (SEQ ID NO: 146).

The invention also encompasses, ACE-2 binding polypeptides that have been modified, for example, to increase or decrease the stability of the molecule, while retaining the ability to bind ACE-2 and/or ACE-2-like polypeptides. An example of a modified ACE-2 binding polypeptide of the invention is a polypeptide in which one of two cysteine residues is substituted with a non-naturally occurring amino acid that is capable of condensing with the remaining cysteine side chain to form a stable thioether bridge, thereby generating a cyclic ACE-2 binding polypeptide. Such cyclic thioether molecules of synthetic peptides may be routinely generated using techniques known in the art and described, e.g., in PCT publication WO 97/46251, incorporated herein by reference.

In another embodiment, the invention provides ACE-2 binding polypeptides of the invention attached, coupled, linked or adhered to a matrix or resin or solid support. Techniques for attaching linking or adhering polypeptides to matrices, resins and solid supports are well known in the art. Suitable matrices, resins or solid supports for these materials may be any composition known in the art to which binding polypeptides are commonly attached, coupled, linked, or adhered, including but not limited to, a chromatographic resin or matrix, such as SEPHAROSE-4 FF agarose beads, the wall or floor of a well in a plastic microtiter dish, such as used in an enzyme-liked immunosorbent assay (ELISA), or a silica based biochip. Materials useful as solid supports on which to immobilize binding polypeptides of the invention include, but are not limited to, polyacrylamide, agarose, silica, nitrocellulose, paper, plastic, nylon, metal, and combinations thereof. An ACE-2 binding polypeptide of the invention may be immobilized on a matrix, resin or solid support material by a non-covalent association or by covalent bonding, using techniques known in the art. Preferably, an ACE-2 binding polypeptide of the invention is immobilized on SEPHAROSE4 FF agarose chromatographic material. More preferably, an ACE-2 binding polypeptide of the invention is coupled to a chromatography material such as SEPHAROSE4FF (agarose). In an even more preferred embodiment, an ACE-2 binding polypeptide of the invention is coupled to a chromatography material using a linker molecule. A preferred linker molecule according to the present invention is a polypeptide comprising the amino acid sequence Pro-Gly-Pro-Glu-Gly-Gly-Gly-Lys (SEQ ID NO:146). Most preferably, the affinity chromatography material of the invention comprises an ACE-2 binding polypeptide comprising an amino acid sequence selected from the group consisting of SEQ ID NOs:23–24 and 36–39, which is linked to a chromatography material by a polypeptide linker molecule having the amino acid sequence Pro-Gly-Pro-Glu-Gly-Gly-Gly-Lys (SEQ ID NO: 146). ACE-2 binding polypeptides of the invention attached, coupled, linked or adhered to a matrix or resin or solid support are useful for methods of detecting, isolating and purifying ACE-2 and/or ACE-2 like polypeptides, particularly for purification of ACE-2 and/or ACE-2-like polypeptides by affinity chromatography.

In certain preferred embodiments, the ACE-2 binding polypeptides of the present invention or phage displaying such inhibitory polypeptides, irreversibly inhibit the ACE-2 protein in its native form.

In certain preferred embodiments, the ACE-2 binding polypeptides of the present invention or phage displaying such inhibiting polypeptides, reversibly inhibit the ACE-2 protein in its native form.

ACE-2 binding polypeptides of the invention inhibit ACE-2 target protein with high affinity. In specific embodiments, ACE-2 binding polypeptides of the invention bind ACE-2 target proteins with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, ACE-2 binding polypeptides of the invention bind ACE-2 target proteins with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, ACE-2 binding polypeptides of the invention bind ACE-2 target proteins with a dissociation constant or $K_D$ less than or equal to $5\times10^{-9}$ M, $10^{-9}$ M, $5\times10^{-10}$ M, $10^{31\ 10}$ M, $5\times10^{31\ 11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In certain preferred embodiments, ACE-2 binding polypeptides of the invention reversibly bind ACE-2 and/or ACE-2-like polypeptides and release bound ACE-2 protein in an active form, preferably in the native form, under specific release conditions. In specific embodiments, ACE-2 binding polypeptides of the invention bind ACE-2 target proteins with off-rates or $k_{off}$ less than or equal to $10^{-1}$ $s^{-1}$, $5\times10^{-1}$ $s^{-1}$, $10^{-2}$ $s^{-1}$, $5\times10^{-2}$ $s^{-1}$, or $5\times10^{-3}$ $s^{-1}$. More preferably, ACE-2 binding polypeptides of the invention bind ACE-2 target proteins with off-rates or $k_{off}$ less than or equal to, $10^{-4}$ $s^{-1}$, $5\times10^{-4}$ $s^{-1}$, $10^{-5}$ $s^{-1}$, $5\times10^{-5}$ $s^{-1}$, $10^{-6}$ $s^{-1}$, $5\times10^{-6}$ $s^{-1}$, or $5\times10^{-7}$ $s^{-1}$.

Binding experiments to determine $K_D$ and off-rates can be performed in a number of conditions including, but not limited to, [pH 6.0, 0.01% Tween 20], [pH 6.0, 0.1% gelatin], [pH5.0, 0.01% Tween 20], [pH9.0, 0.1% Tween 20], [pH6.0, 15% ethylene glycol, 0.01% Tween20], [pH5.0, 15% ethylene glycol, 0.01% Tween 20], and [pH9.0, 15% ethylene glycol, 0.01% Tween 20] The buffers in which to make these solutions can readily be determined by one of skill in the art, and depend largely on the desired pH of the final solution. Low pH solutions (<pH 5.5) can be made, for example, in citrate buffer, glycine-HCl buffer, or in succinic acid buffer. High pH solutions can be made, for example, in Tris-HCl, phosphate buffers, or sodium bicarbonate buffers. A number of conditions may be used to determine $K_D$ and off-rates for the purpose of determining, for example, optimal pH and/or salt concentrations.

In certain embodiments, ACE-2 binding polypeptides of the invention reversibly bind ACE-2 and/or ACE-2-like polypeptides, preferably in the native form.

In preferred embodiments, ACE-2 binding polypeptides of the invention reversibly bind only the native form of ACE-2.

In certain embodiments, ACE-2 binding polypeptides of the invention irreversibly bind ACE-2 and/or ACE-2-like polypeptides, preferably in the native form.

In preferred embodiments, ACE-2 binding polypeptides of the invention irreversibly bind only the native form of ACE-2.

In some screening or assay procedures, it is possible and more convenient to use recombinant bacteriophage that display a particular ACE-2 binding polypeptide instead of using isolated ACE-2 binding polypeptide. Such procedures include phage-based ELISA protocols and immobilization of phage displaying a binding polypeptide to chromatographic materials. Such screening assays and procedures are routine in the art and may be readily adapted for procedures using the recombinant bacteriophage of the present invention.

The invention also encompasses ACE-2 binding polypeptides that competitively inhibit the binding of an ACE-2 binding polypeptide disclosed herein (e.g., a polypeptide having the amino acid sequence of SEQ ID NOS:11–39) for binding to ACE-2. Competitive inhibition can be determined by any suitable method known in the art, for example, using the competitive binding assays described herein. In preferred embodiments, the polypeptide competitively inhibits the binding of an ACE-2 binding polypeptide disclosed herein (e.g., a polypeptide having the amino acid sequence of SEQ ID NOS:11–39) to ACE-2 by at least 95%, at least 90%, at least 85%, at least 80%, at least 75%, at least 70%, at least 60%, or at least 50%. In a more preferred embodiment, the ACE-2 binding polypeptide competitively inhibits the binding of an ACE-2 binding polypeptide disclosed herein (e.g., a polypeptide having the amino acid sequence of SEQ ID NOS:11–39) to the native form of ACE-2, by at least 95%, at least 90%, at least 85%, at least 80%, at least 75%, at least 70%, at least 60%, or at least 50%.

In a further embodiment, the present invention encompasses a composition of matter comprising isolated nucleic acids, preferably DNA, encoding an ACE-2 binding polypeptide of the invention. In a specific embodiment, nucleic acid molecules of the invention encode an ACE-2 binding polypeptide of the invention as provided in SEQ ID NOs: 1–136. In additional embodiments, nucleic acid molecules of the invention encode a polypeptide variant or fragment of a polypeptide having an amino acid sequence of SEQ ID NOs: 1–136. In a further additional embodiment, nucleic acid molecules of the invention encode an ACE-2 binding polypeptide, the complementary strand of which nucleic acid hybridizes to a polynucletide sequence encoding a polypeptide described in Tables 1–2 and in Example 1 (SEQ ID NOs: 1–136), under stringent conditions, e.g., hybridization to filter-bound DNA in 6×sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel et al., eds. , 1989, *Current Protocols in Molecular Biology*, Vol. I, Green Publishing Associates, Inc. and John Wiley & Sons, Inc., New York at pages 6.3.1–6.3.6 and 2.10.3).

The present invention also relates to recombinant vectors that include the isolated nucleic acid molecules encoding the ACE-2 binding polypeptides of the present invention (as well as fragments and variants thereof), and to host cells containing the recombinant vectors, as well as to methods of making such vectors and host cells. The invention further provides for the use of such recombinant vectors in the production of ACE-2 binding polypeptides by recombinant techniques.

The ACE-2 binding polypeptides, nucleic acids, transformed host cells, and genetically engineered viruses and phage of the invention (e.g., recombinant phage), have uses that include, but are not limited to, the detection, isolation, and purification of ACE-2.

In another embodiment of the invention, recombinant bacteriophage displaying ACE-2 binding polypeptides on their surfaces are also provided. Such phage may be routinely generated using techniques known in the art and are useful, for example, as screening reagents and reagents for detecting ACE-2.

The invention also encompasses ACE-2 binding polypeptides (including molecules comprising, or alternatively consisting of, ACE-2 binding polypeptide fragments or variants thereof) that have one or more of the same biological characteristics as one or more of the ACE-2 binding polypeptides described herein. By "biological characteristics" is meant, the in vitro or in vivo activities or properties of the ACE-2 binding polypeptides, such as, for example, the ability to bind to ACE-2 (e.g., the soluble form of ACE-2, the membrane-bound form of ACE-2, the soluble form and membrane-bound form of ACE-2), and/or an antigenic and/or epitope region of ACE-2, the ability to substantially block ACE-2 enzymatic action, preferably the ability to substantially block ACE-2 enzymatic action on Angiotensin, the ability to regulate ACE-2 mediated biological activity (e.g., production of Angiotensin II). Optionally, the ACE-2 binding polypeptides of the invention will bind to the same epitope as at least one of the ACE-2 binding polypeptides specifically referred to herein. Such epitope binding can be routinely determined using assays known in the art.

The present invention also provides for ACE-2 binding polypeptides (including molecules comprising, or alternatively consisting of, ACE-2 binding polypeptide fragments or variants thereof), that neutralize ACE-2 or a fragment thereof, said ACE-2 binding polypeptides comprising, or alternatively consisting of, a polypeptide having an amino acid sequence of any one of SEQ ID NOs:1–136, preferably of SEQ ID NOs: 11–39, most preferably of SEQ ID NOs: 23–24 and 36–39, or a fragment or variant thereof. By an ACE-2 binding polypeptide that "neutralizes ACE-2 or a fragment thereof" is meant an ACE-2 binding polypeptide that inhibits (i.e., is effective to reduce or abolish) or abolishes the ability of ACE-2: cleaving Angiotensin I to Angiotensin 1-9 and regulating the cleavage and/or synthesis of bradykinin, kinetensin, tachykinin, neurotensin, Substance P, and endothelin. Nucleic acid molecules encoding these ACE-2 binding polypeptides are also encompassed by the invention.

The present invention also provides for ACE-2 binding polypeptides (including molecules comprising, or alternatively consisting of, ACE-2 binding polypeptide fragments or variants thereof), that inhibit or abolish ACE-2 mediated cleaving of Angiotensin as determined by any method known in the art such as, for example, the assays described in Example 9, infra, said ACE-2 binding polypeptides comprising, or alternatively consisting of, a polypeptide having an amino acid sequence of any one of SEQ ID NOs:1–136, preferably of SEQ ID NOs: 11–39, most preferably of SEQ ID NOs: 23–24 and 36–39, or a fragment or variant thereof. Nucleic acid molecules encoding these ACE-2 binding polypeptides are also encompassed by the invention.

The present invention also provides: ACE-2 binding polypeptides (including molecules comprising, or alternatively consisting of, ACE-2 binding polypeptide fragments or variants thereof), that specifically bind to the soluble form of ACE-2; ACE-2 binding polypeptides that specifically bind to the membrane-bound form of ACE-2; and ACE-2 binding polypeptides that specifically bind to both the soluble form and membrane-bound form of ACE-2.

The present invention also provides for mixtures of ACE-2 binding polypeptides (including molecules comprising, or alternatively consisting of, ACE-2 binding polypeptide fragments or variants thereof) that specifically bind to ACE-2, wherein the mixture contains at least one, two, three, four, five or more different ACE-2 binding polypeptides of the invention. In particular, the invention provides for mixtures of different ACE-2 binding polypeptides that specifically bind to the soluble form of ACE-2, the membrane-bound form of ACE-2, and/or both the membrane-bound form and soluble form of ACE-2. In specific embodiments, the invention provides mixtures of at least 2, preferably at least 4, at least 6, at least 8, at least 10, at least 12, at least 15, at least 20, or at least 25 different ACE-2 binding polypeptides that specifically bind to ACE-2, wherein at least 1, at least 2, at least 4, at least 6, or at least 10, ACE-2 binding polypeptides of the mixture are ACE-2 binding polypeptides of the invention. In a specific embodiment, each antibody of the mixture is an ACE-2 binding polypeptide of the invention.

The present invention also provides for panels of ACE-2 binding polypeptides (including molecules comprising, or alternatively consisting of, ACE-2 binding polypeptide fragments or variants thereof) that specifically bind to ACE-2, wherein the panel has at least one, two, three, four, five or more different ACE-2 binding polypeptides of the invention. In particular, the invention provides for panels of different ACE-2 binding polypeptides that specifically bind to the soluble form of ACE-2, the membrane-bound form of ACE-2, and/or both the membrane-bound form and soluble form of ACE-2. In specific embodiments, the invention provides for panels of ACE-2 binding polypeptides that have different affinities for ACE-2, different specificities for ACE-2, or different dissociation rates. The invention provides panels of at least 10, preferably at least 25, at least 50, at least 75, or at least 100 ACE-2 binding polypeptides. Panels of ACE-2 binding polypeptides can be used, for example, in 96 well plates for assays such as ELISAs.

The present invention further provides for compositions comprising, one or more ACE-2 binding polypeptides (including molecules comprising, or alternatively consisting of ACE-2 binding polypeptide fragments or variants of the invention). In one embodiment, a composition of the present invention comprises, one, two, three, four, five, or more ACE-2 binding polypeptides that comprise or alternatively consist of, a polypeptide having an amino acid sequence of any one or more of the ACE-2 binding polypeptides contained in SEQ ID NOs:1–136 as disclosed in Tables 1–2 and Example 1, or a variant thereof.

As discussed in more detail below, a composition of the invention may be used either alone or in combination with other compositions. The ACE-2 binding polypeptides (including molecules comprising, or alternatively consisting of ACE-2 binding polypeptide fragments or variants of the present invention) may further be recombinantly fused to a heterologous polypeptide at the N- or C-terminus or chemically conjugated (including covalently and non-covalently conjugations) to polypeptides or other compositions. For example, ACE-2 binding polypeptides of the present invention may be recombinantly fused or conjugated to molecules useful as labels in detection assays and effector molecules such as heterologous polypeptides, polypeptide linkers, drugs, radionuclides, or toxins. See, e.g., PCT publications WO 92/08495; WO 91/14438; WO 89/12624; U.S. Pat. No. 5,314,995; and EP 396,387.

ACE-2 binding polypeptides of the present invention (including molecules comprising, or alternatively consisting of ACE-2 binding polypeptide fragments or variants of the present invention) may be used, for example, but not limited to, to purify and detect ACE-2, and to target the polypeptides of the present invention to cells expressing membrane-bound ACE-2 or ACE-2 receptor, including both in vitro and in vivo diagnostic and therapeutic methods. For example, the ACE-2 binding polypeptides have use in immunoassays for qualitatively and quantitatively measuring levels of ACE-2 in biological samples. See, e.g., Harlow et al., *Antibodies: A Laboratory Manual* (Cold Spring Harbor Laboratory Press, Cold Spring Harbor 1988) (incorporated by reference herein in its entirety).

Production and Modification of ACE-2 Binding Polypeptides

ACE-2 binding polypeptides of the invention may be produced by chemical synthesis, semi-synthetic methods, and recombinant DNA methodologies known in the art.

In certain embodiments, ACE-2 binding polypeptides of the present invention are produced by chemical or semi-synthetic methodologies. known in the art (see, Kelley et al. in *Genetic Engineering Principles and Methods*, Setlow, J. K., ed. (Plenum Press, NY., 1990), vol. 12, pp. 1–19; Stewart et al., *Solid-Phase Peptide Synthesis*, W. H. Freeman Co., San Francisco, 1989). One advantage of these methodologies is that they allow for the incorporation of non-natural amino acid residues into the sequence of the ACE-2 binding polypeptide.

In preferred embodiments, ACE-2 binding polypeptides of the invention are chemically synthesized (see, e.g., Merrifield, *J. Am. Chem. Soc.,* 85: 2149 (1963); Houghten, *Proc. Natl. Acad. Sci. USA,* 82: 5132 (1985)). For example, polypeptides can be synthesized by solid phase techniques, cleaved from the resin, and purified by preparative high performance liquid chromatography (see, e.g., Creighton, *Proteins: Structures and Molecular Properties* (W.H. Freeman and Co., N.Y., 1983), pp. 50–60). ACE-2 binding polypeptides can also be synthesized by use of a peptide synthesizer. The composition of the synthetic polypeptides may be confirmed by amino acid analysis or sequencing (e.g., the Edman degradation procedure; see Creighton, *Proteins: Structures and Molecular Properties* (W.H. Freeman and Co., N.Y., 1983), pp. 34–49). Furthermore, if desired, ACE-2 binding polypeptides of the invention may contain non-classical amino acids or chemical amino acid analogs, which can routinely be introduced during chemical synthesis as a substitution or addition into the ACE-2 binding polypeptides of the invention. Non-classical amino acids include, but are not-limited to, the D-isomers of the common amino acids, 2,4-diaminobutyric acid, alpha-aminoisobutyric acid, 4-aminobutyric acid (4Abu), 2-aminobutyric acid (Abu), 6-aminohexanoic acid (epsilon-Ahx), 2-aminoisobutyric acid (Aib), 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine (bAla), fluoro-amino acids, designer amino acids such as beta-methyl amino acids, Calpha-methyl amino acids, Nalpha-methyl amino acids, and amino acid analogs in general. Furthermore, the amino acid can be D (dextrorotary) or L (levorotary).

Solid phase peptide synthesis begins at the carboxy (C) terminus of the putative polypeptide. by coupling a protected amino acid to a suitable resin, which reacts with the carboxyl group of the C-terminal amino acid to form a bond that is readily cleaved later, for example, a halomethyl resin such as chloromethyl resin, bromomethyl resin, hydroxymethyl resin, aminomethyl resin, benzhydrylamine resin, or t-alkyloxycarbonyl-hydrazide resin. After removal of the α-amino protecting group with, for example, trifluoroacetic acid (TFA) in methylene chloride and neutralization with, for example TEA, the next cycle in the synthesis is ready to proceed. The remaining α-amino and, if necessary, side-chain-protected amino acids are then coupled sequentially in the desired order by condensation to obtain an intermediate compound connected to the resin. Alternatively, some amino acids may be coupled to one another forming an oligopeptide prior to addition to the growing solid phase polypeptide chain.

The condensation between two amino acids, or an amino acid and a peptide, or a peptide and a peptide can be carried out according to condensation methods known in the art, including but not limited to, the azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method), and Woodward reagent K method.

Common to chemical synthesis of peptides is the protection or capping (blocking) of the reactive side chain groups of the various amino acid residues with suitable protecting or capping groups at that site until the group is ultimately removed after the polypeptide chain has been completely assembled. Also common is the protection or capping of the α-amino group on an amino acid or a fragment while that entity reacts at the carboxyl group followed by the selective removal of the α-amino-protecting group to allow subsequent reaction to take place at that location. Accordingly, during synthesis, intermediate compounds are produced which includes each of the amino acid residues located in the desired sequence in the peptide chain with various of these residues having side-chain protecting or capping groups. These protecting or capping groups on amino acid side chains are then removed substantially at the same time so as to produce the desired resultant product following purification.

The typical protective, capping, or blocking groups for α- and ϵ-amino side chain groups found in amino acids are exemplified by benzyloxycarbonyl (Z), isonicotinyloxycarbonyl (iNOC), O-chlorobenzyloxycarbonyl [$Z(NO_2)$], p-methoxybenzyloxycarbonyl [Z(OMe)], t-butoxycarbonyl (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt), and the like.

Protective, capping, or blocking groups for the carboxyl group of amino acids include, for example, benzyl ester (OBzl), cyclohexyl ester (Chx), 4-nitrobenzyl ester (ONb), t-butyl ester (Obut), 4-pyridylmethyl ester (OPic), and the like. It is usually also desirable that side chain groups of specific amino acids such as arginine, cysteine, and serine, are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2,4,6-trimethy-benzyl (Tmb), etc., and the hydroxyl group in the serine can be protected with benzyl, t-butyl, acetyl, tetrahydropyranyl, etc.

After the desired amino acid sequence has been completed, the intermediate polypeptide is removed from the resin support by treatment with a reagent, such as liquid HF and one or more thio-containing scavengers, which cleaves the peptide molecule from the resin and all the remaining side-chain protecting groups. Following HF cleavage, the protein sequence is washed with ether, transferred to a large volume of dilute acetic acid, and stirred at pH adjusted to about 8.0 with ammonium hydroxide. Upon pH adjustment, the polypeptide takes its desired conformational arrangement.

By way of example but not by way of limitation, polypeptides of the invention can be chemically synthesized and purified as follows: Peptides can be synthesized by employing the N-alpha-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection to with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time. of mixing in the initial DMF washes to three 15 minute washes rather than three 30 second washes.

After peptide synthesis, the peptide can be cleaved from the resin as follows: (1) washing the peptide-resin three times for 30 seconds with DMF; (2) removing the Fmoc protective group on the amino terminus by washing two times for 15 minutes it 20% piperdine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether. Specifically, to isolate the peptide, the ether-peptide solution can be allowed to sit at −20° C. for 20 minutes, then centrifuged at 6,000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In other specific embodiments, branched versions of the ACE-2 binding polypeptides described herein are provided, e.g., by substituting one or more amino acids within the ACE-2 binding polypeptide sequence with an amino acid or amino acid analog with a free side chain capable of forming a peptide bond with one or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for ACE-2 binding polypeptide residues within a peptide including an ACE-2 binding polypeptide sequence.

Branched peptides can be prepared by any method known in the art. For example, but not by way of limitation, branched peptides can be prepared as follows: (1) the amino acid to be branched from the main peptide chain can be purchased as an N-alpha-tert-butyloxycarbonyl (Boc) protected amino acid pentafluorophenyl (Opfp) ester and the residue within the main chain to which this branched amino acid will be attached can be an N-Fmoc-alpha-gamma-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the: 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12N HCl; (4) the solution containing the peptide can be dehydrated by adding 2–5 grams magnesium sulfate, filtering out the magnesium sulfate, and evaporating the remaining solution to a volume of about 2–5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-Fmoc coupled form of the amino acid or amino acid analog.

ACE-2 binding polypeptides a peptides of the invention may also be synthesized as multiple antigen peptides (MAPs). MAPs consist of multiple copies of a specific peptide attached to a non-immunogenic lysine core. By way of non-limiting example, MAPs may be synthesized onto a lysine core matrix attached to a polyethylene glycol-polystyrene (PEG-PS) support. The peptide of choice is synthesized onto the lysine residues using 9-fluorenylmethoxycarbonyl (Fmoc) chemistry. For example, PerSeptive Biosystems (Foster City, Calif.) offers MAP supports such as the ([Fmoc-Lys(Aloc)] 4-[Lys] 2-Lys-Ala-PAI-PEG-PS) support which can be used to synthesize MAPs. Cleavage of MAPs from the resin is performed with standard trifloroacetic acid (TFA)-based cocktails. Purification of MAPs, except for desalting, is not necessary. In specific embodiments, ACE-2 binding polypetides of the invention being synthesized as MAPs may be synthesized with additional C terminal "linker" residues. In more specific embodiments, ACE-2 binding polypetides of the invention being synthesized as MAPs may be synthesized with an additional 6, 7, 8, 9, 10, 11, 12, 13 or 14, C terminal residues. In even more specific embodiments, the additional residues are glycine and or serine residues.

ACE-2 binding polypeptides may be synthesized as MAPs in order to create multivalent ACE-2 binding polypeptides. By way of non-limiting example, ACE-2 binding polypeptides synthesized as MAPs may be, for example, labelled with a radiolabel using any method known in the art or described herein, and used to label ACE-2 polypeptides. In a preferred embodiment, ACE-2 binding polypeptides synthesized as MAP peptides comprising one or more DOTA molecules (see below) which are chelating radiometal ions (e.g., $^{90}Y$ or $^{111}In$) are used as a means of radiolabelling ACE-2.

In another non-limiting example, ACE-2 binding polypeptides may be synthesized as MAPs and used as an immunogen to create monoclonal or polyclonal anti-ACE-2 binding polypeptide antibodies using any method known in the art or described herein.

In a preferred embodiment, divalent ACE-2 binding polypeptides may be synthesized by attaching two ACE-2 binding polypeptides to a polyethylene glycol (PEG) molecule. In one embodiment, the two ACE-2 binding polypeptides attached to the PEG molecule are identical. In another embodiment, the two ACE-2 binding polypeptides attached to a PEG molecule are different.

In a preferred embodiment, the ACE-2 binding polypeptide of the invention is a cyclic peptide. Cyclization can be, for example, but not by way of limitation, via a disulfide bond between two cysteine residues or via an amide linkage. For example, but not by way of limitation, disulfide bridge formation can be achieved by (1) dissolving the purified peptide at a concentration of between 0.1–0.5 mg/ml in 0.01 M ammonium acetate, pH 7.5; (2) adding to the dissolved peptide 0.01 M potassium ferricyanide dropwise until the solution appears pale yellow in color and allowing this solution to mix for 24 hours; (3) concentrating the cyclized peptide to 5–10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge. Alternatively, a cyclic peptide can be obtained by generating an amide linkage using, for example but not limited to, the following protocol: An allyl protected amino acid, such as aspartate, glutamate, asparagine or glutamine, can be incorporated into the peptide as the first amino acid, and then the remaining amino acids are coupled on. The allyl protective group can be removed by a two hour mixing of the peptide-resin with a solution of tetrakistriphenylphosphine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the peptide. The peptide can be cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

In addition, according to certain embodiments, it is preferable that the ACE-2 binding polypeptides of the invention are produced having or retaining an amino terminal (N-terminal) and/or a carboxy terminal (C-terminal) capping group, which may protect the N-terminal or C-terminal amino acid from undesirable chemical reactions during use or which may permit further conjugations or manipulations of the binding polypeptide, for example, in conjugating the binding polypeptide to a chromatographic support resin or matrix or to another peptide to tether the binding polypeptide to a resin or support. Such N-terminal and C-terminal groups may also be used to label or tag the binding polypeptide to detect bound complexes or to locate the binding polypeptide (whether bound or unbound to an ACE-2 target protein) for example, at some point in a separation procedure. Accordingly, an ACE-2 binding polypeptide of the invention synthesized in its final form for use in a detection or separation procedure may contain an N-terminal and/or a C-terminal capping group. A particularly preferred N-terminal capping group, which may be present or retained in binding polypeptides of the invention, is an acetyl group (Ac). A particularly preferred C-terminal capping group, which may be present or retained in binding polypeptides of the invention, is an amide group. In a further preferred embodiment, the ACE-2 binding polypeptides of the invention have an acetyl group as an N-terminal capping group and an amide group as a C terminal capping group.

The ACE-2 binding polypeptides of the invention may also be prepared commercially by companies providing polypeptide synthesis as a service (e.g., BACHEM Bioscience, Inc., King of Prussia, Pa.; Quality Controlled Biochemicals, Inc., Hopkinton, Mass.).

The nucleic acid sequence encoding an ACE-2 binding polypeptide of the invention can be produced and isolated using well-known techniques in the art. In one example, nucleic acids encoding the ACE-2 binding polypeptides of the invention are chemically synthesized based on knowledge of the amino acid sequence of the ACE-2 binding polypeptide (preferably the sequence is codon optimized to the host system in which the polypeptide will be expressed). In another example, nucleic acids encoding an ACE-2 binding polypeptide are obtained by screening an expression library (e.g., a phage display library) to identify phage expressing ACE-2 binding polypeptides, and isolating ACE-2 binding polypeptide encoding nucleic acid sequences from the identified library member (e.g., via polymerase chain reaction methodology using primers flanking the polypeptide encoding sequences).

The present invention also relates to vectors which include nucleic acid sequences encoding the ACE-2 binding polypeptides of the invention, host cells which are genetically engineered with the recombinant vectors, or which are otherwise engineered to produce the polypeptides of the invention, and the production of ACE-2 binding polypeptides, or fragments thereof, by recombinant, chemical or synthetic techniques.

Thus, according to the present invention, ACE-2 binding polypeptidess can also be obtained by recombinant expression techniques. (See, e.g., Sambrook et al., 1989, *Molecular Cloning, A Laboratory Manual, 2d Ed.*, Glover, D. M. (ed.), (Cold Spring Harbor Laboratory, Cold Spring Harbor, N.Y., 1989); *DNA Cloning: A Practical Approach* (MRL Press, Ltd., Oxford, U.K., 1985), Vols. I, II.

To produce a recombinant ACE-2 binding polypeptide, a nucleic acid sequence encoding the ACE-2 binding polypeptide is operatively linked to a promoter such that the ACE-2 binding polypeptide is produced from said sequence. For example, a vector can be introduced into a cell, within which cell the vector or a portion thereof is expressed, producing the ACE-2 binding polypeptides. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or, become chromosomally integrated,.as long as it can be transcribed to produce the desired RNA. Such vectors can be constructed by recombinant DNA technology methods standard in the art. Vectors can be bacteriophage, plasmid, viral, retroviral, or others known in the art, used for replication and expression in bacterial, fungal, plant, insect or mammalian cells. Retroviral vectors may be replication competent or replication defective. In the latter case, viral propagation generally will occur only in complementing host cells. Introduction of the vector construct into the host cell can be effected by techniques known in the art which include, but are not limited to, calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, for example, stabilization or simplified purification of expressed recombinant product.

In one embodiment, the nucleic acid encoding an ACE-2 binding polypeptide of the invention is operatively associated with an appropriate heterologous regulatory element (e.g., promoter or enhancer), such as, the phage lambda PL promoter, the *E. coli* lac, trp, phoA, and tac promoters, the SV40 early and late promoters, and promoters of retroviral LTRs, to name a few. Other suitable promoters will be known to the skilled artisan.

As indicated, the expression vectors will preferably include at least one selectable marker. Such markers include dihydrofolate reductase, G418, glutamine synthase or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS, 293, NSO and Bowes melanoma cells; and plant cells. Appropriate culture mediums and conditions for the above-described host cells are known in the art.

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted nucleic acid sequences encoding the ACE-2 polypeptides of the invention, or modifies and processes the ACE-2 binding polypeptide in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed. Selection of appropriate vectors and promoters for expression in a host cell is a well-known procedure and the requisite techniques for expression vector construction, introduction of the vector into the host and expression in the host are routine skills in the art.

Useful expression vectors for bacterial use are constructed by inserting a structural DNA sequence encoding a desired protein together with suitable translation initiation and termination signals in operable reading phase with a functional promoter. The vector will preferably comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium,* and various species within the genera. Pseudomonas, Streptomyces, and Staphylococcus, although others may also be employed as a matter of choice. As a representative, but nonlimiting example, useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Among vectors preferred for use in bacteria are pHE4-5 (ATCC Accession No. 209311) and variations thereof), pQE70, pQE60 and pQE-9, available from QIAGEN, Inc.; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, pPIC9K, and PA0815 (all available from Invitrogen, Carlsbad, Calif.). Among preferred eukaryotic vectors are pWLNEO, pSV2CAT, pOG44, pXT1 and pSG available from Stratagene; and pSVK3, pBPV, pMSG and pSVL (available from Pharmacia). Other suitable vectors will be readily apparent to the skilled artisan.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

In one embodiment, the yeast *Pichia pastoris* is used to express an ACE-2 binding polypeptide in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis et al., *Mol. Cell. Biol.,* 5:1111–21 (1985); Koutz et al., *Yeast,* 5:167–77 (1989); Tschopp et al., *Nucl. Acids Res.,* 15:3859–76 (1987). Thus, a heterologous coding sequence, such as, for example, a polynucleotide encoding a ACE-2 binding polypeptide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding an ACE-2 binding polypeptide of the invention, as set forth herein, in a Pichea yeast system essentially as described in "*Pichia Protocols: Methods in Molecular Biology,*" D. R. Higgins and J. Cregg, eds. (The Humana Press, Totowa, N.J., 1998). This expression vector allows expression and secretion of an ACE-2 binding polypeptide of the invention by virtue of the strong AOXI promoter linked to the *Pichia pastoris* alkaline phosphatase (PHO) secretory signal peptide (i.e., leader) located upstream of a multiple cloning site.

Many other yeast vectors may be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In one embodiment, high-level expression of a heterologous coding sequence, such as, for example, a nucleic acid encoding an ACE-2 binding polypeptide of the invention, may be achieved by cloning the heterologous nucleic acid sequence of the invention into an expression vector such as, for example, pGAPZ or pGAPZalpha, and growing the yeast culture in the absence of methanol.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Various mammalian cell culture systems can also be employed to express recombinant protein. Examples of mammalian expression systems include the COS-7 lines of monkey kidney fibroblasts, described by Gluzman (*Cell,* 23:175 (1981)), and other cell lines capable of expressing a compatible vector, for example, the C127, 3T3, CHO, 293, NSO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NSO) which are glutamine synthase negative. It is also possible to amplify vectors that utilize glutamine synthase selection in glutamine synthase expressing cells (e.g., Chinese Hamster Ovary (CHO) cells), however, by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are herein incorporated by reference.

The host cells described herein may be used in a conventional manner to produce the gene product encoded by the recombinant sequence. Alternatively, cell-free translation systems can also be employed to produce the polypeptides of the invention using RNAs derived from the DNA constructs of the present invention.

The polypeptides of the invention may be expressed or synthesized in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA,* 86:821–824 (1989), for instance, hexa-histidine provides for convenient purification of the fusion protein. Other peptide tags useful for purification include, but are not limited to, the hemagglutinin"HA" tag, which corresponds to an epitope derived from the influenza hemagglutinin protein (Wilson et al., *Cell,* 37:767 (1984)) and the "flag" tag (DYKDDDDK, SEQ ID NO:147) Stratagene, La Jolla, Calif.).

In one embodiment, polynucleotides encoding ACE-2 binding polypeptides of the invention may be fused to signal sequences which will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the polypeptides of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, nucleic acids encoding ACE-2 binding polypeptides of the invention may be fused to the pelB pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to a polypeptide of the invention in order to direct its secretion in mammalian cells include, but are not limited to, the MPIF-1 signal sequence (amino acids 1–21 of GenBank Accession number AAB51134), the stanniocalcin signal sequence (MLQNSAVLLLLVISASA, SEQ ID NO:148), and a consensus signal sequence (MPTWAWWLFLVLLLALWAPARG, SEQ ID NO:149). A suitable signal sequence that may be used in conjunction with baculoviral expression systems is the gp67 signal sequence, (amino acids 1–19 of GenBank Accession Number AAA72759).

A preferred fusion protein comprises a heterologous region from immunoglobulin that is useful to stabilize and purify proteins. For example, EP-A-464 533 (Canadian counterpart 2,045,869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A-232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists. See, Bennett et al., *J. Molecular Recognition,* 8:52–58 (1995) and Johanson et al., *J. Biol. Chem.,* 270:9459–9471.(1995).

Figure 2:
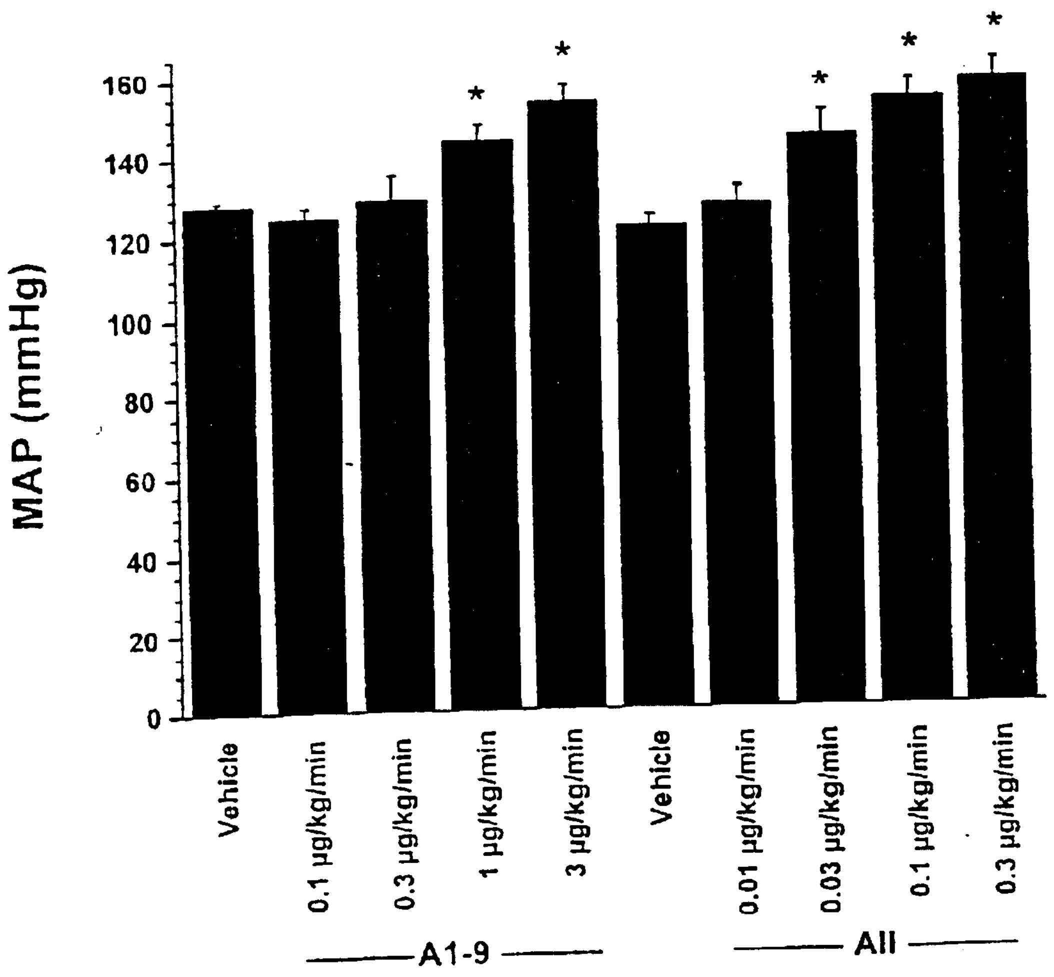
FIG. 2. The effect of A1-9 on (A) mean arterial pressure±SEM in the awake and freely-ranging rat (n=6 rats). Average mean arterial and pulse pressure as well as heart rate data were derived from the last 5 min of a 20 min continuous intravenous infusion period. * indicates a significant difference compared to vehicle-treated rats following analysis of variance and Dunnett's post-hoc test. A1-9 or angiotensin II (AII) continuous infusion doses are in $\mu$g/kg/min.

In another preferred embodiment, ACE-2 binding polypetides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

The present invention encompasses ACE-2 binding polypeptides (including molecules comprising, or alternatively consisting of, ACE-2 binding polypeptide fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, or at least 100 amino acids of the heterologous polypeptide) to generate fusion proteins. The fusion does not necessarily need to be direct, but may occur through linker sequences. For example, ACE-2 binding polypeptides of the invention may be used to target heterologous polypeptides to particular cell types (e.g., smooth muscle cells, endothelial cells, cardiac cells, cardiovascular cells, testicular cells, and renal cells), either in vitro or in vivo, by fusing or conjugating the heterologous polypeptides to ACE-2 binding polypeptides of the invention that are specific for particular cell surface antigens (e.g., membrane-bound ACE-2 on cells of cardiac myocytes and/or proximal tubules of the kidney) or which bind antigens (i.e., ACE-2 binding polypeptides) that bind particular cell surface peptides (e.g., ACE-2 located on cardiac myocytes, proximal convoluted tubules, endothelial cells, and/or epithelial cells of Bowman's capsule). ACE-2 binding polypeptides fused or conjugated to heterologous polypeptides may also be used in in vitro immunoassays and purification methods using methods known in the art. See e.g. Harbor et al., supra, and PCT publication WO 93/2 1232; EP 439 095; Naramura et al., *Immunol. Lett.,* 39:91–99 (1994); U.S. Pat. No. 5,474,981; Gillies et al., *Proc. Nat'l Acad.Sci. USA,* 89:1428–1432 (1992); Fell et al., *J. Immunol.,* 146:2446–2452 (1991), which are incorporated by reference in their entireties.

The present invention further includes compositions comprising, or alternatively consisting of, heterologous polypeptides fused or conjugated to ACE-2 binding polypeptide fragment.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of ACE-2 binding polypeptides (including molecules comprising, or alternatively consisting of, ACE-2 binding polypeptide fragments or variants thereof), such methods can be used to generate ACE-2 binding polypeptides with altered activity (e.g., ACE-2 binding polypeptides with higher affinities and lower dissociation rates). See, generally, U.S. Pat. Nos. 5,605,793; 5,811,238; 5,830,721; 5,834,252; and 5,837,458, and Patten et al., *Curr. Opinion Biotechnol.,* 8:724–33 (1997); Harayama, *Trends Biotechnol.,* 16(2):76–82 (1998); Hansson, et al., *J. Mol. Biol.,* 287:265–76 (1999); and Lorenzo and Blasco, *Biotechniques,* 24(2):308–13 (1998) (each of these patents and publications are hereby incorporated by reference in its entirety). In one embodiment, polynucleotides encoding ACE-2 binding polypeptides of the invention may be altered by being subjected to random mutagenesis by error-prone PCR, random nucleotide insertion or other methods prior to recombination. In another embodiment, one or more portions of a polynucleotide encoding an ACE-2 binding polypeptide which portions specifically bind to ACE-2 may be recombined with one or more components, motifs, sections, parts, domains, fragments, etc. of one or more heterologous molecules.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention encompasses ACE-2 binding polypeptides which are modified during or after synthesis or translation, e.g., by glycosylation, acetylation, benzylation, biotinylation, phosphorylation, amidation, pegylation, formylation, derivatization by known protecting/blocking groups, proteolytic cleavage, linkage to an antibody molecule, hydroxylation, iodination, methylation, myristoylation, oxidation, pegylation, proteolytic processing, phosphorylation, prenylation, racemization, selenoylation, sulfation, ubiquitination, etc. (See, for instance, Creighton, *Proteins: Structures and Molecular Properties, 2d Ed.* (W.H. Freeman and Co., N.Y., 1992); *Postranslational Covalent Modification of Proteins*, Johnson, ed. (Academic Press, New York, 1983), pp. 1–12; Seifter et al., *Meth. Enzymol.,* 182:626–646 (1990); Rattan et al., *Ann. NY Acad. Sci.,* 663:48–62 (1992).) In specific embodiments, the peptides are acetylated at the N-terminus and/or amidated at the C-terminus.

In further embodiments, ACE-2 binding polypeptides of the invention containing two or more residues that have the potential to interact, such as for example, two cysteine residues in a polypeptide, may be treated under oxidizing conditions or other conditions that promote interaction of these residues (e.g, dislulfide bridge formation).

Further ACE-2 binding polypeptide modifications encompassed by the invention include, for example, any of numerous chemical modifications carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational/post-synthesis modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression.

Also provided by the invention are chemically modified derivatives of ACE-2 binding polypetides of the invention which may provide additional advantages such as increased affinity, decreased off-rate, solubility, stability and in vivo or in vitro circulating time of the polypeptide, or decreased immunogenicity (see, U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about I kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any, on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.,* 56:59–72 (1996); Vorobjev et al., *Nucleosides Nucleotides,* 18:2745–2750 (1999); and Caliceti et al., *Bioconjug. Chem.,* 10:638–646 (1999), the disclosures of each of which are incorporated herein by reference.

The polyethylene glycol molecules (or other chemical moieties) should be attached to the ACE-2 binding poypeptide with consideration of effects on functional domains of the polypeptide. There are a number of attachment methods available to those skilled in the art, e.g., EP 0 401 384, herein incorporated by reference (coupling PEG to G-CSF), see also Malik et al., *Exp. Hematol.,* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. In a preferred embodiment, the polyethylene glycol molecule is attached at an amino group, such as attachment at the N-terminus or to a lysine side chain amino group.

As suggested above, polyethylene glycol may be attached to polypeptides via linkage to any of a number of amino acid residues. For example, polyethylene glycol can be linked to a polypeptide via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the polypeptide or to more than one type of amino acid residue (e.g., lysine, histidine, aspartic acid, glutamic acid, cysteine and combinations thereof) of the polypeptide.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to polypeptide molecules in the reaction mix, the type of pegylation reaction to be performed, and the method of obtaining the selected N-terminally pegylated polypeptide. The method of obtaining the N-terminally pegylated preparation (i.e., separating this moiety from other monopegylated moieties if necessary) may be by purification of the N-terminally pegylated material from a population of pegylated polypeptide molecules. Selective N-terminal modification of proteins may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As indicated above, pegylation of the polypeptides of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier*

*Sys.,* 9:249–304 (1992); Francis et al., *Intern. J. of Hematol.,* 68:1–18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of polypeptides without an intervening linker employs tresylated MPEG, which is produced by the modification of monomethoxy polyethylene glycol (MPEG) using tresylchloride ($ClSO_2CH_2CF_3$). Upon reaction of protein with tresylated MPEG, polyethylene glycol is directly attached to amine groups of the polypeptide. Thus, the invention includes polypeptide-polyethylene glycol conjugates produced by reacting polypeptides of the invention with a polyethylene glycol molecule having a 2,2,2-trifluoreothane sulphonyl group.

Polyethylene glycol can also be attached to polypeptides using a number of different intervening linkers. For example, U.S. Pat. No. 5,612,460, the entire disclosure of which is incorporated herein by reference, discloses urethane linkers for connecting polyethylene glycol to polypeptides. Polypeptide-polyethylene glycol conjugates wherein the polyethylene glycol is attached to the polypeptide by a linker can also be produced by reaction of polypeptides with compounds such as MPEG-succinimidylsuccinate, MPEG activated with 1,1'-carbonyldiimidazole, MPEG-2,4,5-trichlorophenylcarbonate, MPEG-p-nitrophenolcarbonate, and various MPEG-succinate derivatives. A number of additional polyethylene glycol derivatives and reaction chemistries for attaching polyethylene glycol to polypeptides are described in WO 98/32466, the entire disclosure of which is incorporated herein by reference. Pegylated ACE-2 binding polypeptide products produced using the reaction chemistries set out herein are included within the scope of the invention.

The number of polyethylene glycol moieties attached to each polypeptide of the invention (i.e., the degree of substitution) may also vary. For example, the pegylated polypeptides of the invention may be linked, on average, to 1, 2, 3, 4, 5, 6, 7, 8, 9, 10, 12, 15, 17, 20, or more polyethylene glycol molecules. Similarly, the average degree of substitution may range within ranges such as 1–3, 2–4, 3–5, 4–6, 5–7, 6–8, 7–9, 8–10, 9–11, 10–12–14, 13–15, 14–16, 15–17, 16–18, 17–19, or 18–20 polyethylene glycol moieties per polypeptide molecule. Methods for determining the degree of substitution are discussed, for example, in Delgado et al., *Crit. Rev. Thera. Drug Carrier Sys.,* 9:249–304 (1992).

The ACE-2 binding polypeptides of the invention can be recovered and purified by known methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The ACE-2 binding polypeptides may also be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of ACE-2 target. The detectable substance may be coupled or conjugated either directly to the polypeptides of the invention or indirectly, through an intermediate (such as, for example, a linker known in the art) using techniques known in the art. Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, 213Bi, or other radioisotopes such as, for example, iodine ($^{131}I$, $^{121}I$, $^{123}I$, $^{121}I$), carbon ($^{14}C$), sulfur ($^{35}S$), tritium ($^{3}H$), indium ($^{115m}I$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}y$, $^{47}Sc$, $^{186}Re$, $^{88}Re$, $^{142}Pr$, $^{105}Rh$, $^{97}Ru$, $^{68}Ge$, $^{57}Co$, $^{65}Zn$, $^{85}Sr$, $^{32}P$, $^{53}Gd$, $^{169}Yb$, $^{51}Cr$, $^{54}Mn$, $^{75}Se$, $^{113}Sn$, and $^{117}Tin$.

In specific embodiments, ACE-2 binding polypetides of the invention are attached either directly or indirectly, to macrocyclic chelators useful for chelating radiometal ions, including but not limited to $^{177}Lu$, $^{90}Y$, $^{166}Ho$, and $^{153}Sm$, to polypeptides. . In a preferred embodiment, the radiometal ion associated with the macrocyclic chelators attached to Neutrokine-alpha and/or Neutrokine-alphaSV polypeptides of the invention is $^{111}In$. In another preferred embodiment, the radiometal ion associated with the macrocyclic chelator attached to Neutrokine-alpha and/or Neutrokine-alphaSV polypeptides of the invention is $^{90}Y$. in specific embodiments, the macrocyclic chelator is 1,4,7,10-tetraazacyclododecane-N,N',N",N'"-tetraacetic acid (DOTA). In one embodiment the side chain moiety of one or more classical or non-classical amino acids in an ACE-2 binding polypeptide comprises a DOTA molecule. In other specific embodiments, the DOTA is attached to the ACE-2 binding polypeptide of the invention via a linker molecule. Examples of linker molecules useful for conjugating DOTA to a polypeptide are commonly known in the art—see, for example, DeNardo et al., *Clin. Cancer Res.,* 4(10):2483–90 (1998); Peterson et al., *Bioconjug. Chem.,* 10(4):553–7 (1999); and Zimmerman et al, *Nucl. Med. Biol.,* 26(8) :943–50 (1999which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the methods disclosed therein in order to conjugate chelating agents to other polypeptides.

In a specific embodiment, ACE-2 binding polypeptides of the invention are labeled with biotin.

The present invention further encompasses ACE-2 binding polypeptides (including molecules comprising, or alternatively consisting of, ACE-2 binding polypeptide fragments or variants thereof), conjugated to a diagnostic or therapeutic agent. The ACE-2 binding polypeptides can be used diagnostically to, for example, monitor or prognose the development or progression of a tumor as part of a clinical testing procedure to, e.g., determine the efficacy of a given treatment regimen. Detection can be facilitated by coupling the ACE-2 binding polypeptide to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions such as, for example, those described herein. The detectable substance may be coupled or conjugated either directly to the ACE-2 binding polypeptide or indirectly, through an intermediate (such as, for example, a linker known in the art) using techniques known in the art. See, for example, U.S. Pat. No. 4,741,900 for metal ions which can be conjugated to ACE-2 binding polypeptides for use as diagnostics according to the present invention.

Further, an ACE-2 binding polypeptide of the invention (including a molecule comprising, or alternatively consisting of, ACE-2 binding polypeptide fragments or variants thereof), may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{53}$Sm, $^{153}$Gd, $^{169}$Yb, $^{51}$Cr, $^{54}$Mn, $^{75}$Se, $^{113}$Sn, $^{9-}$Yttrium, $^{117}$Tin, $^{186}$Rhenium, $^{166}$Holmium, and $^{188}$Rhenium.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and frragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label ACE-2 binding polypeptides of the invention. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990;. 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The ACE-2 binding polypeptides of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity.

An ACE-2 binding polypeptide of the invention (including a molecule comprising, or alternatively consisting of, an ACE-2 binding polypeptide fragment or variant thereof), with or without a therapeutic moiety conjugated to it, administered alone or in combination with cytotoxic factor(s) and/or cytokine(s) can be used as a therapeutic.

Characterization of ACE-2 Binding Polypeptides

ACE-2 binding polypeptides of the present invention (including molecules comprising, or alternatively consisting of, ACE-2 binding polypeptide fragments or variants thereof) may be characterized in a variety of ways. In particular, ACE-2 binding polypeptides and related molecules of the invention may be assayed for the ability to specifically bind to ACE-2 or a fragment of ACE-2 (e.g., to the soluble form or the membrane-bound form of ACE-2) using techniques described herein or routinely modifying techniques known in the art. ACE-2 or ACE-2 fragments that may be specifically bound by the compositions of the invention include, but are not limited to, human ACE-2 (SEQ ID NOs:138, 139, 140 and/or 142) or fragments thereof. Assays for the ability of the ACE-2 binding polypeptides of the invention to specifically bind ACE-2 or a fragment of ACE-2 may be performed in solution (e.g., Houghten, *Bio/Techniques,* 13:412–421(1992)), on beads (e.g., Lam, *Nature,* 354:82–84 (1991)), on chips (e.g., Fodor, *Nature,* 364:555–556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., *Proc. Natl. Acad. Sci. USA,* 89:1865–1869 (1992)) or on phage (e.g., Scott and Smith, *Science,* 249:386–390 (1990); Devlin, *Science,* 249:404–406 (1990); Cwirla et al., *Proc. Natl. Acad. Sci. USA,* 87:6378–6382 (1990); and Felici, *J. Mol. Biol.,* 222:301–310 (1991)) (each of these references is incorporated herein in its entirety by reference). ACE-2 binding polypeptides that have been identified to specifically bind to ACE-2 or a fragment of ACE-2 can then be assayed for their specificity and affinity for ACE-2 or a fragment of ACE-2 using or routinely modifying techniques described herein or otherwise known in the art.

The ACE-2 binding polypeptides of the invention may be assayed for specific binding to ACE-2 and cross-reactivity with other ACE-2-like polypeptides by any method known in the art. In particular, the ability of an ACE-2 binding polypeptide to specifically bind to the soluble form or membrane-bound form of ACE-2 may be determined using or routinely modifying techniques described herein or otherwise known in art.

Assays which can be used to analyze specific binding and cross-reactivity include, but are not limited to, competitive and non-competitive assay systems using techniques such as western blots, radioimmunoassays, ELISA (enzyme linked immunosorbent assay), "sandwich" assays, "immunoprecipitation" assays, precipitin reactions, gel diffusion precipitin reactions, immunodiffusion assays, agglutination assays, complement-fixation assays, radiometric assays, and fluorescent assays, to name but a few. Such assays are routine and well known in the art (see, e.g., *Current Protocols in Molecular Biology, Vol.* 1, Ausubel et al, eds. (John Wiley & Sons, Inc., New York 1994), which is incorporated by reference herein in its entirety) and could easily be adapted to make use of an ACE-2 binding polypeptide (possibly in conjunction with an anti-ACE-2 binding polypeptide antibody) in place of an anti-ACE-2 antibody. Exemplary immunoassays that could be modified to use an ACE-2 binding polypeptide of the invention are described briefly below (but are not intended by way of limitation).

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with ACE-2 binding polypeptide (the ACE-2 binding polypeptide of interest) diluted in blocking buffer, washing the membrane in washing buffer, incubating the membrane with a secondary antibody (which recognizes the ACE-2 binding polypeptide) conjugated to an enzyme (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. Alternatively, the ACE-2 binding polypeptide may be directly conjugated to a detection molecule (e.g., an enzyme or radiolabel), thereby omitting the need for a secondary anti-ACE-2 binding polypeptide antibody. One of skill in the art would be knowledgeable as to the parameters that can be modified to increase the signal detected and to reduce the background noise. For further discussion regarding western blot protocols see, e.g., *Current Protocols in Molecular Biology, Vol.* 1, Ausubel et al, eds. (John Wiley & Sons, Inc., New York 1994) at 10.8.1.

ELISAs comprise preparing antigen (e.g., ACE-2 target), coating the well of a 96-well microtiter plate with the antigen, washing away antigen that did not bind the wells, adding the ACE-2 binding polypeptide of interest conjugated to a detectable compound such as an enzyme (e.g., horseradish peroxidase or alkaline phosphatase) to the wells and incubating for a period of time, washing away unbound ACE-2 binding polypeptides or non-specifically bound ACE-2 binding polypeptides, and detecting the presence of the ACE-2 binding polypeptides specifically bound to the antigen coating the well. In ELISAs the ACE-2 binding polypeptide employed in the assay does not have to be conjugated to a detectable compound; instead, an antibody that recognizes the ACE-2 binding polypeptide and that is conjugated to a detectable compound may be added to the well. Further, instead of coating the well with the antigen, the ACE-2 binding polypeptide. may be coated to the well. In this case, the detectable molecule could be the antigen conjugated to a detectable compound such as an enzyme (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., *Current Protocols in Molecular Biology, Vol.* 1, Ausubel et al, eds. (John Wiley & Sons, Inc., New York 1994) at 11.2.1.

Immunoprecipitation protocols generally use antibody molecules to imunopreciptate a protein of interest. An ACE-2 preciptation protocol could easily be modified to use an ACE-2 binding polypeptide in place of an anti-ACE-2 antibody. Immunopreciptation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. If one wanted to substitute an ACE-2 binding polypeptide for the anti-ACE-2 antibody one could readily do so, and then isolate the ACE-2—ACE-2 binding polypeptide complexes with an antibody that recognizes the ACE-2 binding polypeptide. Then the triple complex of ACE-2, ACE-2 binding polypeptide, and anti-ACE-2 binding polypeptide antibody could be isolated using protein A and/or Protein G as described above. Such a protocol may be desirable if, for example, the anti-ACE-2 binding polypeptide antibody has a higher affinity for the ACE-2 binding polypeptide than the anti-ACE-2 antibody may have for ACE-2.

The effectiveness of incorporating an ACE-2 binding polypeptide in an immunoprecipitation protocol to precipitate ACE-2 can be assessed by, e.g., western blot analysis. One of skill in the art would be knowledgeable as to the parameters that can be modified to increase the binding of the ACE-2 binding polypeptide to an antigen and decrease the background (e.g., pre-clearing the cell lysate with sepharose beads). For further discussion regarding immunoprecipitation protocols see, e.g., *Current Protocols in Molecular Biology, Vol.* 1, Ausubel et al, eds. (John Wiley & Sons, Inc., New York 1994) at 10.16.1.

The binding affinity of an ACE-2 binding polypeptide (including molecules comprising, or alternatively consisting of, ACE-2 binding polypeptide fragments or variants thereof) to an antigen and the off-rate of an ACE-2 binding polypeptide-antigen interaction can be determined by competitive binding assays. One example of a competitive binding assay is a modified radioimmunoassay comprising the incubation of labeled antigen (e.g., $^{3}H$- or $^{125}I$-labeled ACE-2 target) with the ACE-2 binding polypeptide of interest in the presence of increasing amounts of unlabeled antigen, followed by detection of the ACE-2 binding polypeptide bound to the labeled antigen. The affinity of the ACE-2 binding polypeptide of the present invention for ACE-2 and the binding off-rates can be determined from the data by Scatchard plot analysis. Competition with an anti-ACE-2 antibody or ACE-2 binding polypeptide can also be determined using radioimmunoassays. In this case, ACE-2 is incubated with an ACE-2 binding polypeptide of the present invention conjugated to a labeled compound (e.g., with $^{3}H$ or $^{125}I$) in the presence of increasing amounts of an unlabeled ACE-2 binding polypeptide or anti-ACE-2 antibody.

In a preferred embodiment, BIAcore kinetic analysis is used to determine the binding on and off rates of ACE-2 binding polypeptides (including molecules comprising, or alternatively consisting of, ACE-2 binding polypeptide fragments or variants thereof) to ACE-2, or fragments of ACE-2. BIAcore kinetic analysis comprises analyzing the binding and dissociation of ACE-2 from chips with immobilized ACE-2 binding polypeptides on their surface (see Example 3, infra).

The ACE-2 binding polypeptides of the invention (including molecules comprising, or alternatively consisting of, ACE-2 binding polypeptide fragments or variants thereof) can also be assayed for their ability to inhibit, increase, or not significantly alter, the enzymatic activity of ACE-2 using techniques known to those skilled in the art. For example, cells expressing a substrate for ACE-2 (e.g., angiotensin, bradykinin, tachykinin, neurotensin, Substance P, endothelin, and/or kinetensin) can be contacted with ACE-2 in the presence or absence of an ACE-2 binding polypeptide, and the ability of the ACE-2 binding polypeptide to inhibit, increase, or not significantly alter, ACE-2 binding to the cells can be measured. Alternatively, the ACE-2 binding polypeptide may be preincubated with ACE-2 prior to exposure of ACE-2 to cells expressing the ACE-2 receptor. ACE-2 binding to cells can be measured by, for example, flow cytometry or a scintillation assay. ACE-2 or the ACE-2 binding polypeptide can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between ACE-2 and its substrates and/or ACE-2 and an ACE-2 binding polypeptide of the invention.

The ability of ACE-2 binding polypeptides of the invention to inhibit, increase, or not significantly alter, ACE-2 binding to a substrate can also be determined in cell-free assays. For example, native or recombinant ACE-2 (e.g., having the amino acid sequence of SEQ ID NOs:138 and/or 142) or a fragment thereof can be contacted with a ACE-2 binding polypeptide and the ability of the ACE-2 binding polypeptide to inhibit, increase, or not significantly alter, ACE-2 from binding to a substrate can be determined. For example, one could use an ELISA, or other suitable assay to test the ability of ACE-2 binding polypeptides of the invention to inhibit, increase, or not significantly alter, ACE-2 from binding to a substrate. One way to do such an assay would be to immobilize the ACE-2 receptor on a solid support. Then ACE-2 or ACE-2 fragments labeled with a detectable compound which had been preincubated with an ACE-2 binding polypetide of the invention are tested for their ability to bind the ACE-2 substrate immobilized on the solid support. ACE-2 may be partially or completely purified (e.g., partially or completely free of other polypeptides) or part of a cell lysate. Further, the ACE-2 polypeptide may be a fusion protein comprising ACE-2 or a biologically active portion thereof and a domain such as an Immunoglobulin Fc or glutathione-S-transferase. Additionally, the ACE-2 binding polypeptide and/or ACE-2 substrate may be a fusion protein comprising an ACE-2 binding portion of the polypeptide substrate and a domain such as an Immunoglobulin Fc or glutathionine-S-transferase. For example, amino acid residues 1–154 of TACI (GenBank accesion number AAC51790), or 1–48 of BCMA (GenBank accession number NP_001183) may be fused to the Fc region of an IgG molecule and used in a cell free assay to determine the ability of ACE-2 binding polypeptides of the invention to inhibit, increase, or not significantly alter, ACE-2 binding to an ACE-2 substrate. Alternatively, ACE-2 can be biotinylated using techniques well known to those skilled in the art (e.g., biotinylation kit, Pierce Chemicals; Rockford, Ill.).

The ACE-2 binding polypeptides of the invention (including molecules comprising, or alternatively consisting of, ACE-2 binding polypeptide fragments or variants thereof), can also be assayed for their ability to inhibit, stimulate, or not significantly alter, ACE-2-induced enzymatic activity using techniques known to those of skill in the art. For example, ACE-2 activity can be assayed by $^3$H-thymidine incorporation assays and trypan blue cell counts (see, e.g., Moore et al., *Science,* 285: 260–263 (1999)). Additionally, the ACE-2 binding polypeptides of the invention, or fragments or variants thereof, can be assayed for their ability to inhibit, stimulate, or not significantly alter, ACE-2-induced cleavage of angiotensin using techniques known to those of skill in the art (see, e.g., Tipnis et al., *Journal of Biological Chemistry* 275:33238–33243 (2000)). For example, hydrolysis of angiotensin can be determined by analyzing cleavage products detected by high performance liquid chromatography (HPLC). Further, the ACE-2 binding polypeptides of the invention, or fragments or varients thereof, can be assayed for their ability to inhibit, stimulate, or not significantly alter ACE-2 regulation of bradykinin, tachykinin, neurotensin, Substance P, and endothelin synthesis and/or cleavage using the same or similar techniques known to those of skill in the art.

The ACE-2 binding polypeptides of the invention, or fragments or variants thereof can also be assayed for their ability to neutralize, enhance, or not significantly alter, ACE-2 activity. For example, ACE-2 binding polypeptides or fragments or variants thereof, may be routinely tested for their ability to inhibit ACE-2 from enzymatically acting on any of its substrates (e.g., Angiotensin, bradykinin, tachykinin, neurotensin, Substance P, or endothelin).

Uses of the Binding Polypeptides and Recombinant Bacteriophage of the Invention

The ACE-2 binding polypeptides described herein are especially useful to detect, isolate, or remove ACE-2 target proteins in solutions. Such solutions may be simple dispersions or solutions of ACE-2 and/or ACE-2-like polypeptide in water or aqueous buffer or more complex solutions, such as, blood and other biological fluids, tissue homogenates cell extracts, or biopsy samples, and cell culture media containing ACE-2 or ACE-2-like polypeptides. Biological fluids include, but are not limited to sera, plasma, lymph, blood, blood fractions urine, synovial fluid, spinal fluid, saliva, and mucous.

In one embodiment, the present invention provides a method for detecting an ACE-2 protein and/or an ACE-2-like polypeptide in a solution comprising contacting the solution with an ACE-2 binding polypeptide of the invention and detecting binding of ACE-2 or ACE-2-like polypeptide to the ACE-2 binding polypeptide. The ACE-2 binding polypeptide may be either free or immobilized. Preferably, the ACE-2 binding polypeptide is a polypeptide immobilized on a solid surface or chromatographic material or the well of a plastic microtiter assay dish.

Another embodiment of the present invention is a method for isolating ACE-2 protein and/or ACE-2-like polypeptide from a solution containing it, comprising:

contacting the solution with an ACE-2 binding polypeptide under conditions that permit binding of ACE-2 and/or ACE-2-like polypeptides to ACE-2 binding polypeptide, and recovering the ACE-2 and/or ACE-2-like polypeptides.

A further embodiment of the present invention is a method for isolating ACE-2 protein and/or ACE-2-like polypeptide from a solution containing it, comprising:

contacting the solution with an ACE-2 binding polypeptide under conditions that permit binding of ACE-2 and/or ACE-2-like polypeptides to ACE-2 binding polypeptide, and separating the complex(es) formed by the ACE-2 binding polypeptide and ACE-2 and/or ACE-2-like polypeptides from other components of the solution.

Preferably such method also includes the further steps of:

dissociating the ACE-2 binding polypeptide from the ACE-2 and/or ACE-2-like polypeptides, and recovering the dissociated, ACE-2 and/or ACE-2-like polypeptide.

The invention also provides for kits containing a binding polypeptide of the invention for use in methods of detecting or isolating ACE-2 and/or ACE-2-like polypeptides.

According to the invention, detection or isolation of ACE-2 target proteins comprises contacting a solution containing an ACE-2 target protein with an ACE-2 binding polypeptide. Depending on the particular application, the ACE-2 binding polypeptide may be free in solution or immobilized on a solid support or chromatographic material. Sufficient time is allowed to permit binding between the ACE-2 target protein and the binding polypeptides, and non-binding components in the solution or mixture are removed or washed away. The formation of a binding complex between the binding polypeptide and the ACE-2 target protein can then be detected, for example, by detecting the signal from a label on the binding polypeptide, which is one component of the binding complex. A label may be any label that generates a signal that can be detected by standard methods, such as a fluorescent label, a radioactive compound, or an enzyme that reacts with a substrate to generate a detectable signal. Suitable such labels are discussed above. A phage binding polypeptide according to the invention, that is, a recombinant phage displaying an ACE-2 binding polypeptide on its surface, may form a complex with ACE-2 and/or ACE-2-like polypeptides that is detectable as a precipitate or sediment in a reaction tube, which can be detected visually after settling or centrifugation. Alternatively, a sandwich-type assay may be used, wherein an ACE-2 binding polypeptide is immobilized on a solid support such as a plastic tube or well, or a chromatographic support matrix such as agarose beads, then the solution suspected of containing the ACE-2 target is contacted with the immobilized binding polypeptide and non-binding materials or components are removed or washed away.

The binding polypeptides according to this invention are particularly useful for detection and/or isolation of ACE-2 and/or ACE-2-like polypeptides by affinity chromatography methods. Any conventional method of chromatography may be employed. Preferably, an ACE-2 binding polypeptide of the invention will be immobilized on a solid support suitable, for example, for packing a chromatography column. The immobilized ACE-2 binding polypeptide affinity ligand can then be loaded or contacted with a feed stream under conditions favorable to formation of binding polypeptide/ ACE-2 (or ACE-2-like polypeptide) complexes. Non-binding materials can be washed away. Examples of suitable wash conditions can readily be determined by one of skill in the art and include but are not limited to [PBS/0.01% Tween 20, pH7.2] and [1M NaCl/10 mM Tris, pH7.5]. Tris wash buffers may be preferable since phosphates can preciptate in 50% ethylene glycol. In general, non-limiting terms, wash buffers are pH7.0, optionally containing 0.0 to 1.5 M NaCl, more preferably 1M NaCl. Additionally, wash buffers may optionally contain a mild detrgenet, such as, for example, Tween 20, Tween 80, or NP-80. ACE-2 or ACE-2-like polypeptide can be eluted from the ACE-2 binding polypeptide by introducing solution conditions that favor dissociation of the binding complex. Suitable elution solutions can readily be determined by one of skill in the art and include but are not limited to [50% ethylene glycol/100 mM NaOAc]. By way of non-limiting example, useful elution buffers, for the purposes of the present invention contain 40–60% ethylene glycol, preferably 50% ethylene glycol.; and 50–100 mM NaOAc with a pH in the range of pH 4–pH7, more preferably, pH 4–pH 6 and most preferably pH 4.5–pH 5.5. Preferably, a fast flow affinity chromatographic technique is used to bind the molecules and from which purified ACE-2 or ACE-2-like polypeptides are eluted.

Alternatively, batch chromatography can be carried out by mixing a solution containing the ACE-2 target and the ACE-2 binding polypeptide, then isolating complexes of the ACE-2 target and the binding polypeptides. For this type of separation, many methods are known. For example, the binding polypeptide may be immobilized on a solid support such as beads, then separated from the feed stream along with the ACE-2 target by filtration. In another example, the ACE-2 binding polypeptide may be modified with its own affinity tag, such as a polyHis tail or streptavidin binding region, which can be used to isolate the binding polypeptide after complexes have formed using an immobilized metal affinity chromatographic resin or steptavidin-coated substrate. Once separated, the ACE-2 target can be released from the binding polypeptide under elution conditions and recovered in a purified form.

Methods of producing ACE-2 or ACE-2-like polypeptides usually yield ACE-2 or ACE-2-like polypeptides in a feed stream that additionally contains impurities (with respect to the ACE-2 target). One purpose of the present invention is to produce ACE-2 binding polypeptides and preparations (such as affinity chromatography media or surfaces) comprising ACE-2 binding polypeptides that allow rapid and highly specific purification of ACE-2 target proteins from a feed stream. ACE-2 binding polypeptides obtained herein may easily be tailored to isolate ACE-2 target protein from a particular feed stream, using or routinely modifying conditions and techniques known in the art. If an alternate production method for ACE-2 is used, producing a different feed stream, a different set of ACE-2 binding polypeptides and/or conditions may be necessary to achieve the same level of purification. The new set of ACE-2 binding polypeptides and/or conditions can be readily obtained following or modifying procedures outlined herein, or otherwise known in the art.

Use of ACE-2 Binding Polypeptides for Epitope Mapping

The present invention provides ACE-2 binding polypeptides (including molecules comprising, or alternatively consisting of, ACE-2 binding polypeptide fragments or variants thereof), that can be used to identify epitopes of ACE-2. In particular, the ACE-2 binding polypeptides of the present invention can be used to identify epitopes of human ACE-2 (SEQ ID NOs:138 and/or 142) or ACE-2 expressed on human myocytes and/or proximal tubules and/or epithelial cells using techniques described herein or otherwise known in the art. Fragments which function as epitopes may be produced by any conventional means. (See, e.g., Houghten, *Proc. Natl. Acad. Sci. USA,* 82:5131–5135 (1985), further described in U.S. Pat. No. 4,631,211.)

Diagnostic Uses of ACE-2 Binding Polypeptides

Labeled and non-labelled ACE-2 binding polypeptides of the invention (including molecules comprising, or alternatively consisting of, ACE-2 binding polypeptide fragments or variants thereof) which specifically bind to ACE-2 can be used for diagnostic purposes to detect, diagnose, prognose, or monitor diseases and/or disorders associated with the aberrant expression and/or activity of ACE-2. The invention provides for the detection of aberrant expression of ACE-2 comprising: (a) assaying the expression of ACE-2 in a biological sample from an individual using one or more ACE-2 binding polypeptides of the invention that specifically binds to ACE-2; and (b) comparing the level of ACE-2 with a standard level of ACE-2, e.g., in normal biological samples, whereby an increase or decrease in the assayed level of ACE-2 compared to the standard level of ACE-2 is indicative of aberrant expression.

By "biological sample" is intended any fluids and/or cells obtained from an individual, body fluid, body tissue, body cell, cell line, tissue culture, or other source which may contain ACE-2 protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

The invention also provides for the detection of aberrant expression and/or activity of ACE-2 substrates (e.g., angiotensin, bradykinin, tachykinin, neurotensin, Substance P, and endothelin) comprising (a) assaying the expression of ACE-2 substrates in a biological sample from an individual using one or more ACE-2 binding polypeptides or fragments or variants thereof that specifically binds only to soluble ACE-2, but does not inhibit ACE-2/ACE-2 substrate binding. Such an ACE-2 binding polypeptide, by way of an example that is not to be construed as limiting, would be one that is able to capture a biotinylated ACE-2 from solution, but that would not prevent ACE-2 from binding to it receptor expressed, for example on IM-9 cells, and (b) comparing the level of ACE-2 substrate with a standard level of ACE-2 substrate, e.g., in normal tissue or cell samples, whereby an increase or decrease in the assayed level of ACE-2 substrate compared to the standard level of ACE-2 substrate is indicative of aberrant expression.

Angiotensin II is a known potent vasoconstrictor, high concentrations of which are associated with such diseases as hypertension, congestive heart failure, and several other cardiovascular disorders. Production of angiotensin II is under control of the ACE enzyme, which competes with ACE-2 for a common substrate, angiotensin. Thus, an an abnomally high agiotensin II level could result from abnormally low activity of ACE-2, thereby allowing most of all of the angiotensin to be converted to angiotensin II rather than angiotensin 1-9. Conversely, inappropriately low concentrations of angiotensin II, which may play a role in hypotensive disorders and shock, may result from inappropriately high activity of ACE-2, whereby most or all angiotensin is converted to angiotensin 1-9 rather than angiotensin II. Furthermore, angiotensin 1-9 potentiates the vasoconstrictor and pressor action of angiotensin II, indicating a role for angtiotensin 1-9 in the precise regulation of blood pressure and vascular constriction (see Example 9).

Thus, the ACE-2 binding polypeptides of the invention (including molecules comprising, or alternatively consisting of, ACE-2 binding polypeptide fragments or variants thereof) which specifically bind to ACE-2 can be used for diagnostic purposes to detect, diagnose, prognose, or monitor cardiovascular diseases and disorders, including but not limited to hypertension, hypotension, and/or diseases, disorders, or conditions associated therewith. The invention provides for the detection of aberrant expression of ACE-2 comprising: (a) assaying the expression of ACE-2 in a biological sample from an individual using one or more ACE-2 binding polypeptides of the invention that specifically binds to ACE-2; and (b) comparing the level of ACE-2 with a standard level of ACE-2, e.g., in normal biological samples, whereby an increase or decrease in the assayed level of ACE-2 compared to the standard level of ACE-2 is indicative of a cardiovascular disease, disorder, or condition. In specific embodiments, an increase in the assayed level of ACE-2 is indicative of a cardiovascular disease, disorder, or condition. In other specific embodiments, a decrease in the assayed level of ACE-2 is indicative of a cardiovascular disease, disorder, or condition.

ACE-2 binding polypeptides of the invention (including molecules comprising, or alternatively consisting of, ACE-2 binding polypeptide fragments or variants thereof) which specifically bind to ACE-2 but do not inhibit ACE-2/ACE-2 substrate binding can be used for diagnostic purposes to detect, diagnose, prognose, or monitor cardiovascular diseases and disorders, including but not limited to hypertension and/or diseases, disorders, or conditions associated therewith. The invention provides for the detection of aberrant expression of an ACE-2 substrate comprising: (a) assaying the expression of an ACE-2 substrate in a biological sample from an individual using one or more ACE-2 binding polypeptides of the invention that specifically binds to ACE-2; and (b) comparing the level of ACE-2 substrate with a standard level of ACE-2 substrate, e.g., in normal biological samples, whereby an increase or decrease in the assayed level of ACE-2 substrate compared to the standard level of ACE-2 substrate is indicative of a cardiovascular disease, disorder, or condition. In specific embodiments, an increase in the assayed level of ACE-2 substrate is indicative of a cardiovascular disease, disorder, or condition. In other specific embodiments, a decrease in the assayed level of ACE-2 substrate is indicative of a cardiovascular disease, disorder, or condition.

Cardiac and cardiovascular disorders, diseases, or conditions that may be detected, diagnosed, prognosed, or monitored using the ACE-2 binding polypeptides of the invention include, but are not limited to, arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Additional cardiovascular disorders, diseases, or conditions that may be detected, diagnosed, prognosed, or monitored by the ACE-2 binding polypeptides of the invention include, but are not limited to, arrhythmias, such as sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Additional cardiovascular disorders, diseases, or conditions that may be detected, diagnosed, prognosed, or monitored by the ACE-2 binding polypeptides of the invention include, but are not limited to heart valve diseases, such as aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases that may be detected, diagnosed, prognosed, or monitored, using the ACE-2 binding polypeptides of the invention include, but are not limited to alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias that may be detected, diagnosed, prognosed, or monitored, using the ACE-2 binding polypeptides of the invention include, but are not limited to coronary disease, such as angina pectoris, coronary aneurysm, coronary arteriosclerosis, coronary thrombosis, coronary vasospasm, myocardial infarction and myocardial stunning.

Additional cardiovascular diseases that may be detected, diagnosed, prognosed, ormonitored using the ACE-2 binding polypeptides of the invention also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, tel angiectasi a, atacia telangiectasi a, hereditary hemorrhagic telangiectasia, varicocele, varicose veins, varicose ulcer, vasculitis, and venous insufficiency.

Aneurysms that may be detected, diagnosed, prognosed, or monitored using the ACE-2 binding polypeptides of the invention include, but are not limited to dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases that may be detected, diagnosed, prognosed, or monitored using the ACE-2 binding polypeptides of the invention include, but are not limited to include, but are not limited to, arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders that may be detected, diagnosed, prognosed, or monitored using the ACE-2 binding polypeptides of the invention include, but are not limited to, carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms that may be detected, diagnosed, prognosed, or monitored using the ACE-2 binding polypeptides of the invention include, but are not limited to air embolisms, amniotic fluid embolisms, cholesterol embolisms, blue toe syndrome, fat embolisms, pulmonary embolisms, and thromoboembolisms. Thrombosis include, but are not limited to, coronary thrombosis, hepatic vein thrombosis, retinal vein occlusion, carotid artery thrombosis, sinus thrombosis, Wallenberg's syndrome, and thrombophlebitis.

Ischemic disorders that may be detected, diagnosed, prognosed, or monitored using the ACE-2 binding polypeptides of the invention include, but are not limited to, cerebral ischemia, ischemic colitis, compartment syndromes, anterior compartment syndrome, myocardial ischemia, reperfusion injuries, and peripheral limb ischemia. Vasculitis includes, but is not limited to, aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In a specific embodiment, the compositions of the present invention are used to detect, diagnose, prognose, or monitor hypertension.

In another specific embodiment, the compositions of the present invention are used to detect, diagnose, prognose, or monitor congestive heart failure.

In a further specific embodiment, the compositions of the present invention are used to detect, diagnose, prognose, or monitor hypotension.

In an even further specific embodiment, the compositions of the present invention are used to detect, diagnose, prognose, or monitor shock.

Angiotensin II also stimulates the release of aldosterone. Aldosterone is an adrenal cortex hormone that promotes retention of salt and water by the kidneys, which increases plasma volume and, thereby, increases blood pressure. In addition to chronic or acute hypertension and hypotension, aberrant action of aldosterone is known to cause several renal disorders. As discussed previously herein, angiotensin II concentration can be correlated with activity or presence of ACE-2. Thus, the ACE-2 binding polypeptides of the invention (including molecules comprising, or alternatively consisting of, ACE-2 binding polypeptide fragments or variants thereof) which specifically bind to ACE-2 can be used for diagnostic purposes to detect, diagnose, prognose, or monitor diseases and disorders associated with aberrant aldosterone action, including but not limited to renal diseases and disorders, hypertension, hypotension, and/or diseases, disorders, or conditions associated therewith. The invention provides for the detection of aberrant expression of ACE-2 comprising: (a) assaying the expression of ACE-2 in a biological sample from an individual using one or more ACE-2 binding polypeptides of the invention that specifically binds to ACE-2; and (b) comparing the level of ACE-2 with a standard level of ACE-2, e.g., in normal biological samples, whereby an increase or decrease in the assayed level of ACE-2 compared to the standard level of ACE-2 is indicative of a renal disease, disorder, or condition. In specific embodiments, an increase in the assayed level of ACE-2 is indicative of a renal disease, disorder, or condition. In other specific embodiments, a decrease in the assayed level of ACE-2 is indicative of a renal disease, disorder, or condition.

ACE-2 binding polypeptides of the invention (including molecules comprising, or alternatively consisting of, ACE-2 binding polypeptide fragments or variants thereof) which specifically bind to ACE-2 but do not inhibit ACE-2/ACE-2 substrate binding can be used for diagnostic purposes to detect, diagnose, prognose, or monitor diseases and disorders associated with aberrant aldosterone activity, including but not limited to renal diseases and/or disorders, hypertension and/or diseases, disorders, or conditions associated therewith. The invention provides for the detection of aberrant expression of an ACE-2 substrate comprising: (a) assaying the expression of an ACE-2 substrate in a biological sample from an individual using one or more ACE-2 binding polypeptides of the invention that specifically binds to ACE-2; and (b) comparing the level of ACE-2 substrate with a standard level of ACE-2 substrate, e.g., in normal biological samples, whereby an increase or decrease in the assayed level of ACE-2 substrate compared to the standard level of ACE-2 substrate is indicative of a renal disease, disorder, or condition. In specific embodiments, an increase in the assayed level of ACE-2 substrate is indicative of a renal disease, disorder, or condition. In other specific embodiments, a decrease in the assayed level of ACE-2 substrate is indicative of a renal disease, disorder, or condition.

Renal disorders, diseases, and/or conditions that may be detected, diagnosed, prognosed, monitored, treated, prevented, and/or ameliorated using the ACE-2 binding polypeptides of the invention include, but are not limited to acute kidney failure, chronic kidney failure, atheroembolic renal failure, end-stage renal disease, inflammatory diseases of the kidney (e.g., acute glomerulonephritis, postinfectious glomerulonephritis, rapidly progressive glomerulonephritis, nephrotic syndrome, membranous glomerulonephritis, familial nephrotic syndrome, membranoproliferative glomerulonephritis I and II, mesangial proliferative glomerulonephritis, chronic glomerulonephritis, acute tubulointerstitial nephritis, chronic tubulointerstitial nephritis, acute post-streptococcal glomerulonephritis (PSGN), pyelonephritis, lupus nephritis, chronic nephritis, interstitial nephritis, and post-streptococcal glomerulonephritis), blood vessel disorders of the kidneys (e.g., kidney infarction, atheroembolic kidney disease, cortical necrosis, malignant nephrosclerosis, renal vein thrombosis, renal underperfusion, renal retinopathy, renal ischemia-reperfusion, renal artery embolism, and renal artery stenosis), and electrolyte imbalances (e.g., nephrocalcinosis, pyuria, edema, hydronephritis, proteinuria, hyponatremia, hypernatremia, hypokalemia, hyperkalemia, hypocalcemia, hypercalcemia, hypophosphatemia, and hyperphosphatemia).

In a further embodiment, the ACE-2 binding polypeptides of the present invention (including molecules comprising, or alternatively consisting of, ACE-2 binding polypeptide fragments or variants thereof) which specifically bind to ACE-2 can be used for diagnostic purposes to detect, diagnose, prognose, or monitor diseases and/or disorders associated with cell proliferation. Smooth muscle cell proliferation in the intima of muscular arteries is the primary cause of restenosis after vascular surgery (e.g., angioplasty) and in atherosclerosis. Several animal studies have indicated that the renin-angiotensin system plays an important role in this vascular response. Specifically, it has been shown that chronic treatment with inhibitors of ACE (e.g., compositions analagous to Enalapril, Ramipril, and Captopril) reduces myometrial thickening after balloon injury in rat carotid artery or aorta (Powell et al., *Journal of the American College of Cardiology* 17: 137B–142B (1991)). Further, it is known that angiotensin II stimulates cell growth and replication in the cardiovascular system through binding angiotensin II receptors (Rosendorff, *Journal of the American College of Cardiology* 28: 803 (1996)). Thus, the compositions of the present invention may be used to detect, diagnose, prognose, or montior diseases and disorders associated with cell proliferation including, but not limited to, senosis, (e.g., buttonhole stenosis, coronary ostial stenosis, double aortic stenosis, fish-mouth mitral stenosis, bronchial stenosis, hypertrophic pyloric stenosis, pyloric stenosis, infundibular stenosis, idiopathic hypertrophic subaortic stenosis, idiopathic subglottic stenosis, pulmonary stenosis, muscular subaortic stenosis, laryngeal stenosis, mitral stenosis, supravalvar and subvalvar stenosis, subvalvular and supravalvular stenosis, and tricuspid stenosis), myometrial hypertrophy, hypertrophy or hyperplasia of conduit and resistance vessels, atherosclerosis, and several forms of cancer and neoplastic disorders.

In a specific embodiment, the present invention encompasses methods and compositions for detecting, diagnosing and/or prognosing diseases or disorders of smooth muscle cells.

In another specific embodiment, the present invention encompasses methods and compositions for detecting, diagnosing and/or prognosing diseases or disorders of epithelial cells.

In further embodiments, the present invention encompasses methods and compositions for detecting, diagnosing, prognosing and or monitoring growth, progression, and/or metastases of malignancies and proliferative diseases or disorders associated with increased cell survival, or the inhibition of apoptosis. For a review of such disorders, see Fishman et al., *Medicine, 2d Ed.* (J. B. Lippincott Co., Philadelphia 1985). Proliferative diseases and disorders is also extended to include premalignant conditions (e.g., benign tumors, hyperproliferative disorders, and benign proliferative disorders—see below) as well as proliferative disorders of smooth muscle cells and endothelial cells. Other abnormal growth conditions that may be treated, diagnosed, prognosed or monitored include, but are not limited to, hyperplasia, metaplasia, or most particularly, dysplasia has occurred (for review of such abnormal growth conditions, see Robbins and Angell, *Basic Pathology,* 2d Ed. (W. B. Saunders Co., Philadelphia 1976), pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

In another specific embodiment, the present invention encompasses methods and compositions for detecting, diagnosing and/or prognosing growth, progression, and/or metastases of smooth muscle cells.

In another specific embodiment, the present invention encompasses methods and compositions for detecting, diagnosing and/or prognosing growth, progression, and/or metastases of epithelial cells.

As discussed elsewhere herein, bradykinin are believed to also be peptide substrates of ACE-2. Bradykinin are involved in inflammatory reactions of various tissues. For example, in the intestine bradykinin stimulate contraction of smooth muscle and secretion of ions and fluid in response to injury (Manning et al., *Nature* 229: 256 (1982)). Thus, in a another embodiment, the ACE-2 binding polypeptides of the present invention (including molecules comprising, or alternatively consisting of, ACE-2 binding polypeptide fragments or variants thereof) which specifically bind to ACE-2 can be used for diagnostic purposes to detect, diagnose, prognose, or monitor inflammation and diseases and/or disorders associated therewith. Such conditions include, but are in no way limited to, inflammation associated with infection (e.g., septic shock, sepsis, or systemic inflammatory response syndrome (SIRS)), ischemia-reperfusion injury, acute idiopathic inflammation, alterative inflammation, atrophic inflammation, catarrhal inflammation, chronic and chronic active inflammation, fibrinopurulent inflammation, graulomatous inflammation, immune inflammation, interstitial inflammation, necrotic inflammation, proliferative inflammation, pseudomembranous inflammation, purulent inflammation, serofibrinous inflammation, polytrauma, pain, endotoxin lethality, arthritis (e.g., osteoarthritis and rheumatoid arthritis), corhplement-mediated hyperacute rejection, nephritis, cytokine or chemokine induced lung injury, inflammatory bowel disease, Crohn's disease, and resulting from over production of cytokines (e.g., TNF or IL-1.).

The invention provides a diagnostic assay for diagnosing or prognosing a disease or disorder, comprising: (a) assaying for the level of ACE-2 in a biological sample of an individual using one or more ACE-2 binding polypeptides of the invention that specifically bind to ACE-2; and (b) comparing the level of ACE-2 with a standard ACE-2 level, e.g., in a biological sample from a patient without the disease or disorder, whereby an increase or decrease in the assayed ACE-2 level compared to the standard level of ACE-2 is indicative of a particular disease or disorder. With respect to cancer, the presence of a relatively high amount of ACE-2 in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

ACE-2 binding polypeptides of the invention (including molecules comprising, or alternatively consisting of, ACE-2 binding polypeptide fragments or variants thereof) can be used to assay protein levels in a biological sample using classical immunohistological methods as described herein or as known to those of skill in the art (e.g., see Jalkanen et al., *J. Cell. Biol.,* 101:976–985 (1985); Jalkanen et al., *J. Cell. Biol.,* 105:3087–3096 (1987)). Other methods that can be used for detecting protein gene expression that might utilize ACE-2 binding polypeptides or fragments or variants thereof include, but are not limited to, the enzyme linked immunosorbent assay (ELISA) and the radioimmunoassay (RIA). Suitable antibody assay labels are known in the art and include enzyme labels, such as, glucose oxidase, alkaline phophatase, and horseradish peroxidase; radioisotopes, such as iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113m}In$, $^{115m}In$), technetium ($^{99}Tc$,$^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{15f3}Sm$, $^{177}Lu$, $^{159}Gd$, $^{149}Pm$, $^{140}La$, $^{175}Yb$, $^{166}Ho$, $^{90}Y$, $^{47}Sc$, $^{86}Re$, $^{88}Re$, $^{42}Pr$, $^{105}Rh$, and $^{97}Ru$; luminescent labels, such as luminol; and fluorescent labels, such as fluorescein and rhodamine, and biotin.

Certain embodiments of the invention are directed to the detection and diagnosis of a disease or disorder associated with aberrant expression of ACE-2 or ACE-2 substrate in an animal, preferably a mammal and most preferably a human. In one embodiment, diagnosis comprises: (a) administering (for example, parenterally, subcutaneously, or intraperitoneally) to a subject an effective amount of a labeled ACE-2 binding polypeptide of the invention (including molecules comprising, or alternatively consisting of, ACE-2,binding polypeptide fragments or variants thereof) that specifically binds to ACE-2; (b) waiting for a time interval following the administering for permitting the labeled ACE-2 binding polypeptide to preferentially concentrate at sites in the subject where ACE-2 is expressed (and for unbound labeled molecule to be cleared to background level); (c) determining background level; and (d) detecting the labeled ACE-2 binding polypeptide in the subject, such that detection of labeled ACE-2 binding polypeptide or fragment thereof above the background level and above or below the level observed in a person without the disease or disorder indicates that the subject has a particular disease or disorder associated with aberrant expression of ACE-2 or ACE-2 substrate. Background level can be determined by various methods, including comparing the amount of labeled molecule detected to a standard value previously determined for a particular system.

It will be understood by those skilled in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}Tc$. The labeled ACE-2 binding polypeptide will then preferentially accumulate at the location of cells which contain the specific protein. In vivo tumor imaging is described in Burchiel et al., "Immunopharmacokinetics of Radiolabeled Antibodies and Their Fragments," Chapter 13 in *Tumor Imaging: The Radiochemical Detection of Cancer,* S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment for monitoring of the disease or disorder, the method is carried out by repeating the method for diagnosing the disease or disorder, for example, one month after initial diagnosis, six months after initial diagnosis, one year after initial diagnosis, etc. and comparing the results of the successive tests.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (see, e.g., Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Immunophenotyping Using ACE-2 Binding Polypeptides

The ACE-2 binding polypeptides of the invention (including molecules comprising, or alternatively consisting of, ACE-2 binding polypeptide fragments or variants thereof) may be utilized for immunophenotyping of cell lines and biological samples by their ACE-2 expression or ACE-2 substrate expression. Various techniques can be employed utilizing ACE-2 binding polypeptides, fragments, or variants of the invention to screen for cellular populations (i.e., cardiac myocytes, proximal convoluted tubules, endothelial cells, and epithelial cells of Bowman's capsule) expressing ACE-2 or ACE-2 substrate. Such techniques include magnetic separation using ACE-2 binding polypeptide-coated magnetic beads, "panning" with ACE-2 binding polypeptide attached to a solid matrix (i.e., plate), and flow cytometry (see, e.g., U.S. Pat. No. 5,985,660; and Morrison et al., *Cell,* 96:737–49 (1999)). These techniques allow for the screening of particular populations of cells.

In one embodiment, ACE-2 binding polypeptides of the invention (including molecules comprising, or alternatively consisting of, ACE-2 binding polypeptide fragments or variants thereof) are used to identify cells, such as cardiac myocytes, proximal convoluted tubules, endothelial cells, and epithelial cells of Bowman's capsule.

Therapeutic Uses of Peptide Compositions of the Invention

Co-administration of Angiotensin 1-9 and Angiotensin II had the surprising result of increasing vasoconstriction to a significantly greater amount than the sum of the individual peptides administered alone, suggesting a superadditive or synergistic interaction (see Example 9). This effect has great therapeutic potential in treating diseases and disorders related to inappropriate low blood pressure. Thus, in preferred embodiments for raising blood pressure, peptide compositions of the invention comprise angiotensin 1-9 and angiotensin II used, for example, in combination with eachother, either sequentially or simultaneously. Thus, the Therapeutic/Prophylactic Compositions and Administration described below for ACE-2 binding peptides (e.g, dosage amounts and regimens, routes of adminsitration, and co-administered agents), are applied, in accordance with the invention, to Angiotensin 1-9 and Angiotensin II as well, in embodiments relating to raising blood pressure.

The present invention is further directed to therapies with involve administering angiotensin 1-9/angiotensin 1-9-like polypeptides in conjunction with angiotensin II/angiotensin II-like polypeptides to an animal, preferably a mammal, and most preferably a human, patient for treating one or more of the disclosed diseases, disorders, or conditions.

In a preferred embodiment, angiotensin 1-9/angiotensin 1-9-like polypeptides in conjunction with angiotensin II/angiotensin II-like polypeptides is administered to an animal, preferably a mammal, and most preferably a human, patient for treating diseases and/or disorders associated with hypotension, including, for example, shock, syncope, and others as listed herein.

The present invention is further directed to ACE-2 binding polypeptide-based therapies which involve administering ACE-2 binding polypeptides of the invention (including molecules comprising, or alternatively consisting of, ACE-2 binding polypeptide fragments or variants thereof) to an animal, preferably a mammal, and most preferably a human, patient for treating one or more of the disclosed diseases, disorders, or conditions. Therapeutic compounds of the invention include, but are not limited to, ACE-2 binding polypeptides of the invention and nucleic acids encoding ACE-2 binding polypeptides of the invention and antibodies that bind ACE-2 binding polypeptides of the invention as described herein. The ACE-2 binding polypeptides of the invention can be used to treat, ameliorate or prevent diseases, disorders or conditions associated with aberrant expression and/or activity of ACE-2 or ACE-2 substrates, including, but not limited to, any one or more of the diseases, disorders, or conditions described herein. The treatment and/or prevention of diseases, disorders, or conditions associated with aberrant ACE-2 expression and/or activity or aberrant ACE-2 substrate expression and/or activity includes, but is not limited to, alleviating symptoms associated with those diseases, disorders or conditions. ACE-2 binding polypeptides of the invention may be provided in pharmaceutically acceptable compositions as known in the art or as described herein.

ACE-2 binding polypeptides of the present invention (including molecules comprising, or alternatively consisting of, ACE-2 binding polypeptide fragments or variants thereof) that function as agonists or antagonists of ACE-2, preferably of ACE-2-induced signal transduction, can be administered to an animal to treat, prevent or ameliorate a disease or disorder associated with aberrant ACE-2 expression, lack of ACE-2 function, aberrant ACE-2 substrate expression, or lack of ACE-2 substrate function. For example, ACE-2 binding polypeptides of the invention which disrupt the interaction between ACE-2 and one or more of its substrates may be administered to an animal to treat, prevent or ameliorate a disease or disorder associated with aberrant ACE-2 expression, excessive ACE-2 function, aberrant ACE-2 substrate expression, or excessive ACE-2 substrate function. ACE-2 binding polypeptides of the invention which do not prevent ACE-2 from binding its substrate but inhibit or downregulate ACE-2-induced signal transduction can be administered to an animal to treat, prevent or ameliorate a disease or disorder associated with aberrant ACE-2 expression, excessive ACE-2 function, aberrant ACE-2 substrate expression, or excessive ACE-2 substrate function. In particular, ACE-2 binding polypeptides of the present invention which prevent ACE-2-induced signal transduction by specifically recognizing the unbound ACE-2, substrate-bound ACE-2, or both unbound and substrate-bound ACE-2 can be administered to an animal to treat, prevent or ameliorate a disease or disorder associated with aberrant ACE-2 expression, excessive ACE-2 function, aberrant ACE-2 substrates expression, or excessive ACE-2 substrates function.

The ability of an ACE-2 binding polypeptide of the invention to inhibit or downregulate ACE-2-induced signal transduction may be determined by techniques described herein or otherwise known in the art. For example, ACE-2-induced cleavage of ACE-2 substrates can be determined by detecting cleavage products via high performance liquid chromatography (HPLC).

In a specific embodiment, an ACE-2 binding polypeptide of the present invention (including molecules comprising, or alternatively consisting of, ACE-2 binding polypeptide fragments or variants thereof) that inhibits or reduces ACE-2 activity by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to ACE-2 activity in the absence of the ACE-2 binding polypeptide, is administered to an animal to treat, prevent or ameliorate a disease or disorder associated with aberrant ACE-2 expression, excessive ACE-2 function, aberrant ACE-2 receptor expression, or excessive ACE-2 receptor function. In another embodiment, a combination of ACE-2 binding polypeptides, a combination of ACE-2 binding polypeptide fragments, a combination of ACE-2 binding polypeptide variants, or a combination of ACE-2 binding polypeptides, ACE-2 binding polypeptide fragments, and/or variants that inhibit or reduce ACE-2 activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to ACE-2 activity in absence of said ACE-2 binding polypeptides, ACE-2 binding polypeptide fragments, and/or ACE-2 binding polypeptide variants are administered to an animal to treat, prevent or ameliorate a disease or disorder associated with aberrant ACE-2 expression, excessive ACE-2 function, aberrant ACE-2 substrate expression, or excessive ACE-2 substrate function.

Further, ACE-2 binding polypeptides of the present invention (including molecules comprising, or alternatively consisting of, ACE-2 binding polypeptide fragments or variants thereof) which activate ACE-2-induced signal transduction can be administered to an animal to treat, prevent or ameliorate a disease or disorder associated with aberrant ACE-2 expression, lack of ACE-2 function, aberrant ACE-2 substrate expression, or lack of ACE-2 substrate function. These ACE-2 binding polypeptides may potentiate or activate either all or a subset of the biological activities of ACE-2-mediated substrate action, for example, by regulating cleavage or synthesis of ACE-2 substrates. The ACE-2 binding polypeptides of the invention may be administered with or without being pre-complexed with ACE-2. In a specific embodiment, an ACE-2 binding polypeptide of the present invention that increases ACE-2 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% or more relative to ACE-2 activity in absence of the ACE-2 binding polypeptide is administered to an animal to treat, prevent or ameliorate a disease or disorder associated with aberrant ACE-2 expression, lack of ACE-2 function, aberrant ACE-2 substrate expression, or lack of ACE-2 substrate function. In another embodiment, a combination of ACE-2 binding polypeptides, a combination of ACE-2 binding polypeptide fragments, a combination of ACE-2 binding polypeptide variants, or a combination of ACE-2 binding polypeptides, ACE-2 binding polypeptide fragments and/or ACE-2 binding polypeptide variants that increase ACE-2 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% or more relative to ACE-2 activity in absence of the said ACE-2 binding polypeptides or ACE-2 binding polypeptide fragments and/or ACE-2 binding polypeptide variants is administered to an animal to treat, prevent or ameliorate a disease or disorder associated with aberrant ACE-2 expression, lack of ACE-2 function, aberrant ACE-2 substrate expression, or lack of ACE-2 substrate function.

In a specific embodiment, the present invention provides a method of treating, preventing or ameliorating a disease or disorder associated with aberrant ACE-2 or ACE-2 substrate expression or activity, comprising administering to an animal in which such treatment, prevention or amelioration is desired, an ACE-2 binding polypeptide in an amount effective to treat, prevent or ameliorate the disease or disorder. Diseases and disorders which may be treated, prevented or ameliorated by this method include, but are not limited to, cardiovascular disorders (e.g., hypertension, chronic heart failure, left ventricular failure, stroke, cerebral vasospasm after subarachnoid injury, atherosclerotic heart disease, and retinal hemorrhage), renal disorders (e.g., renal vein thrombosis, kidney infarction, renal artery embolism, renal artery stenosis, and edema, hydronephritis), proliferative diseases or disorders (e.g., vascular stenosis, myocardial hypertrophy, hypertrophy and/or hyperplasia of conduit and/or resistance vessels, myocyte hypertrophy, and fibroblast proliferative diseases), inflammatory diseases (e.g., SIRS (systemic Inflammatory Response Syndromes), sepsis, polytrauma, inflammatory bowl disease, acute and chronic pain, rheumatoid arthritis, and osteo arthritis), allergic disorders (e.g., asthma, adult respiratory distress syndrome, wound healing, and scar formation), as well as several other disorders and/or diseases (e.g., periodontal disease, dysmenorrhea, premature labor, brain edema following focal injury, diffuse axonal injury, and reperfusion injury).

In a specific embodiment, the present invention provides a method of treating, preventing or ameliorating diseases or disorders associated with hypertension, comprising administering to an animal in which such treatment, prevention, or amelioration is desired, an ACE-2 binding polypeptide in an amount effective to treat, prevent or ameliorate the disease or disorder. Diseases and disorders associated with hypertension include, for example, accelerated hypertension, episodic hypertension, paroxysmal hypertension, portal hypertension, primary hypertension, secondary hypertensoin, systemic venous hypertension, borderline hypertension, adrenal hypertension, benign hypertension, idiopathic hypertension, pale hypertension, postpartm hypertension, pregnancy-induced hypertension (gestational hypertension), essential hypertension, labile hypertension, pulmonary hypertension, renal and renovascular hypertension, and Goldblatt hypertension, left ventricular failure, atherosclerotic heart disease, stroke, retinal hemorrhage or infarction (Keith-Wagener-Barker changes), renal failure, renovascular disease, chronic heart failure, exudates, papilledema, vascular accidents, myocardial infarction, dissecting aneurysm In a specific embodiment, the present invention provides a method of treating, preventing or ameliorating diseases or disorders associated with hypotension, comprising administering to an animal in which such treatment, prevention, or amelioration is desired, an ACE-2 binding polypeptide in an amount effective to treat, prevent or ameliorate the disease or disorder. Diseases and disorders associated with hypotension include, for example, arterial hypotension, idiopathic orthostatic hypotension, intracranial hypotension, orthostatic hypotension, induced or controlled hypotension, shock (e.g., anaphylactic shock, anaphylactiod shock, anestetic shock, cardiogenic shock, chronic shock, deferred or delayed shock, hemorrhagic shock, hypovolemic shock, oligemic shock, septic shock, and vasogenic shock), and syncope (e.g., local syncope, postural syncope, tussive syncope, and vasodepressor syncope).

One or more ACE-2 binding polypeptides of the present invention (including molecules comprising, or alternatively consisting of, ACE-2 binding polypeptide fragments or variants thereof) that specifically bind to ACE-2 may be used locally or systemically in the body as a therapeutic. The ACE-2 binding polypeptides of the invention (including molecules comprising, or alternatively consisting of, ACE-2 binding polypeptide fragments or variants thereof) may also be advantageously utilized in combination with monoclonal or chimeric antibodies, lymphokines and/or hematopoietic growth factors (such as, e.g., IL-2, IL-3 and IL-7), for example, which serve to increase the number or activity of effector cells which interact with the ACE-2 binding polypeptides.

The ACE-2 binding polypeptides of the invention (including molecules comprising, or alternatively consisting of, ACE-2 binding polypeptide fragments or variants thereof) may be administered alone or in combination with other types of treatments (e.g., radiation therapy, chemotherapy, hormonal therapy, immunotherapy, anti-tumor agents, anti-angiogenesis and anti-inflammatory agents).

It is preferred to use high affinity and/or potent in vivo inhibiting and/or neutralizing ACE-2 binding polypeptides of the invention (including molecules comprising, or alternatively consisting of, ACE-2 binding polypeptide fragments or variants thereof) that specifically bind to ACE-2, or polynucleotides encoding ACE-2 binding polypeptides that specifically bind to ACE-2, for both immunoassays directed to and therapy of disorders related to ACE-2 polynucleotides or polypeptides, including fragments thereof. Such ACE-2 binding polypeptides will preferably have an affinity for ACE-2 and/or ACE-2 fragments. Preferred binding affinities include those with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, ACE-2 binding polypeptides of the invention bind ACE-2 target proteins with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, ACE-2 binding polypeptides of the invention bind ACE-2 target proteins with a dissociation constant or $K_D$ less than or equal to $5\times10^{-9}$ M, $10^{-9}$M, $5\times10^{-10}$ M, $5\times10^{-11}$ M, $10^{-11}$ M, $5\times10^{-12}$ M, $10^{-12}$ M, $5\times^{-13}$ M, $10^{-13}$ M, $5\times10^{-14}$ M, $10^{-14}$ M, $5\times10^{-15}$ M, $10^{-15}$ M.

In a preferred embodiment, ACE-2 binding polypeptides of the invention neutralize ACE-2 activity. In another preferred embodiment, ACE-2 binding polypeptides of the invention inhibit the activity of ACE-2 substrates, including, for example, angiotensin, bradykinin, tachykinin, neurotensin, Substance P, and endothelin. In a further embodiment, the ACE-2 binding polypeptides of the invention are administered in conjunction with an agent known to inhibit ACE (e.g., Enalapril®, Captopril ®, Fosinopril®, and Pramipril®) to inhibit activity of ACE and/or ACE-2 substrates, including, for example, angiotensin, bradykinin, tachykinin, neurotensin, Substance P, and endothelin.

In a preferred embodiment, ACE-2 binding polypeptides of the invention (including molecules comprising, or alternatively consisting of, ACE-2 binding polypeptide fragments or variants thereof) inhibit or reduce binding of the soluble form of ACE-2 to an ACE-2 substrate. In another preferred embodiment ACE-2 binding polypeptides of the invention inhibit or reduce cleavage of ACE-2 substrates induced by the soluble form of ACE-2. In another preferred embodiment ACE-2 binding polypeptides of the invention inhibit or reduce the production of Angiotensin 1-9 and other products of ACE-2 action induced by the soluble form of ACE-2.

In a preferred embodiment, ACE-2 binding polypeptides of the invention (including molecules comprising, or alternatively consisting of, ACE-2 binding polypeptide fragments or variants thereof) inhibit or reduce binding of the membrane-bound form of ACE-2 to an ACE-2 substrate. In another preferred embodiment ACE-2 binding polypeptides of the invention inhibit or reduce cleavage of ACE-2 substrates induced by the membrane-bound form of ACE-2. In another preferred embodiment ACE-2 binding polypeptides of the invention inhibit or reduce the production of Angiotensin 1-9 and other products of ACE-2 action induced by the membrane-bound form of ACE-2.

In a preferred embodiment, ACE-2 binding polypeptides of the invention (including molecules comprising, or alternatively consisting of, ACE-2 binding polypeptide fragments or variants thereof) inhibit or reduce binding of both the soluble and membrane-bound forms of ACE-2 to an ACE-2 substrate. In another preferred embodiment, ACE-2 binding polypeptides of the invention inhibit or reduce cleavage of ACE-2 substrates induced by either or both forms of ACE-2. In another preferred embodiment, ACE-2 binding polypeptides of the invention inhibit or reduce the production of Angiotensin 1-9 and other products of ACE-2 action induced by either or both forms of ACE-2.

In one embodiment, the invention provides a method of delivering radiolabelled ACE-2 binding polypeptide and/or ACE-2 binding polypeptide conjugates of the invention to targeted cells, such as, for example, cardiac myocytes cells expressing the membrane-bound form of ACE-2, or proximal tubules expressing an ACE-2 substrate.

In one embodiment, the invention provides methods and compositions for inhibiting or reducing angiotensin 1-9 production, comprising, or alternatively consisting of, contacting an effective amount of ACE-2 binding polypeptide with ACE-2, wherein the effective amount of ACE-2 binding polypeptide inhibits or reduces ACE-2 mediated production of angiotensin 1-9. In another embodiment, the invention provides methods and compositions for inhibiting or reducing angiotensin 1-9 production, comprising, or alternatively consisting of, administering to an animal in which such inhibition or reduction is desired, an ACE-2 binding polypeptide in an amount effective to inhibit or reduce production of angiotensin 1-9.

Additionally, angiotensin 1-9 can be hydrolyzed by ACE into angiotensin 1-5. Thus, in another embodiment, the present invention provides methods and compositions for inhibiting or reducing angiotensin 1-5 production, comprising, or alternatively consisting of, contacting an effective amount of ACE-2 binding polypeptide with ACE-2, wherein the effective amount of ACE-2 binding polypeptide inhibits or reduces ACE-2 mediated production of angiotensin 1-5. In another embodiment, the invention provides methods and compositions for inhibiting or reducing angiotensin 1-5 production, comprising, or alternatively consisting of, administering to an animal in which such inhibition or reduction is desired, an ACE-2 binding polypeptide in an amount effective to inhibit or reduce production of angiotensin 1-5.

Further, ACE-2 and ACE compete for the substrate angiotensin, hydrolyzing angiotensin to angiotensin 1-9 and angiotensin II, respectively. Thus, the present invention provides for methods and compositions for enhancing or increasing angiotensin II production, comprising, or alternatively consisting of, contacting an effective amount of ACE-2 binding polypeptide with ACE-2, wherein the effective amount of ACE-2 binding polypeptide enhances or increases ACE mediated production of angiotensin II. In another embodiment, the invention provides methods and compositions for enhancing or increasing angiotensin II production, comprising, or alternatively consisting of, administering to an animal in which such enhancing or increasing is desired, an ACE-2 binding polypeptide in an amount effective to enhance or increase production of angiotensin II. Determination of angiotenin II levels are most often performed by comparing the level of angiotensin II in a sample to a standard containing a known amount of angiotensin II using ELISA assays. Determination of angiotensin II levels in a given sample, can readily be determined using ELISA or other method known in the art.

Additionally, ACE-2 has significant sequence homologies with ACE functional domains, suggesting that both types of enzymes share additional similar substrates beyond angiotensin. Thus, the present invention provides for methods and compositions for enhancing or increasing bradykinin activity, comprising, or alternatively consisting of, contacting an effective amount of ACE-2 binding polypeptide with ACE-2, wherein the effective amount of ACE-2 binding polypeptide inhibits or reduces ACE-2 mediated degradation of bradykinin. In another embodiment, the invention provides methods and compositions for enhancing or increasing bradykinin activity, comprising, or alternatively consisting of, administering to an animal in which such enhancing or increasing is desired, an ACE-2 binding polypeptide in an amount effective to enhance or increase activity of bradykinin. Determination of bradykinin levels are most often performed by comparing the level of bradykinin in a sample to a standard containing a known amount of bradykinin using ELISA assays. Determination of bradykinin levels in a given sample, can readily be determined using ELISA or other method known in the art.

Additionally, the present invention provides for methods and compositions for enhancing or increasing tachykinin activity, comprising, or alternatively consisting of, contacting an effective amount of ACE-2 binding polypeptide with ACE-2, wherein the effective amount of ACE-2 binding polypeptide inhibits or reduces ACE-2 mediated degradation of tachykinin. In another embodiment, the invention provides methods and compositions for enhancing or increasing tachykinin activity, comprising, or alternatively consisting of, administering to an animal in which such enhancing or increasing is desired, an ACE-2 binding polypeptide in an amount effective to enhance or increase activity of tachykinin. Determination of tachykinin levels are most often performed by comparing the level of tachykinin in a sample to a standard containing a known amount of tachykinin using ELISA assays. Determination of tachykinin levels in a given sample, can readily be determined using ELISA or other method known in the art.

Additionally, the present invention provides for methods and compositions for enhancing or increasing neurotensin activity, comprising, or alternatively consisting of, contacting an effective amount of ACE-2 binding polypeptide with ACE-2, wherein the effective amount of ACE-2 binding polypeptide inhibits or reduces ACE-2 mediated degradation of neurotensin. In another embodiment, the invention provides methods and compositions for enhancing or increasing neurotensin activity, comprising, or alternatively consisting of, administering to an animal in which such enhancing or increasing is desired, an ACE-2 binding polypeptide in an amount effective to enhance or increase activity of neurotensin. Determination of neurotensin levels are most often performed by comparing the level of neurotensin in a sample to a standard containing a known amount of neurotensin using ELISA assays. Determination of neurotensin levels in a given sample, can readily be determined using ELISA or other method known in the art.

Moreover, the present invention provides for methods and compositions for enhancing or increasing Substance P activity, comprising, or alternatively consisting of, contacting an effective amount of ACE-2 binding polypeptide with ACE-2, wherein the effective amount of ACE-2 binding polypeptide inhibits or reduces ACE-2 mediated degradation of Substance P. In another embodiment, the invention provides methods and compositions for enhancing or increasing Substance P activity, comprising, or alternatively consisting of, administering to an animal in which such enhancing or increasing is desired, an ACE-2 binding polypeptide in an amount effective to enhance or increase activity of Substance P. Determination of Substance P levels are most often performed by comparing the level of Substance P in a sample to a standard containing a known amount of Substance P using ELISA assays. Determination of Substance P levels in a given sample, can readily be determined using ELISA or other method known in the art.

In addition, the present invention provides for methods and compositions for enhancing or increasing endothelin activity, comprising, or alternatively consisting of, contacting an effective amount of ACE-2 binding polypeptide with ACE-2, wherein the effective amount of ACE-2 binding polypeptide inhibits or reduces ACE-2 mediated degradation of endothelin. In another embodiment, the invention provides methods and compositions for enhancing or increasing endothelin activity, comprising, or alternatively consisting of, administering to an animal in which such enhancing or increasing is desired, an ACE-2 binding polypeptide in an amount effective to enhance or increase activity of endothelin. Determination of endothelin levels are most often performed by comparing the level of endothelin in a sample to a standard containing a known amount of endothelin using ELISA assays. Determination of endothelin levels in a given sample, can readily be determined using ELISA or other method known in the art.

Angiotensin, angiotenin II, bradykinin, tachykinin, neurotensin, Substance P, and endothelin all are well known in the art to regulate blood pressure, sodium homeostasis, and inflammatory processes (for review see Kramer et al., Journal of Cardiovascular Pharmacology 15 Suppl. 6: 591–598 (1990); Johnson et al., Journal of Hypertension Supplement 15: S3–S6 (1997); Regoli et al., Regulatory Peptides 45: 323–340 (1993); Textor et al., Liver Transplant 6:521–530 (2000)). Errant regulation of blood pressure, sodium homeostasis, or inflammatory responses affects several physiological systems, including the cardiovascular system, renal system, and the immune system. By modulating activity of angiotensin, angiotenin II, bradykinin, tachykinin, neurotensin, Substance P, and endothelin, compositions of the present invention can be used as therapeutic or pharmaceutical agent to treat, prevent, or ameliorate diseases and/or disorders associated with aberrant blood pressure, sodium homeostasis, or inflammatory processes.

In one embodiment, therapeutic or pharmaceutical compositions of the present invention are administered to an animal to treat, prevent, or ameliorate diseases and/or disorders associated with hypertension including, but not limited to, accelerated hypertension, episodic hypertension, paroxysmal hypertension, portal hypertension, primary hypertension, secondary hypertensoin, systemic venous hypertension, borderline hypertension, adrenal hypertension, benign hypertension, idiopathic hypertension, pale hypertension, postpartm hypertension, pregnancy-induced hypertension (gestational hypertension), essential hypertension, labile hypertension, pulmonary hypertension, renal and renovascular hypertension, and Goldblatt hypertension, left ventricular failure, atherosclerotic heart disease, stroke, retinal hemorrhage or infarction (Keith-Wagener-Barker changes), renal failure, renovascular disease, exudates, papilledema, vascular accidents, myocardial infarction, dissecting aneurysm.

In another embodiment, therapeutic or pharmaceutical compositions of the present invention are administered to an animal to treat, prevent, or ameliorate diseases and/or disorders associated with hypotension including, but not limited to, arterial hypotension, idiopathic orthostatic hypotension, induced or controlled hypotension, shock (e.g., anaphylactic shock, anaphylactoid shock, anestetic shock, cardiogenic shock, chronic shock, deferred or delayed shock, hemorrhagic shock, hypovolemic shock, oligemic shock, septic shock, and vasogenic shock), and syncope (e.g., local syncope, postural syncope, tussive syncope, and vasodepressor syncope).

In a preferred embodiment, therapeutic compositions of the present invention are administered to an animal (preferrably administered to a human) to treat, prevent, or ameliorate diseases and/or disorders associated with shock.

In a further preferred embodiment, shock is treated, prevented, or ameliorated by administering to an animal (preferrably administered to a human) angiotensin 1-9/angiotensin 1-9-like polypeptides in conjunction with angiotensin II/angiotensin II-like polypeptides (see Example 9).

In another preferred embodiment, shock is treated, prevented, or ameliorated by administering to an animal (preferrably administered to a human) compositions of the invention that increase concentrations of angiotensin 1-9/angiotensin 1-9-like polypeptides and/or angiotensin II/angiotensin II-like polypeptides.

In another embodiment, therapeutic or pharmaceutical compositions of the present invention are administered to an animal to treat, prevent, or ameliorate diseases and/or disorders associated with cardiovascular disease including, but not limited to, arrhythmias (e.g., sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias (e.g., paroxysmal tachycardia, supraventricular tachycardia, accelerated idioventricular rhythm, atrioventricular nodal reentry tachycardia, ectopic atrial tachycardia, .ectopic junctional tachycardia, sinoatrial nodal reentry tachycardia, sinus tachycardia, Torsades de Pointes, and ventricular tachycardia), and ventricular fibrillation), carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases (e.g., aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis), myocardial diseases (e.g., alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis), myocardial ischemia (e.g., coronary disease, such as angina pectoris, coronary aneurysm, coronary arteriosclerosis, coronary thrombosis, coronary vasospasm, myocardial infarction and myocardial stunning), pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, cardiovascular tuberculosis, aneurysms (e.g., dissecting aneurysms, false aneurysms, infected aneurysms, ruptured aneurysms, aortic aneurysms, cerebral aneurysms, coronary aneurysms, heart aneurysms, and iliac aneurysms), angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases (e.g., arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans), arteritis, enarteritis, polyarteritis nodosa, cerebrovascular disorders (e.g., carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural. hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency), diabetic angiopathies, diabetic retinopathy, embolisms (e.g., air embolisms, amniotic fluid embolisms, cholesterol embolisms, blue toe syndrome, fat embolisms, pulmonary embolisms, and thromoboembolisms), thrombosis (e.g., coronary thrombosis, hepatic vein thrombosis, retinal vein occlusion, carotid artery thrombosis, sinus thrombosis, Wallenberg's syndrome, and thrombophlebitis), erythromelalgia, hemorrhoids, hepatic veno-occlusive disease, hypertension, hypotension, ischemia (e.g., cerebral ischemia, ischemic colitis, compartment syndromes, anterior compartment syndrome, myocardial ischemia, reperfusion injuries, and peripheral limb ischemia), peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis (e.g., aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis), and venous insufficiency.

In a further embodiment, therapeutic or pharmaceutical compositions of the present invention are administered to an animal to treat, prevent, or ameliorate diseases and/or disorders associated with the renal system including, but not limited to, acute kidney failure, chronic kidney failure, atheroembolic renal failure, end-stage renal disease, inflammatory diseases of the kidney (e.g., acute glomerulonephritis, postinfectious glomerulonephritis, rapidly progressive glomerulonephritis, nephrotic syndrome, membranous glomerulonephritis, familial nephrotic syndrome, membranoproliferative glomerulonephritis I and II, mesangial proliferative glomerulonephritis, chronic glomerulonephritis, acute tubulointerstitial nephritis, chronic tubulointerstitial nephritis, acute post-streptococcal glomerulonephritis (PSGN), pyelonephritis, lupus nephritis, chronic nephritis, interstitial nephritis, and post-streptococcal glomerulonephritis), blood vessel disorders of the kidneys (e.g., kidney infarction, atheroembolic kidney disease, cortical necrosis, malignant nephrosclerosis, renal vein thrombosis, renal underperfusion, renal retinopathy, renal ischemia-reperfusion, renal artery embolism, and renal artery stenosis), and electrolyte imbalances (e.g., nephrocalcinosis, pyuria, edema, hydronephritis, proteinuria, hyponatremia, hypernatremia, hypokalemia, hyperkalemia, hypocalcemia, hypercalcemia, hypophosphatemia, and hyperphosphatemia).

In an even further embodiment, therapeutic or pharmaceutical compositions of the present invention are administered to an animal to treat, prevent, or ameliorate diseases and/or disorders associated with inflammatory responses.

Such inflammatory conditions include,.but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

Similarly, polynucleotides, polypeptides, antibodies, and/or agonists or antagonists of the present invention may also be used to treat, prevent, or ameliorate inflammation, including, but not limited to, inflammation associated with infection (e.g., septic shock, sepsis, or systemic inflammatory response syndrome (SIRS)), ischemia-reperfusion injury, polytrauma, pain, endotoxin lethality, arthritis (e.g., osteoarthritis and rheumatoid arthritis), complement-mediated hyperacute rejection, nephritis, cytokine or chemokine induced lung injury, inflammatory bowel disease, Crohn's disease, and resulting from over production of cytokines (e.g., TNF or IL-1.).

Additionally, many autoimmune disorders are in part manifested as inappropriate inflammation resulting from inappropriate recognition of self as foreign material by immune cells. Therefore, the administration of polynucleotides and polypeptides of the invention that can inhibit an inappropriate inflammatory response may be an effective therapy in preventing autoimmune disorders.

Autoimmune diseases and/or disorders that may be treated, prevented, or ameliorated by compositions of the present invention include, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Autism, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

Similarly, in specific embodiments, polypeptides, antibodies, or polynucleotides of the invention, and/or agonists or antagonists thereof, are useful to treat, diagnose, and/or prevent transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD.

Further, allergic reactions and conditions, such as asthma (particularly allergic asthma) or other respiratory problems, may also be treated, prevented, and/or diagnosed using polypeptides, antibodies, or polynucleotides of the invention, and/or agonists or antagonists thereof. Moreover, these molecules can be used to treat, prevent, and/or diagnose anaphylaxis, hypersensitivity to an antigenic molecule, or blood group incompatibility.

Beyond its role as a neuromodulator, neurotensin is found in high concentrations in gut endocrine cells of the ileum and is released following ingestion of food. Since ACE-2 has been found to hydrolyze neurotensin (as described herein), the invention provides for methods and compositions that can be used for digestive purposes.

Thus, in one embodiment, the invention can be used to treat, prevent, or ameliorate diseases and disorders of the digestive system including, but not limited to, disorders of the small intestine, such as malabsorption syndromes, distension, irritable bowel syndrome, sugar intolerance, celiac disease, duodenal ulcers, duodenitis, tropical sprue, Whipple's disease, intestinal lymphangiectasia, Crohn's disease, appendicitis, obstructions of the ileum, Meckel's diverticulum, multiple diverticula, failure of complete rotation of the small and large intestine, lymphoma, and bacterial and parasitic diseases (such as Traveler's diarrhea, typhoid and paratyphoid, cholera, infection by Roundworms (*Ascariasis lumbricoides*), Hookworms (*Ancylostoma duodenale*), Threadworms (*Enterobius vermicularis*), Tapeworms (*Taenia saginata, Echinococcus granulosus,* Diphyllobothrium spp., and *T. solium*).

The invention can also be used to treat, prevent, or ameliorate diseases and disorders disorders of the large intestine, including antibiotic-associated colitis, diverticulitis, ulcerative colitis, acquired megacolon, abscesses, fungal and bacterial infections, anorectal disorders (e.g., fissures, hemorrhoids), colonic diseases (colitis, colonic neoplasms [colon cancer, adenomatous colon polyps (e.g., villous adenoma), colon carcinoma, colorectal cancer], colonic diverticulitis, colonic diverticulosis, megacolon [Hirschsprung disease, toxic megacolon]; sigmoid diseases [proctocolitis, sigmoin neoplasms]), constipation, Crohn's disease, diarrhea (infantile diarrhea, dysentery), duodenal diseases (duodenal neoplasms, duodenal obstruction, duodenal ulcer, duodenitis), enteritis (enterocolitis), HIV enteropathy, ileal diseases (ileal neoplasms, ileitis), immunoproliferative small intestinal disease, inflammatory bowel disease (ulcerative colitis, Crohn's disease), intestinal atresia, parasitic diseases (anisakiasis, balantidiasis, blastocystis infections, cryptosporidiosis, dientamoebiasis, amebic dysentery, giardiasis), intestinal fistula (rectal fistula), intestinal neoplasms (cecal neoplasms, colonic neoplasms, duodenal neoplasms, ileal neoplasms, intestinal polyps, jejunal neoplasms, rectal neoplasms), intestinal obstruction (afferent loop syndrome, duodenal obstruction, impacted feces, intestinal pseudo-obstruction [cecal volvulus], intussusception), intestinal perforation, intestinal polyps (colonic polyps, gardner syndrome, peutz-jeghers syndrome), jejunal diseases (jejunal neoplasms), malabsorption syndromes (blind loop syndrome, celiac disease, lactose intolerance, short bowl syndrome, tropical sprue, whipple's disease), mesenteric vascular occlusion, pneumatosis cystoides intestinalis, protein-losing enteropathies (intestinal lymphagiectasis), rectal diseases (anus diseases, fecal incontinence, hemorrhoids, proctitis, rectal fistula, rectal prolapse, rectocele), peptic ulcer (duodenal ulcer, peptic esophagitis, hemorrhage, perforation, stomach ulcer, Zollinger-Ellison syndrome), postgastrectomy syndromes (dumping syndrome), stomach diseases (e.g., achlorhydria, duodenogastric reflux (bile reflux), gastric antral vascular ectasia, gastric fistula, gastric outlet obstruction, gastritis (atrophic or hypertrophic), gastroparesis, stomach dilatation, stomach diverticulum, stomach neoplasms (gastric cancer, gastric polyps, gastric adenocarcinoma, hyperplastic gastric polyp), stomach rupture, stomach ulcer, stomach volvulus), tuberculosis, visceroptosis, vomiting (e.g., hematemesis, hyperemesis gravidarum, postoperative nausea and vomiting) and hemorrhagic colitis.

Additionally, the invention can be used to treat, prevent, or ameliorate diseases and disorders disorders of the liver, such as intrahepatic cholestasis (alagille syndrome, biliary liver cirrhosis), fatty liver (alcoholic fatty liver, reye syndrome), hepatic vein thrombosis, hepatolentricular degeneration, hepatomegaly, hepatopulmonary syndrome, hepatorenal syndrome, portal hypertension (esophageal and gastric varices), liver abscess (amebic liver abscess), liver cirrhosis (alcoholic, biliary and experimental), alcoholic liver diseases (fatty liver, hepatitis, cirrhosis), parasitic (hepatic echinococcosis, fascioliasis, amebic liver abscess), jaundice (hemolytic, hepatocellular, and cholestatic), cholestasis, portal hypertension, liver enlargement, ascites, hepatitis (alcoholic hepatitis, animal hepatitis, chronic hepatitis (autoimmune, hepatitis B, hepatitis C, hepatitis D, drug induced), toxic hepatitis, viral human hepatitis (hepatitis A, hepatitis B, hepatitis C, hepatitis D, hepatitis E), Wilson's disease, granulomatous hepatitis, secondary biliary cirrhosis, hepatic encephalopathy, portal hypertension, varices, hepatic encephalopathy, primary biliary cirrhosis, primary sclerosing cholangitis, hepatocellular adenoma, hemangiomas, bile stones, liver failure (hepatic encephalopathy, acute liver failure), and liver neoplasms (angiomyolipoma, calcified liver metastases, cystic liver metastases, epithelial tumors, fibrolamellar hepatocarcinoma, focal nodular hyperplasia, hepatic adenoma, hepatobiliary cystadenoma, hepatoblastoma, hepatocellular carcinoma, hepatoma, liver cancer, liver hemangioendothelioma, mesenchymal hamartoma, mesenchymal tumors of liver, nodular regenerative hyperplasia, benign liver tumors (Hepatic cysts [Simple cysts, Polycystic liver disease, Hepatobiliary cystadenoma, Choledochal cyst], Mesenchymal tumors [Mesenchymal hamartoma, Infantile hemangioendothelioma, Hemangioma, Peliosis hepatis, Lipomas, Inflammatory pseudotumor, Miscellaneous], Epithelial tumors [Bile duct epithelium (Bile duct hamartoma, Bile duct adenoma), Hepatocyte (Adenoma, Focal nodular hyperplasia, Nodular regenerative hyperplasia)], malignant liver tumors [hepatocellular, hepatoblastoma, hepatocellular carcinoma, cholangiocellular, cholangiocarcinoma, cystadenocarcinoma, tumors of blood vessels, angiosarcoma, Karposi's sarcoma, hemangioendothelioma, other tumors, embryonal sarcoma, fibrosarcoma, leiomyosarcoma, rhabdomyosarcoma, carcinosarcoma, teratoma, carcinoid, squamous carcinoma, primary lymphoma]), peliosis hepatis, erythrohepatic porphyria, hepatic porphyria (acute intermittent porphyria, porphyria cutanea tarda), Zellweger syndrome).

Moreover, the invention can be used to treat, prevent, or ameliorate diseases and disorders disorders of the gallbladder, such as gallstones (cholelithiasis and choledocholithiasis), postcholecystectomy syndrome, diverticulosis of the gallbladder, acute cholecystitis, chronic cholecystitis, bile duct tumors, and mucocele.

Further, the invention can be used to treat, prevent, or ameliorate diseases and disorders disorders of the pancreas including, but not limited to, acute pancreatitis, chronic pancreatitis (acute necrotizing pancreatitis, alcoholic pancreatitis), neoplasms (adenocarcinoma of the pancreas, cystadenocarcinoma, insulinoma, gastrinoma, and glucagonoma, cystic neoplasms, islet-cell tumors, pancreoblastoma), and other pancreatic diseases (e.g., cystic fibrosis, cyst (pancreatic pseudocyst, pancreatic fistula, insufficiency)).

Other diseases and disoders of the gastroinstestinal system that can be treated, prevented, or ameliorated by compositions of the present invention include dysphagia, odynophagia, inflammation of the esophagus, peptic esophagitis, gastric reflux, submucosal fibrosis and stricturing, Mallory-Weiss lesions, leiomyomas, lipomas, epidermal cancers, adeoncarcinomas, gastric retention disorders, gastroenteritis, gastric atrophy, gastric/stomach cancers, polyps of the stomach, autoimmune disorders such as pernicious anemia, pyloric stenosis, gastritis (bacterial, viral, eosinophilic, stress-induced, chronic erosive, atrophic, plasma cell, and Ménétrier's), peritoneal diseases (e.g., chyloperioneum, hemoperitoneum, mesenteric cyst, mesenteric lymphadenitis, mesenteric vascular occlusion, panniculitis, neoplasms, peritonitis, pneumoperitoneum, bubphrenic abscess,), biliary tract diseases, such as, gastroschisis, fistula (e.g., biliary fistula, esophageal fistula, gastric fistula, intestinal fistula, pancreatic fistula), neoplasms (e.g., biliary tract neoplasms, esophageal neoplasms, such as adenocarcinoma of the esophagus, esophageal squamous cell carcinoma, gastrointestinal neoplasms, pancreatic neoplasms, such as adenocarcinoma of the pancreas, mucinous cystic neoplasm of the pancreas, pancreatic cystic neoplasms, pancreatoblastoma, and peritoneal neoplasms), esophageal disease (e.g., bullous diseases, candidiasis, glycogenic acanthosis, ulceration, barrett esophagus varices, atresia, cyst, diverticulum (e.g., Zenker's diverticulum), fistula (e.g., tracheoesophageal fistula), motility disorders (e.g., CREST syndrome, deglutition disorders, achalasia, spasm, gastroesophageal reflux), neoplasms, perforation (e.g., Boerhaave syndrome, Mallory-Weiss syndrome), stenosis, esophagitis, diaphragmatic hernia (e.g., hiatal hernia); gastrointestinal diseases, such as, gastroenteritis (e.g., cholera morbus, norwalk virus infection), hemorrhage (e.g., hematemesis, melena, peptic ulcer hemorrhage), stomach neoplasms (gastric cancer, gastric polyps, gastric adenocarcinoma, stomach cancer)), hernia (e.g., congenital diaphragmatic hernia, femoral hernia, inguinal hernia, obturator hernia, umbilical hernia, ventral hernia), and intestinal diseases (e.g., cecal diseases (appendicitis, cecal neoplasms)).

Several in vivo studies have indicated that the renin-angiotensin system plays an important role in the proliferation of smooth muscle cells. For example, recent evidence indicates that Angiotensin II stimulates the growth of vascular smooth muscle cells in response to injury (see Inagami and Eguchi, Brazilian Journal of Medical and Biological Research 33: 619–624 (2000)). Specifically, endogenous angiotensin II stimulates the progression from G1 to S phase in vascular smooth muscle cells (Kubo et al., American Journal of Hypertension, 13:1117–1124 (2000)). This poses a particular problem relative to many surgical procedures, such as angioplasty, where smooth muscle cell proliferation is a primary cause of artery restenosis.

ACE-2 directly competes with ACE for angiotensin to produce angiotensin 1-9 and angiotensin II, respectively. Thus, it is logical to assume that regulation of ACE-2 activity affects production of angiotensin II. Specifically, inhibition of ACE-2 prevents the conversion of angiotenin to angiotensin 1-9, making available an increased concentration of angiotenin for conversion to angiotensin II. Conversely, stimulation of ACE-2 increases utlization of angiotensin, decreasing the amount available for conversion to angiotensin II. Thus, the invention provides methods and compositions for regulating angiotenin II-mediated cell proliferation.

Hence, in another embodiment, therapeutic or pharmaceutical compositions of the present invention are administered to an animal to treat, prevent, or ameliorate diseases and/or disorders associated with cell proliferation including, but not limited to, neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tissues; and lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an aforementioned organ system.

In a preferred embodiment, the compositions of the present invention can be used to treat, prevent, or ameliorate stenosis, restenosis, myocardial hypertrophy, hypertrophy or hyperplasia of conduit and resistance vessels, and atherosclerosis.

Pain and hyperalgesia, the perceptual companions of tissue injury and inflammation, are in part attributable to the sensitization of primary afferent nociceptors by endogenously released chemicals, such as bradykinin. Application of exogenous bradykinin or stimulation of endogenous bradykinin production has been demonstrated to cause hyperalgesia in animal models of pain (for review see Burch and Kyle, Life Sciences 50: 829–838 (1992)). Additionally, a number of studies have shown that bradykinin antagonists are capable of blocking or ameliorating pain in both animal models and humans (for review see Burch et al., Medical Research Review 10: 237–269 (1990); Sharma, Genetic Pharmacology 24: 267–274 (1993)). As discussed elsewhere herein, the compositions of the invention may be used to regulate the hydrolysis (and, therefore, activity) of bradykinin. Thus, the invention provides methods and compositions for regulating bradykinin-mediated pain and hyperalgesia.

In one embodiment, therapeutic or pharmaceutical compositions of the present invention can be used as analgesics to reduce or inhibit pain. For example, therapeutic or pharmaceutical compositions of the present invention can be used to treat, prevent, or ameliorate perioperative pain and/or for use in surgical procedures and labor.

Additionally, therapeutic or pharmaceutical compositions of the present invention can be used to treat, prevent, or ameliorate pain associated with cancer and treatment of cancer (e.g., radiation therapy, surgery, and/or chemotherapy).

Moreover, therapeutic or pharmaceutical compositions of the present invention can be used to treat, prevent, or ameliorate neuropathic pain disorders including, but not limited to, reflex sympathetic dystrophy, causalgia, phantom limb pain, trigeminal neuralgia, atypical trigeminal neuralgia, geniculate neuralgia, glossopharyngeal neuralgia, hallucinatory neuralgia, idiopathic neuralgia, intercostal neuralgia, mammary neuralgia, Morton neuralgia, occipital neuralgia, periodic migrainous neuralgia, sciatic neuralgia, sphenopalatine neuralgia, suboccipital neuralgia, supraorbital neuralgia, and symptomatic neuralgia.

Therapeutic or pharmaceutical compositions of the present invention can also be used to treat, prevent, or ameliorate idiopathic pain.

Additionally, therapeutic or pharmaceutical compositions of the present invention can be used to treat, prevent, or ameliorate pain associated with diseases and/or disorders including, but in no way limited to, burns, angina, myocardial ischemia, minor or severe trauma, migraine, shock, arthritis, rheumatoid arthritis, infection (e.g., herpes zoster, AIDS and AIDS-related conditions, sepsis, and pneumonia), and rhinitis.

Further, therapeutic or pharmaceutical compositions of the present invention can be used to treat pain of the body including, for example, abdominal pain, back pain (particularly lower back pain), pelvic pain, joint pain, headache, facial pain, and muscular pain, as well as bodily pain due to trauma, stings, bites, and central nervous system injury.

In another embodiment, the presence of ACE-2 in the testis suggests that the present invention may also have utility in treating infertility or other disorders relating to male reproduction (e.g., erectile dysfunction) and/or gamete formation and maturation.

In a further embodiment, compositions of the present invention can be useful in treating, preventing, or ameliorating cognitive diseases.

In another embodiment, the invention provides a method for the specific delivery of ACE-2 binding polypeptides and ACE-2 binding polypeptide conjugates of the invention to cells by administering molecules of the invention that are associated with heterologous polypeptides or nucleic acids. In one example, the invention provides for a method for delivering a therapeutic protein into the targeted cell. In another example, the invention provides a method for delivering a single strand nucleic acid (e.g., antisense or ribozymes) or double stranded nucleic acid (e.g., DNA that can integrate into the cell's genome or replicate episomally and that can be transcribed) in the target cell.

Gene Therapy

In a specific embodiment, nucleic acids comprising sequences encoding ACE-2 binding polypeptides or functional derivatives thereof, are administered to treat, inhibit or prevent a disease or disorder associated with aberrant expression and/or activity of ACE-2 and/or its substrates, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., *Clinical Pharmacy,* 12:488–505 (1993); Wu and Wu, *Biotherapy,* 3:87–95 (1991); Tolstoshev, *Ann. Rev. Pharmacol. Toxicol.,* 32:573–596 (1993); Mulligan, *Science,* 260:926–932 (1993); and Morgan and Anderson, *Ann. Rev. Biochem.,* 62:191–217 (1993); May, TIBTECH, 1 1(5):155–215 (1993). Methods commonly known in the art of recombinant DNA technology which can be used are described in *Current Protocols in Molecular Biology*, Ausubel et al., eds. (John Wiley & Sons, NY 1993); and Kriegler, *Gene Transfer and Expression, A Laboratory Manual* (Stockton Press, NY 1990).

In a preferred aspect, a composition of the invention comprises, or alternatively consists of, nucleic acids encoding an ACE-2 binding polypeptide, said nucleic acids being part of an expression vector that expresses the ACE-2 binding polypeptide or fragment thereof or chimeric protein including it in a suitable host. In particular, such nucleic acids have promoters, preferably heterologous promoters, operably linked to the ACE-2 binding polypeptide coding region, said promoter being inducible or constitutive, and, optionally, tissue-specific. In another particular embodiment, nucleic acid molecules are used in which the ACE-2 binding polypeptide coding sequences and any other desired sequences are flanked by regions that promote homologous recombination at a desired site in the genome, thus providing for intrachromosomal expression of the ACE-2 binding polypeptide encoding nucleic acids (Koller and Smithies, *Proc. Natl. Acad. Sci. USA,* 86:8932–8935 (1989); Zijlstra et al., *Nature,* 342:435–438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.,* 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT publications WO 92/06180; WO 92/22635; WO 92/20316; WO 93/14188, WO 93/20221). Alternatively, the nucleic acid can be introduced intracellularly and incorporated within host cell DNA for expression, by homologous recombination (Koller and Smithies, *Proc. Natl. Acad. Sci. USA,* 86:8932–8935 (1989); Zijlstra et al., *Nature,* 342:435–438 (1989)).

In a specific embodiment, viral vectors that contains nucleic acid sequences encoding an ACE-2 binding polypeptide of the invention or fragments or variants thereof are used. For example, a retroviral vector can be used (see Miller et al., *Meth. Enzymol.,* 217:581–599 (1993)). These retroviral vectors contain the components necessary for the correct packaging of the viral genome and integration into the host cell DNA. The nucleic acid sequences encoding the ACE-2 binding polypeptide to be used in gene therapy are cloned into one or more vectors, which facilitates delivery of the gene into a patient. Additional details concerning retroviral vectors can be found in Boesen et al., *Biotherapy,* 6:29 1–302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., *J. Clin. Invest.,* 93:644–651 (1994); Klein et al., *Blood,* 83:1467–1473 (1994); Salmons and Gunzberg, *Human Gene Therapy,* 4:129–141 (1993); and Grossman and Wilson, *Curr. Opin. in Genetics and Devel.,* 3:110–114 (1993).

Other viral vectors that can be used in gene therapy are adenoviruses. Adenoviruses are especially attractive vehicles for delivering genes to respiratory epithelia. Adenoviruses naturally infect respiratory epithelia, where they cause a mild disease. Other targets for adenovirus-based delivery systems are liver, the central nervous system, endothelial cells, and muscle. Adenoviruses have the advantage of being capable of infecting non-dividing cells. See, Kozarsky and Wilson, *Current Opinion in Genetics and Development,* 3:499–503 (1993), presenting a review of adenovirus-based gene therapy. Bout et al., *Human Gene Therapy,* 5:3–10 (1994) demonstrated the use of adenovirus vectors to transfer genes to the respiratory epithelia of rhesus monkeys. Other instances of the use of adenoviruses in gene therapy can be found in Rosenfeld et al., *Science,* 252:431–434 (1991); Rosenfeld et al., *Cell,* 68:143–155 (1992); Mastrangeli et al., *J. Clin. Invest.,* 91:225–234 (1993); PCT publication WO 94/12649; and Wang et al., *Gene Therapy,* 2:775–783 (1995). In a preferred embodiment, adenovirus vectors are used.

Adeno-associated virus (AAV) has also been proposed for use in gene therapy (Walsh et al., *Proc. Soc. Exp. Biol. Med.,* 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.,* 217:599–618 (1993); Cohen et al., *Meth. Enzymol.,* 217:618–644 (1993); *Clin. Pharma. Ther.,* 29:69–92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to cardiac myocytes, proximal tubules, endothelial cells, epithelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an ACE-2 binding polypeptide or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells that can be isolated and maintained in vitro can potentially be used in accordance with this embodiment of the present invention (see, e.g., PCT publication WO 94/08598; Stemple and Anderson, *Cell,* 7 1:973–985 (1992); Rheinwald, *Meth. Cell Bio.,* 21A:229 (1980); and Pittelkow and Scott, *Mayo Clinic Proc.,* 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific ACE-2 binding polypeptide or composition of the present invention is indicated, include in vitro cell culture assays in which a patient tissue sample is grown in culture, and exposed to, or otherwise administered, an ACE-2 binding polypeptide or composition of the present invention, and the effect of such an ACE-2 binding polypeptide or composition of the present invention upon the tissue sample is observed. In various specific embodiments, in vitro assays can be carried out with representative cells of cell types involved in a patient's disorder, to determine if an ACE-2 binding polypeptide or composition of the present invention has a desired effect upon such cell types. Preferably, the ACE-2 binding polypeptides or compositions of the invention are also tested in in vitro assays and animal model systems prior to administration to humans.

ACE-2 binding polypeptides or compositions of the present invention for use in therapy can be tested for their toxicity in suitable animal model systems, including but not limited to rats, mice, chicken, cows, monkeys, and rabbits. For in vivo testing of an ACE-2 binding polypeptide or composition's toxicity any animal model system known in the art may be used.

Efficacy in treating or preventing vasoconstriction may be demonstrated by detecting the ability of an ACE-2 binding polypeptide or composition of the invention to prevent or treat hypertension, which can be defined as a diastolic blood pressure greater than 90 mmHg and/or a systolic blood pressure of greater than 140 mmHg, as measured in an adult over 18 years of age. Since children and pregnant women have a lower avaerage blood pressure, a mean diastolic blood pressure over 80 mmHg and systolic blood pressure over 120 mmHg is considered indicative of hypertension.

ACE-2 binding polypeptides or compositions of the invention can be tested for the ability to inhibit or prevent smooth muscle cell proliferation, such as occurs in vascular stenosis and tumor formation, in in vitro, ex vivo, and in vivo assays. For example, cellular proliferation can be assayed by $^3$H-thymidine incorporation assays and trypan blue cell counts.

ACE-2 binding polypeptides or compositions of the invention can be tested for the ability to modulate inflammatory responses by contacting cells involved in inflammatory responses, preferably human cells involved inflammatory responses (e.g., basophils and mast cells), with an ACE-2 binding polypeptide or composition of the invention to modulate (i.e., increase or decrease) the inflammatory response. The ability of an ACE-2 binding polypeptide or composition of the invention to modulate inflammatory responses can be assessed by detecting the proliferation of cells involved in the immune response (e.g., basophile and mast cells), detecting the activation of signalling molecules (e.g, bradykinin), detecting secretion of fluid and/or ions, detecting functio laesa, detecting changes in calor or rubor at affected site, detecting the expression of antigens, or detecting changes in blood flow to the affected site. Techniques known to those of skill in the art can be used for measuring these activities. For example, antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the ability of an ACE-2 binding polypeptide or composition of the invention to enhance or increase bradykinin concentrations and/or activity is measured.

ACE-2 binding polypeptides or compositions of the invention can also be tested for their ability to alleviate of one or more symptoms associated with cancer, a cardiovascular disorder (e.g., hypertension or hypotension), a neurological disorder, or a digestive disorder. Further, ACE-2 binding polypeptides or compositions of the invention can be tested for their ability to increase the survival period of animals suffering from disease or disorder, including cancer, a cardiovascular disorder, a neurological disorder, or a digestive disorder. Techniques known to those of skill in the art can be used to analyze the function of the ACE-2 binding polypeptides or compositions of the invention in vivo.

Therapeutic/Prophylactic Compositions and Administration

The invention provides methods of treatment, inhibition and prophylaxis by administration to a subject of an effective amount of ACE-2 binding polypeptide (or fragment or variant thereof) or pharmaceutical composition of the invention, preferably an ACE-2 binding polypeptide of the invention. In a preferred aspect, an ACE-2 binding polypeptide or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer ACE-2 binding polypeptide or fragment or variant thereof of the invention, e.g., encapsulation in liposomes, microparticles, microcapsules, recombinant cells capable of expressing the ACE-2 binding polypeptide or ACE-2 binding polypeptide fragment, receptor-mediated endocytosis (see, e.g., Wu and Wu, *J. Biol. Chem.,* 262:4429–4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an ACE-2 binding polypeptide, of the invention, care must be taken to use materials to which the protein does not absorb.

In another embodiment, the composition can be delivered in a vesicle, in particular a liposome (see, Langer, *Science,* 249:1527–1533 (1990); Treat et al., in *Liposomes in the Therapy of Infectious Disease and Cancer*, Lopez-Berestein and Fidler, eds. (Liss, New York 1989), pp. 353–365; Lopez-Berestein, ibid., pp. 317–327; see, generally, ibid.).

In yet another embodiment, the composition can be delivered in a controlled release system. In one embodiment, a pump may be used (see Langer, supra; Sefton, *CRC Crit. Ref. Biomed. Eng.,* 14:201 (1987); Buchwald et al., *Surgery,* 88:507 (1980); Saudek et al., *N. Engl. J. Med.,* 321:574 (1989)). In another embodiment, polymeric materials can be used (see, *Medical Applications of Controlled Release*, Langer and Wise, eds. (CRC Press, Boca Raton, Fla. 1974); *Controlled Drug Bioavailability, Drug Product Design and Performance*, Smolen and Ball, eds. (Wiley, New York 1984); Ranger and Peppas, *Macromol. Sci. Rev. Macromol. Chem.,* 23:61 (1983); see also Levy et al., *Science,* 228:190 (1985); During et al., *Ann. Neurol.,* 25:35 1 (1989); Howard et al., *J.Neurosurg.,* 7 1:105 (1989)). In yet another embodiment, a controlled release system can be placed in proximity of the therapeutic target, e.g., the brain, thus requiring only a fraction of the systemic dose (see, e.g., Goodson, in *Medical Applications of Controlled Release*, supra, vol. 2, pp. 115–138 (1984)). Other controlled release systems are discussed in the review by Langer (*Science,* 249:1527–1533 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or. transfecting agents, or by administering it in linkage to a homeobox-like peptide which is known to enter the nucleus (see, e.g., Joliot et al., *Proc. Natl. Acad. Sci. USA,* 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an ACE-2 binding polypeptide or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences,* 18*th Ed*., Gennaro, ed. (Mack Publishing Co., 1990). Such compositions will contain a therapeutically effective amount of the ACE-2 binding polypeptide or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Generally, the ingredients are supplied either separately or mixed together in unit dosage form, for example, as a dry lyophilized powder or water free concentrate in. a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For ACE-2 binding polypeptides, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Further, the dosage and frequency of administration of therapeutic or pharmaceutical compositions of the invention may be reduced by enhancing uptake and tissue penetration (e.g., into the brain) of the ACE-2 binding polypeptides by modifications such as, for example, lipidation.

The ACE-2 binding polypeptides and ACE-2 binding polypeptide compositions of the invention may be administered alone or in combination with other molecules including ACE-2. In further embodiments of the invention, the ACE-2 binding polypeptides are administered in complex with ACE-2. Preferably the ACE-2 binding polypeptide is radiolabelled or in complex with a radioisotope, toxin, or prodrug. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The ACE-2 binding polypeptides and ACE-2 binding polypeptide compositions of the invention may be administered alone or in combination with other adjuvants. Adjuvants that may be administered with the ACE-2 binding polypeptides and ACE-2 binding polypeptide compositions of the invention include, but are not limited to, alum, alum plus deoxycholate (ImmunoAg), MTP-PE (Biocine Corp.), QS21 (Genentech, Inc.), BCG, and MPL. In a specific embodiment, ACE-2 binding polypeptides and ACE-2 binding polypeptide compositions of the invention are administered in combination with alum. In another specific embodiment, ACE-2 binding polypeptides and ACE-2 binding polypeptide compositions of the invention are administered in combination with QS-21. Further adjuvants that may be administered with the ACE-2 binding polypeptides and ACE-2 binding polypeptide compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the ACE-2 binding polypeptides and ACE-2 binding polypeptide compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™.

The ACE-2 binding polypeptides and ACE-2 binding polypeptide compositions of the invention may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the ACE-2 binding polypeptides and ACE-2 binding polypeptide compositions of the invention are administered in combination with antihypertensives including, but not limited to, diuretics, beta-blockers, calcium channel blockers, ACE inhibitors, angiotensin II receptor blockers, alpha blockers, combined alpha and beta blockers, central agonists, peripheral adrenergic inhibitors, and blood vessel dilators.

In a preferred embodiment, the ACE-2 binding polypeptides and ACE-2 binding polypeptide compositions of the invention are administered in combination with diuretics including, but not limited to, bumetanide (Bumex®), chlorothiazide (Diuril®), chlorthalidone (Hygroton®), furosemide (Lasix®), hydrochlorothiazide (Esidrix®, Hydrodiuril®), mannitol, metolazone (Diulo®, Zaroxolyn®), amiloride and hydrochlorothiazide mix (Moduretic®), triamterene and hydrochlorothiazide mix (Dyazide®, Maxzide®), and potassium-sparring diuretics, such as amiloride (Midamor®), spironolactone (Aldactone®), and triamterene (Dyrenium®).

In a preferred embodiment, the ACE-2 binding polypeptides and ACE-2 binding polypeptide compositions of the invention are administered in combination with beta blockers including, but not limited to, atenolol (Tenormin®), esmolol (Brevibloc®), labetalol (Normodyne®, Trandate®), metoprolol (Lopressor®), propranolol (Inderal®), sotalol (Betapace®), acebutolol (Sectral®), nadolol (Corgard®), pindolol (Visken®), and timolol (Blocadren®).

In a preferred embodiment, the ACE-2 binding polypeptides and ACE-2 binding polypeptide compositions of the invention are administered in combination with ACE inhibitors including, but not limited to, benazepril (Lotensin®), captopril (Capoten®), enalapril (Vasotec®), fosinopril (Monopril®), lisinopril (Zestril®, Prinivil®), and quinapril (Accupril®).

In a preferred embodiment, the ACE-2 binding polypeptides and ACE-2 binding polypeptide compositions of the invention are administered in combination with angiotensin II blockers including, but not limited to losartan (Cozaar®).

In a preferred embodiment, the ACE-2 binding polypeptides and ACE-2 binding polypeptide compositions of the invention are administered in combination with calcium channel blockers including, but not limited to, amlodipine (Norvasc®), diltiazem (Cardizem®), felodipine (Plendil®), isradipine (Dynacirc®), nicardipine (Cardene®), nifedipine (Procardia®), and verapamil (Calan®, Isoptin®).

In a preferred embodiment, the ACE-2 binding polypeptides and ACE-2 binding polypeptide compositions of the invention are administered in combination with alpha blockers including, but not limited to, doxazosin (Cardura®), prazosin (Minipress®), and tamsulosin (Flomax®).

In a preferred embodiment, the ACE-2 binding polypeptides and ACE-2 binding polypeptide compositions of the invention are administered in combination with central agonists including, but not limited to, clonidine (Catapres®), methyldopa (Aldomet®), guanabenz (Wytensin®), and guanfacine (Tenex®).

In a preferred embodiment, the ACE-2 binding polypeptides and ACE-2 binding polypeptide compositions of the invention are administered in combination with peripheral adrenergic inhibitors including, but not limited to, reserpine, guanadrel (Hylorel®), and guanethidine (Ismelin®).

In a preferred embodiment, the ACE-2 binding polypeptides and ACE-2 binding polypeptide compositions of the invention are administered in combination with blood vessel dilators including, but not limited to, hydralzine (Apresoline®) and minoxidil (Loniten®).

In another preferred embodiment, the ACE-2 binding polypeptides and ACE-2 binding polypeptide compositions of the invention are administered in combination with vasodilating agents including, but not limited to, alprostadil (PGE-1, prostaglandin E-1, Prostin VR Pediatric®), amyl nitrite, dipyridamole (Persantin®), epoprostenol (Flolan®), isosorbide dinitrate (Isordil®, Sorbitrate®), isosorbide monomitrate (IMDUR®), nimodipine (nimotop®), nitric oxide gas (INOmax®), nitroglycerin (glyceryl trinitrate, Nitro-Dur®, Nitroligual®, Nitrostat®, NTG, Transderm-Nirto®), papaverine, and tolazoline (Priscoline®).

Antilipemic agents that may be administered in combination with the ACE-2 binding polypeptides and ACE-2 binding polypeptide compositions of the present invention include, but are not limited to, atorvastatin (Lipitor®), cholestyramine(Questran®), colestipol (Colestid®), fluvastatin (Lescol®), gemfibrozil (Lopid®), niacin (nicotinic acid), prevastatin (Pravachol®), and simvastatin (Zocor®).

In another preferred embodiment, a therapeutically effective amount of angiotensin 1-9 is administered in combination with a therapeutically effective amount of angiotensin II or other hypotensive agents (see Example 9).

Additionally, in another embodiment, the ACE-2 binding polypeptides and ACE-2 binding polypeptide compositions of the invention are administered in combination with intravascular radiation to prevent, treat, or ameliorate restenosis. In a preferred embodiment, the ACE-2 binding polypeptides and ACE-2 binding polypeptide compositions of the invention are administered in combination with beta-emitting phosphorus-32. In another preferred ambodiment, the ACE-2 binding polypeptides and ACE-2 binding polypeptide compositions of the invention are administered in combination with iridium-192.

In a further embodiment, the ACE-2 binding polypeptides and ACE-2 binding polypeptide compositions of the invention are administered in combination with analgesics and anti-inflammatory agents. Analgesic agents that may be administered in combination with the ACE-2 binding polypeptides and ACE-2 binding polypeptide compositions of the invention include, but are not limited to, opioids, such as codeine, fentanyl (Actig®, Duragesic®, Oralet®, Sublimaze®), hydromorphone (Dilaudid®), meperidine (Demerol®), methadone (Dolophine®), morphine (Duramorph®, Infomorph®, morphine sulfate, MSO4), oxycodone, remifentanil (Ultiva®), and sufentanil (Sufenta®); opiate partial agonists, such as butorphanol (Stadol®), nalbuphine (Nubain®), and tramadol (Ultram®). Anti-inflammatory agents that may be administered in combination with the ACE-2 binding polypeptides and ACE-2 binding peptide compositions of the invention include, but are not limited to, NSAIDs (non-steroidal anti-inflammatory drugs), such as aspirin (ASA®, Empirin®), choline magnesium trisalicylate (Trilisate®), diclofenac, diflunisal, fenoprofen, flurbiprofin (Ocufen®), ibuprofin (Advil®, Motrin®, Rufen®), indomethacin (Indocin®), ketoprofen, meclofenamate, nabumetone (Relafen®), naproxen (Naprosyn®), naproxen sodium (Aleve®, Anaprox®), oxaprozin, phenylbutazone, piroxicam (Feldene®), salsalate (Disalcid®), sulindac (Clinoril®), tolmetin, celecoxib (Celebrex®), and ketorolac (Toradol®).

In an even further embodiment, the ACE-2 binding polypeptides and ACE-2 binding polypeptide compositions of the invention are administered alone or in combination with other anti-inflammatory agents. Anti-inflammatory agents that may be administered with the ACE-2 binding polypeptides and ACE-2 binding polypeptide compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the ACE-2 binding polypeptides and ACE-2 binding polypeptide compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, ACE-2 binding polypeptides and ACE-2 binding polypeptide compositions of the invention are administered in combination with CHOP (cyclophosphamide, doxorubicin, vincristine, and prednisone) or any combination of the components of CHOP. In one embodiment, the compositions of the invention are administered in combination with anti-CD20 antibodies, human monoclonal anti-CD20 antibodies. In another embodiment, the compositions of the invention are administered in combination with anti-CD20 antibodies and CHOP, or anti-CD20 antibodies and any combination of one or more of the components of CHOP, particularly cyclophosphamide and/or prednisone. In a specific embodiment, compositions of the invention are administered in combination with Rituximab. In a further embodiment, compositions of the invention are administered with Rituximab and CHOP, or Rituximab and any combination of one or more of the components of CHOP, particularly cyclophosphamide and/or prednisone. In a specific embodiment, compositions of the invention are administered in combination with tositumomab. In a further embodiment, compositions of the invention are administered with tositumomab and CHOP, or tositumomab and any combination of one or more of the components of CHOP, particularly cyclophosphamide and/or prednisone. The anti-CD20 antibodies may optionally be associated with radioisotopes, toxins or cytotoxic prodrugs.

In another specific embodiment, the compositions of the invention are administered in combination Zevalin™. In a further embodiment, compositions of the invention are administered with Zevalin™ and CHOP, or Zevalin™ and any combination of one or more of the components of CHOP, particularly cyclophosphamide and/or prednisone. Zevalin™ may be associated with one or more radisotopes. Particularly preferred isotopes are $^{90}$Y and $^{111}$In.

Additionally, the ACE-2 binding polypeptides and ACE-2 binding polypeptide compositions of the invention may be administered alone or in combination with other therapeutic regimens, including but not limited to, radiation therapy. Such combinatorial therapy may be administered sequentially and/or concomitantly.

Kits for Detecting and/or Quantitating ACE-2 or ACE-2-like Polypeptides

The present invention is also directed to an assay kit which can be useful in screening for the presence of ACE-2 and/or quantitating ACE-2 concentrations in a fluid, such as, for example, a biological fluid (e.g., blood, serum, synovial fluid).

In a particular embodiment of the present invention, an assay kit is contemplated which comprises in one or more containers one or more ACE-2 binding polypeptides of the invention and optionally, a detection means for determining the presence of an ACE-2-ACE-2 binding polypeptide interaction or the absence thereof. The kit further optionally contains ACE-2 protein that may be used, for example as a control. The ACE-2 binding polypeptide may be free or expressed on the surface of a phage.

In a specific embodiment, either the ACE-2 binding polypeptide or the ACE-2 protein is labeled. As further discussed herein, a wide range of labels can be used accordance with the present invention, including but not limited to conjugating the recognition unit to biotin by conventional means. Alternatively, the label may comprise, e.g., a fluorogen, an enzyme, an epitope, a chromogen, or a radionuclide. Preferably, the biotin is conjugated by covalent attachment to either the ACE-2 binding polypeptide or the ACE-2 protein. Preferably, the ACE-2 binding polypeptide is immobilized on a solid support. The detection means employed to detect the label will depend on the nature of the label and can be any known in the art, e.g., film to detect a radionuclide, an enzyme substrate that gives rise to a detectable signal to detect the presence of an enzyme, antibody to detect the presence of an epitope, etc.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In one preferred embodiment the kit comprises a vial containing ACE-2 binding polypeptides conjugated to a toxin or a label (as described herein). Such conjugated binding polypeptide may be used to kill a particular population of cells or to quantitate a particular population of cells. In a preferred embodiment, such conjugated ACE-2 binding polypeptides are used to kill cells expressing the membrane-bound form of ACE-2. In another preferred embodiment, such conjugated ACE-2 binding polypeptides are used to quantitate cells expressing the membrane-bound form of ACE-2.

In one embodiment, the present invention provides a pharmaceutical pack or kit comprising a first container containing ACE-2 binding polypetides attached to a macrocyclic chelator (e.g., DOTA), a second container containing ACE-2 polypeptide, and a third container containing radiometal ions (e.g., $^{90}$Y, $^{111}$In, or $^{131}$I,). The contents of these containers could then be mixed, and incubated for a period of time to allow the reagents to associate with one another, prior to administration to a patient. In addition it may also be desirable to purify the ACE-2/ACE-2 binding polypeptide-macrocyclic chelator/radiometal ion complexes from excess reagents that did not form into complexes, for example, by filtration in a spin column based on a size exclusion principle (e.g. Bio-Spin columns available from Biorad Laboratories, Inc.) Thus in another embodiment, the present invention provides a pharmaceutical pack or kit comprising a first container containing ACE-2 binding polypetides attached to a macrocyclic chelator (e.g., DOTA), a second container containing ACE-2 polypeptide, and a third container containing radiometal ions (e.g., $^{90}Y$, $^{111}In$, or 131I), and a means for purifying ACE-2/ACE-2 binding polypeptide-macrocyclic chelator/radiometal ion complexes.

In other embodiments, the present invention provides a pharmaceutical pack or kit comprising a first container containing ACE-2 and ACE-2 binding poypeptides, and a second container containing radiometal ions (e.g., $^{90}Y$, $^{111}In$, or $^{131}I$). In a specific embodiment, the present invention provides a pharmaceutical pack or kit comprising a first container containing ACE-2 and ACE-2 binding poypeptides, a second container containing radiometal ions (e.g., $^{90}Y$, $^{111}In$, or $^{131}I$), and a means for purifying ACE-2/ACE-2 binding polypeptide-macrocyclic chelator/radiometal ion complexes.

In still other embodiments, the present invention provides a pharmaceutical pack or kit comprising a first container containing ACE-2 binding polypetides attached to a macrocyclic chelator (e.g., DOTA) and a second container containing radiometal ions (e.g., $^{90}Y$, $^{111}In$, or $^{131}I$,). In a specific embodiment, the present invention provides a pharmaceutical pack or kit comprising a first container ACE-2 binding polypetides attached to a macrocyclic chelator (e.g., DOTA), a second container containing radiometal ions (e.g., $^{90}Y$, $^{111}In$, or $^{131}I$,) and a means for purifying ACE-2 binding polypeptide-macrocyclic chelator/radiometal ion complexes.

The present invention provides kits that can be used in the above. methods. In one embodiment, a kit comprises an ACE-2 binding polypeptide of the invention, preferably a purified ACE-2 binding polypeptide, in one or more containers. In an alterative embodiment, a kit comprises an ACE-2 binding polypeptide fragment that specifically binds to ACE-2. In a specific embodiment, the kits of the present invention contain a substantially isolated ACE-2 polypeptide as a control. Preferably, the kits of the present invention further comprise a control binding polypeptide which does not react with ACE-2. In another specific embodiment, the kits of the present invention contain a means for detecting the binding of an ACE-2 binding polypeptide to ACE-2 (e.g., the ACE-2 binding polypeptide may be conjugated to a detectable substrate such as a fluorescent compound, an enzymatic substrate, a radioactive compound or a luminescent compound, or a second antibody which recognizes the ACE-2 binding polypeptide may be conjugated to a detectable substrate). In specific embodiments, the kit may include a recombinantly produced or chemically synthesized ACE-2. The ACE-2 provided in the kit may also be attached to a solid support. In a more specific embodiment the detecting means of the above-described kit includes a solid support to which ACE-2 is attached. Such a kit may also include a non-attached reporter-labeled anti- ACE-2 binding polypeptide antibody. In this embodiment, binding of the ACE-2 binding polypeptide to ACE-2 can be detected by binding of the said reporter-labeled antibody. Alternatively, or in addition, the detecting means may include a labeled, competing antigen.

In an additional embodiment, the invention includes a diagnostic kit for use in screening serum containing ACE-2 or ACE-2-like polypeptides. The diagnostic kit includes a substantially isolated ACE-2 binding polypeptide specifically reactive with ACE-2 target, and means for detecting the binding of ACE-2 target to the ACE-2 binding polypeptide. In one embodiment, the ACE-2 binding polypeptide is attached to a solid support.

In one diagnostic configuration, test serum is reacted with a solid phase reagent having a surface-bound ACE-2 binding polypeptide according to the present invention. After ACE-2 binds to a specific ACE-2 binding polypeptide, the unbound serum components are removed by washing, reporter-labeled anti-ACE-2 binding polypeptide antibody is added, unbound anti-ACE-2 binding polypeptide antibody is removed by washing, and a reagent is reacted with reporter-labeled anti-ACE-2 binding polypeptide antibody to bind reporter to the reagent in proportion to the amount of bound ACE-2 binding polypeptide on the solid support. Typically, the reporter is an enzyme which is detected by incubating the solid phase in the presence of a suitable fluorometric, luminescent or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated ACE-2 binding polypeptides.

Thus, the invention provides an assay system or kit for carrying out this diagnostic method. The kit generally includes a support with surface-bound recombinant ACE-2, and a reporter-labeled anti-ACE-2 binding polypeptide antibody for detecting surface-bound anti-ACE-2 binding polypeptide.

Methods of Screening for ACE-2 Binding Molecules

The invention also encompasses screening methods for identifying polypeptides and nonpolypeptides that bind ACE-2, and the ACE-2 binding molecules identified thereby. This method comprises the steps of:

(a) contacting ACE-2 or ACE-2-like polypeptide with a plurality of molecules; and (b) identifying molecule(s) that binds the ACE-2 or ACE-2-like polypeptide.

The step of contacting the ACE-2 protein or ACE-2-like protein with the plurality of molecules may be effected in a number of ways. For example, one may contemplate immobilizing ACE-2 target on a solid support and bringing a solution of the plurality of molecules in contact with the immobilized ACE-2 target. Such a procedure would be akin to an affinity chromatographic process, with the affinity matrix being comprised of the immobilized ACE-2 protein or ACE-2-like polypeptide. The molecules having a selective affinity for the ACE-2 or ACE-2-like polypeptide can then be purified by affinity selection. The nature of the solid support, process for attachment of the ACE-2 or ACE-2-like polypeptide to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" using an ACE-2 target protein, optionally in the presence of an inducer should one be required for expression, to determine if any selective affinity interaction takes place between the ACE-2 target protein and the individual clone. Prior to contacting the ACE-2 target protein with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for ACE-2 or ACE-2-like polypeptide. Furthermore, the amino acid sequence of the polypeptide having a selective affinity for the ACE-2 protein or ACE-2-like protein can be determined directly by conventional means, or the coding sequence of the DNA encoding the polypeptide can frequently be determined more conveniently. The primary amino acid sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any ACE-2 or ACE-2-like polypeptide, or alterntatively, unbound polypeptides, from a mixture of ACE-2 or ACE-2-like polypeptide and the plurality of polypeptides prior to attempting to determine or to detect the presence of a selective affinity interaction. One or more such a wash steps may be particularly desirable when the ACE-2 or ACE-2-like polypeptide or the plurality of polypeptides is bound to a solid support.

The plurality of molecules provided according to this method may be provided by way of diversity libraries, such as random or combinatorial peptide or non-peptide libraries which can be screened for molecules that specifically bind to ACE-2. Peptide libraries may be designed such that the polypeptides encoded by the libraries are automatically fused to a polypeptide linker moiety, for example. Many libraries are known in the art that can be used, e.g., chemically synthesized libraries, recombinant (e.g., phage display libraries), and in vitro translation-based libraries. Examples of chemically synthesized libraries are described in Fodor et al., *Science,* 251:767–773 (1991); Houghten et al., *Nature,* 354:84–86 (1991); Lam et al., *Nature,* 354:82–84 (1991); Medynski, *Bio/Technology,* 12:709–710 (1994); Gallop et al., *J. Medicinal Chemistry,* 37(9):1233–1251 (1994); Ohlmeyer et al., *Proc. Natl. Acad. Sci. USA,* 90:10922–10926 (1993); Erb et al., *Proc. Natl. Acad. Sci. USA,* 91:11422–11426 (1994); Houghten et al., *Biotechniques,* 13:412 (1992); Jayawickreme et al., *Proc. Natl. Acad. Sci. USA,* 91:1614–1618 (1994); Salmon et al., *Proc. Natl. Acad. Sci. USA,* 90:11708–11712 (1993); PCT publication WO 93/20242; and Brenner and Lerner, *Proc. Natl. Acad. Sci. USA,* 89:5381–5383 (1992).

Examples of phage display libraries are described in Scott and Smith, *Science,* 249:386–390 (1990); Devlin et al., *Science,* 249:404–406 (1990); Christian et al., *J. Mol. Biol.,* 227:711–718 (1992); Lenstra, *J. Immunol. Meth.,* 152:149–157 (1992); Kay et al., *Gene,* 128:59–65 (1993); and PCT publication WO 94/18318.

In vitro translation-based libraries include but are not limited to those described in PCT publication WO 91/05058 and Mattheakis et al., *Proc. Natl. Acad. Sci. USA,* 91:9022–9026 (1994).

By way of examples of non-peptide libraries, a benzodiazepine library (see, e.g., Bunin et al., *Proc. Natl. Acad. Sci. USA,* 91:4708–4712 (1994) can be adapted for use. Peptoid libraries (Simon et al., *Proc. Natl. Acad. Sci. USA,* 89:9367–9371 (1992)) can also be used. Another example of a library that can be used, in which the amide functionalities in peptides have been permethylated to generate a chemically transformed combinatorial library, is described by Ostresh et al. (*Proc. Natl. Acad. Sci. USA,* 91:11138–11142 (1994)).

The variety of non-peptide libraries that are useful in the present invention is great. For example, Ecker and Crooke, *Bio/Technology,* 13:351–360 (1995) list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, *Adv. Exp. Med. Biol.,* 251:215–218 (1989); Scott and Smith, *Science,* 249:386–390 (1990); Fowlkes et al., *BioTechniques,* 13:422–427 (1992); Oldenburg et al., *Proc. Natl. Acad. Sci. USA,* 89:5393–5397 (1992); Yu et al., *Cell,* 76:933–945 (1994); Staudt et al., *Science,* 241:577–580 (1988); Bock et al., *Nature,* 355:564–566 (1992); Tuerk et al., *Proc. Natl. Acad. Sci. USA,* 89:6988–6992 (1992); Ellington et al., *Nature,* 355:850–852 (1992); U.S. Pat. Nos. 5,096,815; 5,223,409; and 5,198,346, all to Ladner et al.; Rebar and Pabo, *Science,* 263:671–673 (1993); and PCT publication WO 94/18318.

In a specific embodiment, screening to identify a molecule that binds ACE-2 can be carried out by contacting the library members with ACE-2 or ACE-2-like polypeptide immobilized on a solid phase and harvesting those library members that bind to the ACE-2 or ACE-2-like polypeptide. Examples of such screening methods, termed "panning" techniques are described by way of example in Parmley and Smith, *Gene,* 73:305–318 (1998); Fowlkes et al., *BioTechniques,* 13:422–427 (1992); PCT publication WO 94/18318; and in references cited therein.

In another embodiment, the two-hybrid system for selecting interacting proteins in yeast (Fields and Song, *Nature,* 340:245–246 (1989); Chien et al., *Proc. Natl. Acad. Sci. USA,* 88:9578–9582 (1991)) can be used to identify molecules that specifically bind to ACE-2 or ACE-2-like polypeptides.

Where the ACE-2 binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid, that certain amino acid positions in a peptide remain fixed (e.g., as cysteine), or that positions 4, 8, and 9, for example, of a decapeptide library be limited to permit several but less than all of the twenty naturally-occurring amino acids. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of an ACE-2 binding molecule that is a polypeptide, the polypeptide may have about 6 to less than about 60 amino acid residues, preferably about 6 to about 10 amino acid residues, and most preferably, about 6 to about 22 amino acids. In another embodiment, an ACE-2 binding polypeptide has in the range of 15–100 amino acids, or 20–50 amino acids.

The selected ACE-2 binding polypeptide can be obtained by chemical synthesis or recombinant expression.

The specific ACE-2 binding polypeptides disclosed herein were isolated using phage display technology, to identify ACE-2 binding polypeptides exhibiting particular preselected binding properties. These ACE-2 binding polypeptides were isolated initially by screening nine phage display libraries, that is, populations of recombinant bacteriophage transformed to express an exogenous recombinant polypeptide on their surface. In order to isolate new polypeptide binding moieties for a particular target, such as ACE-2, screening of peptide libraries, for example using phage display techniques, is especially advantageous, in that very large numbers (e.g., $5\times10^9$) of potential binders can be tested and successful binders isolated in a short period of time.

In order to prepare a phage library of potential binding polypeptides to screen for members of the library that are ACE-2 binding polypeptides, a candidate binding domain is selected to serve as a structural template for the polypeptides to be displayed in the library. The phage library is made up of polypeptide analogues of this template or "parental binding domain." The parental binding domain is a polypeptide molecule that may be a naturally occurring or synthetic protein or polypeptide, or polypeptide region or domain of a protein. The parental binding domain may be selected based on knowledge of a known interaction between the parental binding domain and a target protein, but this is not critical. In fact, it is not essential that the parental binding domain have any affinity for a target at all because its purpose is to provide a structure from which a multiplicity of polypeptide analogues (a "library") can be generated, which multiplicity of polypeptide analogues will include one or more binding polypeptides that exhibit the desired binding and release properties with respect to ACE-2 target proteins (and any other properties selected).

Knowledge of the exact polypeptide that will serve as the parental binding domain, or knowledge of a class of proteins or domains to which the parental binding domain belongs can be useful in determining the conditions under which ACE-2 binding polypeptides optimally bind ACE-2 target proteins as well as the conditions under which ACE-2 binding polypeptides optimally release ACE-2 target proteins. Similarly, the binding and/or release conditions may be selected with regard to known interactions between a binding domain and the ACE-2 target protein, for example, to favor the interaction under the binding and/or release conditions, or they may be selected without regard to such known interactions. Likewise, the parental binding domain can be selected taking into account a desired binding and/or release condition or not. It is understood that if the binding domain analogues of a library are unstable under a proposed or desired binding or release condition, no useful binding polypeptides may be obtained.

In selecting the parental binding domain, the most important consideration is how the analogue domains will be presented to the ACE-2 target protein, that is, in what conformations the ACE-2 target and the polypeptide analogues will contact one another. In preferred embodiments, for example, the polypeptide analogues will be generated by insertion of synthetic DNA encoding the polypeptide analogue into a replicable genetic package, resulting in display of the domain on the surface of a microorganism, such as M13 phage, using techniques as described in Kay et al., *Phage Display of Peptides and Proteins: A Laboratory Manual* (Academic Press, Inc.; San Diego 1996) and U.S. Pat. No. 5,223,409 (Ladner et al.), incorporated herein by reference. For formation of phage display libraries, it is preferred to use structured polypeptides as the parental binding domain or template, as opposed to unstructured, linear peptides. Mutation of surface residues in a protein domain or polypeptide molecule will usually have little effect on the overall structure or general properties (such as size, stability, and temperature of denaturation) of the protein; while at the same time mutation of surface residues may profoundly affect the binding properties of the molecule. The more tightly a polypeptide segment is constrained, the less likely it is to bind to any particular target. If it does bind, however, the binding is likely to be tighter and more specific. Thus, it is preferred to select a parental binding domain wherein the parental polypetide has structure and, thereby in turn, select a structure for the polypeptide analogues of the library, which is constrained within a framework having some degree of rigidity.

Preferably the protein domain that is used as the template or parental domain for generating the library of domain analogues will be a peptide molecule that is a relatively small protein or polypeptide. Small polypeptides offer several advantages over large proteins: First, the mass per binding site is reduced. Highly stable protein domains having low molecular weights, for example, Kunitz domains (~7 kilodaltons, kDa), Kazal domains (~7 kDa), *Cucurbida maxima* trypsin inhibitor (CMTI) domains (~3.5 kDa), and endothelin (~2 kDa), can show much higher binding per gram than do antibodies (150 kDa) or single chain scFv antibodies (30 kDa). Second, the possibility of non-specific binding is reduced because there is less molecular surface available for nonspecific binding. Third, small polypeptides can be engineered to have unique tethering sites in a way that is impracticable for larger proteins or antibodies. For example, small proteins and polypeptides can be engineered to have lysines only at sites suitable for tethering to a chromatography matrix. This is not feasible for antibodies. Fourth, a constrained polypeptide structure is more likely to retain its functionality when transferred (with the structural domain intact) from one framework to another. For instance, the binding domain structure is likely to be transferable from the framework used for presentation in a library, such as displayed on a phage, to an isolated protein removed from the presentation framework or immobilized on a chromatographic substrate.

In specific embodiments, the ACE-2 binding polypeptides of the invention are immobilized. ACE-2 binding polypeptide molecules according to the invention may be immobilized, for example, on chromatographic support materials to form efficient ACE-2 separation or affinity chromatographic media. Immobilized ACE-2 binding polypeptides of the invention have uses that include, but are not limted to, detecting, isolating or removing ACE-2 target proteins from solutions. One strategy for generating ACE-2 binding polypeptide molecules that can be immobilized, for example, on matrices, resins, or supports, involves selecting appropriate binding domain templates such that ACE-2 binding polypeptide molecules are generated that have one or more amino acids that may be used to covalently link the ACE-2 binding polypeptide to a chromatographic resin or substrate to form an affinity resin. Similarly, the N-terminal amino group or the C-terminal carboxyl group of a peptide molecule may be modified by adding a capping group to render it inert or a functional group, which permits linkage to a support medium. For example, the C-terminal carboxyl group of a protein domain may be converted to an amide or a hydrazide (—NH—$NH_2$) group for reaction with an aldehyde-functional substrate or other amine-reactive substrate. This technique is preferred. Another preferred modification of ACE-2 binding polypeptides useful for linking an ACE-2 binding polypeptide molecule of the invention to a chromatography material is a polypeptide linker comprising, or alternatively consisting of, the amino acid sequence Pro-Gly-Pro-Glu-Gly-Gly-Gly-Lys (SEQ ID NO:13).

In one non-limiting example of a screening procedure to obtain ACE-2 binding polypeptides encompassed by the invention, the phage in a phage display library are contacted with and allowed to bind an ACE-2 target protein that is immobilized on a solid support. Those phage that display non-binding polypeptides are separated from those that bind the ACE-2 target protein. Any of various techniques known in the art may be applied to dissociate the bound phage from the immobilized ACE-2 protein, and to collect and/or amplify the phage and/or their nucleic acid contents. Using these techniques it is possible to identify a ACE-2 binding phage that is about 1 in 20 million in the population. Libraries, displaying 10–20 million or more potential binding peptide molecules each, are rapidly screened to find high-affinity ACE-2 binding polypeptides.

In each round of screening, the diversity of a population falls until only efficient binding polypeptides remain, that is, the process converges. Typically, a phage display library will contain several closely related binding polypeptides (10 to 50 different binding polypeptides out of 10 million). Indications of convergence include increased binding (measured by phage titers) and recovery of closely related sequences. After a first set of binding polypeptide molecules is identified, the sequence information can be used to design other libraries biased for members having additional desired properties, for example, discrimination between different forms of ACE-2 (e.g., the membrane form and the soluble form of ACE-2) and fragments thereof, or discrimination between ACE-2 and closely related impurities in a feed stream.

Such techniques make it possible not only to screen a large number of potential binding polypeptides, but make it practical to repeat the binding and elution cycles and to build secondary, biased libraries for screening polypeptide analogue-displaying phage that meet specific criteria. Using these techniques, a polypeptide analogue biased library may be screened to reveal members that bind tightly, that is, have high affinity for ACE-2 target protein, under the screening conditions.

In the present invention target ACE-2 protein molecules were biotinylated and then bound to streptavidin-coated magnetic particles. Eight phage display libraries of different design were screened for the ability to bind the immobilized ACE-2. Six of the libraries were characterized by M13 phage displaying a variegated exogenous peptide loop of different lengths and overall structure: The TN6/6 library was constructed to display a single microprotein binding loop contained in a 12-amino acid template. The TN7/4 library was constructed to display a single microprotein binding loop contained in a 13-amino acid template. The TN8/9 library was constructed to display a single microprotein binding loop contained in a 14-amino acid template. The TN9/4 library was constructed to display a single microprotein binding loop contained in a 15-amino acid template. The TN10/9 library was constructed to display a single microprotein binding loop contained in a 16-amino acid template. The TN12/1 library was constructed to display a single microprotein binding loop contained in an 18-amino acid template. Two commercially available linear phage display libraries were also screened, designated PhD 7 and PhD 12 (New England Biolabs). The PhD 7 library displayed a linear random-sequence 7-mer and the PhD 12 library displayed a random-sequence 12-mer.

ACE-2 binding phage were not isolated from either of the comercially available libraries, PhD 7 and PhD 12.

After analysis of the sequences isolated from the library screenings, several families of ACE-2 binding peptides were defined. The amino acid sequences of the ACE-2-binding "hits" are set forth in Example 1 (infra).

As it within the scope of the present invention to screen phage libraries that bind one or more of the various forms of ACE-2, the following outlines some assays that may be used in screening for ACE-2 binding polypeptides that bind the soluble form of ACE-2, the membrane-bound form of ACE-2, or both the soluble and the membrane-bound forms of ACE-2. Assays to determine the specificity of binding polypeptides for different forms of a protein are commonly known in the art and may be readily adapted for determining the specificity of ACE-2 binding polypeptides for different forms of ACE-2.

ACE-2 binding polypeptides of the invention (including molecules comprising, or alternatively consisting of, ACE-2 binding polypeptide fragments or variants thereof) may be screened in a variety of assays to identify those ACE-2 binding polypeptides that specifically bind to the soluble form of ACE-2. ACE-2 binding polypeptides may be assayed in neutralization assays described herein (see Example 4) or otherwise known in the art. For example, ACE-2 binding polypeptides may be tested for their ability to inhibit soluble ACE-2 from binding an ACE-2 substrate.

ACE-2 binding polypeptides of the invention (including molecules comprising, or alternatively consisting of, ACE-2 binding polypeptide fragments or variants thereof) may be screened in a variety of assays commonly known in the art to identify those ACE-2 binding polypeptides that specifically bind to the membrane-bound form of ACE-2. For example, ACE-2 binding polypeptides may be assayed for binding ACE-2 protein present on cell membranes of cells that express ACE-2.

ACE-2 binding polypeptides of the invention (including molecules comprising, or alternatively consisting of, ACE-2 binding polypeptide fragments or variants) may be screened in a variety of assays to identify those ACE-2 binding polypeptides or ACE-2 binding polypeptide fragments or variants that specifically bind to the soluble form and membrane-bound form of ACE-1. This can readily be determined by performing assays to distinguish binding to the soluble form and assays to distinguish binding to the membrane-bound form (such as the assays described herein or otherwise known in the art), and identifying the ACE-2 binding polypeptides that bind both forms.

Additionally, ACE-2 binding polypeptides of the invention may be screened for the ability to inhibit, stimulate or not significantly alter ACE-2 activity, e.g., the ability of ACE-2 to bind to its substrate (e.g., angiotensin).

Anti-ACE-2 Binding Polypeptide Antibodies

Further polypeptides of the invention relate to antibodies and T-cell antigen receptors (TCR) which immunospecifically bind an ACE-2 binding polypeptide of the present invention (as determined by immunoassays well known in the art for assaying specific antibody-antigen binding). Antibodies of the invention include, but are not limited to, polyclonal, monoclonal, multi specific, human, humanized or chimeric antibodies, single chain antibodies, Fab fragments, F(ab') fragments, fragments produced by a Fab expression library, anti-idiotypic (anti-id) antibodies (including, e.g., anti-id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins may have both a heavy and light chain. In specific embodiments, the immunoglobulin molecules of the invention are IgG1. In other specific embodiments, the immunoglobulin molecules of the invention are IgG4. An array of IgG, IgE, IgM, IgD, IgA, and IgY heavy chains may be paired with a light chain of the kappa or lambda forms.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human. immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 to Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715, WO 92/08802, WO 91/00360, WO 92/05793; Tutt et al., *J. Immunol.,* 147:60–69 (1991); U.S. Pat. Nos. 4,474,893; 4,714,681; 4,925,648; 5,573,920; 5,601,819; Kostelny et al., *J. Immunol.,* 148:1547–1553 (1992).

Antibodies of the present invention may be described or specified in terms of the epitope(s) or portion(s) of an ACE-2 binding polypeptide of the present invention which they recognize or specifically bind. Antibodies which specifically bind any epitope or polypeptide of the present invention may also be excluded. Therefore, the present invention includes antibodies that specifically bind ACE-2 binding polypeptides of the present invention, and allows for the exclusion of the same.

In further preferred, nonexclusive embodiments, the antibodies of the invention (e.g., anti-idiotypic antibodies) inhibit one or more biological activities of ACE-2 through specific binding to ACE-2. In another preferred embodiment, the antibody of the invention inhibits ACE-2-mediated vasoconstriction.

Antibodies of the present invention may also be described or specified in terms of their cross-reactivity. Antibodies that do not bind any other ACE-2 binding polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to an ACE-2 binding polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to an ACE-2 binding polypeptide of the present invention are also included in the present invention. Further included in the present invention are antibodies which bind polypeptides encoded by polynucleotides, the complement of which hybridize to a polynucleotides of the present invention under stringent hybridization conditions (as described herein). Antibodies of the present invention may also be described or specified in terms of their binding affinity to an ACE-2 binding polypeptide of the invention. Preferred binding affinities include those with a dissociation constant or Kd less than $5\times10^{-5}$ M, $10^{-5}$ M, $5\times10^{-6}$ M, $10^{-6}$M, $5\times10^{-7}$ M, $10^{7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15 \text{ M, or}}$ $10^{-15}$ M.

The invention also provides antibodies that competitively inhibit binding of an antibody to an ACE-2 binding polypeptide of the invention as determined by any method known in the art for determining competitive binding. In preferred embodiments, the antibody competitively inhibits binding to the ACE-2 binding polypeptide by at least 95%, at least 90%, at least 85%, at least 80%, at least 75%, at least 70%, at least 60%, or at least 50%.

Antibodies of the present invention (e.g., anti-idiotypic antibodies) may act as agonists or antagonists of ACE-2 or alternatively may not significantly alter ACE-2 mediated activity. For example, the present invention includes antibodies (e.g., anti-idiotypic antibodies) which disrupt ACE-2/ACE-2 substrate (e.g., angiotensin, bradykinin, tachykinin, endothelin, neurotensin, or Substance P) interactions either partially or fully. In another example, antibodies of the invention enhance ACE-2/ACE-2 receptor interactions either partially or fully. Such activity may be the result of, for example, the antibody binding to an ACE-2 binding polypeptide of the invention, or alternatively as a result of direct binding of the antibody (e.g., an anti-idiotypic antibody to ACE-2).

Preferrably, antibodies of the present invention bind an ACE-2 binding polypeptide disclosed herein, a portion thereof, or an antibody that binds an ACE-2 binding polypeptide disclosed herein, or a portion thereof. The invention features both ACE-2 binding polypeptide-specific antibodies and antibodies that are specific to ACE-2 binding polypeptide/ACE-2 complexes. The invention features antibodies that enhance ACE-2/ACE-2 binding polypeptide binding and/or ACE-2/ACE-2 substrate binding. The invention also features antibodies that do not inhibit or reduce ACE-2/ACE-2 binding polypeptide binding and/or ACE-2/ACE-2 substrate binding. The invention also features ACE-2 binding polypeptide specific antibodies that inhibit binding of the ACE-2 binding polypeptide to ACE-2 or ACE-2 binding to an ACE-2 substrate. In specific embodiments, antibodies are provided that inhibit ACE-2 activity or ACE-2 substrate activity by at least 95%, at least 90%, at least 85%, at least 80%, at least 75%, at least 70%, at least 60%, or at least 50% of the activity in absence of the antibody. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra).

The antibodies of the present invention may be used, for purposes including, but not limited to, purify, detect, and target the ACE-2 binding polypeptides of the present invention, including both in vitro and in vivo diagnostic and therapeutic methods. For example, the antibodies have use in immunoassays for qualitatively and quantitatively measuring levels of ACE-2 in biological samples. See, e.g., Harlow et al., *Antibodies: A Laboratory Manual* (Cold Spring Harbor Laboratory Press, Cold Spring Harbor 1988).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugated) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396 387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

According to certain embodiments of the invention, multivalent ACE-2 binding polypeptides are administered to the host animal. Multivalent ACE-2 binding polypeptide complexes may be prepared using techniques and materials known in the art such as, for example, by cross-linking the polypeptide to a carrier protein (e.g., bovine serum albumin (BSA), human albumin, keyhole limpet hemocyanin (KLH), or succinylated KLH) by use of conventional cross-linking reagents.

In specific embodiments multivalent ACE-2 binding polypeptides of the invention are administered in the form of multiple antigen peptides (MAP) (Tam, *J. Imm. Meth.*, 124:53–61 (1989); Tam, *Proc. Natl. Acad. Sci. USA*, 85:5409–5413 (1988)). In this form, the multivalent ACE-2 binding polypeptide is synthesized on a branching lysyl matrix using solid-phase peptide synthesis methods. Recognition units in the form of MAP may be prepared by methods known in the art (Tam, 1989, supra; Tam, 1988, supra), or, for example, by a stepwise solid-phase procedure on MAP resins (Applied Biosystems), utilizing methodology established by the manufacturer. MAP peptides may be synthesized comprising (ACE-2 binding polypeptide)$_2$ Lys$_1$, (ACE-2 binding polypeptide)$_4$ Lys$_3$, (ACE-2 binding polypeptide)$_8$ Lys$_7$ or more levels of branching.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, Cold Spring Harbor 1988); Hammerling et al., in *Monoclonal Antibodies and T-Cell Hybridomas* (Elsevier, N.Y. 1981), pp. 563–681 (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

A "monoclonal antibody" may comprise, or alternatively consist of, two proteins, i.e., a heavy and a light chain.

Methods for producing and screening for specific antibodies using hybridoma technology are routine and well known in the art and are discussed in detail in the Examples (e.g., Degradation). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC), to form hybridoma cells. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and $F(ab')_2$ fragments of the invention may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles that carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods,* 182:41–50 (1995); Ames et al., *J. Immunol. Methods,* 184:177–186 (1995); Kettleborough et al., *Eur. J. Immunol.,* 24:952–958 (1994); Persic et al., *Gene,* 187 9–18 (1997); Burton et al., *Advances in Immunology,* 57:191–280 (1994); PCT international application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and $F(ab')_2$ fragments can also be employed using methods known in the art such as those disclosed in PCT publication WO 92/22324; Mullinax et al., *BioTechniques,* 12(6):864–869 (1992); and Sawai et al., *AJRI,* 34:26–34 (1995); and Better et al., *Science,* 240:1041–1043 (1988) (said references incorporated herein by reference in their entireties).

Examples of techniques which can be used to produce single-chain Fvs and antibodies include those described in U.S. Pat. Nos. 4,946,778 and 5,258,498; Huston et al., *Methods in Enzymology,* 203:46–88 (1991); Shu et al., *Proc. Natl. Acad. Sci. USA,* 90:7995–7999 (1993); and Skerra et al., *Science,* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science,* 229:1202 (1985); Oi et al., *BioTechniques,* 4:214 (1986); Gillies et al., *J. Immunol. Methods,* 125:191–202 (1989); U.S. Pat. Nos. 5,807,715; 4,816,567; and 4,816,397, which are incorporated herein by reference in their entirety. A humanized antibody is an antibody molecule made using one or more complementarity determining regions (CDRs) from a non-human species antibody that binds the desired antigen and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature,* 332:323 (1988), which are incorporated herein by reference in their entireties.) Antibodies can be humanized using a variety of techniques known in the art including, for example, CDR-grafting (EP 239 400; PCT publication WO 91/09967; U.S. Pat. Nos. 5,225,539; 5,530,101; and 5,585,089), veneering or resurfacing (EP 592 106; EP 519 596; Padlan, *Molecular Immunology,* 28(4/5):489–498 (1991); Studnicka et al., *Protein Engineering,* 7(6):805–814 (1994); Roguska. et al., *Proc. Natl. Acad. Sci. USA,* 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.,* 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent 598 877; U.S. Pat. Nos. 5,413,923; 5,625,126; 5,633,425; 5,569,825; 5,661,016; 5,545,806; 5,814,318; 5,885,793; 5,916,771; and 5,939,598, each of which is incorporated by reference herein in its entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope. (See, Jespers et al., *Bio/technology,* 12:899–903 (1988).)

Further, antibodies to the ACE-2 binding polypeptides of the invention can, in turn, be utilized to generate anti-idiotype antibodies that "mimic" polypeptides of the invention using techniques well known to those skilled in the art. (See, e.g., Greenspan & Bona, *FASEB J.,* 7(5):437–444 (1989) and Nissinoff, *J. Immunol.,* 147(8):2429–2438 (1991).) For example, antibodies which bind to and competitively inhibit the binding of ACE-2 binding polypeptide to ACE-2 can be used to generate anti-idiotypes that "mimic" the ACE-2/ACE-2 binding polypeptide binding domain and, as a consequence, bind to and neutralize or enhance ACE-2 binding to an ACE-2 substrate (e.g., angiotensin, bradykinin, tachykinin, endothelin, neurotensin, or Substance P). Such neutralizing anti-idiotypes or Fab fragments of such anti-idiotypes can be used in therapeutic regimens to bind ACE-2 and/or neutralize or enhance ACE-2 mediated acitivity. In a specific embodiment, anti-idiotypic antibodies can be used to bind ACE-2, and thereby block its biological activity. In another specific embodiment, anti-idiotypic antibodies can be used to bind ACE-2, and thereby enhance its biological activity (e.g., via multimerization of ACE-2).

Polynucleotides Encoding Antibodies

The invention further provides polynucleotides comprising a nucleotide sequence encoding an antibody of the invention and fragments thereof. The invention also encompasses polynucleotides that hybridize under stringent hybridization conditions, e.g., as defined supra, to polynucleotides that encode an antibody, preferably, that specifically binds to ACE-2 or an ACE-2 binding polypeptide of the invention.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques,* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning: A Laboratory Manual, 2d Ed.* (Cold Spring Harbor Laboratory, Cold Spring Harbor, N.Y. 1990) and *Current Protocols in Molecular Biology*, Ausubel et al., eds. (John Wiley & Sons, NY 1993), which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.,* 278: 457–479 (1998) for a listing of human framework regions). Preferably, the polynucleotide generated by the combination of the framework regions and CDRs encodes an antibody that specifically binds ACE-2 or an ACE-2 binding polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci. USA,* 81:851–855 (1984); Neuberger et al., *Nature,* 312:604–608 (1984); Takeda et al., *Nature,* 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine antibody and a human immunoglobulin constant region, e.g., humanized antibodies.

Alternatively, techniques described for the production of single chain antibodies (U.S. Pat. No. 4,946,778; Bird, *Science,* 242:423–42 (1988); Huston et al., *Proc. Natl. Acad. Sci. USA,* 85:5879–5883 (1988); and Ward et al., *Nature,* 334:544–54 (1989)) can be adapted to produce single chain antibodies. Single chain. antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science,* 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody or portion thereof (preferably containing the heavy or light chain variable domain) of the invention has been obtained, the vector for the production of the antibody molecule may be produced by recombinant DNA technology using techniques well known in the art. Thus, methods for preparing a protein by expressing a polynucleotide containing an antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT publication WO 86/05807; PCT publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene,* 45:101 (1986); Cockett et al., *Bio/Technology,* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.,* 2:1791 (1983)), in which the antibody coding sequence may be ligated individually into the vector in frame with the lacZ coding region so that a fusion protein is produced; pIN vectors (Inouye & Inouye, *Nucleic Acids Res.,* 13:3101–3109 (1985); Van Heeke & Schuster, *J. Biol. Chem.,* 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. See, e.g., Logan & Shenk, *Proc. Natl. Acad. Sci. USA,* 81:355–359 (1984). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, Bittner et al., *Methods in Enzymol.,* 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, NSO, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell,* 11:223 (1977)), hypoxanthine-guanine phosphoribosyltransferase (Szybalska & Szybalski, *Proc. Natl. Acad. Sci. USA,* 48:202 (1992)), and adenine phosphoribosyltransferase (Lowy et al., *Cell,* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Proc. Natl. Acad. Sci. USA,* 77:357 (1980); O'Hare et al., *Proc. Natl. Acad. Sci. USA,* 78:1527 (1981)); gpt, which confers resistance to mycophenolic acid (Mulligan & Berg, *Proc. Natl. Acad. Sci. USA,* 78:2072 (1981)); neo, which confers resistance to the aminoglycoside G-418; Wu and Wu, *Biotherapy,* 3:87–95 (1991); Tolstoshev, *Ann. Rev. Pharmacol. Toxicol.,* 32:573–596 (1993); Mulligan, *Science,* 260:926–932 (1993); and Morgan and Anderson, *Ann. Rev. Biochem.,* 62:191–217 (1993); May, 1993, TIB TECH 11(5):155–215); and hygro, which confers resistance to hygromycin (Santerre et al., *Gene,* 30:147 (1984)). Methods commonly known in the art of recombinant DNA technology may be routinely applied to select the desired recombinant clone, and such methods are described, for example, in *Current Protocols in Molecular Biology*, Ausubel et al., eds. (John Wiley & Sons, NY 1993); Kriegler, *Gene Transfer and Expression, A Laboratory Manual* (Stockton Press, NY 1990); and *Current Protocols in Human Genetics*, Dracopoli et al., eds. (John Wiley & Sons, NY 1994), Chapters 12 and 13; Colberre-Garapin et al., *J. Mol. Biol.,* 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.,* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature,* 322:52 (1986); Kohler, *Proc. Natl. Acad. Sci. USA,* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalent and non-covalent conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than ACE-2 binding polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.,* 39:91–99 (1994); U.S. Pat. No. 5,474,981; Gillies et al., *Proc. Natl. Acad. Sci. USA,* 89:1428–1432 (1992); Fell et al., *J. Immunol.,* 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307 434; EP 367 166; PCT publications WO 96/04388; WO 91/06570; Ashkenazi et al., *Proc. Natl. Acad. Sci. USA,* 88:10535–10539 (1991); Zheng et al., J. Immunol. 154:5590–5600 (1995); and Vil et al., *Proc. Natl. Acad. Sci. USA,* 89:11337–11341(1992) (said references incorporated by reference in their entireties).

As discussed, supra, the polypeptides corresponding to an ACE-2 binding polypeptide of the invention may be fused or conjugated to the above antibody portions to increase the in vivo half life of the polypeptides or for use in immunoassays using methods known in the art. Further, the ACE-2 binding polypeptides of the invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394 827; Traunecker et al., *Nature,* 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.,* 270:3958–3964 (1995)). In many cases, the Fc part in a fusion protein is beneficial in therapy and diagnosis, and thus can result in, for example, improved pharmacokinetic properties (see, EP-A-232 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., *J. Molecular Recognition,* 8:52–58 (1995); Johanson et al., *J. Biol. Chem.,* 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA,* 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell,* 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See,PCT publication WO 97/33899), AIM II (See, PCT publication WO 97/34911), Fas Ligand (Takahashi et al., *Int. Immunol.,* 6:1567–1574 (1994)), VEGI (See, PCT publication WO 99/23105), CD40 Ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al., eds. (Alan R. Liss, Inc. 1985), pp. 243–56; Hellstrom et al., "Antibodies For Drug Delivery", in *Controlled Drug Delivery* (*2nd Ed.*), Robinson et al., eds. (Marcel Dekker, Inc. 1987), pp. 623–53; Thorpe, "Antibody Carriers Of Cytotoxic Agents In Cancer Therapy: A Review", in *Monoclonal Antibodies '84: Biological And Clinical Applications*, Pinchera et al., eds., pp. 475–506 (1985); "Analysis, Results, And Future Prospective Of The Therapeutic Use Of Radiolabeled Antibody in Cancer Therapy", in *Monoclonal Antibodies For Cancer Detection And Therapy*, Baldwin et al., eds. (Academic Press 1985), pp. 303–16; and Thorpe et al., "The Preparation And Cytotoxic Properties Of Antibody-Toxin Conjugates", *Immunol. Rev.,* 62:119–58 (1982).

Antibodies may also be attached to solid supports, which are particularly useful for immunoassays or purification of the ACE-2 binding polypeptide. Such solid supports include, but are not limited to, glass, cellulose, polyacrylamide, nylon, polystyrene, polyvinyl chloride or polypropylene.

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., *Current Protocols in Molecular Biology*, Ausubel et al., eds. (John Wiley & Sons, NY 1993), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., *Current Protocols in Molecular Biology*, Ausubel et al., eds. (John Wiley & Sons, NY 1993) at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., *Current Protocols in Molecular Biology*, Ausubel et al., eds. (John Wiley & Sons, NY 1993) at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., *Current Protocols in Molecular Biology*, Ausubel et al., eds. (John Wiley & Sons, NY 1993) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3H$ or $^{125}I$) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the diseases, disorders, or conditions disclosed herein. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant ACE-2 expression and/or activity, including, but not limited to, any one or more of the diseases, disorders, or conditions described herein.

The treatment and/or prevention of diseases, disorders, or conditions associated with aberrant expression and/or activity of ACE-2 or an ACE-2 substrate includes, but is not limited to, alleviating symptoms associated with those diseases, disorders or conditions. The antibodies of the invention may also be used to target and kill cells expressing ACE-2 on their surface and/or cells having ACE-2 bound to their surface. This targeting may be the result of binding of the antibody to ACE-2 binding polypeptides of the invention that have been coadministered, or alternatively, the result of direct binding of the antibody to ACE-2. Antibodies of the invention may be provided in pharmaceutically acceptable compositions as known in the art or as described herein.

Non-limiting examples of the ways in which the antibodies of the present invention may be used therapeutically includes binding ACE-2 binding polypeptides. of the present invention that have been coadministered in order to bind or neutralize ACE-2, or by direct cytotoxicity of the antibody, e.g., as mediated by complement (CDC) or by effector cells (ADCC). ACE-2 binding polypeptides and anti-ACE-2 binding polypeptide antibodies may be administered either locally or systemically. Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, antibiotics, and immunoglobulin). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides of the present invention, fragments or regions thereof, for both immunoassays directed to and therapy of disorders related to polypeptides, including fragments thereof, of the present invention. Such antibodies, fragments, or regions, will preferably have an affinity for polypeptides of the invention, including fragments thereof. Preferred binding affinities include those with a dissociation constant or KD less than $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{15}$ M, and $10^{-15}$ M.

Demonstration of Therapeutic or Prophylactic Activity of Antibodies

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic and/or Prophylactic Administration and Composition

The invention provides methods of treatment, inhibition and prophylaxis by administration to a subject of an effective amount of a compound or pharmaceutical composition of the invention, preferably an antibody of the invention. In a preferred embodiment, the compound is substantially purified (e.g., substantially free from substances that limit its effect or produce undesired side effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.,* 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, *Science,* 249:1527–1533 (1990); Treat et al., in *Liposomes in the Therapy of Infectious Disease and Cancer*, Lopez-Berestein and Fidler, eds. (Liss, New York 1989), pp. 353–365; Lopez-Berestein, ibid., pp. 317–327; see generally ibid.)

In yet another embodiment, the compound or composition can be delivered in a controlled release system. In one embodiment, a pump may be used (see Langer, supra; Sefton, *CRC Crit. Ref. Biomed. Eng.,* 14:201 (1987); Buchwald et al., *Surgery,* 88:507 (1980); Saudek et al., *N. Engl. J. Med.,* 321:574 (1989)). In another embodiment, polymeric materials can be used (see *Medical Applications of Controlled Release*, Langer and Wise, eds. (CRC Press, Boca Raton, Fla. 1974); *Controlled Drug Bioavailability, Drug Product Design and Performance*, Smolen and Ball, eds. (Wiley, New York 1984); Ranger and Peppas, *J. Macromol. Sci. Rev. Macromol. Chem.,* 23:61 (1983); see also Levy et al., *Science,* 228:190 (1985); During et al., *Ann. Neurol.,* 25:351 (1989); Howard et al., *J.Neurosurg.,* 71:105 (1989)). In yet another embodiment, a controlled release system can be placed in proximity of the therapeutic target, thus requiring only a fraction of the systemic dose (see, e.g., Goodson, in *Medical Applications of Controlled Release*, Langer and Wise, eds. (CRC Press, Boca Raton, Fla. 1974), vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA,* 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences, 18th Ed.*, Gennaro, ed. (Mack Publishing Co., 1990). Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses. may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to an ACE-2 binding polypeptide of interest can be used for diagnostic purposes to detect, diagnose, or monitor diseases and/or disorders associated with the aberrant expression and/or activity of ACE-2. The invention provides for the detection of aberrant expression of ACE-2, comprising (a) contacting cells or body fluid with an ACE-2 binding polypeptide; (b) assaying the expression of ACE-2 in cells or body fluid of an individual using one or more antibodies specific to the ACE-2 binding polypeptide and (c) comparing the level of ACE-2 expression with a standard ACE-2 expression level, whereby an increase or decrease in the assayed ACE-2 expression level compared to the standard expression level is indicative of aberrant expression.

The invention provides a diagnostic assay for diagnosing a disorder, comprising (a) contacting cells or body fluid with an ACE-2 binding polypeptide; (b) assaying the expression of ACE-2 in cells or body fluid of an individual using one or more antibodies specific to the ACE-2 binding polypeptide of interest and (c) comparing the level of ACE-2 expression with a standard ACE-2 expression level, whereby an increase or decrease in the assayed ACE-2 expression level compared to the standard expression level is indicative of a particular disorder. With respect to cancer, the presence of a relatively high amount of ACE-2 in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay ACE-2 protein levels in a biological sample using or routinely modifying classical immunohistological methods known to those of skill in the art (e.g., see Jalkanen et al., *J. Cell. Biol.,* 101:976–985 (1985); Jalkanen et al., *J. Cell. Biol.,* 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, 105Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One embodiment of the invention is the detection and diagnosis of a disease or disorder associated with aberrant expression of ACE-2 in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to ACE-2 (e.g., an ACE-2 binding polyptide of the invention) or which specifically binds to a molecule that specifically binds to ACE-2 (e.g., an anti- ACE-2 binding polypeptide antibody of the invention); (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood by those skilled in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain the specific polypeptide. In vivo tumor imaging is described in S. W. Burchiel et al., "Immunopharmacokinetics of Radiolabeled Antibodies and Their Fragments." (Chapter 13 in *Tumor Imaging: The Radiochemical Detection of Cancer*, S. W. Burchiel and B. A. Rhodes, eds. (Masson Publishing Inc. 1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In a further embodiment, monitoring of the disease or disorder is carried out by repeating the method for diagnosing the disease or disorder, for example, one month after initial diagnosis, six months after initial diagnosis, one year after initial diagnosis, etc. and comparing the results.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include but are not limited to computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Antibody Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention comprise two or more antibodies (monoclonal and/or polyclonal) that recognize the same and/or different sequences or regions of a polypeptide according to the invention. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated protein(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

In another specific embodiment, any of the antibodies listed above are conjugated to a toxin or a label (as described supra). Such conjugated antibodies are used to kill a particular population of cells or to quantitate a particular population of cells. In a preferred embodiment, such conjugated antibodies are used to kill smooth muscle cells expressing ACE-2 on their surface. In another preferred embodiment, such conjugated antibodies are used to quantitate smooth muscle cells expressing ACE-2 on their surface. In a further preferred embodiment, such conjugated antibodies are used to kill endothelial cells expressing ACE-2 on their surface. In a further preferred embodiment, such conjugated antibodies are used to quantitate endothelial cells expressing ACE-2 on their surface.

In another specific embodiment, any of the antibodies listed above are conjugated to a toxin or a label (as described supra). Such conjugated antibodies are used to kill a particular population of cells or to quantitate a particular population of cells. In a preferred embodiment, such conjugated antibodies are used to kill smooth muscle cells expressing the membrane-bound form of ACE-2. In another preferred embodiment, such conjugated antibodies are used to quantitate smooth muscle cells expressing the membrane-bound form of ACE-2. In a further preferred embodiment, such conjugated antibodies are used to kill endothelial cells expressing the membrane-bound form of ACE-2. In a further preferred embodiment, such conjugated antibodies are used to quantitate endothelial cells expressing the membrane-bound form of ACE-2.

The antibodies of the invention also have uses as therapeutics and/or prophylactics which include, but are not limited to, regulation of vasoconstriction, as an analgesic agent, regulation of smooth muscle cell proliferation, and in activating cells or blocking cell activation and/or killing cell lineages that express the membrane bound form of ACE-2 on their cell surfaces (e.g., to treat, prevent, and/or diagnose atherosclerosis, restenosis, and other diseases or conditions). In a specific embodiment, the antibodies of the invention fix complement. In other specific embodiments, as further described herein, the antibodies of the invention (or fragments thereof) are associated with heterologous polypeptides or nucleic acids (e.g. toxins, such as, compounds that bind and activate endogenous cytotoxic effecter systems, and radioisotopes; and cytotoxic prodrugs).

As discussed above, antibodies to the ACE-2 binding polypeptides of the invention can, in turn, be utilized to generate anti-idiotype antibodies that "mimic" the ACE-2 binding polypeptide, using techniques well known to those skilled in the art. (See, e.g., Greenspan & Bona, *FASEB J.,* 7(5):437–444 (1989), and Nissinoff, J. Immunol., 147(8):2429–2438 (1991)). For example, antibodies which bind to ACE-2 binding polypeptides and competitively inhibit ACE-2/ACE-2 binding polypeptide binding can be used to generate anti-idiotypes that "mimic" the ACE-2 binding polypeptide/ACE-2 binding domain and, as a consequence, bind to and, for example, neutralize ACE-2. Such neutralizing anti-idiotypes or Fab fragments of such anti-idiotypes can be used in therapeutic regimens to neutralize ACE-2. For example, such anti-idiotypic antibodies can be used to bind ACE-2 and thereby block ACE-2 mediated vasoconstriction.

EXAMPLES

Isolation of ACE-2 binding polypeptides and their use in accordance with this invention will be further illustrated below. The specific parameters included in the following examples are intended to illustrate the practice of the invention, and they are not presented to in any way limit the scope of the invention.

Example 1

Screening of Phage Display Libraries

The specific polypeptides according to this invention were selected from screening eight phage display libraries. Six of the libraries each displayed a short, variegated exogenous peptide loop of 6, 7, 8, 9, 10, or 12 amino acids on the surface of M13 phage, at the amino terminus of protein III. The libraries are designated TN6/6 (having a potential $3.3\times10^{12}$ amino acid sequence diversity); TN7/4 (having a potential $1.2\times10^{14}$ amino acid sequence diversity), TN8/9 (having a potential $2.2\times10^{15}$ amino acid sequence diversity), TN9/4 (having a potential $4.2\times10^{16}$ amino acid sequence diversity, TN10/9 (having a potential $3.0\times10^{16}$ amino acid sequence diversity), and TN12/1 (having a sequence diversity of $4.6\times10^{19}$).

The TN6/6 library was constructed to display a single microprotein binding loop contained in a 12-amino acid template. The TN6/6 library utilized a template sequence of Xaa-Xaa-Xaa-Cys-Xaa-Xaa-Xaa-Xaa-Cys-Xaa-Xaa-Xaa (SEQ ID NO:153). The amino acids at positions 2, 3, 5, 6, 7, 8, 10, and 11 of the template were varied to permit any amino acid except cysteine (C). The amino acids at positions 1 and 12 of the template were varied to permit any amino acid except cysteine (C), glutamic acid (E), isoleucine (I), Lysine (K), methionine (M), and threonine (T).

The TN7/4 library was constructed to display a single microprotein binding loop contained in a 13-amino acid template. The TN7/4 library utilized a template sequence of Xaa-Xaa-Xaa-Cys-Xaa-Xaa-Xaa-Xaa-Xaa-Cys-Xaa-Xaa-Xaa (SEQ ID NO:154). The amino acids at amino acid positions 1, 2, 3, 5, 6, 7, 8, 9, 11, 12, and 13 of the template were varied to permit any amino acid except cysteine (C).

The TN8/9 library was constructed to display a single microprotein binding loop contained in a 14-amino acid template. The TN8/9 library utilized a template sequence of Xaa-Xaa-Xaa-Cys-Xaa-Xaa-Xaa-Xaa-Xaa-Xaa-Cys-Xaa-Xaa-Xaa (SEQ ID NO:155). The amino acids at positions 1, 2, 3, 5, 6, 7, 8, 9, 10, 12, 13, and 14 in the template were varied to permit any amino acid except cysteine (C).

The TN9/4 library was constructed to display a single microprotein binding loop contained in an 15-amino acid template. The TN9/1 library utilized a template sequence Xaa-Xaa-Xaa-Cys-Xaa-Xaa-Xaa-Xaa-Xaa-Xaa-Xaa-Cys-Xaa-Xaa-Xaa (SEQ ID NO:156). The amino acids at positions 1, 2, 3, 5, 6, 7, 8, 9, 10, 11, 13, 14 and 15 in the template were varied to permit any amino acid except cysteine (C).

The TN10/9 library was constructed to display a single microprotein binding loop contained in a 16-amino acid template. The TN10/9 library utilized a template sequence Xaa-Xaa-Xaa-Cys-Xaa-Xaa-Xaa-Xaa-Xaa-Xaa-Xaa-Xaa-Cys-Xaa-Xaa-Xaa (SEQ ID NO:157). The amino acids at positions 1, 2, 15, and 16 in the template were varied to permit any amino acid selected from a group of 10 amino acids: D, F, H, L, N, P, R, S, W, or Y). The amino acids at positions 3 and 14 in the template were varied to permit any amino acid selected from a group of 14 amino acids: A, D, F, G, H, L, N, P, Q, R, S, V, W, or Y). The amino acids at positions 5, 6, 7, 8, 9, 10, 11, and 12 in the template were varied to permit any amino acid except cysteine (C).

The TN12/1 library was constructed to display a single microprotein binding loop contained in an 18-amino acid template. The TN12/1 library utilized a template sequence Xaa-Xaa-Xaa-Cys-Xaa-Xaa-Xaa-Xaa-Xaa-Xaa-Xaa-Xaa-Xaa-Xaa-Cys-Xaa-Xaa-Xaa (SEQ ID NO:158). The amino acids at position 1, 2, 17, and 18 in the template were varied to permit any amino acid selected from a group of 12 amino acids: A, D, F, G, H, L, N, P, R, S, W, or Y). The amino acids at positions 3, 5, 6, 7, 8, 9, 10, 11, 12, 13, 14, and 16 were varied to permit any amino acid except cysteine (C).

We also endeavored to select ACE-2 binding polypeptides from two commercially available linear phage display libraries, designated PhD 7 and PhD 12, respectively (New England Biolabs). The PhD 7 library displays a linear random-sequence 7-mer; the PhD 12 libary displays a random-sequence 12-mer. No ACE-2 binding phage were isolated from these two linear libraries.

The libraries were selected against a FLAG-tagged ACE-2 target, which was immobilized to streptoavidin-coated paramagnetic beads (Seradyn, Ramsey, Minn.) via biotinylated anti-FLAG antibody (M2 antibody, Sigma, St. Louis, Mo.). Before selection against the target, the libraries were depleted 5 times with FLAG peptide/anti-FLAG antibody-immobilized beads, to remove binders to the streptoavidin beads, the anti-FLAG antibody and the FLAG peptide. The depleted libraries were incubated with 6 μg FLAG-ACE-2 (obtained from Human Genome Sciences, Inc.) in solution for 1 hour at room temperature (RT), and then incubated with anti-FLAG antibody-immobilized beads for 1 hour. The beads were washed 7 times with PBS, 0.2% Tween 20 (PBST) to remove unbound phage. After washing, the bound phage were eluted by introducing free FLAG peptide (100 μg/ml). Eluted phage were amplified, and underwent two more similar rounds of selection. In round 1, the six constrained peptide libraries, TN6/6, TN7/4, TN8/9, TN9/4, TN 10/9, and TN12/1, were selected separately. To accelerate the selection procedures, in the subsequent rounds of selection, these six libraries were combined into two pools: TN6/6, TN7/4, and TN8/9 were combined to form pool A, whereas TN9/4, TN 10/9, and TN12/1 were combined to form pool B. The two linear peptide libraries, PhD7 and PhD12 (New England BioLabs) were combined together at round 1.

Phage enriched from the third round of selection were screened by ELISA for strong ACE-2 binders. Immulon 2 96-well plates (Dynatech) were coated with streptavidin for 1 hour at 37° C. and subsequently coated with anti-FLAG antibody for 1 hour at room temperature. Half of the plates were further coated with FLAG-ACE-2 as the target plates, and the other half of the plates were coated with FLAG peptide as background plates. The amount of each protein or peptide coated was 100 ng per well. The coated plates were then incubated for 1 hour at room temperature with 1:2 diluted overnight phage cultures that were made by inoculating phage from individual plaques into bacterial host cells. After being washed 7 times with PBST, the plates were incubated with HRP-conjugated anti-M13 antibody (Pharmacia) for 1 hour at room temperature, washed 5 times, developed with TMB peroxidase substrate solution (Kirkegaad & Perry Laboratories, Gaithersburg, Md.), and read at 630 nm on an ELISA plate reader.

DNA sequences encoding peptides from positive phage binders were amplified by PCR and sequenced by automatic sequencing. A number of ACE-2-binding polypeptides were identified, with ACE-2 binders being isolated from five of the cyclic peptide libraries screened (i.e., all except TN9/4). Analysis of recurring amino acid sequences among the ACE-2 binding polypeptides revealed a series of polypeptide "families" exhibiting common core structures:

| | SEQ ID NO: |
|---|---|
| Sequence Family I | |
| N R E C H **A** **L** **F** C M **D** **F** | 20 |
| S P T C R **A** **L** **F** C **V** **D** **F** | 21 |
| S E N C Q **A** **L** **F** C **V** **D** **F** | 22 |
| S P T C R **A** **L** **F** C **V** **D** **F** | 23 |
| L E M C E **A** **L** **F** C **V** **E** **F** | 24 |
| N P E C G **A** **L** **F** C M **E** **F** | 25 |
| D F G C N **A** M **F** C **V** **E** **F** | 26 |
| D Q N C F **A** M Y C F **E** **F** | 27 |
| N D Y C T V F T G **A** **L** **F** C L **D** **F** | 28 |
| P N Q C G V D I W **A** **L** **F** C **V** **D** **F** | 29 |
| Sequence Family II | |
| E G N C F L I G P **W** C **F** **E** **F** | 30 |
| E G N C F L I G P **W** C **F** **E** **F** | 31 |
| H I E C E E W G Y **W** C **I** **E** M | 32 |
| W E D C L W I G M M C V **E** **F** | 33 |
| Y E D C I G H A L **F** C M T **F** | 34 |
| D D K C F G W A H **F** C **F** **D** **F** | 35 |
| G G Q C G T S Y L **F** C **I** **D** **F** | 36 |
| Y S G C A D M Y M **F** C **I** **D** **F** | 37 |
| G G Q C G T S Y L **F** C **I** **D** **F** | 38 |
| K F E C M P S S L **F** C V **D** **F** | 39 |
| D D Y C F N I S S Y S **Y** C **F** **D** **F** | 40 |
| L H D C F I Y A D Y E **Y** C **F** **D** **F** | 41 |
| N H H C L E F S S F E **Y** C **F** **D** **F** | 42 |
| D N L C M S G G S F D **Y** C **F** **D** **F** | 43 |
| S D Y C V G N N A V T **Y** C **F** **D** **F** | 44 |
| N L D C I Y L Q N H S **Y** C **F** **D** **F** | 45 |
| D D D C M M L P L T M **F** C **F** **D** **F** | 46 |
| Y D N C L G L A N L N **F** C **F** **D** **F** | 47 |
| H L D C Y N L V D N M **F** C **F** **D** **F** | 48 |
| N W N C L G T N E L Q **F** C **L** **D** **F** | 49 |
| Y F A C T N N D S Y L **F** C **L** **D** **F** | 50 |
| Y N F C M L I G E R D **Y** C **L** **D** **F** | 51 |
| D D V C Y S L I M A D **Y** C **L** **D** **F** | 52 |
| Y F A C T N N D S Y L **F** C **L** **D** **F** | 53 |
| Sequence Family III | |
| **D** **D** M C R **W** Y P **F** A S F Y M C L F - | 54 |
| **D** **D** H C **E** **W** A S **Y** W K W D L C L H D | 55 |
| **D** **D** V C **E** N A D **F** A W L G W C M H F | 56 |
| **D** **D** **D** C G **W** I G **F** A N F H L C L H G | 57 |
| F **D** **D** C Q T S W F Q G **F** W L C I D D | 58 |
| F H **D** C S **W** G P **W** G P W E I C T R L | 59 |
| S N **D** C V **W** L Q **F** W G G D M C F L P | 60 |
| N A **D** C **E** **W** V N **F** N H V D L C M W N | 61 |
| G S **D** C **E** **W** V N **F** T M F Q M C I S N | 62 |
| A W **D** C **E** **W** N L **F** D S T F F C P G F | 63 |
| L Y **E** C **E** **W** K Q **F** G P V E M C L N F | 64 |
| H S **E** C R **W** E W **F** G R T M I C M S F | 65 |
| S G **E** C N **W** Q Q **F** S G W E I C L R D | 66 |
| A Y L C **D** **W** I L **F** D S F E M C L A P | 67 |
| P F **E** C **D** **W** G P **W** T L E M L C G P P | 68 |
| Sequence Family IV | |
| **R** G H C **R** **D** **S** **R** C M M N A P G | 69 |
| **R** I G C **R** **D** **S** **R** C N W W A P G | 70 |
| **R** G F C **R** **D** **S** S C S F P | 71 |
| **R** G W C L **D** **S** **R** C K V F | 72 |
| F L F C **R** L A S **R** **D** **S** **R** C A S P | 73 |
| F N P C **R** L Q S **R** **D** **S** A C R F R | 74 |
| F F P C **R** A L E K **D** **S** **R** C S F F | 75 |

-continued

| | SEQ ID NO: |
|---|---|
| H F S C **R** L P S L **D** **S** **R** C Q L W | 76 |
| Sequence Family V | |
| N D V C L N D **D** C **V** Y G | 77 |
| W P T C L **T** M **D** C **V** Y N | 78 |
| H Y N C H **T** N **D** C **V** V L | 79 |
| H L R C M **T** S **D** C I H F | 80 |
| Sequence Family VI | |
| W V L C **F** **E** **W** **E** D C D E K | 81 |
| Y E Y C **F** **E** **W** **E** Q C W E K | 82 |
| G I F C **F** **E** **W** **E** T C Y Q A | 83 |
| P Q F C **F** **E** **W** **E** P C F - - | 84 |
| I G F C **F** **E** **W** **E** V C Y E G | 85 |
| S I Y C **F** **D** **W** **E** D C W D E | 86 |
| Y D W C **F** **D** **W** **E** Q C W D Q | 87 |
| V G F C **F** **D** **W** **E** P C D E L | 88 |
| M D F C **F** **D** **W** **E** E C W T N | 89 |
| N I F C **F** **D** **W** **E** P C H F G | 90 |
| F E I C **F** **D** **W** **E** V C H E Q | 91 |
| D Y L C **F** **D** **W** **E** A C W L S | 92 |
| Y A M C **F** **D** **W** **D** E C F L G | 93 |
| W ? W C **F** **E** **W** **E** D W C L V E | 94 |
| Y Q F C **F** **D** **W** **E** T T C W L D | 95 |
| V Y F C **F** **D** **W** **E** Q D C D E M | 96 |
| F Q L C **F** **D** **W** **E** E E C E E S | 97 |
| W A V C **F** **D** **W** **E** N - C G D K | 98 |
| W Q F C **F** **D** **W** **D** L N C D L R | 99 |
| Y W F C **F** **D** **W** **E** E D A N G H C G G N | 100 |
| F L L C **F** **D** **W** **D** I D W E Y G C Q H H | 101 |
| Sequence Family VII | |
| **Y** **E** E C **H** W R **P** M A C S T H | 102 |
| **W** **E** V C **H** **W** A **P** M M C K H G | 103 |
| **Y** **E** F C **H** **Y** A **P** Q E C K H M | 104 |
| Sequence Family VIII | |

-continued

| | SEQ ID NO: |
|---|---|
| ? **K** **E** C **K** **F** **G** **Y** S ? C **L** **A** **W** | 105 |
| Q **K** **E** C **K** **F** **G** **Y** P H C **L** **P** **W** | 106 |
| Sequence Family IX | |
| E H N C **T** **W** W N **P** C W T T | 107 |
| M **D** H C **T** **W** Y Q **P** C V L K | 108 |
| W **D** H C N **W** A H **P** C S R K | 109 |
| S **D** W CG**T** **W** N N **P** C F H Q | 110 |
| Sequence Family X | |
| R Y L C L **P** Q **R** D K **P** **W** K F C N W F | 111 |
| R L H C K **P** Q **R** Q S **P** **W** M K C Q H L | 112 |
| Y S H C S **P** L **R** Y Y **P** **W** W K C T Y P | 113 |
| L H A C R **P** V **R** G D **P** **W** W A C T L G | 114 |
| G F T C S **P** I **R** M F **P** **W** F R C D L G | 115 |
| F S P C K A L **R** H S **P** **W** W V C P S G | 116 |

In the foregoing peptide families, the amino acids in bold type are either invariant at that position or are preferred (i.e., recurrent in multiple sequences) in a position relative to an invariant residue. Analysis of the structures of the above families of ACE-2 binding polypeptides revealed the general formulae I to X for ACE-2 binders discussed above (SEQ ID NOs: 1–10).

Based on the sequence families identified by sequence cluster analysis, representative peptides from each motif were synthesized for further analysis and testing (see Table 1, below). The crude peptides were ordered from Sigma (St. Louis, Mo.). The peptides were then cleaved from resin, purified, oxidized, and lyophilized. The purity of oxidized peptides was great than 90%.

TABLE 1

Peptide Sequences Synthesized for Further Testing

| Peptide Designation | Library | Sequence | SEQ ID NO: |
|---|---|---|---|
| DX500 | TN6 | Ac-GSNRECHALFCMDFAPGEGGG-NH2 | 11 |
| DX501 | TN6 | Ac-GSSPTCRALFCVDFAPGEGGG-NH2 | 12 |
| DX502 | TN6 | Ac-GSLEMCEALFCVEFAPGEGGG-NH2 | 13 |
| DX503 | TN6 | Ac-GSDQNCFAMYCFEFAPGEGGG-NH2 | 14 |
| DX507 | TN10 | Ac-GSNDYCTVFTGALFCLDFAPEGGG-NH2 | 18 |
| DX514 | TN10 | Ac-GSPNQCGVDIWALFCVDFAPEGGGK-NH2 | 25 |
| DX504 | TN8 | Ac-AGEGNCFLIGPWCFEFGTEGGG-NH2 | 15 |
| DX505 | TN8 | Ac-AGYEDCIGHALFCMTFGTEGGG-NH2 | 16 |
| DX508 | TN10 | Ac-GSYDNCLGLANLNFCFDFAPEGGG-NH2 | 19 |
| DX509 | TN12 | Ac-GDDDHCEWASYWKWDLCLHDDPEGGG-NH2 | 20 |
| DX510 | TN12 | Ac-GDDDDCGWIGFANFHLCLHGDPEGGG-NH2 | 21 |
| DX511 | TN12 | Ac-GDPFECDWGPWTLEMLCGPPDPEGGG-NH2 | 22 |
| DX524 | TN6 | Ac-GSRIGCRDSRCNWWAPGEGGG-NH2 | 27 |
| DX525 | TN6 | Ac-GSRGFCRDSSCSFPAPGEGGG-NH2 | 28 |
| DX526 | TN6 | Ac-GSWPTCLTMDCVYNAPGEGGG-NH2 | 29 |
| DX527 | TN7 | Ac-AGWVLCFEWEDCDEKGTEGGG-NH2 | 30 |
| DX528 | TN8 | Ac-AGVYFCPDWEQDCDEMGTEGGG-NH2 | 31 |
| DX529 | TN8 | Ac-AGWEVCHWAPMMCKHGGTEGGG-NH2 | 32 |
| DX530 | TN8 | Ac-AGQKECKFGYPHCLPWGTEGGG-NH2 | 33 |
| DX531 | TN8 | Ac-AGSDWCGTWNNPCFHQGTEGGG-NH2 | 34 |
| DX512 | TN12 | Ac-GDRLHCKPQRQSPWMKCQHLDPEGGG-NH2 | 23 |
| DX513 | TN12 | Ac-GDLHACRPVRGDPWWACTLGDPEGGG-NH2 | 24 |
| DX599 | TN12 | Ac-GDRYLCLPQRDKPWKFCNWFDPEGGG-NH2 | 36 |
| DX600 | TN12 | Ac-GDYSHCSPLRYYPWWKCTYPDPEGGG-NH2 | 37 |
| DX601 | TN12 | Ac-GDGFTCSPIRMFPWFRCDLGDPEGGG-NH2 | 38 |
| DX602 | TN12 | Ac-GDFSPCKALRHSPWWVCPSGDPEGGG-NH2 | 39 |

"Ac-" denotes N-terminal acetylation; "-NH2" denotes C-terminal amidation.

Lead peptide inhibitor candidates were identified from in vitro studies utilizing peptide M-2195 as a substrate. Assay mixture was prepared first by pre-incubating (30 minutes, room temperature) the enzyme with the inhibitor (0.45 μg (50 pmoles) ACE-2, 0–0.5 μM inhibitor rage, up to 90 μL volume with 100 mM TRIS pH 7.4, 0.1% Tween-20, 0.4% DMSO) in each well, in triplicate, by dispensing volumes using a repeat pipetter (Rainin) into a 96-well clear-bottom back plate (Costar, 07-200-590). The layout of the plate was such that M-2195 substrate concentration were varied by column and inhibitor concentrations were varied by row. Substrate stock (10 μL of 10× concentration) was added to each well to be tested in blocks of three vertically down the plate. The reaction was monitored on a Spectrafluor Plus (Tecan) at an excitation wavelength of 340 nm and an emission wavelength of 400 nm (+/−35 nm) every 30 seconds for a time period of 10 minutes. All data points were transferred to and analysed by Prism 2.01 software. The results are shown in table 2.

TABLE 2

| DX-No. | Clone Name | Sequence | #of Res. | Inhibi-tion | IC50 μM | Ki nM | SEQ ID NO: |
|---|---|---|---|---|---|---|---|
| DX-500 | A-B5 | Ac-GSNRECHALFCMDFAPGEGGG-NH2 | 21 | + | | | 11 |
| DX-501 | A-H2 | Ac-GSSPTCRALFCVDFAPGEGGG-NH2 | 21 | + | | | 12 |
| DX-502 | A-B6 | Ac-GSLEMCEALFCVEFAPGEGGG-NH2 | 21 | − | | | 13 |
| DX-503 | A-C11 | Ac-GSDQNCFAMYCFEFAPGEGGG-NH2 | 21 | − | | | 14 |
| DX-504 | A-F12 | Ac-AGEGNCFLIGPWCFEFGTEGGG-NH2 | 22 | − | | | 15 |
| DX-505 | A3-E12 | Ac-AGYEDCIGHALFCMTFGTEGGG-NH2 | 22 | + | | | 16 |
| *DX-506 | ACEH10-A6 | Ac-AGWELCNGVMALFCVEFGTEGGG-NH2 | 23 | n./d. | | | 17 |
| DX-507 | ACEH5-H8 | Ac-GSNDYCTVFTGALFCLDFAPEGGG-NH2 | 24 | − | | | 18 |
| DX-508 | ACEH1-C1 | Ac-GSYDNCLGLANLNFCFDFAPEGGG-NH2 | 24 | + | | | 19 |
| DX-509 | ACEH6-D12 | Ac-GDDDHCEWASYWKWDLCLHDDPEGGG-NH2 | 26 | + | | | 20 |
| DX-510 | ACEH4-H9 | Ac-GDDDDCGWIGFANFHLCLHGDPEGGG-NH2 | 26 | − | | | 21 |
| DX-511 | ACEH1-D3 | Ac-GDPFECDWGPWTLEMLCGPPDPEGGG-NH2 | 26 | + | | | 22 |
| DX-512 | B-H7 | Ac-GDRLHCKPQRQSPWMKCQHLDPEGGG-NH2 | 26 | ++++ | 0.06 | 150 | 23 |
| DX-513 | ACEH2-D8 | Ac-GDLHACRPVRGDPWWACTLGDPEGGG-NH2 | 26 | ++++ | 0.09 | 150 | 24 |
| DX-514 | ACEH2-A2 | Ac-GSPNQCGVDIWALFCVDFAPEGGGK-NH2 | 25 | + | | | 25 |
| DX-515 | ACEH2-A2 | Ac-GSPNQCGVDIWALFCVDFAPEGGGK(fitc)-NH2 | 25 | | | | 26 |
| DX-524 | 360c-7-G10 | Ac-GSRIGCRDSRCNWWAPGEGGG-NH2 | 21 | +++ | 0.6 | | 27 |
| DX-525 | 360c-8-H9 | Ac-GSRGFCRDSSCSFPAPGEGGG-NH2 | 21 | +++ | 1 | | 28 |
| DX-526 | 360c-7-C3 | Ac-GSWPTCLTMDCVYNAPGEGGG-NH2 | 21 | + | | | 29 |
| DX-527 | 360c-7-D4 | Ac-AGWVLCFEWEDCDEKGTEGGG-NH2 | 21 | − | | | 30 |
| DX-528 | 360c-2-A12 | Ac-AGVYFCFDWEQDCDEMGTEGGG-NH2 | 22 | − | | | 31 |
| DX-529 | 360c-4-E5 | Ac-AGWEVCHWAPMMCKHGGTEGGG-NH2 | 22 | +++ | 0.4 | | 32 |
| DX-530 | 360c-7-D8 | Ac-AGQKECKFGYPHCLPWGTEGGG-NH2 | 22 | ++ | 30 | | 33 |
| DX-531 | 360c-8-G11 | Ac-AGSDWCGTWNNPCFHQGTEGGG-NH2 | 22 | +++ | 0.5 | | 34 |
| DX-537 | ACEH2-D8 | Ac-GDLHACRPVRGDPWWACTLGDPEGGGK(fitc)-NH2 | 26 | | | | 35 |
| DX-599 | ACEH2-F6 | Ac-GDRYLCLPQRDKPWKFCNWFDPEGGG-NH2 | 26 | ++++ | 0.14 | | 36 |
| DX-600 | ACEH1-F11 | Ac-GDYSHCSPLRYYPWWKCTYPDPEGGG-NH2 | 26 | ++++ | 0.025 | | 37 |
| DX-601 | ACEH1-G10 | Ac-GDGFTCSPIRMFPWFRCDLGDPEGGG-NH2 | 26 | ++++ | 0.068 | | 38 |
| DX-602 | B-G09 | Ac-GDFSPCKALRHSPWWVCPSGDPEGGG-NH2 | 26 | ++++ | 0.12 | | 39 |

−: signifies no inhibition on ACE-2 activity
+: signifies weak inhibition (20–60% inhibition at ~100 μM)
++: signifies moderate inhibition (at least 80% inhibition at ~100 μM; with IC50 of ~30 μM)
+++: signifies strong inhibition (~99% inhibition at ~100 μM; with IC50 between 0.4–1 μM)
++++: signifies very strong inhibition (~100% inhibition at 100 μM; with IC50 0.15 μM)
n./d.: not determined, due to difficulties in sythesizing
DX515: fluorescence-labeled version of DX514
DX537: fluorescence-labeled version of DX513.

Example 2

Synthesis of Further ACE-2 Binding Peptides

Once a promising ACE-2 binding polypeptide has been isolated, improvements to that polypeptide can be made by changing, adding or removing individual or multiple amino acid residues from the polypeptide. Amino acid substitutions can be conservative or non conservative. Conservative amino acid exchanges include, for example, the exchange of aromatic residues (e.g., phenylalanine, tryptophan, and tyrosine) for one another, the exchange of hydrophobic residues (e.g, leucine, isoleucine, and valine) for one another, the exchange of polar residues (e.g., glutamine and asparagine) for one another, the exchange of acidic residues (e.g., arginine, lysine, and histidine) for one another, and the exchange of small residues (e.g., alanine, serine, threonine, methionine, and glycine) for one another, the exchange of aromatic residues for one another. Additionally, nonclassical amino acids, chemical amino acid analogs, or chemically modified classical amino acids can be introduced as a substitution or addition to an ACE-2 binding polypeptide of the invention. Non-classical amino acids include, but are not limited to, the D-isomers of the common amino acids, 2,4-diaminobutyric acid (Dbu), 4-aminobutyric acid (bAbu), 2-aminobutyric acid (Abu), 6-amino hexanoic acid (epsilon-Ahx), 2-aminoisobutyric acid (Aib), 3-aminoisobutyric acid (bAib), 3-aminopropanoic acid (bAla), ornithine (Orn), nor-leucine (Nle), norvaline (Nva), 3-hydroxyproline (3Hyp), 4-hydroxyproline (4Hyp), sarcosine (MeGly), citrulline, homocitrulline, cysteic acid, t-butylglycine, t-butylalanine, phenylglycine, cyclohexylalanine, fluoro-amino acids, designer amino acids such as β-methyl amino acids, Cα-methyl amino acids, Nα-methyl amino acids, and amino acid analogs in general.

Example 3

Biacore Analysis of the Affinity of ACE-2 Binding Polypeptides

Binding of ACE-2 binding polypeptides to ACE-2, for example, can be analyzed by BIAcore analysis. Either ACE-2 (or another antigen for which one wants to know the affinity of an ACE-2 binding polypeptide) or ACE-2 binding polpeptide can be covalently immobilized to a BIAcore sensor chip (CM5 chip) via amine groups using N-ethyl-N'-(dimethylaminopropyl)carbodiimide/N-hydroxysuccinimide chemistry. Various dilutions of ACE-2 binding polypeptides or ACE-2 (or other antigen for which one wants to know the affinity of an ACE-2 binding polypeptide), respectively are flowed over the derivatized CM5 chip in flow cells at 15 microlters/min. for a total volume of 50 microliters. The amount of bound protein is determined during washing of the flow cell with HBS buffer (10 mM HEPES, pH7.4, 150 mM NaCl, 3.4 mM EDTA, 0.005% surfactant P20). Binding specificty for the protein of inerest is determined by competition with soluble competitor in the presence the protein of ineterest.

The flow cell surface can be regenerated by displacing bound protein by washing with 20 microliters of 10 mM glycine-HCl, pH2.3. For kinetic analysis, the flow cells are tested at different flow rates and different polypetide densities on the CM5 chip. The on-rates and off-rates can be determined using the kinetic evaluation program in BIAevaluation 3 software.

Example 4

In Vitro Screening of ACE-2 Antagonists

The bioassay for assessing the effects of putative ACE-2 antagonists is performed in triplicate in 96 well format by mixing equal volumes of ACE-2, responder cells, and putative antagonist each of which is prepared as a 3× stock reagent.

Endothelial cells of coronary vessels are washed and resuspended in complete medium (CM) (RPMI 1640 with 10% FBS containing 100 U/ml penicillin, 100 μg/ml streptomycin, 4 mM glutamine, 5x10E-5 M beta-mercaptoethanol) at a concentration of 3x10e6 cells/mL. Staphylococcus aureus, Cowan I (SAC, CalBiochem) is added to cells at 3× concentration (3×=1:33,333 dilution of stock).

Meanwhile, eight serial dilutions (3-fold) of potential antagonists are prepared in CM such that the diluted antagonists are at 3× the final concentrations to be tested in the assay. ACE-2 binding polypeptides are routinely tested starting at a final concentration of 10μg/mL and going down to about 1.5 ng/mL.

Human rACE-2 is prepared in CM to 3× concentration (3×=300 ng/mL, 30 ng/mL, and 3 ng/mL) in CM. Potential inhibitors are routinely tested at several concentrations of ACE-2 to avoid false negatives due to unexpectedly low affinity or antagonist concentration.

Fifty microliters of diluted antagonist and 50 μL of diluted ACE-2 are added to the putative antagonist dilution series. Cells are then incubated for 72 hours (37° C., 5% $CO_2$) in a fully humidified chamber. After 72 hrs., the cells are supplemented with 0.5 μCi/well 3H-thymidine (e.g., 6.7 Ci/mmol) and incubated for an additional 24 hours. Plates are harvested using a Tomtec Cell Harvester and filters counted in a TopCount Scintillation counter (Packard).

Example 5

Protein Fusions of ACE-2 Binding Polypeptides

ACE-2 binding polypeptides of the invention are optionally fused to other proteins. These fusion proteins can be used for a variety of applications. For example, fusion of ACE-2 binding polypeptides to His-tag, HA-tag, protein A, IgG domains, and maltose binding protein facilitates purification. (See, EP A 394 827; Traunecker et al., *Nature,* 331:84–86 (1988)). Similarly, fusion to IgG-1, IgG-3, and albumin increases the half-life time in vivo. Nuclear localization signals fused to ACE-2 binding polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below (SEQ ID NO:184). These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and ACE-2 binding polynucleotide is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891)

Human IgG Fc region:

GGGATCCGGAGCCCAAATCTTCTGA-
CAAAACTCACACATGCCCACCGTGC-
CCAGCACCTGAATTCGAGGGTGCACCGT-
CAGTCTTCCTCTTCCCCCCAAAACCCAAGGAC
ACCCTCATGATCTCCCGGACTCCTGAG-
GTCACATGCGTGGTGGTGGACGTAAGC-
CACGAAGACCCTGAGGTCAAGT-
TCAACTGGTACGTGGACGGCGTGGAGGTGCAT
AATGCCAAGACAAAGCCGCGGGAGGAG-
CAGTACAACAGCACGTACCGTGTGGT-
CAGCGTCCTCACCGTCCTGCACCAG-
GACTGGCTGAATGGCAAGGAGTACAAGTGCAA
GGTCTCCAACAAAGCCCTCCCAAC-
CCCCATCGAGAAAACCATCTCCAAAGC-
CAAAGGGCAGCCCCGAGAACCACAGGTG-
TACACCCTGCCCCCATCCCGGGATGAGCTGACC
AAGAACCAGGTCAGCCTGACCTGCCTG-
GTCAAAGGCTTCTATCCAAGCGA-
CATCGCCGTGGAGTGGGAGAG-
CAATGGGCAGCCGGAGAACAACTACAAGACCA
CGCCTCCCGTGCTGGACTCCGACGGCTC-
CTTCTTCCTCTACAGCAAGCTCACCGTG-
GACAAGAGCAGGTGGCAGCAGGG-
GAACGTCTTCTCATGCTCCGTGATGCATGAGGC
TCTGCACAACCACTACACGCAGAAGAGC-
CTCTCCCTGTCTCCGGGTAAATGAGTGC-
GACGGCCGCGACTCTAGAGGAT (SEQ ID NO:150)

Example 6

Isolation of scFV Molecules Recognizing ACE-2 Binding Polypeptides

Naturally occuring V-genes isolated from human PBLs are constructed into a large library of antibody fragments which contain reactivities against polypeptides of the present invention to which the donor may or may not have been exposed (see, e.g., U.S. Pat. No. 5,885,793, incorporated herein by reference in its entirety).

Rescue of the Library

A library of scFvs is constructed from the RNA of human PBLs as described in WO 92/01047. To rescue phage displaying antibody fragments, approximately $10^9$ *E. coli* harbouring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×108 TU of Δ gene 3 helper phage (M13 Δ gene III, see WO 92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 μg/ml ampicillin and 50 μg/mI kanamycin and grown overnight. Phage are prepared as described in WO92/01047.

M13 Δ gene III is prepared as follows: M13 Δ gene III helper phage does not encode gene III protein, hence the phage(mid) displaying antibody fragments have a greater avidity of binding to antigen. Infectious M13 Δ gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (EC-Centra 8, 4000 revs/min. for 10 min.), resuspended in 300 ml 2×TY broth containing 100 μg ampicillin/ml and 25 μg kanamycin/mi (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately 1013 TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with Δ gene III helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect *E. coli* HB 2151 and soluble scFv is produced (Marks et al., 1991) from single colonies for assay. ELISAs are performed with microtitre plates coated with either 10 pg/ml of the polypeptide of the present invention in 50 mM bicarbonate, pH 9.6. Clones positive in ELISA are further characterized by PCR fingerprinting (see, e.g., WO 92/01047) and then by sequencing.

Additionaly, scFvs may be converted to complete Ig molecules using techniques which are commonly known in the art.

Example 7

Production of an anti-ACE-2 Binding Polypeptide Antibody Hybridoma Technology The antibodies of the present invention can be prepared by a variety of methods. (See, Current Protocols, Chapter 2.) As one example of such methods, cells expressing ACE-2 binding polypeptides are administered to an animal to induce the production of sera containing polyclonal antibodies. In a preferred method, a preparation of ACE-2 binding polypeptide is prepared and purified to render it substantially free of natural contaminants which is then conjugated to a carrier molecule such as keyhole limpet hemocyanin (KLH), suucinylated KLH, or chicken gamma globulin (CGG). Such a preparation is then introduced into an animal in order to produce polyclonal antisera of greater specific activity.

In the most preferred method, the antibodies of the present invention are monoclonal antibodies (or ACE-2 protein binding fragments thereof). Such monoclonal antibodies can be prepared using hybridoma technology. (Kohler et al., *Nature,* 256:495 (1975); Kohler et al., *Eur. J. Immunol.,* 6:511 (1976); Kohler et al., *Eur. J. Immunol.,* 6:292 (1976); Hammerling et al., in *Monoclonal Antibodies and T-Cell Hybridomas* (Elsevier, N.Y. 1981), pp. 563–681.) In general, such procedures involve immunizing an animal (preferably a mouse) with ACE-2 binding polypeptide or, more preferably, with a secreted ACE-2 binding polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2/0), available from the ATCC. After fusion, the resulting hybridoma cells are selectively maintained in HAT medium, and then cloned by limiting dilution as described by Wands et al. (*Gastroenterology,* 80:225–232 (1981).) The hybridoma cells obtained through such a selection are then assayed to identify clones which secrete antibodies capable of binding the ACE-2 binding polypeptide.

Alternatively, additional antibodies capable of binding to ACE-2 binding polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the ACE-2 binding polypeptide-specific antibody can be blocked by ACE-2 binding polypeptide. Such antibodies comprise anti-idiotypic antibodies to the ACE-2 binding protein-specific antibody and can be used to immunize an animal to induce formation of further ACE-2 binding polypeptide-specific antibodies.

It will be appreciated that Fab and $F(ab')_2$ and other fragments of the antibodies of the present invention may be used according to the methods disclosed herein. Such fragments are typically produced by proteolytic cleavage, using enzymes such as papain (to produce Fab fragments) or pepsin (to produce $F(ab')_2$ fragments). Alternatively, secreted ACE-2 binding protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, *Science,* 229:1202 (1985); Oi et al., *BioTechniques,* 4:214 (1986); Cabilly et al., U.S. Pat. No. 4,816,567; Taniguchi et al., EP 171 496; Morrison et al., EP 173 494; Neuberger et al., WO 86/01533; Robinson et al., WO 87/02671; Boulianne et al., *Nature,* 312:643 (1984); Neuberger et al., *Nature,* 314:268 (1985)).

Example 8

Fluorometric Assays for ACE-2

The activity of ACE-2 was measured utilizing a fluorometric assay in which peptide M-2195 (BACHEM) is used as a substrate. ACE-2 cleaves off the C-terminal lysine from the peptide with a concomitant increase in fluorescence signal.

The assays were performed in 96-well clear-bottom black plates (Costar, 07-200-590). In each well, 0.45 μg (5 pmoles) of ACE-2 is added to 90 μL of an assay solution containing 100 mM TRIS at pH 7.4, 0.1% Tween, and 0.4% DMSO. Substrate stock at 10 μL of 10× concentration is added to each well (for example, 10 μL of 1 mM stock for a final 100 μM concentration). The reaction was monitored on a Spectrafluor Plus (Tecan) at an excitation wavelength of 340 nm and an emission wavelength of 400 nm (+/−35 nm) every 30 seconds up to 10 minutes. All samples were measured in triplicate. The data points were transferred to and analysed on Prism 2.01 software.

Degradation: Identification and Analysis of the Functional Roles of ACE-2 Inhibitory Peptides The effects of graded doses of A1-9 (Fields et al., *Peptide Research* 4: 95–101 (1991)) or A1-10 (substrate control) alone or in combination (Tallarida, *Drug Synergism and Dose-Effect Data Analysis*, Chapman and Hall/CRC, New York (2000), Tallarida et al., *Life Science* 61: PL417–425 (1997)) with angiotensin II were examined on isolated aortic vascular rings developed tension in response to vasoactive substances. Aortas were removed from mature male Sprague-Dawley rats, cleared of connective tissue, and cut into 1 mm rings. Rings were mounted to an isometric force transducer and placed in Krebs-Henseleit solution bubbled with 95% 02/5% CO2 at 37° C. Rings were exposed to a 2 g preload, relaxed and then exposed to various concentrations of angiotensin peptides alone or in combination. Following angiotensin peptide dosing, rings were fully constricted with KCl to determine the maximum degree of vasoconstriction.

Table 3 shows the maximum developed isometric force (Emax) following treatment with A1-9, angiotensin II or the combination of the two over a dose range from 1–30 nM (alone or in combination) in mature rat aortic rings. The maximum tension developed by A1-9 animal and always less than that of angiotensin II. When A1-9 was combined with angiotensin II, the resulting Emax was greater than the sum of the individual peptide Emax values, suggesting a superadditive or synergistic interaction. Because A1-9 is virtually devoid of activity, the quantitation of its constrictor-enhancing action on angiotensin II was derived from the shift in the angiotensin II dose-effect curve as seen in FIG. 1. The slopes of the dose-effect curves did not differ; however, the relative potency of angiotensin II was increased by a factor of 11.6 (95% confidence limits of 3.02–44.7) beyond that of simple additive potentiation, indicative of synergism for the combination. In control experiments, angiotensin I failed to potentiate angiotensin II-mediated vasoconstriction. This indicates that the synergy observed between A1-9 and angiotensin II is specific for A1-9 and is not a of the ACE and ACE-2 substrate, angiotensin I.

TABLE 3

| Experiment | A1-9 % Max. Developed Force | AII % Max. Developed Force | AI-9 + AII % Max. Developed Force |
|---|---|---|---|
| 1 | 3.5 | 22 | 82 |
| 2 | 0 | 8.6 | 18 |
| 3 | 7.5 | 17 | 24 |
| 4 | 6.4 | 9.9 | 34 |
| 5 | 3.2 | 41 | 48 |

To investigate the effects of A1-9 on arterial pressure, A1-9 was administered to awake, free-ranging Sprague-Dawley rats via indwelling intravenous and arterial catheters. Intravenous infusion of A1-9 (1–3 μg/kg/min) in the awake rat produced a dose-dependent tonic increase in mean arterial pressure to a maximum of approximately 30 mmHg (FIG. 2). Pulse pressure (systolic-diastolic) was also elevated and heart rate was decreased in a dose-dependent manner by A1-9 infusion (data not shown). These responses seen with A1-9 were similar in magnitude to those induced by angiotensin II. The observed bradycardia (presumed to be reflexive) in association with the increase in mean arterial and pulse pressure suggests that A1-9 increases vascular tone in vivo, perhaps through potentiating the activity of angiotensin II.

Figure 3:
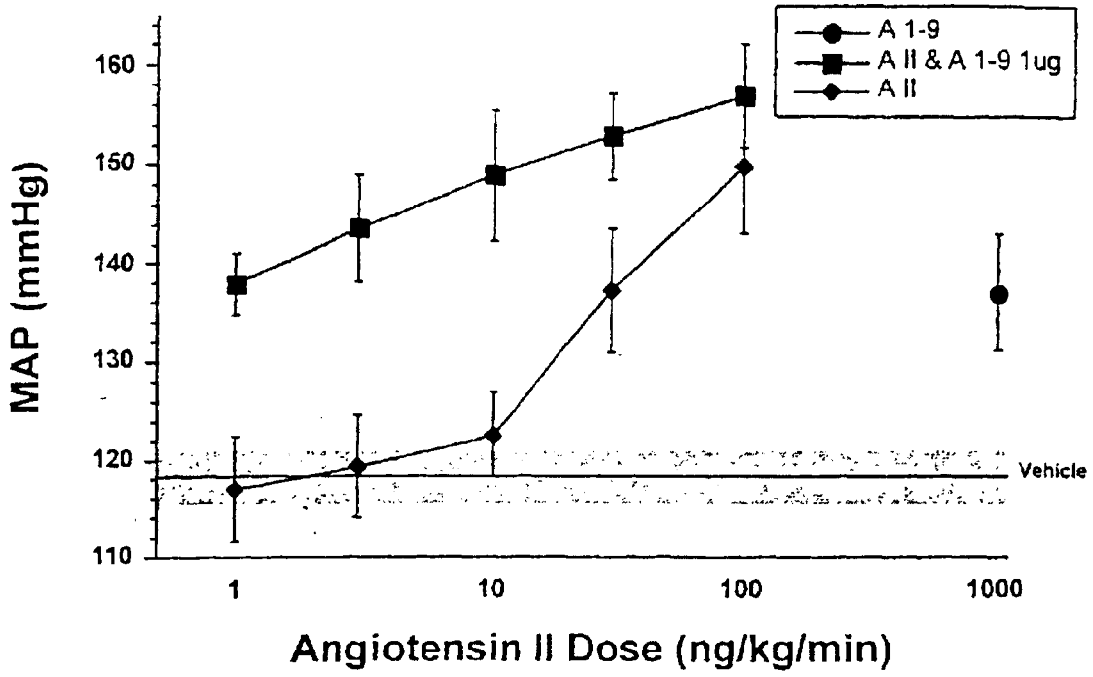
FIG. 3. The effect of A1-9 on angiotensin II-mediated pressor responses in normotensive awake male rats. Data are reported as average mean arterial pressure±SEM (n=6 rats).

To examine any interactions induced by coadministration of A1-9 and angiotensin II, arterial pressure was monitored in the awake rat after they received either A1-9 (1 μg/kg/min) or saline coinfused with angiotensin II (1–100 ng/kg/min). The submaximal infusion of A1-9 potentiated the pressor response elicted by angiotensin II in an additive fashion (FIG. 3). Angiotensin II coinfused with a control nonapeptide with no intrinsic hemodynamic activity in awake rats produced a dose-effect curve similar to that of angiotensin II alone (data not shown).

To test further the hypothesis that downregulating ACE-2 activity would decrease arterial pressure, tagged human ACE-2 was generated in order to identify potential peptide ACE-2 inhibitors whose sequences were derived from phage display. The human ACE-2 cDNA was used as template for amplification by PCR of the nucleotides corresponding to the extracellular domain (M1-S740). The 5' primer:

5' ATGGATGATCAGCCATCATGTCAAGCTCTTCCTG 3' (SEQ ID NO:151)

and 3' primer:

5' GTATGCTCTAGATTAGGAAA-CAGGGGGCTGGTTAG 3' (SEQ ID NO:152)

generate a 2200 bp fragment which was digested with BclI and XbaI and cloned into the BamHI and XbaI sites of a baculovirus transfer vector pA2. Following DNA sequence confirmation, the plasmid (A2:Ace-H) was transfected into Sf9 cells to generate a recombinant baculovirus (Coleman et al, *Gene* 190:163–170 (1997)). Metabolic labeling was used to confirm the presence of a novel band of ~85 Kd corresponding to the human Ace-H protein in conditioned media from Sf9 cells. For protein production, Sf9 cells were seeded in serum-free media and infected at a multiplicity of infection of 1–2 with the recombinant baculovirus. Conditioned media was harvested, clarified by filtration, and used for subsequent enzyme purification. Initially, FLAG peptide was attached to streptavidin beads using bead-immobilized biotinylated anti-FLAG antibody. Proprietary phage display libraries were depleted on these beads 5 times to remove phages bound to the FLAG peptide. Depleted libraries were incubated with FLAG-ACE-2 and then immobilized on streptavidin beads. The beads were washed stringently and the bound phage was eluted with FLAG peptide. Eluted phages were amplified and characterized by ELISA using FLAG-ACE-2 coated in microtiter plates. Positive binders were sequenced and collapsed into several families based on amino acid sequences.

A phage display technology was used to identify families of peptide inhibitors of rhACE-2. FLAG-ACE-2 (above) was used for panning peptides binding to ACE-2. Peptide binders were sequenced and collapsed into several families based upon amino acid sequences. Several members from the peptide families were synthesized and their inhibitory activities were tested using recombinant human-ACE-2. Using M-2195 peptide as substrate, multiple inhibitors were identified and the most active ACE-2 inhibitor peptide was chosen for further studies. Another ACE-2 binding peptide that failed to inhibit rhACE-2 was identified, synthesized and used as a control for in vivo experiments. The Ki for the ACE-2 inhibitor peptide was 250 nM, acting as a mixed-type inhibitor for ACE-2 when M-2195 was used as a substrate. This peptide also inhibited conversion of angiotensin I to A1-9 by ACE-2. The ACE-2 inhibitor peptide was specific for ACE-2 and did not inhibit the activity of ACE. For example, the inhibitor did not affect the hydrolysis of the substrate, hip-his-leu (250 mM) by ACE (1.5 nM), even at 25 mM. In comparison, the hydrolytic activity of ACE was completely inhibited by 25 mM captopril. Thus, the ACE-2 inhibitor peptide was found to be specific for ACE-2 and blocked conversion of angiotensin I to A1-9.

Figure 4:
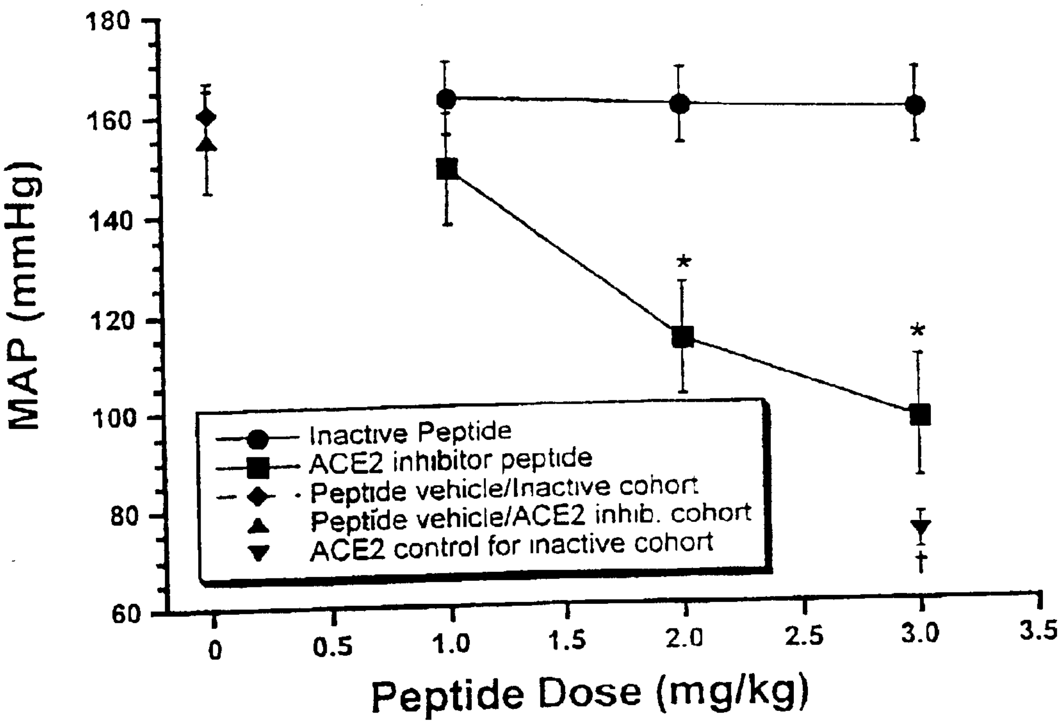
FIG. 4. Arterial pressure responses to ACE-2 inhibitor or inactive peptide in spontaneously hypertensive rats for 2.5 min following bolus injection. Data are reported as mean MAP±SEM. Since ACE-2 and inactive peptides were tested in different cohorts of rats, separate vehicle treatment groups are plotted. The inactive peptide treated group was also treated with ACE-2 inhibitory peptide at the end of the experiment for control. * indicates significant difference between ACE-2 inhibitor and vehicle treatment (ANOVA followed by Dunnett's). t indicates significant difference between ACE-2 inhibitor and control peptide treated groups. The control peptide had no effect on MAP.

A lead inhibitor peptide candidate identified from in vitro studies caused a dose-dependent depressor response upon iv bolus administration in the awake SHR (FIG. 4). As the peptide inhibitor dose was increased, the magnitude and duration of the depressor response increased. This depressor response was characterized by an initial transient fall in MAP lasting approximately 1–2 min at the lower doses and approximately 6 min in duration at the 3 mg/kg dose level. The maximal average depressor response at a dose of 3 mg/kg was 70.5±4.6 mmHg from an average MAP of 155±10 mmHg. Transient tachycardia (average maximal change between 50–70 bpm at a dose level of 2–3 mg/kg) was observed to coincide with the depressor response (data not shown). At no dose level was the MAP or HR altered by the control peptide.

In terms of cardiovascular function, the expression pattern of ACE-2 suggests a potential role in the regulation of local circulation in the kidney and heart. However, our results indicate that ACE-2 may play a role in regulating systemic circulatory homeostasis. A1-9, known to be produced from ACE-2 mediated catabolism of angiotensin I, potentiated angiotensin II-mediated vasoconstriction in isolated rat aortic rings and pressor responses in the awake rat. Although there has been speculation that A1-9 might serve to inhibit ACE and lead to vasodilation (Donoghue, *Circulation Research* 87:e1-e9 (2000), Snyder et al., *The Journal of Biological Chemistry* 260:7857–7860 (1985)), the present results support the hypothesis that ACE-2 upregulates systemic arterial pressure under conditions where intact cardiovascular reflexes are present. An unlikely possibility is that the observed effects of A1-9 were due to its conversion to angiotensin II in vivo since biochemical and in vivo evidence supports that this mechanism is not a major contributor to the normal formation of angiotensin II (Johnson et al., *Peptides* 10:489–492 (1989); Donoghue et al., *Circulation Research* 87:e1-e9 (2000); Oparil et al., *Circulation Research* 29:682–690 (1971)).

The identification of a peptide inhibitor of ACE-2 has enabled the study of the effects of ACE-2 inhibition in a model of spontaneous hypertension in vivo. The current results indicate that the inhibition of ACE-2 reduces arterial pressure through decreasing circulating and/or levels of A1-9, an angiotensin II synergizing peptide. Supporting this is the demonstration that blockade of ACE-2 causes a depressor response in awake spontaneously hypertensive rats.

Following the foregoing description, the characteristics important for affinity binding polypeptides permitting detection or separation of ACE-2 or ACE-2-like polypeptides (ACE-2 target protein) in or from any solution can be appreciated. Additional binding polypeptide embodiments of the invention and alternative methods adapted to a particular solution or feed stream will be evident from studying the foregoing description. All such embodiments and obvious alternatives are intended to be within the scope of this invention, as defined by the claims that follow.

Publications referred to above are hereby incorporated by reference.

What is claimed is:

1. A method of increasing vasoconstriction comprising administering to an individual a therapeutically effective amount of angiotensin II (SEQ ID NO:144) in combination with angiotensin 1-9 (SEQ ID NO:145), wherein the angiotensin 1-9 potentiates the effect of angiotensin II.

2. A method of ameliorating a disorder resulting from low blood pressure comprising administering a therapeutically effective amount of angiotensin II SEQ ID No:144)in combination with angiotensin 1-9 (SEQ ID NO:145), wherein the angiotensin 1-9 potentiates the effect of angiotensin II.

3. The method of claim 2 wherein the disorder is hypotension.

4. The method of claim 2 wherein the disorder is shock.

5. The method of claim 2 wherein the disorder is syncope.

* * * * *